US012305227B2

(12) United States Patent
Roudebush et al.

(10) Patent No.: US 12,305,227 B2
(45) Date of Patent: May 20, 2025

(54) IMPLANTATION SUCCESS AS DETERMINED BY BLASTOCOEL FLUID COMPONENTS

(71) Applicant: University of South Carolina, Columbia, SC (US)

(72) Inventors: William Roudebush, Mount Pleasant, SC (US); Renee Chosed, Greer, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 16/594,192

(22) Filed: Oct. 7, 2019

(65) Prior Publication Data

US 2020/0109438 A1 Apr. 9, 2020

Related U.S. Application Data

(60) Provisional application No. 62/741,617, filed on Oct. 5, 2018.

(51) Int. Cl.
*C12Q 1/686* (2018.01)
*G01N 21/64* (2006.01)

(52) U.S. Cl.
CPC ......... *C12Q 1/686* (2013.01); *G01N 21/6428* (2013.01); *G01N 21/6486* (2013.01)

(58) Field of Classification Search
CPC ......... C12Q 2600/158; G01N 21/6486; G01N 21/6428
See application file for complete search history.

(56) References Cited

PUBLICATIONS

Gianaroli et al., "Blastocentesis: a source of DNA for preimplantation genetic testing. Results from a pilot study," Fertility and Sterility, December, vol. 102, No. 6, pp. 1692-1699. (Year: 2014).*
Rule et al., "Relationship between blastocoel cell-free DNA and day-5 blastocyst morphology," Journal of Assisted Reproduction and Genetics, June, vol. 35, pp. 1497-1501. (Year: 2018).*
Chang et al., "Blastocoel cell-free DNA, a marker of embryonic quality," Reproductive Biology 2, Nov. 1, vol. 108, No. 3, e106. (Year: 2017).*
Palini et al., "Genomic DNA in human blastocoel fluid," Reproductive BioMedicine Online, vol. 26, pp. 603-610. (Year: 2013).*
Li et al., "Preimplantation Genetic Screening with Spent Culture Medium/Blastocoel Fluid in Vitro Fertilization," Scientific Report, June, vol. 8, pp. 1-10. (Year: 2018).*
Rehman et al., "Late stages of embryo progression are a much better predictor of clinical pregnancy than early cleavage in intracytoplasmic sperm injection and in vitro fertilization cycles with blastocyst-stage transfer," Fertility and Sterility, May, vol. 87, No. 5, pp. 1041-1052 (Year: 2007).*
Skryabin et al., "Molecular Karyotyping of Cell-Free DNA from Blastocoele Fluid as a Basis for Noninvasive Preimplantation Genetic Screening of Aneuploidy," Russian Journal of Genetics, vol. 51, No. 11, pp. 1123-1128. (Year: 2015).*

* cited by examiner

*Primary Examiner* — Young J Kim
(74) *Attorney, Agent, or Firm* — Offit Kurman; Douglas L. Lineberry

(57) ABSTRACT

The current disclosure explains that cfDNA levels, specific gene expression profiles (assessed via altered mRNA levels of specific gene transcripts), specific protein levels, and potentially noncoding RNAs in blastocoel fluid are all factors that can be used to forecast/determine the implantation potential in IVF patients.

17 Claims, 13 Drawing Sheets

Specification includes a Sequence Listing.

| Morphology Score (mean) | Percent positive for cfDNA | cfDNA content [ng/mL] | Percent positive for Caspase-3 | Caspase Activity (AFU) |
| --- | --- | --- | --- | --- |
| 21.125 | 100 | 133.55 | 78.1 | 383.8 |

FIGURE 1

TABLE 2

| Sample Number | PGT-A | Age | Implantation result? |
|---|---|---|---|
| 1 | 46, XY | 26 | Yes |
| 2 | 46, XY | 30 | Yes |
| 3 | 46, XY | 41 | Yes |
| 4 | 46, XX | 38 | Yes |
| 5 | 46, XY | 39 | Yes |
| 6 | 46, XX | 37 | Yes |
| 7 | 46, XY | 36 | No |
| 8 | 46, XX | 36 | No |
| 9 | 46, XX | 35 | No |
| 10 | 46, XX | 33 | No |
| 11 | 47, XY +21 | 41 | N/A |
| 12 | 47, XY +21 | 33 | N/A |
| 13 | 47, XY +21 | 39 | N/A |
| 14 | 47, XX +21 | 39 | N/A |
| 15 | 45, XO | 32 | N/A |
| 16 | 45, XO | 32 | N/A |
| 17 | 47, XY +18 | 36 | N/A |
| 18 | 47, XXY | 38 | N/A |
| 19 | 46, XX -17 +21 | 39 | N/A |
| 20 | 45, XY -21 | 39 | N/A |
| 21 | 47, XY +4 | 31 | N/A |

FIGURE 5

SEQUENCE LISTING

<160> NUMBER OF SEQ ID NOS: 93

<210> SEQ ID NO 1
<211> LENGTH: 1285
<212> TYPE: DNA
<213> ORGANISM: Homo sapiens

<400> SEQUENCE: 1
gctctctgct cctcctgttc gacagtcagc cgcatcttct tttgcgtcgc cagccgagcc 60
acatcgctca gacaccatgg ggaaggtgaa ggtcggagtc aacggatttg gtcgtattgg 120
gcgcctggtc accagggctg cttttaactc tggtaaagtg gatattgttg ccatcaatga 180
ccccttcatt gacctcaact acatggttta catgttccaa tatgattcca cccatggcaa 240
attccatggc accgtcaagg ctgagaacgg gaagcttgtc atcaatggaa atcccatcac 300
catcttccag gagcgagatc cctccaaaat caagtggggc gatgctggcg ctgagtacgt 360
cgtggagtcc actggcgtct tcaccaccat ggagaaggct ggggctcatt tgcagggggg 420
agccaaaagg gtcatcatct ctgccccctc tgctgatgcc cccatgttcg tcatgggtgt 480
gaaccatgag aagtatgaca acagcctcaa gatcatcagc aatgcctcct gcaccaccaa 540
ctgcttagca cccctggcca aggtcatcca tgacaacttt ggtatcgtgg aaggactcat 600
gaccacagtc catgccatca ctgccaccca gaagactgtg gatggcccct ccgggaaact 660
gtggcgtgat ggccgcgggg ctctccagaa catcatccct gcctctactg gcgctgccaa 720
ggctgtgggc aaggtcatcc ctgagctgaa cgggaagctc actggcatgg ccttccgtgt 780
ccccactgcc aacgtgtcag tggtggacct gacctgccgt ctagaaaaac ctgccaaata 840
tgatgacatc aagaaggtgg tgaagcaggc gtcggagggc cccctcaagg gcatcctggg 900

```
ctacactgag caccaggtgg tctcctctga cttcaacagc gacacccact cctccacctt    960

tgacgctggg gctggcattg ccctcaacga ccactttgtc aagctcattt cctggtatga   1020

caacgaattt ggctacagca acagggtggt ggacctcatg gcccacatgg cctccaagga   1080

gtaagacccc tggaccacca gccccagcaa gagcacaaga ggaagagaga gaccctcact   1140

gctggggagt ccctgccaca ctcagtcccc caccacactg aatctcccct cctcacagtt   1200

gccatgtaga ccccttgaag aggggagggg cctagggagc cgcaccttgt catgtaccat   1260

caataaagta ccctgtgctc aacca                                         1285
```

<210> SEQ ID NO 2
<211> LENGTH: 3813
<212> TYPE: DNA
<213> ORGANISM: Homo sapiens

<400> SEQUENCE: 2

```
aacgctggtc ctcggccggg cgcgctgacg tcatcgtgcg tcagagtgag cccggatggg     60

gcggcgggct tcgggagcgc ccgggctgat ccgagccgag cgggccgtat ctccttgtcg    120

gcgccgctga ttcccggctc tgcggaggcc tctaggcagc cgcgcagctt ccgtgtttgc    180

tgcgcccgca ctgcgattta caaccctgaa gaatctccct atccctattt tgtcccccctg    240

cagtaataaa tcccattatg gagatctcga aactttataa agggatatag tttgaattct    300

atggagtgta attttgtgta tgaattatat ttttaaaaca ttgaagagtt ttcagaaaga    360

aggctagtag agttgattac tgatacttta tgctaagcag tactttttttg gtagtacaat    420

attttgttag gcgtttctga taacactaga aaggacaagt tttatcttgt gataaattga    480

ttaatgttta caacatgact gataattata gctgaatagt ccttaaatga tgaacaggtt    540

atttagtttt taaatgcagt gtaaaaagtg tgctgtggaa attttatggc taactaagtt    600

tatggagaaa ataccttcag ttgatcaaga ataatagtgg tatacaaagt taggaagaaa    660

gtcaacatga tgctgcagga aatggaaaca aatacaaatg atatttaaca aagatagagt    720

ttacagtttt tgaactttaa gccaaattca tttgacatca agcactatag caggcacagg    780

ttcaacaaag cttgtgggta ttgacttccc ccaaaagttg tcagctgaag taatttagcc    840

cacttaagta aatactatga tgataagctg tgtgaactta gcttttaaat agtgtgacca    900

tatgaaggtt ttaattactt ttgtttattg gaataaaatg agatttttttg ggttgtcatg    960

ttaaagtgct tatagggaaa gaagcctgca tataattttt taccttgtgg cataatcagt   1020

aattggtctg ttattcaggc ttcatagctt gtaaccaaat ataaataaaa ggcataattt   1080

aggtattcta tagttgctta gaattttgtt aatataaatc tctgtgaaaa atcaaggagt   1140

tttaatattt tcagaagtgc atccaccttt cagggcttta agttagtatt actcaagatt   1200

atgaacaaat agcacttagg ttacctgaaa gagttactac aaccccaaag agttgtgttc   1260

taagtagtat cttggtaatt cagagagata ctcatcctac ctgaatataa actgagataa   1320

atccagtaaa gaaagtgtag taaattctac ataagagtct atcattgatt tctttttgtg   1380

gtaaaaatct tagttcatgt gaagaaattt catgtgaatg ttttagctat caaacagtac   1440

tgtcacctac tcatgcacaa aactgcctcc caaagacttt tcccaggtcc ctcgtatcaa   1500

aacattaaga gtataatgga agatagcacg atcttgtcag attggacaaa cagcaacaaa   1560

caaaaaatga agtatgactt ttcctgtgaa ctctacagaa tgtctacata ttcaactttc   1620

cccgccgggg tgcctgtctc agaaaggagt cttgctcgtg ctggttttta ttatactggt   1680
```

gtgaatgaca aggtcaaatg cttctgttgt ggcctgatgc tggataactg gaaactagga 1740
gacagtccta ttcaaaagca taaacagcta tatcctagct gtagctttat tcagaatctg 1800
gtttcagcta gtctgggatc cacctctaag aatacgtctc caatgagaaa cagttttgca 1860
cattcattat ctcccacctt ggaacatagt agcttgttca gtggttctta ctccagcctt 1920
tctccaaacc ctcttaattc tagagcagtt gaagacatct cttcatcgag gactaacccc 1980
tacagttatg caatgagtac tgaagaagcc agatttctta cctaccatat gtggccatta 2040 actttttttgt caccatcaga attggcaaga gctggttttt attatatagg acctggagat 2100
agggtagcct gctttgcctg tggtgggaag ctcagtaact gggaaccaaa ggatgatgct 2160
atgtcagaac accggaggca ttttcccaac tgtccatttt tggaaaattc tctagaaact 2220
ctgaggttta gcatttcaaa tctgagcatg cagacacatg cagctcgaat gagaacattt 2280
atgtactggc catctagtgt tccagttcag cctgagcagc ttgcaagtgc tggtttttat 2340
tatgtgggtc gcaatgatga tgtcaaatgc ttttgttgtg atggtggctt gaggtgttgg 2400
gaatctggag atgatccatg ggtagaacat gccaagtggt ttccaaggtg tgagttcttg 2460
atacgaatga aaggccaaga gtttgttgat gagattcaag gtagatatcc tcatcttctt 2520
gaacagctgt tgtcaacttc agataccact ggagaagaaa atgctgaccc accaattatt 2580
cattttggac ctggagaaag ttcttcagaa gatgctgtca tgatgaatac acctgtggtt 2640
aaatctgcct tggaaatggg ctttaataga gacctggtga aacaaacagt tcaaagtaaa 2700
atcctgacaa ctggagagaa ctataaaaca gttaatgata ttgtgtcagc acttcttaat 2760
gctgaagatg aaaaaagaga agaggagaag gaaaaacaag ctgaagaaat ggcatcagat 2820
gatttgtcat taattcggaa gaacagaatg gctctctttc aacaattgac atgtgtgctt 2880
cctatcctgg ataatctttt aaaggccaat gtaattaata aacaggaaca tgatattatt 2940
aaacaaaaaa cacagatacc tttacaagcg agagaactga ttgataccat tttggttaaa 3000
ggaaatgctg cggccaacat cttcaaaaac tgtctaaaag aaattgactc tacattgtat 3060
aagaacttat ttgtggataa gaatatgaag tatattccaa cagaagatgt ttcaggtctg 3120
tcactggaag aacaattgag gaggttgcaa gaagaacgaa cttgtaaagt gtgtatggac 3180
aaagaagttt ctgttgtatt tattccttgt ggtcatctgg tagtatgcca ggaatgtgcc 3240
ccttctctaa gaaaatgccc tatttgcagg ggtataatca agggtactgt tcgtacattt 3300
ctctcttaaa gaaaaatagt ctatatttta acctgcataa aaaggtcttt aaaatattgt 3360
tgaacacttg aagccatcta aagtaaaaag ggaattatga gtttttcaat tagtaacatt 3420
catgttctag tctgctttgg tactaataat cttgtttctg aaaagatggt atcatatatt 3480
taatcttaat ctgtttattt acaagggaag atttatgttt ggtgaactat attagtatgt 3540
atgtgtacct aagggagtag tgtcactgct tgttatgcat catttcagga gttactggat 3600
ttgttgttct ttcagaaagc tttgaatact aaattatagt gtagaaaaga actggaaacc 3660
aggaactctg gagttcatca gagttatggt gccgaattgt ctttggtgct tttcacttgt 3720
gttttaaaat aaggattttt ctcttatttc tccccctagt ttgtgagaaa catctcaata 3780
aagtgcttta aaaagaaaaa aaaaaaaaaa aaa 3813

<210> SEQ ID NO 3
<211> LENGTH: 3744
<212> TYPE: DNA
<213> ORGANISM: Homo sapiens

<400> SEQUENCE: 3

```
ggaagatgga tgcaaaagct cgaaattgtt tgcttcaaca tagagaagct ctggaaaagg     60
acatcaagac atcctacatc atggatcaca tgattagtga tggattttta acaatatcag    120
aagaggaaaa agtaagaaat gagcccactc aacagcaaag agcagctatg ctgattaaaa    180
tgatacttaa aaaagataat gattcctacg tatcattcta caatgctcta ctacatgaag    240
gatataaaga tcttgctgcc cttctccatg atggcattcc tgttgtctct tcttccagtg    300
gtaaagattc agttagtgga ataacttcgt atgtaaggac agtcctgtgt gaaggtggag    360
taccacagag gccagttgtt tttgtcacaa ggaagaagct ggtgaatgca attcagcaga    420
agctctccaa attgaaaggt gaaccaggat gggtcaccat acatggaatg gcaggctgtg    480
ggaagtctgt attagctgca gaagctgtta gagatcattc ccttttagaa ggttgtttcc    540
caggggggagt gcattgggtt tcagttggga aacaagacaa atctgggctt ctgatgaaac    600
tgcagaatct ttgcacacgg ttggatcagg atgagagttt ttcccagagg cttccactta    660
atattgaaga ggctaaagac cgtctccgca ttctgatgct tcgcaaacac ccaaggtctc    720
tcttgatctt ggatgatgtt tgggactctt gggtgttgaa agcttttgac agtcagtgtc    780
agattcttct tacaaccaga gacaagagtg ttacagattc agtaatgggt cctaaatatg    840
tagtccctgt ggagagttcc ttaggaaagg aaaaaggact tgaaatttta tccctttttg    900
ttaatatgaa gaaggcagat ttgccagaac aagctcatag tattataaaa gaatgtaaag    960
gctctcccct tgtagtatct ttaattggtg cacttttacg tgattttccc aatcgctggg   1020
agtactacct caaacagctt cagaataagc agtttaagag aataaggaaa tcttcgtctt   1080
atgattatga ggctctagat gaagccatgt ctataagtgt tgaaatgctc agagaagaca   1140
tcaaagatta ttacacagat ctttccatcc ttcagaagga cgttaaggtg cctacaaagg   1200
tgttatgtat tctctgggac atggaaactg aagaagttga agacatactg caggagtttg   1260
taaataagtc tcttttattc tgtgatcgga atggaaagtc gtttcgttat tatttacatg   1320
atcttcaagt agattttctt acagagaaga attgcagcca gcttcaggat ctacataaga   1380
agataatcac tcagtttcag agatatcacc agccgcatac tctttcacca gatcaggaag   1440
actgtatgta ttggtacaac tttctggcct atcacatggc cagtgccaag atgcacaagg   1500
aactttgtgc tttaatgttt tccctggatt ggattaaagc aaaaacagaa cttgtaggcc   1560
ctgctcatct gattcatgaa tttgtggaat acagacatat actagatgaa aaggattgtg   1620
cagtcagtga gaattttcag gagtttttat ctttaaatgg acaccttctt ggacgacagc   1680
catttcctaa tattgtacaa ctgggtctct gtgagccgga aacttcagaa gtttatcagc   1740
aagctaagct gcaggccaag caggaggtcg ataatggaat gctttacctg gaatggataa   1800
acaaaaaaaa catcacgaat ctttcccgct tagttgtccg cccccacaca gatgctgttt   1860
accatgcctg cttttctgag gatgatcaga gaatagcttc ttgtggagct gataaaacct   1920
tacaggtgtt caaagctgaa acaggaggga aacttctaga aatcaaggct catgaggatg   1980
aagtgctttg ttgtgcattc tctacagatg acagatttat agcaacctgc tcagtggata   2040
aaaaagtgaa gatttggaat tctatgactg gggaactagt acacacctat gatgagcact   2100
cagagcaagt caattgctgc catttcacca acagtagtca tcatcttctc ttagccactg   2160
ggtcaagtga ctgcttcctc aaactttggg atttgaatca aaaagaatgt cgaaatacca   2220
tgtttggtca tacaaattca gtcaatcact gcagattttc accagatgat aagcttttgg   2280
ctagttgttc agctgatgga accttaaagc tttgggatgc gacatcagca aatgagagga   2340
```

```
aaagcattaa tgtgaaacag ttcttcctaa atttggagga ccctcaagag gatatggaag   2400

tgatagtgaa gtgttgttcg tggtctgctg atggtgcaag gataatggtg gcagcaaaaa   2460

ataaaatctt tttgtggaat acagactcac gttcaaaggt ggctgattgc agaggacatt   2520

taagttgggt tcatggtgtg atgttttctc ctgatggatc atcatttttg acatcttctg   2580

atgaccagac aatcaggctc tgggagacaa agaaagtatg taagaactct gctgtaatgt   2640

taaagcaaga agtagatgtt gtgtttcaag aaaatgaagt gatggtcctt gcagttgacc   2700

atataagacg tctgcaactc attaatggaa gaacaggtca gattgattat ctgactgaag   2760

ctcaagttag ctgctgttgc ttaagtccac atcttcagta cattgcattt ggagatgaaa   2820

atggagccat tgagatttta gaacttgtaa acaatagaat cttccagtcc aggtttcagc   2880

acaagaaaac tgtatggcac atccagttca cagccgatga gaagactctt atttcaagtt   2940

ctgatgatgc tgaaattcag gtatggaatt ggcaattgga caaatgtatc tttctacgag   3000

gccatcagga aacagtgaaa gactttagac tcttgaaaaa ttcaagactg ctttcttggt   3060

catttgatgg aacagtgaag gtatggaata ttattactgg aaataaagaa aaagactttg   3120

tctgtcacca gggtacagta ctttcttgtg acatttctca cgatgctacc aagttttcat   3180

ctacctctgc tgacaagact gcaaagatct ggagttttga tctccttttg ccacttcatg   3240

aattgagggg ccacaacggc tgtgtgcgct gctctgcctt ctctgtggac agtaccctgc   3300

tggcaacggg agatgacaat ggagaaatca ggatatggaa tgtctcaaac ggtgagcttc   3360

ttcatttgtg tgctccgctt tcagaagaag gagctgctac ccatggaggc tgggtgactg   3420

acctttgctt ttctccagat ggcaaaatgc ttatctctgc tggaggatat attaagtggt   3480

ggaacgttgt cactggggaa tcctcacaga ccttctacac aaatggaacc aatcttaaga   3540

aaatacacgt gtcccctgac ttcaaaacat atgtgactgt ggataatctt ggtattttat   3600

atattttaca gactttagaa taaaatagtt aagcattaat gtagttgaac tttttaaatt   3660

tttgaattgg aaaaaaattc taatgaaacc ctgatatcaa ctttttataa agctcttaat   3720

tgttgtgcag tattgcattc atta                                          3744


<210> SEQ ID NO 4
<211> LENGTH: 507
<212> TYPE: DNA
<213> ORGANISM: Homo sapiens

<400> SEQUENCE: 4

atgttccaga tcccagagtt tgagccgagt gagcaggaag actccagctc tgcagagagg     60

ggcctgggcc ccagccccgc aggggacggg ccctcaggct ccggcaagca tcatcgccag    120

gccccaggcc tcctgtggga cgccagtcac cagcaggagc agccaaccag cagcagccat    180

catggaggcg ctggggctgt ggagatccgg agtcgccaca gctcctaccc cgcggggacg    240

gaggacgacg aagggatggg ggaggagccc agcccctttc ggggccgctc gcgctcggcg    300

ccccccaacc tctgggcagc acagcgctat ggccgcgagc tccggaggat gagtgacgag    360

tttgtggact cctttaagaa gggacttcct cgcccgaaga gcgcgggcac agcaacgcag    420

atgcggcaaa gctccagctg gacgcgagtc ttccagtcct ggtgggatcg gaacttgggc    480

aggggaagct ccgccccctc ccagtga                                        507


<210> SEQ ID NO 5
<211> LENGTH: 2170
<212> TYPE: DNA
<213> ORGANISM: Homo sapiens
```

<400> SEQUENCE: 5

```
acagagcaac ttcctctaga gggagctgat tggagccggg tgccgctggc acctctatga     60
tcactggagt ctcgcgggtc cctcgggctg cacagggaca agtaaaggct acatccagat    120
gccgggaatg cactgacgcc cattcctgga aactgggctc ccactcagcc cctgggagca    180
gcagccgcca gcccctcggg acctccatct ccaccctgct gagccacccg ggttgggcca    240
ggatcccggc aggctgatcc cgtcctccac tgagacctga aaaatggctt cggggcaagg    300
cccaggtcct cccaggcagg agtgcggaga gcctgccctg ccctctgctt ctgaggagca    360
ggtagcccag gacacagagg aggttttccg cagctacgtt ttttaccgcc atcagcagga    420
acaggaggct gaaggggtgg ctgcccctgc cgacccagag atggtcacct tacctctgca    480
acctagcagc accatggggc aggtgggacg gcagctcgcc atcatcgggg acgacatcaa    540
ccgacgctat gactcagagt tccagaccat gttgcagcac ctgcagccca cggcagagaa    600
tgcctatgag tacttcacca agattgccac cagcctgttt gagagtggca tcaattgggg    660
ccgtgtggtg gctcttctgg gcttcggcta ccgtctggcc ctacacgtct accagcatgg    720
cctgactggc ttcctaggcc aggtgacccg cttcgtggtc gacttcatgc tgcatcactg    780
cattgcccgg tggattgcac agaggggtgg ctgggtggca gccctgaact tgggcaatgg    840
tcccatcctg aacgtgctgg tggttctggg tgtggttctg ttgggccagt ttgtggtacg    900
aagattcttc aaatcatgac tcccaagggt gccctttggg gtcccggttc agacccctgc    960
ctggacttaa gcgaagtctt tgccttctct gttcccttgc aggggtcccc cctcaagagt   1020
acagaagctt tagcaagtgt gcactccagc ttcggagggc cctgcgtggg gggccagtca   1080
ggctgcagag gcacctcaac attgcatggt gctagtgggc cctctctctg ggcccagggg   1140
ctgtggccgt ctcctccctc agctctctgg gacctcctta gccctgtctg ctaggcgctg   1200
gggagactga taacttgggg aggcaagaga ctgggagcca cttctcccca gaaagtgttt   1260
aacggtttta gctttttata atacccttgt gagagcccat tcccaccatt ctacctgagg   1320
ccaggacgtc tggggtgtgg ggattggtgg gtctatgttc cccaggattc agctattctg   1380
gaagatcagc accctaagag atgggactag gacctgagcc tggtcctggc cgtccctaag   1440
catgtgtccc aggagcagga cctactagga gaggggggcc aaggtcctgc tcaactctac   1500
ccctgctccc attcctccct ccggccatac tgcctttgca gttggactct cagggattct   1560
gggcttgggg tgtggggtgg ggtggagtcg cagaccagag ctgtctgaac tcacgtgtca   1620
gaagcctcca agcctgcctc ccaaggtcct ctcagttctc tcccttcctc tctccttata   1680
gacacttgct cccaacccat tcactacagg tgaaggctct cacccccatc cctgggggcc   1740
ttgggtgagt ggcctgctaa ggctcctcct tgcccagact acagggctta ggacttggtt   1800
tgttatatca gggaaaagga gtagggagtt catctggagg gttctaagtg ggagaaggac   1860
tatcaacacc actaggaatc ccagaggtgg gatcctccct catggctctg gcacagtgta   1920
atccaggggt gtagatgggg gaactgtgaa tacttgaact ctgttccccc accctccatg   1980
ctcctcacct gtctaggtct cctcagggtg gggggtgaca gtgccttctc tattgggcac   2040
agcctagggt cttgggggtc agggggagaa agttcttgat tcagccaaat gcagggaggg   2100
gaggcagatg gagcccatag gccacccccct atcctctgag tgtttggaaa taaactgtgc   2160
aatcccctca                                                          2170
```

<210> SEQ ID NO 6

<211> LENGTH: 795
<212> TYPE: DNA
<213> ORGANISM: Homo sapiens

<400> SEQUENCE: 6
gcgctgcggc cgcccgcgcg gacccggcga gaggcggcgg cgggagcggc ggtgatggac 60
gggtccgggg agcagcccag aggcgggggg cccaccagct ctgagcagat catgaagaca 120
ggggcccttt tgcttcaggg tttcatccag gatcgagcag ggcgaatggg gggggaggca 180
cccgagctgg ccctggaccc ggtgcctcag gatgcgtcca ccaagaagct gagcgagtgt 240
ctcaagcgca tcggggacga actggacagt aacatggagc tgcagaggat gattgccgcc 300
gtggacacag actccccccg agaggtcttt ttccgagtgg cagctgacat gttttctgac 360
ggcaacttca actggggccg ggttgtcgcc cttttctact ttgccagcaa actggtgctc 420
aaggccctgt gcaccaaggt gccggaactg atcagaacca tcatgggctg gacattggac 480
ttcctccggg agcggctgtt gggctggatc caagaccagg gtggttggga cggcctcctc 540
tcctactttg ggacgcccac gtggcagacc gtgaccatct ttgtggcggg agtgctcacc 600
gcctcactca ccatctggaa gaagatgggc tgaggccccc agctgccttg gactgtgttt 660
ttcctccata aattatggca tttttctggg aggggtgggg attgggggac gtgggcattt 720
ttcttacttt tgtaattatt ggggggtgtg gggaagagtg gtcttgaggg ggtaataaac 780
ctccttcggg acaca 795

<210> SEQ ID NO 7
<211> LENGTH: 1639
<212> TYPE: DNA
<213> ORGANISM: Homo sapiens

<400> SEQUENCE: 7 ccgcccccctc cggcgtgttc atgcccccgg ggccccaggg agcgccatgg cccgcgcacg 60
ccaggagggc agctccccgg agcccgtaga gggcctggcc cgcgacggcc cgcgcccctt 120
cccgctcggc cgcctggtgc cctcggcagt gtcctgcggc ctctgcgagc ccggcctggc 180
tgccgccccc gccgccccca ccctgctgcc cgctgcctac ctctgcgccc ccaccgcccc 240
acccgccgtc accgccgccc tggggggttc ccgctggcct gggggtcccc gcagccggcc 300
ccgaggcccg cgcccggacg gtcctcagcc ctcgctctcg ctggcggagc agcacctgga 360
gtcgcccgtg cccagcgccc cgggggctct ggcgggcggt cccacccagg cggccccggg 420
agtccgcggg gaggaggaac agtgggcccg ggagatcggg gcccagctgc ggcggatggc 480
ggacgacctc aacgcacagt acgagcggcg gagacaagag gagcagcagc ggcaccgccc 540
ctcaccctgg agggtcctgt acaatctcat catgggactc ctgcccttac ccaggggcca 600
cagagccccc gagatggagc ccaattaggt gcctgcaccc gcccggtgga cgtcagggac 660
tcggggggca ggcccctccc acctcctgac accctggcca gcgcggggga ctttctctgc 720
accatgtagc atactggact cccagccctg cctgtcccgg gggcgggccg gggcagccac 780
tccagcccca gcccagcctg gggtgcactg actgagatgc ggactcctgg gtccctggcc 840
aagaagccag gagagggacg gctgatggac tcagcatcgg aaggtggcgg tgaccgaggg 900
ggtggggact gagccgcccg cctctgccgc ccaccaccat ctcaggaaag gctgttgtgc 960
tggtgcccgt tccagctgca ggggtgacac tggggggggg gggggctctc ctctcggtgc 1020
tccttcactc tgggcctggc ctcaggcccc tggtgcttcc ccccctcctc ctgggagggg 1080
gcccgtgaag agcaaatgag ccaaacgtga ccactagcct cctggagcca gagagtgggg 1140

```
ctcgtttgcc ggttgctcca gcccggcgcc cagccatctt ccctgagcca gccggcgggt   1200

ggtgggcatg cctgcctcac cttcatcagg gggtggccag gaggggccca gactgtgaat   1260

cctgtgctct gcccgtgacc gccccccgcc ccatcaatcc cattgcatag gtttagagag   1320

agcacgtgtg accactggca ttcatttggg gggtgggaga ttttggctga agccgcccca   1380

gccttagtcc ccagggccaa gcgctggggg gaagacgggg agtcagggag ggggggaaat   1440

ctcggaagag ggaggagtct gggagtgggg agggatggcc cagcctgtaa gatactgtat   1500

atgcgctgct gtagataccg gaatgaattt tctgtacatg tttggttaat tttttttgta   1560

catgattttt gtatgtttcc ttttcaataa aatcagattg gaacagtgga aaaaaaggcc   1620

ttcgtggcct cgagagatc                                                1639
```

<210> SEQ ID NO 8
<211> LENGTH: 1284
<212> TYPE: DNA
<213> ORGANISM: Homo sapiens

<400> SEQUENCE: 8

```
gtgggagagt tctgttgctg cggcggggcc tgcacgttga ctgtgggaaa ctcggaaaca     60

agctcacatc ttcctgtggg aaaccttcta gcaacaggat gagtctgcag tggactgcag    120

ttgccacctt cctctatgcg gaggtctttg ttgtgttgct tctctgcatt cccttcattt    180

ctcctaaaag atggcagaag attttcaagt cccggctggt ggagttgtta gtgtcctatg    240

gcaacacctt ctttgtggtt ctcattgtca tccttgtgct gttggtcatc gatgccgtgc    300

gcgaaattcg gaagtatgat gatgtgacgg aaaaggtgaa cctccagaac aatcccgggg    360

ccatggagca cttccacatg aagcttttcc gtgcccagag gaatctctac attgctggct    420

tttccttgct gctgtccttc ctgcttagac gcctggtgac tctcatttcg cagcaggcca    480

cgctgctggc ctccaatgaa gcctttaaaa agcaggcgga gagtgctagt gaggcggcca    540

agaagtacat ggaggagaat gaccagctca agaagggagc tgctgttgac ggaggcaagt    600

tggatgtcgg gaatgctgag gtgaagttgg aggaagagaa caggagcctg aaggctgacc    660

tgcagaagct aaaggacgag ctggccagca ctaagcaaaa actagagaaa gctgaaaacc    720

aggttctggc catgcggaag cagtctgagg gcctcaccaa ggagtacgac cgcttgctgg    780

aggagcacgc aaagctgcag gctgcagtag atggtcccat ggacaagaag gaagagtaag    840

ggcctccttc ctcccctgcc tgcagctggc ttccacctgg cacgtgcctg ctgcttcctg    900

agagcccggc ctctccctcc agtacttctg tttgtgccct tctgcttccc ccattccctt    960

ccacagctca tagctcgtca tctcggccct tgtccacact ctccaagcac attacagggg   1020

acctgattgc tacacgttca gaatgcgttt gctgtcatcc tgcttggcct ggccaggcct   1080

ggcacagcct tggcttccac gcctgagcgt ggagagcacg agttagttgt agtccggctt   1140

gcggtggggc tgacttcctg ttggtttgag cccctttttg ttttgccctc tgggtgtttt   1200

ctttggtccc gcaggagggt gggtggagca ggtggactgg agtttctctt gagggcaata   1260

aaagttgtca tggtgtgtac gtgg                                          1284
```

<210> SEQ ID NO 9
<211> LENGTH: 2833
<212> TYPE: DNA
<213> ORGANISM: Homo sapiens

<400> SEQUENCE: 9

-continued

```
tgcctgcgcc tgagcctcta cgagagggaa ggaacgctgc tccgagctcc gcgtcgcgtc      60
gcgtagattc gcgtcgccgt cgacctcaga ggcggggccg gaagcgctac ggtttgaccc     120
ccgagtccct ctgttcccga aggggcggcc gtctttctcc cgacccgctc cgcctcctct     180
ccttcttccc cattacccgg aggccgaagc cccagccag ggcggggcgg cgcagcccga      240
gctcccggac ccggaagaag cgccatctcc cgcctccacc atggagccca ccgcaccgtc     300
cctcaccgag gaggacctca ctgaagtgaa gaaggacgcc ttagaaaatt tacgtgtata     360
cctgtgtgag aaaatcatag ctgagagaca ttttgatcat ctacgtgcaa aaaaaatact     420
cagtagagaa gacactgaag aaatttcttg tcgaacatca agtagaaaaa gggctggaaa     480
attgttagac tacttacagg aaaacccaaa aggtctggac acccttgttg aatctattcg     540
gcgagaaaaa acacagaact tcctgataca gaagattaca gatgaagtgc tgaaacttag     600
aaatataaaa ctagaacatc tgaaaggact aaaatgtagc agttgtgaac cttttccaga     660
tggagccacg aacaacctct ccagatcaaa ttcagatgag agtaatttct ctgaaaaact     720
gagggcatcc actgtcatgt accatccaga aggagaatcc agcacgacgc cctttttttc     780
tactaattct tctctgaatt tgcctgttct agaagtaggc agaactgaaa ataccatctt     840
ctcttcaact acacttccca gacctgggga cccaggggct cctcctttgc caccagatct     900
acagttagaa gaagaaggaa cttgtgcaaa ctctagtgag atgtttcttc ccttaagatc     960
acgtactgtt tcacgacaat gacactttat tgccttttaa tttttaatga tgacaaaaaa    1020
tgttttaaag aatatgactt tttataaaat ggctgtaatc atttgtttac atttgatgca    1080
tgtcttttaa aatgcaatgt aagcatactt tgtaaatagg atttttagaa ttaaaaaagc    1140
atacttctag gatagctaac tgtaaatcat gttgatcatg tactttttag taatttcttt    1200
ttttcctttt taaggtcttt cagtactttt ttaaatattt tctattttaa gactgatttt    1260
aatagggaat atatctctat ttgagaatag acccttacta ggaagaacgt tttttcctca    1320
gtgcatttgt gctagaaatt ttcaagagtc taatagtctt tgccagtcat tcagcagcaa    1380
attttcagca ttaagctgtt cctgttcagt aataaaaccg gtcactgatg ggaaaactgc    1440
caatatagaa aaataaaaat ctcttttcca ctccattgtc gtataggcat gtaaacagcc    1500
tctttttgat actggaggaa cacttgatgg agtgtgagcc acctaagatc tcggtttgcc    1560
aaaattcatt tctaattaac cttactaatt atactacttt gttaggattt tcacattctt    1620
ggcttaatca ttttcattcc taaagaaaaa tatcttggcc taaacctcag ttattacatg    1680
taatttgatg aggtattttt tccttttttc tttttttttt tttttttttt ttgagacagt    1740
cttgctctat cgcccaggct ggagtgcagt ggcgcattct aggctcactg caacttctgc    1800
ctcccatgct tacgtgatcc tctcacctca gcctctcaag taatatagct gagactacaa    1860
gtgtgtgcca ccatgcctca ctaatttttg tattattttt gtagagacgg tgttttgcca    1920
tgttggccag gctggtcttg aactcctgga ctcaagcaac ctacccagcg tggcctccca    1980
aagtgctggg attacagaca cgagccacct cacctagcct gatgagattt ttaaaaaata    2040
ttttctctgt acttttcatt ctcttttaat gaggaccaat gtacagttga aataactgga    2100
acaaattatt tttggtgtgt gtgacaattc tgtttttaat gctatttgaa caagtgggcc    2160
attagccaga tttgtctttt tgttgtaaaa caaaatttga ctaattttac atgtttataa    2220
atcttatgct ctcactgttt gtttttattt aaattacaat tttatctgtt tcctgacatt    2280
gtctcctata tatttctatt attaattgca aaaacataga aatggaaatt ttgctatcaa    2340
caataaaatt tttttaaagt agtgagtgct attttggagt tccaaatttt cagtaggaag    2400
```

```
tatctaaaac ttttttaat acgtgccatt atctatagaa aacattactt caggttgtga   2460

gattgagttg catttctgga tggactgatg aatttatccg acatgaagaa gattggcata   2520

ttagctttaa aaatttttaa agattggatt ttttttagta taagcacttt ctaaggatta   2580

tagagaaatg tttcacctcc aatgcatagc aaaaatagtg gtgttagaaa gaaaataggt   2640

tacatttaag gaaggtgctt taaaaagcag aagcagactt taaaattaaa tttgtggaca   2700

ccttttaaa aattgaatca aagattataa tttagatata caataacacc tatatataga   2760

taagttttaa cactgagttt tctttcagac tgttttctaa ctacatagac aataaaatta   2820

agctttgcat aaa                                                     2833
```

<210> SEQ ID NO 10
<211> LENGTH: 6492
<212> TYPE: DNA
<213> ORGANISM: Homo sapiens

<400> SEQUENCE: 10

```
tttctgtgaa gcagaagtct gggaatcgat ctggaaatcc tcctaatttt tactccctct     60

ccccgcgact cctgattcat tgggaagttt caaatcagct ataactggag agtgctgaag    120

attgatggga tcgttgcctt atgcatttgt tttggtttta caaaaaggaa acttgacaga    180

ggatcatgct gtacttaaaa aatacaacat cacagaggaa gtagactgat attaacaata    240

cttactaata ataacgtgcc tcatgaaata aagatccgaa aggaattgga ataaaaattt    300

cctgcatctc atgccaaggg ggaaacacca gaatcaagtg ttccgcgtga ttgaagacac    360

cccctcgtcc aagaatgcaa agcacatcca ataaaatagc tggattataa ctcctcttct    420

ttctctgggg gccgtggggt gggagctggg gcgagaggtg ccgttggccc ccgttgcttt    480

tcctctggga aggatggcgc acgctgggag aacagggtac gataaccggg agatagtgat    540

gaagtacatc cattataagc tgtcgcagag ggctacgag tgggatgcgg gagatgtggg    600

cgccgcgccc ccgggggccg cccccgcacc gggcatcttc tcctcccagc ccgggcacac    660

gccccatcca gccgcatccc gggacccggt cgccaggacc tcgccgctgc agaccccggc    720

tgccccggc gccgccgcgg ggcctgcgct cagcccggtg ccacctgtgg tccacctgac    780

cctccgccag gccggcgacg acttctcccg ccgctaccgc cgcgacttcg ccgagatgtc    840

cagccagctg cacctgacgc ccttcaccgc gcggggacgc tttgccacgg tggtggagga    900

gctcttcagg gacggggtga actgggggag gattgtggcc ttctttgagt tcggtggggt    960

catgtgtgtg gagagcgtca accgggagat gtcgcccctg gtggacaaca tcgccctgtg   1020

gatgactgag tacctgaacc ggcacctgca cacctggatc caggataacg gaggctggga   1080

tgcctttgtg gaactgtacg gccccagcat gcggcctctg tttgatttct cctggctgtc   1140

tctgaagact ctgctcagtt tggccctggt gggagcttgc atcaccctgg gtgcctatct   1200

gggccacaag tgaagtcaac atgcctgccc caaacaaata tgcaaaaggt tcactaaagc   1260

agtagaaata atatgcattg tcagtgatgt accatgaaac aaagctgcag gctgtttaag   1320

aaaaaataac acacatataa acatcacaca cacagacaga cacacacaca cacaacaatt   1380

aacagtcttc aggcaaaacg tcgaatcagc tatttactgc caaagggaaa tatcatttat   1440

tttttacatt attaagaaaa aaagatttat ttatttaaga cagtcccatc aaaactcctg   1500

tctttggaaa tccgaccact aattgccaag caccgcttcg tgtggctcca cctggatgtt   1560

ctgtgcctgt aaacatagat tcgctttcca tgttgttggc cggatcacca tctgaagagc   1620
```

-continued

```
agacggatgg aaaaaggacc tgatcattgg ggaagctggc tttctggctg ctggaggctg   1680
gggagaaggt gttcattcac ttgcatttct ttgccctggg ggctgtgata ttaacagagg   1740
gagggttcct gtggggggaa gtccatgcct ccctggcctg aagaagagac tctttgcata   1800
tgactcacat gatgcatacc tggtgggagg aaaagagttg ggaacttcag atggacctag   1860
tacccactga gatttccacg ccgaaggaca gcgatgggaa aaatgccctt aaatcatagg   1920
aaagtatttt tttaagctac caattgtgcc gagaaaagca ttttagcaat ttatacaata   1980
tcatccagta ccttaagccc tgattgtgta tattcatata ttttggatac gcacccccca   2040
actcccaata ctggctctgt ctgagtaaga aacagaatcc tctggaactt gaggaagtga   2100
acatttcggt gacttccgca tcaggaaggc tagagttacc cagagcatca ggccgccaca   2160
agtgcctgct tttaggagac cgaagtccgc agaacctgcc tgtgtcccag cttggaggcc   2220
tggtcctgga actgagccgg ggccctcact ggcctcctcc agggatgatc aacagggcag   2280
tgtggtctcc gaatgtctgg aagctgatgg agctcagaat tccactgtca agaaagagca   2340
gtagaggggt gtggctgggc ctgtcaccct ggggccctcc aggtaggccc gttttcacgt   2400
ggagcatggg agccacgacc cttcttaaga catgtatcac tgtagaggga aggaacagag   2460
gccctgggcc cttcctatca gaaggacatg gtgaaggctg ggaacgtgag gagaggcaat   2520
ggccacggcc cattttggct gtagcacatg gcacgttggc tgtgtggcct tggcccacct   2580
gtgagtttaa agcaaggctt taaatgactt tggagagggt cacaaatcct aaaagaagca   2640
ttgaagtgag gtgtcatgga ttaattgacc cctgtctatg gaattacatg taaaacatta   2700
tcttgtcact gtagtttggt tttatttgaa aacctgacaa aaaaaaagtt ccaggtgtgg   2760
aatatggggg ttatctgtac atcctggggc attaaaaaaa aaatcaatgg tggggaacta   2820
taaagaagta acaaaagaag tgacatcttc agcaaataaa ctaggaaatt tttttttctt   2880
ccagtttaga atcagccttg aaacattgat ggaataactc tgtggcatta ttgcattata   2940
taccatttat ctgtattaac tttggaatgt actctgttca atgtttaatg ctgtggttga   3000
tatttcgaaa gctgctttaa aaaaatacat gcatctcagc gtttttttgt ttttaattgt   3060
atttagttat ggcctataca ctatttgtga gcaaaggtga tcgttttctg tttgagattt   3120
ttatctcttg attcttcaaa agcattctga gaaggtgaga taagccctga gtctcagcta   3180
cctaagaaaa acctggatgt cactggccac tgaggagctt tgtttcaacc aagtcatgtg   3240
catttccacg tcaacagaat tgtttattgt gacagttata tctgttgtcc ctttgacctt   3300
gtttcttgaa ggtttcctcg tccctgggca attccgcatt taattcatgg tattcaggat   3360
tacatgcatg tttggttaaa cccatgagat tcattcagtt aaaaatccag atggcaaatg   3420
accagcagat tcaaatctat ggtggtttga cctttagaga gttgctttac gtggcctgtt   3480
tcaacacaga cccacccaga gccctcctgc cctccttccg cgggggcttt ctcatggctg   3540
tccttcaggg tcttcctgaa atgcagtggt gcttacgctc caccaagaaa gcaggaaacc   3600
tgtggtatga agccagacct ccccggcggg cctcagggaa cagaatgatc agacctttga   3660
atgattctaa tttttaagca aaatattatt ttatgaaagg tttacattgt caaagtgatg   3720
aatatggaat atccaatcct gtgctgctat cctgccaaaa tcattttaat ggagtcagtt   3780
tgcagtatgc tccacgtggt aagatcctcc aagctgcttt agaagtaaca atgaagaacg   3840
tggacgtttt taatataaag cctgttttgt cttttgttgt tgttcaaacg ggattcacag   3900
agtatttgaa aaatgtatat atattaagag gtcacggggg ctaattgctg gctggctgcc   3960
ttttgctgtg ggttttgtt acctggtttt aataacagta aatgtgccca gcctcttggc   4020
```

-continued

```
cccagaactg tacagtattg tggctgcact tgctctaaga gtagttgatg ttgcattttc   4080

cttattgtta aaaacatgtt agaagcaatg aatgtatata aaagcctcaa ctagtcattt   4140

ttttctcctc ttcttttttt tcattatatc taattatttt gcagttgggc aacagagaac   4200

catccctatt ttgtattgaa gagggattca catctgcatc ttaactgctc tttatgaatg   4260

aaaaaacagt cctctgtatg tactcctctt tacactggcc agggtcagag ttaaatagag   4320

tatatgcact ttccaaattg gggacaaggg ctctaaaaaa agccccaaaa ggagaagaac   4380

atctgagaac ctcctcggcc ctcccagtcc ctcgctgcac aaatactccg caagagaggc   4440

cagaatgaca gctgacaggg tctatggcca tcgggtcgtc tccgaagatt tggcaggggc   4500

agaaaactct ggcaggctta agatttggaa taaagtcaca gaattaagga agcacctcaa   4560

tttagttcaa acaagacgcc aacattctct ccacagctca cttacctctc tgtgttcaga   4620

tgtggccttc catttatatg tgatctttgt tttattagta aatgcttatc atctaaagat   4680

gtagctctgg cccagtggga aaaattagga agtgattata aatcgagagg agttataata   4740

atcaagatta aatgtaaata atcagggcaa tcccaacaca tgtctagctt tcacctccag   4800

gatctattga gtgaacagaa ttgcaaatag tctctatttg taattgaact tatcctaaaa   4860

caaatagttt ataaatgtga acttaaactc taattaattc caactgtact tttaaggcag   4920

tggctgtttt tagactttct tatcacttat agttagtaat gtacacctac tctatcagag   4980

aaaaacagga aaggctcgaa atacaagcca ttctaaggaa attagggagt cagttgaaat   5040

tctattctga tcttattctg tggtgtcttt tgcagcccag acaaatgtgg ttacacactt   5100

tttaagaaat acaattctac attgtcaagc ttatgaaggt tccaatcaga tctttattgt   5160

tattcaattt ggatctttca gggatttttt ttttaaatta ttatgggaca aaggacattt   5220

gttggagggg tgggagggag gaagaatttt taaatgtaaa acattcccaa gtttggatca   5280

gggagttgga agttttcaga ataaccagaa ctaagggtat gaaggacctg tattggggtc   5340

gatgtgatgc ctctgcgaag aaccttgtgt gacaaatgag aaacattttg aagtttgtgg   5400

tacgaccttt agattccaga gacatcagca tggctcaaag tgcagctccg tttggcagtg   5460

caatggtata aatttcaagc tggatatgtc taatgggtat ttaaacaata aatgtgcagt   5520

tttaactaac aggatattta atgacaacct tctggttggt agggacatct gtttctaaat   5580

gtttattatg tacaatacag aaaaaaattt tataaaatta agcaatgtga aactgaattg   5640

gagagtgata atacaagtcc tttagtctta cccagtgaat cattctgttc catgtctttg   5700

gacaaccatg accttggaca atcatgaaat atgcatctca ctggatgcaa agaaaatcag   5760

atggagcatg aatggtactg taccggttca tctggactgc cccagaaaaa taacttcaag   5820

caaacatcct atcaacaaca aggttgttct gcataccaag ctgagcacag aagatgggaa   5880

cactggtgga ggatggaaag gctcgctcaa tcaagaaaat tctgagacta ttaataaata   5940

agactgtagt gtagatactg agtaaatcca tgcacctaaa ccttttggaa aatctgccgt   6000

gggccctcca gatagctcat ttcattaagt ttttccctcc aaggtagaat ttgcaagagt   6060

gacagtggat tgcatttctt ttggggaagc tttcttttgg tggttttgtt tattatacct   6120

tcttaagttt tcaaccaagg tttgcttttg ttttgagtta ctggggttat ttttgtttta   6180

aataaaaata agtgtacaat aagtgttttt gtattgaaag cttttgttat caagattttc   6240

atacttttac cttccatggc tctttttaag attgatactt ttaagaggtg gctgatattc   6300

tgcaacactg tacacataaa aaatacggta aggatacttt acatggttaa ggtaaagtaa   6360
```

```
gtctccagtt ggccaccatt agctataatg gcactttgtt tgtgttgttg gaaaaagtca   6420

cattgccatt aaactttcct tgtctgtcta gttaatattg tgaagaaaaa taaagtacag   6480

tgtgagatac tg                                                       6492


<210> SEQ ID NO 11
<211> LENGTH: 528
<212> TYPE: DNA
<213> ORGANISM: Homo sapiens

<400> SEQUENCE: 11

atgacagact gtgaatttgg atatatttac aggctggctc aggactatct gcagtgcgtc     60

ctacagatac cacaacctgg atcaggtcca agcaaaacgt ccagagtgct acaaaatgtt    120

gcgttctcag tccaaaaaga agtggaaaag aatctgaagt catgcttgga caatgttaat    180

gttgtgtccg tagacactgc cagaacacta ttcaaccaag tgatggaaaa ggagtttgaa    240

gacggcatca ttaactgggg aagaattgta accatatttg catttgaagg tattctcatc    300

aagaaacttc tacgacagca aattgccccg gatgtggata cctataagga gatttcatat    360

tttgttgcgg agttcataat gaataacaca ggagaatgga taaggcaaaa cggaggctgg    420

gaaaatggct ttgtaaagaa gtttgaacct aaatctggct ggatgacttt tctagaagtt    480

acaggaaaga tctgtgaaat gctatctctc ctgaagcaat actgttga                 528


<210> SEQ ID NO 12
<211> LENGTH: 699
<212> TYPE: DNA
<213> ORGANISM: Homo sapiens
<220> FEATURE:
<221> NAME/KEY: misc_feature
<222> LOCATION: (566)..(567)
<223> OTHER INFORMATION: n is a, c, g, or t

<400> SEQUENCE: 12

atgtctcaga gcaaccggga gctggtggtt gactttctct cctacaagct ttcccagaaa     60

ggatacagct ggagtcagtt tagtgatgtg gaagagaaca gaactgaggc cccagaaggg    120

actgaatcag agatggagac ccccagtgcc atcaatggca acccatcctg gcacttggcg    180

gacagccctg cggtgaatgg agccactggc cacagcagca gcttggatgc ccgggaggtg    240

atccccatgg cagcggtgaa gcaggcgctg agggaggccg gggatgagtt tgaactgagg    300

taccggcggg cattcagcga cctgacatcc cagcttcaca tcaccccagg gacagcatat    360

cagagctttg agcaggtagt gaacgaactc ttccgggatg gggtgaactg gggtcgcatt    420

gtggcctttt tctccttcgg tggggcactg tgcgtggaaa gcgtagacaa ggagatgcag    480

gtattggtga gtcggatcgc aacttggatg gccacttacc tgaacgacca cctagagcct    540

tggatccagg agaacggcgg ctgggnnact tttgtggaac tctacgggaa caatgcagcg    600

gccgagagcc ggaagggcca ggagcgcttc aaccgctggt tcctgacagg catgactgtg    660

gctggcgtgg ttctgctggg ctcactcttc agtcggaaa                           699


<210> SEQ ID NO 13
<211> LENGTH: 876
<212> TYPE: DNA
<213> ORGANISM: Homo sapiens

<400> SEQUENCE: 13

aagaaaacca gcgaaggccc ggccccccag cagaggccgg accatggttg accagttgcg     60

ggagcgcacc accatggccg acccgctgcg ggagcgcacc gagctgttgc tggccgacta    120
```

```
cctggggtac tgcgcccggg aacccggcac ccccgagccg gcgccatcca cgcccgaggc    180

cgccgtgctg cgctccgtgg ccgcctggtt acggcagatt caccggtcct ttttctccgc    240

ctacctcggc taccccggga accgcttcga gctggtggcg ctgatggcgg attccgtgct    300

ctccgacagc cccggcccca cctggggcag agtggtgacg ctcgtgacct tcgcagggac    360

gctgctggag agagggccgc tggtgaccgc ccggtggaag aagtggggct tccagccgcg    420

gctaaaggag caggagggcg acgtcgcccg ggactgccag cgcctggtgg ccttgctgag    480

ctcgcggctc atggggcagc accgcgcctg gctgcaggct cagggcggct gggatggctt    540

ttgtcacttc ttcaggaccc cctttccact ggctttttgg agaaaacagc tggtccaggc    600

ttttctgtca tgcttgttaa caacagcctt catttatctc tggacacgat tattatgagt    660

tttaaaactt ttaacccgct tctacctgcc caactgtgac caactaaatg acagatgtgt    720

gagaacaaga actgagggaa agcaccttcc cccaccccag acgtttttat ctgaatgcat    780

acaaggagtc ctgaggtggt gatttggcca gtgttttaac ttgtgacaag tactcaggtg    840

tgaggacaag aatgcaaatg gctcttcctt gagtga                              876
```

<210> SEQ ID NO 14
<211> LENGTH: 726
<212> TYPE: DNA
<213> ORGANISM: Homo sapiens

<400> SEQUENCE: 14

```
gttcgttgca acaaattgat gagcaatgct tttttataat gccaactttg tacaaaaaag     60

ttggcatggc aaagcaacct tctgatgtaa gttctgagtg tgaccgagaa ggtagacaat    120

tgcagcctgc ggagaggcct ccccagctca gacctggggc ccctacctcc ctacagacag    180

agccacaagg taatcctgaa ggcaatcacg gaggtgaagg ggacagctgc ccccacggca    240

gccctcaggg cccgctggcc ccacctgcca gccctggccc ttttgctacc agatccccgc    300

ttttcatctt tatgagaaga tcctccctgc tgtctcgatc ctccagtggg tatttctctt    360

ttgacacaga caggagccca gcacccatga gttgtgacaa atcaacacaa accccaagtc    420

ctccttgcca ggccttcaac cactatctca gtgcaatggc ttccatgagg caggctgaac    480

ctgcagatat gcgcccagag atatggatcg cccaagagtt gcggcgtatt ggagacgagt    540

ttaacgctta ctatgcaagg agggtatttt tgaataatta ccaagcagcc gaagaccacc    600

cacgaatggt tatcttacga ctgttacgtt acattgtccg cctggtgtgg agaatgcatt    660

gcccaacttt cttgtacaaa gttggcatta taagaaagca ttgcttatca atttgttgca    720

acgaac                                                               726
```

<210> SEQ ID NO 15
<211> LENGTH: 1587
<212> TYPE: DNA
<213> ORGANISM: Homo sapiens

<400> SEQUENCE: 15

```
gttcgttgca acaaattgat gagcaatgct tttttataat gccaactttg tacaagaaag     60

ttggcatggc gtcctcttct actgtgcctc tgggatttca ctatgaaaca aagtatgttg    120

ttctcagcta cttgggactc ctctctcaag agaagctgca agagcaacat ctttcctcac    180

cccaaggggt tcaactagat atagcttcac aatctctgga tcaagaaatt ttattaaaag    240

ttaaaactga aattgaagaa gagctaaaat ctctggacaa agaaatttct gaagccttca    300
```

```
ccagcacagg ctttgaccgt cacacttctc cagtgttcag ccctgccaat ccagaaagct    360

caatggaaga ctgcttggcc catcttggag aaaaagtgtc ccaggaactg aaagagcctc    420

tccataaagc attgcaaatg ctcctgagcc agccagtgac atatcaggca tttcgggaat    480

gtacactgga gaccacagtt catgccagcg gctggaataa gattttggtg cctctggttt    540

tgctacgaca aatgcttttg gaattgacaa gacgtggtca agaacctttg agcgcactgc    600

tgcagtttgg cgtgacatac ctggaggact attcggcaga gtacatcatt cagcaaggtg    660

gctggggcac tgtgtttagt cttgagtcag aggaggagga ataccctgga atcactgcag    720

aagatagcaa tgacatttac atcctgccca gcgacaactc tggacaagtc agtcccccag    780

agtctccaac tgtgaccact tcctggcagt ctgagagctt acctgtgtca ctgtcagcta    840

gccagagttg gcacacagaa agcctgccag tgtcactagg ccctgagtcc tggcagcaga    900

ttgcaatgga tcctgaagaa gtgaaaagct tagacagcaa cggagctgga gagaagagtg    960

agaacaactc ctctaattct gacattgtgc acgtggagaa agaagaggtg cccgagggca   1020

tggaagaggc tgctgtggct tctgtggtct tgccagcgcg ggagctgcaa gaggcacttc   1080

ctgaagcccc agctcccttg cttccacata tcactgccac ctccctgctg gggacaaggg   1140

aatctgacac agaagtgatc acagttgaga aatccagccc tgctacatct ctgtttgtag   1200

aacttgatga agaagaggtg aaagcagcaa caactgaacc tactgaagtg gaggaggtgg   1260

tccccgcact ggaacccaca gaaacgctgc tgagtgagaa ggagataaac gcaagggaag   1320

agagccttgt ggaagagctg tcccctgcca gcgagaagaa gcccgtgccg ccgtctgagg   1380

gcaagtctag actgtccccc gccggtgaga tgaagcccat gccgctgtct gagggcaagt   1440

ctatactgct gtttggaggg gctgctgctg ttgccatcct ggcagtggcc atcggggtag   1500

ccctggctct gagaaagaaa tacccaaatt tcttgtacaa agttggcatt ataagaaagc   1560

attgcttatc aatttgttgc aacgaac                                        1587
```

```
<210> SEQ ID NO 16
<211> LENGTH: 1113
<212> TYPE: DNA
<213> ORGANISM: Homo sapiens
<220> FEATURE:
<221> NAME/KEY: misc_feature
<222> LOCATION: (47)..(47)
<223> OTHER INFORMATION: n is a, c, g, or t

<400> SEQUENCE: 16

gttcgttgca acaaattgat gagcaatgct tttttataat gccactnttg tacaaaaaag     60

ttggcatgtg tagcaccagt gggtgtgacc tggaagaaat ccccctagat gatgatgacc    120

taaacaccat agaattcaaa atcctcgcct actacaccag acatcatgtc ttcaagagca    180

cccctgctct cttctcacca aagctgctga gaacaagaag tttgtcccag aggggcctgg    240

ggaattgttc agcaaatgag tcatggacag aggtgtcatg gccttgcaga aattcccaat    300

ccagtgagaa ggccataaac cttggcaaga aaaagtcttc ttggaaagca ttctttggag    360

tagtggagaa ggaagattcg cagagcacgc ctgccaaggt ctctgctcag ggtcaaagga    420

cgttggaata ccaagattcg cacagccagc agtggtccag gtgtctttct aacgtggagc    480

agtgcttgga gcatgaagct gtggacccca aagtcatttc cattgccaac cgagtagctg    540

aaattgttta ctcctggcca ccaccacaag cgacccaggc aggaggcttc aagtccaaag    600

agatttttgt aactgagggt ctctccttcc agctccaagg ccacgtgcct gtagcttcaa    660

gttctaagaa agatgaagaa gaacaaatac tagccaaaat tgttgagctg ctgaaatatt    720
```

caggagatca gttggaaaga aagctgaaga aagataaggc tttgatgggc cacttccagg 780
atgggctgtc ctactctgtt ttcaagacca tcacagacca ggtcctaatg ggtgtggacc 840
ccaggggaga atcagaggtc aaagctcagg gctttaaggc tgcccttgta atagacgtca 900
cggccaagct cacagctatt gacaaccacc cgatgaacag ggtcctgggc tttggcacca 960
agtacctgaa agagaacttc tcgccatgga tccagcagca cggtggatgg gaaaaaatac 1020
ttgggatatc acatgaagaa gtagactgcc caactttctt gtacaaagtt ggcattataa 1080
gaaagcattg cttatcaatt tgttgcaacg aac 1113

<210> SEQ ID NO 17
<211> LENGTH: 1428
<212> TYPE: DNA
<213> ORGANISM: Homo sapiens

<400> SEQUENCE: 17
ggccccagct gggggctttc atccgcctga cccggctcca cgctggcctt tcatcctcct 60
ggccagcgtg gagccgggtc aggccgggag gatgaaaggc cccagctggg ggctccttgc 120
caccagtgct gtgtcttaag agctgccatc ccggctggcc gcccggatgg cgaccccagc 180
ctcggcccca gacacacggg ctctggtggc agactttgta ggttataagc tgaggcagaa 240
gggttatgtc tgtggagctg gccccgggga gggcccagca gctgacccac tgcaccaagc 300
catgcgggca gctggagatg agttcgagac ccgcttccgg cgcaccttct ctgatctggc 360
ggctcagctg catgtgaccc caggctcagc ccaacaacgc ttcacccagg tctccgatga 420
actttttcaa gggggcccca actggggccg ccttgtagcc ttctttgtct ttggggctgc 480
actgtgtgct gagagtgtca acaaggagat ggaaccactg gtgggacaag tgcaggagtg 540
gatggtggcc tacctggaga cgcggctggc tgactggatc cacagcagtg gggggctgggc 600 ggagttcaca gctctatacg gggacggggc cctggaggag gcgcggcgtc tgcgggaggg 660
gaactgggca tcagtgagga cagtgctgac gggggccgtg gcactggggg ccctggtaac 720
tgtaggggcc ttttttgcta gcaagtgaaa gtccagggcc aggtggggct aggtgtggct 780
gggggccagg agagcaggaa cagaacagag aaatgccctt ggaagaagtg gagttggtgg 840
atgggtgggc atggaacagg atgggcagag aaagggtagt gtgtgaggga gctgagtagg 900
ccaggtaggc gattggaaga gtgagcagga cacagagggg aggggaatgt tttggcaagt 960
ttaggggcac aggagatgta gtcgttccag ggctgggggga ggtgggaggg atcacgccta 1020
taggtgtggg cacatgaaac gacctggaac ttgcttcaca gccctgagga aggtggactt 1080
acataagcag ctgtattcca ttagatgagt gggatttagg gaacgcagaa ggcacatccc 1140
tttggaatgg aagcttaggg gttctcaggt gatagggaga ggtggctgtt aacagtgggc 1200
tgcttggaca cgcgtgtgca tgtgcacgca tgctggtgtg catgctgggc tgcctggcaa 1260
atctggtggt ggtgggattc ctcaaggaga aaacattccc tcttgcaatg gcaagaacta 1320
ggggcagttc tctgtccctc ctcccaaccc ctcctttccc ctgcccttgt cctgatgcct 1380
caaggcttag agagaaacat tgtatccaga aaaaaaaaaa aaaaaaaa 1428

<210> SEQ ID NO 18
<211> LENGTH: 1877
<212> TYPE: DNA
<213> ORGANISM: Homo sapiens

<400> SEQUENCE: 18

-continued

```
aggggaagtc ccggcgcccg gcgaaaccac cctcccgtgc agccgagccc agccgctctc     60
cggccgccgt ccccggcggc cccatgcccc gatgccccgc gggggccatg gacgaggggc    120
ccgtggacct gcgcacccgg cccaaggccg ccggactccc gggcgccgcg ctgccgctcc    180
gcaagcgccc gctgcgcgcg ccctccccgg agcccgccgc tccccgcggc gctgcgggcc    240
ttgtcgtccc cctggaccct ctgcgcggcg gctgcgacct gccggcggtc cccgggcccc    300
cccacggcct ggcccggccg gaggcgcttt actaccccgg agccttactg cctttgtacc    360
ccactcgggc catgggctcc ccgtttcctc tggtgaacct gcctacaccc ctatacccca    420
tgatgtgccc catggaacac cccctttctg ctgacatcgc catggccacc cgtgcagatg    480
aggacggaga cacgcctctc catattgctg tggtgcaggg taacctgcca gctgtgcacc    540
ggctggtcaa cctcttccag cagggggggcc gggagctcga catctacaac aacctacggc    600
agacaccgct ccacctggct gtgatcacca cattaccgtc tgtggtccgg ctcctggtga    660
cagctggtgc cagccccatg gcgctggacc gccatggcca gacggccgct cacctggcgt    720
gcgagcaccg cagcccgacc tgcctgcgag ccctgctgga cagcgcagct ccgggcacgt    780
tggacctgga ggcccgcaat tatgacgggc tcaccgccct gcacgtggca gtgaacaccg    840
agtgccaaga aaccgtgcag ctcttgctag agcgcggtgc cgacatcgac gcagtggaca    900
ttaagagcgg ccgctccccg ctcatccacg ccgtggaaaa caacagcctt agcatggtgc    960
agctgctgct gcagcacggc gccaacgtga acgcgcaaat gtactccggc agctccgccc   1020
tgcactcagc gtccggccgc gggctcctcc cgctggtgcg cacgctggtc cgcagcggcg   1080
ctgacagcag cctcaagaac tgccacaacg acacgccgct catggtggcg cgcagccgca   1140
gggtcatcga catcctgagg gggaaggcca cccggcctgc ttccacctcc cagccagacc   1200
cctcccctga ccggagcgcc aacacctccc ccgagagcag cagccgcctc agctccaatg   1260
gtcttctctc cgcatcacca tcctcctcac cctcccagtc tccccccagg gaccccccctg   1320
gattccccat ggctcctccc aatttcttcc ttccttcccc atctccaccc gccttcctgc   1380
cctttgctgg ggtcctccga ggccctggcc ggccggtgcc cccctcccca gctccaggag   1440
gcagctgagg gggatggggg ggcagatctt ggactcatga ggaggggccc ccctgccctg   1500
tggggtcaac ccttctggaa actgtgaaga tctcactctg cccccccccc ccatcttcgg   1560
gaccaggatt tgcacagaag cacatgcacc tacccataca ccccctcttc tgagcacaga   1620
tgttccccca tctcgctccc tcccaggact ctgaccccag cattctcagg caccagtccc   1680
tgtccggaat gccacccaca tcttccattt ccatgtcccc tcccagagct ggtggaccca   1740
gggaacagcc actcccctcc actctctacc agataactga ggaggggaga ggtgggccgt   1800
aacgggcacg gatcacgatg taaattatta agcattttgg ttggatttct tttgtaataa   1860
actatttttg taccata                                                  1877
```

<210> SEQ ID NO 19
<211> LENGTH: 682
<212> TYPE: DNA
<213> ORGANISM: Homo sapiens

<400> SEQUENCE: 19

```
tgtgaaccag gagtgagtcg gagctgccgc gctgcccagg ccatggactg tgaggtcaac     60
aacggttcca gcctcaggga tgagtgcatc acaaacctac tggtgtttgg cttcctccaa    120
agctgttctg acaacagctt ccgcagagag ctggacgcac tgggccacga gctgccagtg    180
ctggctcccc agtgggaggg ctacgatgag ctgcagactg atggcaaccg cagcagccac    240
```

```
tcccgcttgg gaagaataga ggcagattct gaaagtcaag aagacatcat ccggaatatt    300

gccaggcacc tcgcccaggt cggggacagc atggaccgta gcatccctcc gggcctggtg    360

aacggcctgg ccctgcagct caggaacacc agccggtcgg aggaggaccg gaacagggac    420

ctggccactg ccctggagca gctgctgcag gcctacccta gagacatgga gaaggagaag    480

accatgctgg tgctggccct gctgctggcc aagaaggtgg ccagtcacac gccgtccttg    540

ctccgtgatg tctttcacac aacagtgaat tttattaacc agaacctacg cacctacgtg    600

aggagcttag ccagaaatgg gatggactga acggacagtt ccagaagtgt gactggctaa    660

agctcgatgt ggtcacagct gt                                             682
```

<210> SEQ ID NO 20
<211> LENGTH: 923
<212> TYPE: DNA
<213> ORGANISM: Homo sapiens

<400> SEQUENCE: 20

```
cagcatcgcc gccgccagag gagaaatgtc tgaagtaaga cccctctcca gagacatctt     60

gatggagacc ctcctgtatg agcagctcct ggaacccccg accatggagg ttcttggcat    120

gactgactct gaagaggacc tggaccctat ggaggacttc gattctttgg aatgcatgga    180

gggcagtgac gcattggccc tgcggctggc ctgcatcggg gacgagatgg acgtgagcct    240

cagggccccg cgcctggccc agctctccga ggtggccatg cacagcctgg gtctggcttt    300

catctacgac cagactgagg acatcaggga tgttcttaga agtttcatgg acggtttcac    360

cacacttaag gagaacataa tgaggttctg gagatccccg aaccccgggt cctgggtgtc    420

ctgcgaacag gtgctgctgg cgctgctgct gctgctggcg ctgctgctgc cgctgctcag    480

cgggggcctg cacctgctgc tcaagtgagc ccccggcggc tcaggcgtgg ctggccccac    540

ccccatgacc actgccctga ggtggcggcc tgctgctgtt atctttttaa ctgttttctc    600

atgatgcctt ttatattaac cccgtgatag tgctggaaca ctgctgaggt tttatactca    660

ggtttttgt tttttttta ttccagtttt cgttttttct aaaagatgaa ttcctatggc    720

tctgcaattg tcaccggtta actgtggcct gtgcccagga agagccattc actcctgccc    780

ctgcccacac ggcaggtagc agggggagtg ctggtcacac ccctgtgtga tatgtgatgc    840

cctcggcaaa gaatctactg gaatagattc cgaggagcag gagtgctcaa taaaatgttg    900

gtttccagca aaaaaaaaaa aaa                                            923
```

<210> SEQ ID NO 21
<211> LENGTH: 4153
<212> TYPE: DNA
<213> ORGANISM: Homo sapiens

<400> SEQUENCE: 21

```
tccactggcc agcattctcc tctattagac tagaactgtg gataaacctc agaaaatggc     60

cacccagcag aaagcctctg acgagaggat ctcccagttt gatcacaatt tgctgccaga    120

gctgtctgct cttctgggcc tagatgcagt tcagttggca aaggaactag aagaagagga    180

gcagaaggag cgagcaaaaa tgcagaaagg ctacaactct caaatgcgca gtgaagcaaa    240

aaggttaaag actttttgtga cttatgagcc gtacagctca tggataccac aggagatggc    300

ggccgctggg ttttacttca ctggggtaaa atctgggatt cagtgcttct gctgtagcct    360

aatcctcttt ggtgccggcc tcacgagact ccccatagaa gaccacaaga ggtttcatcc    420
```

```
agattgtggg ttccttttga acaaggatgt tggtaacatt gccaagtacg acataagggt    480
gaagaatctg aagagcaggc tgagaggagg taaaatgagg taccaagaag aggaggctag    540
acttgcatcc ttcaggaact ggccatttta tgtccaaggg atatcccctt gtgtgctctc    600
agaggctggc tttgtcttta caggtaaaca ggacacggta cagtgttttt cctgtggtgg    660
atgtttagga aattgggaag aaggagatga tccttggaag gaacatgcca aatggttccc    720
caaatgtgaa tttcttcgga gtaagaaatc ctcagaggaa attacccagt atattcaaag    780
ctacaaggga tttgttgaca taacgggaga acattttgtg aattcctggg tccagagaga    840
attacctatg gcatcagctt attgcaatga cagcatcttt gcttacgaag aactacggct    900
ggactctttt aaggactggc cccgggaatc agctgtggga gttgcagcac tggccaaagc    960
aggtcttttc tacacaggta taaaggacat cgtccagtgc ttttcctgtg gagggtgttt   1020
agagaaatgg caggaaggtg atgacccatt agacgatcac accagatgtt ttcccaattg   1080
tccatttctc caaaatatga agtcctctgc ggaagtgact ccagaccttc agagccgtgg   1140
tgaactttgt gaattactgg aaaccacaag tgaaagcaat cttgaagatt caatagcagt   1200
tggtcctata gtgccagaaa tggcacaggg tgaagcccag tggtttcaag aggcaaagaa   1260
tctgaatgag cagctgagag cagcttatac cagcgccagt ttccgccaca tgtctttgct   1320
tgatatctct tccgatctgg ccacggacca cttgctgggc tgtgatctgt ctattgcttc   1380
aaaacacatc agcaaacctg tgcaagaacc tctggtgctg cctgaggtct ttggcaactt   1440
gaactctgtc atgtgtgtgg agggtgaagc tggaagtgga aagacggtcc tcctgaagaa   1500
aatagctttt ctgtgggcat ctggatgctg tcccctgtta aacaggttcc agctggtttt   1560
ctacctctcc cttagttcca ccagaccaga cgaggggctg gccagtatca tctgtgacca   1620
gctcctagag aaagaaggat ctgttactga aatgtgcatg aggaacatta tccagcagtt   1680
aaagaatcag gtcttattcc ttttagatga ctacaaagaa atatgttcaa tccctcaagt   1740
cataggaaaa ctgattcaaa aaaaccactt atcccggacc tgcctattga ttgctgtccg   1800
tacaaacagg gccagggaca tccgccgata cctagagacc attctagaga tcaaagcatt   1860
tccettttat aatactgtct gtatattacg gaagctcttt tcacataata tgactcgtct   1920
gcgaaagttt atggtttact ttggaaagaa ccaaagtttg cagaagatac agaaaactcc   1980
tctctttgtg gcggcgatct gtgctcattg gtttcagtat ccttttgacc catcctttga   2040
tgatgtggct gttttcaagt cctatatgga acgcctttcc ttaaggaaca aagcgacagc   2100
tgaaattctc aaagcaactg tgtcctcctg tggtgagctg gccttgaaag ggtttttttc   2160
atgttgcttt gagtttaatg atgatgatct cgcagaagca ggggttgatg aagatgaaga   2220
tctaaccatg tgcttgatga gcaaatttac agcccagaga ctaagaccat tctaccggtt   2280
tttaagtcct gccttccaag aatttcttgc ggggatgagg ctgattgaac tcctggattc   2340
agataggcag gaacatcaag atttgggact gtatcatttg aaacaaatca actcacccat   2400
gatgactgta agcgcctaca acaatttttt gaactatgtc tccagcctcc cttcaacaaa   2460
agcagggccc aaaattgtgt ctcatttgct ccatttagtg gataacaaag agtcattgga   2520
gaatatatct gaaaatgatg actacttaaa gcaccagcca gaaatttcac tgcagatgca   2580
gttacttagg ggattgtggc aaatttgtcc acaagcttac ttttcaatgg tttcagaaca   2640
tttactggtt cttgccctga aaactgctta tcaaagcaac actgttgctg cgtgttctcc   2700
atttgttttg caattccttc aagggagaac actgactttg ggtgcgctta acttacagta   2760
ctttttcgac cacccagaaa gcttgtcatt gttgaggagc atccacttcc caatacgagg   2820
```

```
aaataagaca tcacccagag cacatttttc agttctggaa acatgttttg acaaatcaca   2880

ggtgccaact atagatcagg actatgcttc tgcctttgaa cctatgaatg aatgggagcg   2940

aaatttagct gaaaaagagg ataatgtaaa gagctatatg gatatgcagc gcagggcatc   3000

accagacctt agtactggct attggaaact ttctccaaag cagtacaaga ttccctgtct   3060

agaagtcgat gtgaatgata ttgatgttgt aggccaggat atgcttgaga ttctaatgac   3120

agttttctca gcttcacagc gcatcgaact ccatttaaac cacagcagag gctttataga   3180

aagcatccgc ccagctcttg agctgtctaa ggcctctgtc accaagtgct ccataagcaa   3240

gttggaactc agcgcagccg aacaggaact gcttctcacc ctgccttccc tggaatctct   3300

tgaagtctca gggacaatcc agtcacaagt aaaattaatt caaaattctc caaaccttca   3360

tgttttccat ctgaagtgta acttcttttc ggattttggg tctctcatga ctatgcttgt   3420

ttcctgtaag aaactcacag aaattaagtt ttcggattca ttttttcaag ccgtcccatt   3480

tgttgccagt ttgccaaatt ttatttctct gaagatatta aatcttgaag gccagcaatt   3540

tcctgatgag gaaacatcag aaaaatttgc ctacatttta ggttctctta gtaacctgga   3600

agaattgatc cttcctactg gggatggaat ttatcgagtg gccaaactga tcatccagca   3660

gtgtcagcag cttcattgtc tccgagtcct ctcattttc aagactttga atgatgacag    3720

cgtggtggaa attgccaaag tagcaatcag tggaggtttc cagaaacttg agaacctaaa   3780

gctttcaatc aatcacaaga ttacagagga aggatacaga aatttctttc aagcactgga   3840

caacatgcca aacttgcagg agttggacat ctccaggcat ttcacagagt gtatcaaagc   3900

tcaggccaca acagtcaagt ctttgagtca atgtgtgtta cgactaccaa ggctcattag   3960

actgaacatg ttaagttggc tcttggatgc agatgatatt gcattgctta atgtcatgaa   4020

agaaagacat cctcaatcta agtacttaac tattctccag aaatggatac tgccgttctc   4080

tccaatcatt cagaaataaa agattcagct aaaaactgct gaatcaataa tttgtcttgg   4140

ggcatattga gga                                                      4153
```

<210> SEQ ID NO 22
<211> LENGTH: 6877
<212> TYPE: DNA
<213> ORGANISM: Homo sapiens

<400> SEQUENCE: 22

```
ggcacggaaa aggccaggcg acaggtgtcg cttgaaaaga ctgggcttgt ccttgctggt     60

gcatgcgtcg tcggcctctg ggcagcaggt ttacaaagga ggaaaacgac ttcttctaga    120

ttttttttc agtttcttct ataaatcaaa acatctcaaa atggagacct aaaatcctta     180

aagggactta gtctaatctc gggaggtagt tttgtgcatg ggtaaacaaa ttaagtatta    240

actggtgttt tactatccaa agaatgctaa ttttataaac atgatcgagt tatataaggt    300

ataccataat gagtttgatt ttgaatttga tttgtggaaa taaaggaaaa gtgattctag    360

ctggggcata ttgttaaagc attttttca gagttggcca ggcagtctcc tactggcaca     420

ttctcccatt atgtagaata gaaatagtac ctgtgtttgg gaaagatttt aaaatgagtg    480

acagttattt ggaacaaaga gctaataatc aatccactgc aaattaaaga aacatgcaga    540

tgaaagtttt gacacattaa aatacttcta cagtgacaaa gaaaaatcaa gaacaaagct    600

ttttgatatg tgcaacaaat ttagaggaag taaaaagata aatgtgatga ttggtcaaga    660

aattatccag ttatttacaa ggccactgat attttaaacg tccaaaagtt tgtttaaatg    720
```

```
ggctgttacc gctgagaatg atgaggatga gaatgatggt tgaaggttac attttaggaa    780
atgaagaaac ttagaaaatt aatataaaga cagtgatgaa tacaaagaag atttttataa    840
caatgtgtaa aatttttggc cagggaaagg aatattgaag ttagatacaa ttacttacct    900
ttgagggaaa taattgttgg taatgagatg tgatgtttct cctgccacct ggaaacaaag    960
cattgaagtc tgcagttgaa aagcccaacg tctgtgagat ccaggaaacc atgcttgcaa   1020
accactggta aaaaaaaaaa aaaaaaaaaa aaaaagccac agtgacttgc ttattggtca   1080
ttgctagtat tatcgactca gaacctcttt actaatggct agtaaatcat aattgagaaa   1140
ttctgaattt tgacaaggtc tctgctgttg aaatggtaaa tttattattt tttttgtcat   1200
gataaattct ggttcaaggt atgctatcca tgaaataatt tctgaccaaa actaaattga   1260
tgcaatttga ttatccatct tagcctacag atggcatctg gtaacttttg actgttttaa   1320
aaaataaatc cactatcaga gtagatttga tgttggcttc agaaacattt agaaaaacaa   1380
aagttcaaaa atgttttcag gaggtgataa gttgaataac tctacaatgt tagttctttg   1440
agggggacaa aaaatttaaa atctttgaaa ggtcttattt tacagccata tctaaattat   1500
cttaagaaaa tttttaacaa agggaatgaa atatatatca tgattctgtt tttccaaaag   1560
taacctgaat atagcaatga agttcagttt tgttattggt agtttgggca gagtctcttt   1620
ttgcagcacc tgttgtctac cataattaca gaggacattt ccatgttcta gccaagtata   1680
ctattagaat aaaaaaactt aacattgagt tgcttcaaca gcatgaaact gagtccaaaa   1740
gaccaaatga acaaacacat taatctctga ttatttattt taaatagaat atttaattgt   1800
gtaagatcta atagtatcat tatacttaag caatcatatt cctgatgatc tatgggaaat   1860
aactattatt taattaatat tgaaaccagg ttttaagatg tgttagccag tcctgttact   1920
agtaaatctc tttatttgga gagaaatttt agattgtttt gttctcctta ttagaaggat   1980
tgtagaaaga aaaaaatgac taattggaga aaaattgggg atatatcata tttcactgaa   2040
ttcaaaatgt cttcagttgt aaatcttacc attattttac gtacctctaa gaaataaaag   2100
tgcttctaat taaaatatga tgtcattaat tatgaaatac ttcttgataa cagaagtttt   2160
aaaatagcca tcttagaatc agtgaaatat ggtaatgtat tattttcctc ctttgagtta   2220
ggtcttgtgc tttttttcc tggccactaa atttcacaat ttccaaaaag caaaataaac   2280
atattctgaa tatttttgct gtgaaacact tgacagcaga gctttccacc atgaaaagaa   2340
gcttcatgag tcacacatta catctttggg ttgattgaat gccactgaaa cattctagta   2400
gcctggagaa gttgacctac ctgtggagat gcctgccatt aaatggcatc ctgatggctt   2460
aatacacatc actcttctgt gaagggtttt aattttcaac acagcttact ctgtagcatc   2520
atgtttacat tgtatgtata aagattatac aaaggtgcaa ttgtgtattt cttccttaaa   2580
atgtatcagt ataggattta gaatctccat gttgaaactc taaatgcata gaaataaaaa   2640
taataaaaaa tttttcattt tggcttttca gcctagtatt aaaactgata aaagcaaagc   2700
catgcacaaa actacctccc tagagaaagg ctagtccctt ttcttcccca ttcatttcat   2760
tatgaacata gtagaaaaca gcatattctt atcaaatttg atgaaaagcg ccaacacgtt   2820
tgaactgaaa tacgacttgt catgtgaact gtaccgaatg tctacgtatt ccacttttcc   2880
tgctggggtt cctgtctcag aaaggagtct tgctcgtgct ggtttctatt acactggtgt   2940
gaatgacaag gtcaaatgct tctgttgtgg cctgatgctg gataactgga aaagaggaga   3000
cagtcctact gaaaagcata aaaagttgta tcctagctgc agattcgttc agagtctaaa   3060
ttccgttaac aacttggaag ctacctctca gcctactttt ccttcttcag taacaaattc   3120
```

```
cacacactca ttacttccgg gtacagaaaa cagtggatat ttccgtggct cttattcaaa   3180
ctctccatca aatcctgtaa actccagagc aaatcaagat tttctgcct tgatgagaag    3240
ttcctaccac tgtgcaatga ataacgaaaa tgccagatta cttacttttc agacatggcc   3300
attgactttt ctgtcgccaa cagatctggc aaaagcaggc ttttactaca taggacctgg   3360
agacagagtg gcttgctttg cctgtggtgg aaaattgagc aattgggaac cgaaggataa   3420
tgctatgtca gaacacctga gacattttcc caaatgccca tttatagaaa atcagcttca   3480
agacacttca agatacacag tttctaatct gagcatgcag acacatgcag cccgctttaa   3540
aacattcttt aactggccct ctagtgttct agttaatcct gagcagcttg caagtgcggg   3600
tttttattat gtgggtaaca gtgatgatgt caaatgcttt tgctgtgatg gtggactcag   3660
gtgttgggaa tctggagatg atccatgggt tcaacatgcc aagtggtttc caaggtgtga   3720
gtacttgata agaattaaag gacaggagtt catccgtcaa gttcaagcca gttaccctca   3780
tctacttgaa cagctgctat ccacatcaga cagcccagga gatgaaaatg cagagtcatc   3840
aattatccat tttgaacctg gagaagacca ttcagaagat gcaatcatga tgaatactcc   3900
tgtgattaat gctgccgtgg aaatgggctt tagtagaagc ctggtaaaac agacagttca   3960
gagaaaaatc ctagcaactg gagagaatta tagactagtc aatgatcttg tgttagactt   4020
actcaatgca gaagatgaaa taagggaaga ggagagagaa agagcaactg aggaaaaaga   4080
atcaaatgat ttattattaa tccggaagaa tagaatggca ctttttcaac atttgacttg   4140
tgtaattcca atcctggata gtctactaac tgccggaatt attaatgaac aagaacatga   4200
tgttattaaa cagaagacac agacgtcttt acaagcaaga gaactgattg atacgatttt   4260
agtaaaagga aatattgcag ccactgtatt cagaaactct ctgcaagaag ctgaagctgt   4320
gttatatgag catttatttg tgcaacagga cataaaatat attcccacag aagatgtttc   4380
agatctacca gtggaagaac aattgcggag actacaagaa gaaagaacat gtaaagtgtg   4440
tatggacaaa gaagtgtcca tagtgtttat tccttgtggt catctagtag tatgcaaaga   4500
ttgtgctcct tctttaagaa agtgtcctat ttgtaggagt acaatcaagg gtacagttcg   4560
tacatttctt tcatgaagaa gaaccaaaac atcgtctaaa ctttagaatt aatttattaa   4620
atgtattata actttaactt ttatcctaat ttggtttcct taaaattttt atttatttac   4680
aactcaaaaa acattgtttt gtgtaacata tttatatatg tatctaaacc atatgaacat   4740
atatttttta gaaactaaga gaatgatagg cttttgttct tatgaacgaa aaagaggtag   4800
cactacaaac acaatattca atcaaaattt cagcattatt gaaattgtaa gtgaagtaaa   4860
acttaagata tttgagttaa cctttaagaa ttttaaatat tttggcattg tactaatacc   4920
gggaacatga agccaggtgt ggtggtatgt gcctgtagtc ccaggctgag gcaagagaat   4980
tacttgagcc caggagtttg aatccatcct gggcagcata ctgagaccct gcctttaaaa   5040
acaaacagaa caaaaacaaa acaccaggga cacatttctc tgtctttttt gatcagtgtc   5100
ctatacatcg aaggtgtgca tatatgttga atgacatttt agggacatgg tgtttttata   5160
aagaattctg tgagaaaaaa tttaataaag caacaaaaat tactcttatt cttcattgct   5220
ttatttcaat gacattggat agtttagtca ctcccagact ctttccatac cttcttaaag   5280
cctctcaaat attgaactac agtttatact ccttcccata agatgcttct tcattgacac   5340
ttgtagaaca cggggtcaac acatcataaa atctattatg gaatgcctga gacaagaatc   5400
aaacagtccc tttagtaagt ttgtttattc acttctctat tgattcattc aagaagtctc   5460
```

```
atgccagccc cacctattgg aagaaggtct gagttttatt cttatctctt tggtattaat   5520

tctgaaactt agaaagtaca ctggttagca atgcttggga ccaacaggtt gttctggtaa   5580

ataaatctgt ttcatattgt cagtgcaaca aaatgtcccc ctctgcatta tgttattggt   5640

actcaacacg tccgagtcat aactctgtcc tttgcttctt atagaggtat taggtcttca   5700

agagcagaag taagactgta atagggaata ctcaggggaa ggcaggcaaa ggctagtcat   5760

ctaaaccagt tctagatgtc tgtatagggg cagatggctc tgtaagggca gaagggaaag   5820

accccttcat aagggtcaca gctgacaatc ctataacaaa agacaggtta acaagagaaa   5880

aacttaacaa atttatttaa tcacagattt acatcaccgg ggagccttcg taatgaagat   5940

ccaaaattac aggggaaact gtgcattttt atgcttaggt ttgataatga atggacagcc   6000

ctgaagaata gtgattggaa aaaaaggata tgatctaatg ggaatagaca caggttgggg   6060

acccagcaag gcctgtctgt tcagattatt cttggtctct gtgcagcatt ccttcctcct   6120

ggatataggg cagggcctgt atgggatggg gatattataa cctgctatca agcaaggtag   6180

gtcagagaat ttatttatgg ccagctctta catagttagg tgaggaaaga ttagagtact   6240

atctttaaga tgtaagtctg gcattgtgga aagatggttc cagtttctat gacctacctt   6300

ggggaagagg aattcaagtt tctgtggctt gccttcaggg agaatgaggc tgagacagga   6360

gggcaggata acatcagaga aaaactttgc ttctgaggcc ttcactttgg gttttctgag   6420

ccccaacatc tgctagtgtt gtaaagagaa caattaggga ccaagtgagg ggaggaaaga   6480

atccatctct gcattctgat gctgggagac ttatttcctt gaaatgcaat tgattttgcc   6540

tctgctaaga ggctctgctg gctacccatg tactagccag tgtcctgcat gggtgctagg   6600

ctgaattatt tgtaattgtg cttaggtgat ttgtaactca ggtatagggt atttaaatag   6660

taggcaccct ttttgcacca tgtgtttttt tttttatcta gttcttgtat actacagata   6720

atatttgaac tttgtcatct cactgtaaaa cttttgttca tttctcatta tggtaataaa   6780

tagctattat aaccaaccca tttattcaaa tatgttattt ccctaagtgt tattttgaca   6840

ttttgttttg gaaaaaataa atcaccatag ataataa                            6877
```

```
<210> SEQ ID NO 23
<211> LENGTH: 8427
<212> TYPE: DNA
<213> ORGANISM: Homo sapiens

<400> SEQUENCE: 23
```

```
ttcttactgc ccccatccgg ttcggggagg tggcgggacc ttggcggcgc ccggagccgg     60

cgtggcgctc atcgagggac gcccggccca agtgaaaagg tggacaagtc ctattttcaa    120

gagaagatga cttttaacag ttttgaagga tctaaaactt gtgtacctgc agacatcaat    180

aaggaagaag aatttgtaga agagtttaat agattaaaaa cttttgctaa ttttccaagt    240

ggtagtcctg tttcagcatc aacactggca cgagcagggt ttctttatac tggtgaagga    300

gataccgtgc ggtgctttag ttgtcatgca gctgtagata gatggcaata tggagactca    360

gcagttggaa gacacaggaa agtatcccca aattgcagat ttatcaacgg cttttatctt    420

gaaaatagtg ccacgcagtc tacaaattct ggtatccaga atggtcagta caaagttgaa    480

aactatctgg gaagcagaga tcattttgcc ttagacaggc catctgagac acatgcagac    540

tatcttttga gaactgggca ggttgtagat atatcagaca ccatataccc gaggaaccct    600

gccatgtata gtgaagaagc tagattaaag tcctttcaga actggccaga ctatgctcac    660

ctaaccccaa gagagttagc aagtgctgga ctctactaca caggtattgg tgaccaagtg    720
```

```
cagtgctttt gttgtggtgg aaaactgaaa aattgggaac cttgtgatcg tgcctggtca    780
gaacacaggc gacactttcc taattgcttc tttgttttgg gccggaatct taatattcga    840
agtgaatctg atgctgtgag ttctgatagg aatttcccaa attcaacaaa tcttccaaga    900
aatccatcca tggcagatta tgaagcacgg atctttactt ttgggacatg gatatactca    960
gttaacaagg agcagcttgc aagagctgga ttttatgctt taggtgaagg tgataaagta   1020
aagtgctttc actgtggagg agggctaact gattggaagc ccagtgaaga cccttgggaa   1080
caacatgcta aatggtatcc agggtgcaaa tatctgttag aacagaaggg acaagaatat   1140
ataaacaata ttcatttaac tcattcactt gaggagtgtc tggtaagaac tactgagaaa   1200
acaccatcac taactagaag aattgatgat accatcttcc aaaatcctat ggtacaagaa   1260
gctatacgaa tggggttcag tttcaaggac attaagaaaa taatggagga aaaaattcag   1320
atatctggga gcaactataa atcacttgag gttctggttg cagatctagt gaatgctcag   1380
aaagacagta tgcaagatga gtcaagtcag acttcattac agaaagagat tagtactgaa   1440
gagcagctaa ggcgcctgca agaggagaag ctttgcaaaa tctgtatgga tagaaatatt   1500
gctatcgttt ttgttccttg tggacatcta gtcacttgta aacaatgtgc tgaagcagtt   1560
gacaagtgtc ccatgtgcta cacagtcatt actttcaagc aaaaaatttt tatgtcttaa   1620
tctaactcta tagtaggcat gttatgttgt tcttattacc ctgattgaat gtgtgatgtg   1680
aactgacttt aagtaatcag gattgaattc cattagcatt tgctaccaag taggaaaaaa   1740
aatgtacatg gcagtgtttt agttggcaat ataatctttg aatttcttga tttttcaggg   1800
tattagctgt attatccatt ttttttactg ttatttaatt gaaaccatag actaagaata   1860
agaagcatca tactataact gaacacaatg tgtattcata gtatactgat ttaatttcta   1920
agtgtaagtg aattaatcat ctggattttt tattcttttc agataggctt aacaaatgga   1980
gctttctgta tataaatgtg gagattagag ttaatctccc caatcacata atttgttttg   2040
tgtgaaaaag gaataaattg ttccatgctg gtggaaagat agagattgtt tttagaggtt   2100
ggttgttgtg ttttaggatt ctgtccattt tcttttaaag ttataaacac gtacttgtgc   2160
gaattatttt tttaaagtga tttgccattt ttgaaagcgt atttaatgat agaatactat   2220
cgagccaaca tgtactgaca tggaaagatg tcaaagatat gttaagtgta aaatgcaagt   2280
ggcaaaacac tatgtatagt ctgagccaga tcaaagtatg tatgttttta atatgcatag   2340
aacaaaagat ttggaaagat atacaccaaa ctgttaaatg tggtttctct tcggggaggg   2400
ggggattggg ggaggggccc cagaggggtt ttatagggc cttttcactt tctacttttt   2460
tcattttgtt ctgttcgaat tttttataag tatgtattac ttttgtaatc agaattttta   2520
gaaagtattt tgctgattta aaggcttagg catgttcaaa cgcctgcaaa actacttatc   2580
actcagcttt agtttttcta atccaagaag gcagggcagt taaccttttt ggtgccaatg   2640
tgaaatgtaa atgattttat gtttttcctg ctttgtggat gaaaaatatt tctgagtggt   2700
agtttttga caggtagacc atgtcttatc ttgtttcaaa ataagtattt ctgattttgt   2760
aaaatgaaat ataaaatatg tctcagatct tccaattaat tagtaaggat tcatccttaa   2820
tccttgctag tttaagcctg cctaagtcac tttactaaaa gatctttgtt aactcagtat   2880
tttaaacatc tgtcagctta tgtaggtaaa agtagaagca tgtttgtaca ctgcttgtag   2940
ttatagtgac agctttccat gttgagattc tcatatcatc ttgtatctta aagtttcatg   3000
tgagttttta ccgttaggat gattaagatg tatataggac aaaatgttaa gtctttcctc   3060
```

-continued

```
tacctacatt tgttttcttg gctagtaata gtagtagata cttctgaaat aaatgttctc   3120
tcaagatcct taaaacctct tggaaattat aaaaatattg gcaagaaaag aagaatagtt   3180
gtttaaatat tttttaaaaa acacttgaat aagaatcagt agggtataaa ctagaagttt   3240
aaaaatgctt catagaacgt ccagggttta cattacaaga ttctcacaac aaacctattg   3300
tagaggtgag taaggcatgt tactacagag gaaagtttga gagtaaaact gtaaaaaatt   3360
atatttttgt tgtactttct aagagaaaga gtattgttat gttctcctaa cttctgttga   3420
ttactacttt aagtgatatt catttaaaac attgcaaatt tattttattt atttaatttt   3480
ctttttgaga tggagtcttg cttgtcaccc aggctggagt gcagtggagt gatctctgct   3540
cactgcaacc tccgccttct gggttcaagc gattctcgtg cctcagcttc ctgagtagct   3600
ggaattacag gcaggtgcca ccatgcccga ctaatttttt tttattttta gtagagacgg   3660
ggtttcacca tgttggccag gctggtatca aactcctgac ctcaagagat ccactcgcct   3720
tgccctccca aagtgctggg attacaggct tgagccacca cgcccggcta aaacattgca   3780
aatttaaatg agagttttaa aaattaaata atgactgccc tgtttctgtt ttagtatgta   3840
aatcctcagt tcttcacctt tgcactgtct gccacttagt ttggttatat agtcattaac   3900
ttgaatttgg tctgtatagt ctagacttta aatttaaagt tttctacaag gggagaaaag   3960
tgttaaaatt tttaaaatat gttttccagg acacttcact tccaagtcag gtaggtagtt   4020
caatctagtt gttagccaag gactcaagga ctgaattgtt ttaacataag gcttttcctg   4080
ttctgggagc cgcacttcat taaaattctt ctaaaacttg tatgtttaga gttaagcaag   4140
actttttttc ttcctctcca tgagttgtga aatttaatgc acaacgctga tgtggctaac   4200
aagtttattt taagaattgt ttagaaatgc tgttgcttca ggttcttaaa atcactcagc   4260
actccaactt ctaatcaaat ttttggagac ttaacagcat ttgtctgtgt ttgaactata   4320
aaaagcaccg gatcttttcc atctaattcc gcaaaaattg atcatttgca aagtcaaaac   4380
tatagccata tccaaatctt ttccccctcc caagagttct cagtgtctac atgtagacta   4440
ttccttttct gtataaagtt cactctagga tttcaagtca ccacttattt tacattttag   4500
tcatgcaaag attcaagtag ttttgcaata agtacttatc tttatttgta ataatttagt   4560
ctgctgatca aaagcattgt cttaattttt gagaactggt tttagcattt acaaactaaa   4620
ttccagttaa ttaattaata gctttatatt gcctttcctg ctacatttgg ttttttcccc   4680
tgtccctttg attacgggct aaggtagggt agagtgggtg tagtgagtgt atataatgtg   4740
atttggccct gtgtattatg atattttgtt atttttgttg ttatattatt tacatttcag   4800
tagttgtttt ttgtgtttcc attttagtgg ataaaatttg tattttgaac tatgaatgga   4860
gactaccgcc ccagcattag tttcacatga tataccettt aaacccgaat cattgtttta   4920
tttcctgatt acacaggtgt tgaatgggga aaggggctag tatatcagta ggatatacta   4980
tgggatgtat atatatcatt gctgttagag aaatgaaata aaatggggct gggctcagtg   5040
gctcacgcct gtaatcccag cactttggga ggctgaggca ggtggatcac gaggtcagga   5100
gatcgagacc atcctggcta acacggtgaa accccgtctc tactaaaaaa cagaaaatta   5160
gccgggcgtg gtggcgggcg cctgtagtcc cagctactcg ggaggctgag gcaggagaat   5220
ggtgtgaacc cgggaggcag agcttgcagt gagccgagat ctcgccactg cactccagcc   5280
tgggcaacag agcaagactc tgtctcaaaa aaaaaaaaaa aagaaataag aaaatgggaa   5340
gcaatatttg acatagttct ttttagtcaa atctacttgt taaaaaaagg gtagcagttt   5400
attcatctgt gaaaggaaaa taatacttat cttacaaggt tgcaagagct caaggagacc   5460
```

```
atgtatgtaa agttcctgct gtaaatatga actcccatcc taataccctt ttacctctct   5520
gtgggtttgt cttgacctgg aaatttgggc taaaacttag aaaaaattct tacatgataa   5580
ctcagtgatg cttactcata gtttttggtg tttctcatag ataagatata aatcagctgg   5640
gcgcggtggc tcatgcctgt aatcccagca ctttgggagg ccgaggcggg cagatcacct   5700
gaggtcggga ggtcgagacc agcctgacca acatggagaa accccgtctc tactaaaaat   5760
acaaaattag ctgggcgtgg tggctcatgc ctgtaatccc agctacttgg gaggctgagg   5820
caggagaatc gcttgaaccc aggaggcgga ggttgtggtg agcgaagatc gtgccattgc   5880
actccagcct gggcaacaag agcaaaactc tgtctcaaaa aaaaaaaaag atataaatca   5940
caataaataa ataggtcaat acaaatgtta gccaggcgtg gtggcacatg cccatagtcg   6000
cagctactct ggaggcagag gcaggaggat cacttgagcc catgaatttg aggcagcagt   6060
gagctatgat tgtgccactg tactccagtc tgggtgacag agtgagaccc catctctaaa   6120
taaataggtc aaacccttaa aaatatttaa attcttaaaa aattgaaaag attattcttc   6180
tcaaatttag ttgagctttc taagagaagc aattggcttt ttcccacttc aataatcatt   6240
ttcagtttga ctcatacagt taacacaatg tgaatttctt cctcagcata acagagttat   6300
agaatgacag ggctggaagt gaccttagag agtatccagt tctttcattt tacaggtgag   6360
gcaactgaga ctcaaaggtg atgtaatttg tgcaaagatt atagctaatt agtagcagag   6420
ccctgactgg gacatagttt gaaggtgaaa aacttcacca agctaccttt cttgaaaggt   6480
ccaaatgttt atgttttcaa ctactctttc cactgtacca taactttcac tacatattaa   6540
atgacacttt ataactaata taataggaca atcatcaatg catatatagc cagcccttca   6600
tatctgtggg ttttgcatcc atggattcaa ccaaggagga attgaaaaca ctgagaaaaa   6660
aaaaaaagac cacacaataa aaaaaaaaaa tacaaaataa tacaaagaaa aagccaaaat   6720
tgtcatactg ttgttaagca acagtataac aactatttac atagcattaa ggttggtgca   6780
aaaatgcaaa aaaaaaaaaa gcaattattt ttaaaccaac ctaatatatt gtattaggta   6840
ttaaagtcat ctggacatga attaaagtat atgatgccag cctggacaaa aggcaaaacc   6900
ctgtctctac aaaaaataca aaaattagct gggcatggtg gtgtgtgcct gtagtcctgg   6960
ctactccgga gcctgaggtg ggaggatcgc ttgagtctgg gaggcagagg ctgcattgag   7020
ctatgatcat ggcactgcat tccagcctgg gtgacagtgc aagaccttgt ctcagaataa   7080
ataaagtatg tgatgaagat gtgcatacat tatatgcaaa tactgttttt ttttttttta   7140
atttaaacag tctcactgtg ttgcccagga tggagtgcaa tggcacaatc ttggctcatg   7200
gcaaactctg cctcgcaagc agctgggact acaggcatgc tccacggtgc ccagttaatt   7260
tttttgtat tcttagtaga gacagggttt caccatgttg gccaggctag tcttgaattt    7320
ctgacctcaa gtgattcatc tcccaaagtg ctgggattac aggcgtgagc caccacggcc   7380
ggctaatttt tgtatttttt agtagtgact ggtttcgcgg tgttgaccag gctggtctcg   7440
aactcctgat ctcaggtgat ctgcctgcct cggcctcaca aagtgctggg attacaggtg   7500
tgaaccactg ctcccggcct tgtgtgattt tatctaaggg acttaagcgt cctcaggtcc   7560
tagggggtcg tgaaaccaaa accccaggga tagcaaggga caattgtatc ttcaaagtag   7620
acaaatggcg ccgggcacgg tggctcacgc ctgtaatccc agcagtttcc gaggctgagg   7680
caggcggctc acctgaggtc aggagttgga gaccagcctg gccaacatgc tgaaaccctg   7740
tctgtacaaa aatacaaaaa tagctgggca tggtggcgca tgcctgtagt cccagctact   7800
```

```
agagcgactg aggcaggaga attgcttgaa cctgggaggc ggaggttgca gggagccaag   7860

atggcgccac cgcactccag cctaggtgat agagtgagac tccctctcaa aaacaaaaca   7920

aaacaaaaaa attagacaaa tgctacatta atgtttgggt ggtcagattc tactttgaat   7980

ctgaagtttg cagatatgcc tatagatttt tggagtttac cactttctta ttctgtatca   8040

ttaatgtaat attttaaatt actatatatg ttaccatttt tctggattta gtaagaaatt   8100

tgcagttttg gtttgatgta acaagggttt taatgtaatt tatgttagat tttgcatttt   8160

tttcattact gttatatttt aacctgactg actgatctaa ttgtattagt attgtgaata   8220

atcatgtgaa atgttttgag acagagtact atatttgtga atataatttt atggtttttt   8280

tcacttagaa cctttctgtg tggaaaacta agaaaattgc tttctgctgt ataatctggc   8340

attcattgta gattaaagct tatttttctg tgaataaaac gtattcaata aaatactatt   8400

ctttaaaatt atatcataaa aaaaaaa                                       8427
```

<210> SEQ ID NO 24
<211> LENGTH: 429
<212> TYPE: DNA
<213> ORGANISM: Homo sapiens

<400> SEQUENCE: 24

```
atgggtgccc cgacgttgcc ccctgcctgg cagccctttc tcaaggacca ccgcatctct     60

acattcaaga actggccctt cttggagggc tgcgcctgca ccccggagcg gatggccgag    120

gctggcttca tccactgccc cactgagaac gagccagact tggcccagtg tttcttctgc    180

ttcaaggagc tggaaggctg ggagccagat gacgacccca tagaggaaca taaaaagcat    240

tcgtccggtt gcgctttcct ttctgtcaag aagcagtttg aagaattaac ccttggtgaa    300

tttttgaaac tggacagaga aagagccaag aacaaaattg caaaggaaac caacaataag    360

aagaaagaat ttgaggaaac tgtgaagaaa gtgcgccgtg ccatcgagca gctggctgcc    420

atggattga                                                            429
```

<210> SEQ ID NO 25
<211> LENGTH: 15718
<212> TYPE: DNA
<213> ORGANISM: Homo sapiens

<400> SEQUENCE: 25

```
tccctgcttc tccccctctc ccgtcagcct ccctccgagt ttggcccctc cggccgggcg     60

atcgacgttc cgcgtgcgtg cgggcgcctg acttcacttc cggctaacgc gctcggcttg    120

ccccctggcc ccggatggtg actggtggtg gtgctgcacc tcccgggact gtcactgagc    180

cgcttcccag tgtgattgtg ctgagcgcag gccggaagat ggcggctgcg gctgcggcgg    240

cctcgggccc cggctgctcc tcggcggcgg gggcgggggc ggccggggtc tcagagtggc    300

tggtgctgcg ggacggctgc atgcactgcg acgccgacgg gctgcacagc ctgtcctacc    360

accctgcgct caacgccatc ctggccgtca ctagccgcgg gaccatcaaa gtcatcgacg    420

gcacctcggg ggccacactg caggcctccg cgctcagtgc taaaccaggt ggacaggtga    480

aatgtcagta tatctctgct gtggataaag ttatatttgt ggatgattat gcagtagggt    540

gtaggaagga ccttaatgga atcttgttgt tagacactgc tctgcaaact ccagtttcaa    600

agcaggatga tgtggttcag cttgaattac ccgttacaga ggcacagcag ctcttatcag    660

catgtttaga aaaggtagat atttctagta cagagggtta tgatttgttc atcacacagc    720

tcaaagatgg tttaaaaaat acatctcatg agactgcagc aaaccacaaa gttgctaagt    780
```

```
gggccacagt tacatttcat cttcctcatc atgtgttgaa gtccattgcc agtgccattg    840
taaatgaact caagaaaata aatcaaaatg ttgctgcctt acctgtggcg tcctcagtga    900
tggacagatt gtcttacctc ttacctagtg cacgtccaga actcggagtg ggccaggcc     960
gttctgtaga cagatcactg atgtatagtg aagctaacag acgggagaca tttacctcat   1020
ggcctcatgt aggctatagg tgggcacaac cagatcccat ggctcaagct ggattttatc   1080
atcagcctgc ctcatctgga gatgatagag ccatgtgttt tacttgtagt gtatgcctcg   1140
tttgttggga acctactgat gaaccttggt ctgaacacga aagacattcc ccaaactgcc   1200
catttgtgaa aggtgagcac acacagaatg tgccattgtc agtcactctt gcaacaagtc   1260
ctgcacagtt tccttgtacg gatggaactg acagaatatc ttgctttggg tcggggagct   1320
gccctcattt tctagctgct gcaactaaac gaggaaagat ctgcatatgg gatgtttcca   1380
aacttatgaa ggtgcactta aagtttgaaa ttaatgccta tgatccagca attgtacaac   1440
agcttattct atcaggagac ccaagctcag gagttgattc aaggagacca actttggcgt   1500
ggctggagga ctcctctagt tgctcagata taccaaaatt ggaaggagat agtgatgatt   1560
tactggagga ttcagacagt gaagagcatt ccagatcaga ttctgtgaca gggcatacat   1620
cacagaagga agccatggaa gtaagccttg atataacagc actcagcatt ctccaacagc   1680
cagaaaaact tcagtgggag attgttgcaa atgtgcttga agatactgtt aaggatcttg   1740
aagaacttgg ggcaaatcct tgtttaacaa actctaagag tgaaaagaca aaggaaaagc   1800
accaggagca acacaacatt ccttttccat gtttattagc tggaggttta ttaacatata   1860
aatctcctgc tacctcaccc attagtagta attctcacag gtcactggat ggtttaagca   1920
gaactcaggg tgaaagtata tcagaacaag ggtcaactga caatgaatcc tgcactaatt   1980
cagaactaaa ttctcctctg gtaaggagga ctttaccggt tttgcttctt tatagcatca   2040
aggaatctga tgagaaagca ggaaagatct tttcacagat gaacaatatt atgagtaaaa   2100
gtttgcatga tgatggtttt actgttccac agattattga aatggagctg gatagtcagg   2160
agcagttgtt attgcaggat cctcctgtga cttacattca gcaatttgca gatgcagcag   2220
ccaaccttac ctctccggat tctgagaagt ggaactctgt gtttcccaag cctgggactt   2280
tggttcagtg cttgaggctg ccaaagtttg cagaggagga gaatctttgt atagactcaa   2340
taactccttg tgctgacgga attcatttgt tggtaggact gcggacatgc cctgttgaat   2400
ccttgagtgc aataaatcaa gtagaggcct tgaataattt aaataaatta aactctgcac   2460
tatgtaatag acggaaaggt gagctggaat caaatcttgc tgtagtgaat ggtgcaaata   2520
ttagtgtaat ccaacatgaa tcaccagcag atgtacagac tcctttaata attcagcctg   2580
agcagaggaa tgttagtggt ggatatttag tgctttataa aatgaattat gccactcgga   2640
tagtgacttt agaagaggag ccaataaaaa tacaacatat caaagatccc caggacacaa   2700
ttacctcgct cattttgctt ccacccgata tattggataa tcgagaggat gactgtgagg   2760
aacctattga ggacatgcag ttaacctcaa agaatggttt tgagagagaa aaaacgtctg   2820
acatttctac tcttggacac ctggtaataa ccactcaggg aggatatgta aaaatactag   2880
atctttcaaa ctttgaaatt ttggccaaag tggagcctcc caaaaaggag ggcactgagg   2940
aacaggacac atttgtttct gtgatttact gttctggcac agacaggctg tgtgcatgca   3000
ccaaaggtgg tgagcttcat ttttctccaaa ttggaggaac ctgtgatgat attgatgaag   3060
ctgatatact agtggatgga tctctttcta aaggaataga accatcttca gaaggttcca   3120
```

```
aacctttatc aaatccttca agtcctggca tttcaggagt tgatttattg gtggaccagc   3180

cattcaccct tgaaatcttg acatccctag tggagctaac ccgctttgag actttgactc   3240

caaggttttc agcgactgtt cctccatgct gggtagaagt tcaacaagaa cagcagcaaa   3300

ggaggcatcc tcaacatttg catcagcaac accatggtga tgctgctcag catactcgaa   3360

cttggaaact acagaccgac agcaacagct gggatgaaca tgtatttgaa ttagtactac   3420

ctaaagcttg tatggttgga catgtggact tcaaattcgt tttgaactca aacatcacca   3480

atattccaca gatacaagtg acactgctga aaaataaagc tccaggatta gggaaagtca   3540

atgctcttaa cattgaagtg gaacaaaatg ggaaaccgtc cctggttgat ttgaatgaag   3600

aaatgcagca catggatgta gaggaatcac agtgtcttag attatgtcca tttttggagg   3660

atcataaaga agacattcta tgtgggccag tatggcttgc tagtggcctt gatctatcag   3720

ggcatgctgg aatgttgacg ttaacaagcc ccaaacttgt taaaggtatg gcaggaggaa   3780

aatatcgttc gtttttaatc catgtcaagg cagtgaatga aagaggaaca gaagagattt   3840

gtaatggtgg tatgcgtcct gtagtaaggc ttccatccct aaaacaccag agtaacaagg   3900

gttattcact tgcttcactt ttggctaaag ttgcagcagg caaggaaaaa tcatctaatg   3960

ttaagaatga aaatacaagt ggcacccgta aatctgaaaa cctccggggc tgtgatttac   4020

ttcaagaggt ctcagtcacc attcgaagat ttaagaaaac ctcaatttct aaggaaagag   4080

tgcaacgatg tgccatgtta cagttttcag aatttcatga gaagcttctt aatactcttt   4140

gcagaaaaac agatgatggc cagatcacag aacatgccca gagccttgtg ttggatactc   4200

tctgttggtt agctggagtt cattcaaatg gacccggaag ctcaaaggaa ggaaatgaga   4260

acctactttc aaaaacacga aaatttctgt cagacatcgt acgtgtttgc ttctttgagg   4320

caggacgaag tatagcccat aagtgtgccc gatttctagc cttgtgcatt agtaatggca   4380

aatgtgaccc atgtcaacca gcatttggac ctgttctgtt gaaggcttta cttgataata   4440

tgtcattttt acctgcagca acaactggtg gttctgtcta ttggtatttt gtcttactga   4500

attatgtgaa agatgaagat ctggctggat gcagtacagc ttgtgcatct ttgcttactg   4560

cagtgtccag acagttacag gacaggctaa caccaatgga ggctttactt cagacaagat   4620

atggattata tagctcacca tttgatccag tcctctttga tttggagatg agtggctctt   4680

cttgtaaaaa tgtttataac agcagcattg gtgtccagtc agatgaaatt gatttatcag   4740

atgtcctttc aggaaatgga aaggtcagta gttgcacagc tgctgagggt agtttcacat   4800

ctctcactgg actttggaa gttgaacctc tgcactttac ttgtgtgtca actagtgatg    4860

gaaccagaat agaaagggat gatgcaatga gttccttcgg ggttactcct gcagtaggtg   4920

gactatcatc tgggacagtt ggggaagcct cgacagccct gagttcagca gcccaggtag   4980

ctttgcagtc tctctctcat gcaatggctt cagccgagca acagctacag gtgctgcaag   5040

agaaacagca gcagcttttg aagcttcagc aacagaaagc aaagctggaa gccaagttac   5100

atcagacaac agctgcagca gctgcagcag catcagcagt aggtcctgtt cacaactctg   5160

tgccttccaa cccagtggct gcccctggat tcttcattca tccatctgat gttattccac   5220

ccactccaaa aacaacacct ctttttatga ctccaccact cactccaccc aatgaagcag   5280

tttccgttgt gattaatgcc gaacttgcac agcttttccc aggctcagtc attgatcccc   5340

cagcagtcaa tcttgctgca cataacaaaa attccaacaa gtccagaatg aatccacttg   5400

gttctggtct agcccttgca atttctcatg cttcacattt tcttcaacct ccgcctcacc   5460

agtccattat tatagagcga atgcattcag gagcaagaag atttgtgacc ttggattttg   5520
```

```
ggaggcctat attgttgact gatgtattga ttcccacttg tggagacttg gcctctttgt   5580
caattgacat ttggacatta ggagaagagg tggatggaag gcggttggta gtggcaactg   5640
atataagcac tcattcacta attcttcatg acttaatacc acctcccgtg tgcagattca   5700
tgaagatcac tgttattgga cgttacggga gtacaaatgc cagagccaaa atcccattag   5760
gattttacta tggtcatacc tacatcttgc cttgggaaag tgaactgaag ttaatgcatg   5820
atcctctaaa gggagaggga gaatctgcaa accagccaga aattgaccag catttagcaa   5880
tgatggttgc tttgcaggag gatatacagt gcaggtataa cttggcttgt catcgtctgg   5940
aaacccttt gcaaagtatt gatcttcctc ctctaaacag tgctaacaat gcacagtact   6000
ttttacgaaa accagataag gcagttgagg aagacagtag ggttttttct gcttatcaag   6060
attgtattca gctacagctt caactaaatt tggctcataa tgcagtgcag aggctcaaag   6120
tggcgctagg tgcaagccgg aagatgttga gtgaaacatc aaatccagaa gatttaattc   6180
agacatcttc cacagagcag ttacgtacta tcatcagata tttactggac actttgctca   6240
gcctgcttca tgcttctaat ggacactctg ttcctgcagt tttgcagagc acatttcatg   6300
cccaggcctg tgaagagctc tttaaacact tgtgcatcag tggaacccca aagatacggt   6360
tacatactgg tcttcttctt gttcaactgt gtggtggtga aaggtggtgg ggtcaatttc   6420
tttctaatgt ccttcaggaa ttgtacaatt cggaacagct tctcatcttt ccacaggata   6480
gggtcttcat gttactttcc tgcattggtc aaagatcact tagtaatagt ggagtattag   6540
aaagcttact taatctcttg gataatttat tgtcacctct tcagccacag ttacccatgc   6600
ataggaggac agaaggagta ctagatattc ccatgatcag ttgggttgtt atgctggtgt   6660
ccaggttgct ggattatgtg gcaactgttg aagatgaagc agcagctgca aagaaacctt   6720
tgaatggtaa tcagtggagt tttattaaca ataatctaca cactcagagc ttaaatagat   6780
cttctaaagg cagcagtagc cttgatagat tatattccag aaaaatcaga aagcagcttg   6840
ttcatcataa acagcaactt aacctactaa aagcaaagca gaaggcattg gtagaacaga   6900
tggaaaaaga aaaaatacaa agtaacaaag gatcatcata taaactcctg gtagaacaag   6960
caaaactaaa gcaggccact tcaaagcact ttaaggattt aattcgttta cgtcggacag   7020
cagaatggtc ccgttctaat ttagacacag aagttacaac agcaaaagaa agtcctgaga   7080
tagaaccact tccatttact ctggcccatg agcgttgtat ctcagtagtc cagaaacttg   7140
ttctgtttct tctctccatg gactttacat gtcatgcaga tctcttattg tttgtttgta   7200
aggttcttgc acgcattgca aatgccacga ggccaactat tcatctgtgt gagattgtga   7260
acgaacccca gctggaaaga ctgctgttac ttttggttgg aactgacttc aatagaggag   7320
atatatcttg ggtggtgct tgggctcagt attccttaac ttgcatgcta caagatattt   7380
tagcaggaga attactggct ccagtagccg cagaagccat ggaggaagga acagtgggtg   7440
atgatgtagg tgcgacagct ggtgactctg atgactccct tcaacagtcc tcagttcagt   7500
tgctggaaac tatagatgaa cctttgacac atgacataac aggtgcacct cctctgtcct   7560
ctttggaaaa agataaagaa attgaccttg agttacttca ggatctaatg gaagttgaca   7620
ttgatccttt agatattgat ttggaaaagg accctcttgc agccaaggtt tttaagccaa   7680
taagcagtac atggtatgat tattggggtg ctgattatgg gacctacaat tacaaccctt   7740
acattggagg tctgggaatt cctgtagcaa agccaccagc aaacacggag aagaacggat   7800
cacagacagt tagcgtttca gtctctcagg ccctggatgc tcgcctagaa gttggacttg   7860
```

-continued

```
aacagcaagc agaactgatg ttgaaaatga tgtctactct ggaggcagat tccattttac   7920
aggcattaac aaatacatct cctacattat cacagtctcc cactggaaca gatgattcac   7980
ttctaggggg tttacaagca gcaaaccaaa ccagccagct tattatacag ttatcatctg   8040
tcccaatgtt aaatgtttgt ttcaacaaac ttttttccat gcttcaagtc catcatgttc   8100
agttggagtc acttctccaa ttgtggctca cactgagcct gaattctagt tcaactggaa   8160
acaaagaaaa tggagcagac atatttttat ataatgctaa taggatacct gttatttcat   8220
taaatcaagc atcaataact agctttctca cagtgttagc ttggtatccc aatactttgc   8280
tccggacatg gtgccttgtg cttcatagcc taacactcat gacaaacatg cagcttaatt   8340
ctggttccag cagtgccatt ggaactcagg agagtactgc tcatttgttg gtttcagatc   8400
caaacctaat tcatgtatta gtgaaatttc tttctggcac cagtccacat ggaacaaatc   8460
aacacagtcc acaggttggt cctacagcta cacaagctat gcaagaattt cttactcgat   8520
tacaagtgca tctttcttca acatgtcctc agatattcag tgaatttttg ctcaagctaa   8580
ttcatatact ttcaactgaa aggggtgctt tccagacagg ccaaggacct ctcgatgccc   8640
aagtgaagct cttagaattc actctggagc agaattttga agtcgtttca gttagtacta   8700
tttctgccgt gatagaatcg gttacatttt tagtgcacca ctatatcact tgctcagaca   8760
aagtaatgtc aagaagtgga tcagatagct ccgtgggtgc tcgagcatgc tttgggggac   8820
tctttgccaa tcttattcgt ccgggtgatg caaaagcagt ttgtggcgaa atgacaagag   8880
atcaactcat gtttgatttg ttaaaacttg ttaacatttt agtgcagctg cctctttcag   8940
gcaataggga atacagtgca agagtgtctg tgaccacaaa tacaacagat agtgtttcag   9000
atgaagaaaa agtctcagga ggcaaagatg gcaatggaag cagtaccagt gttcaaggat   9060
cgcctgcata tgttgctgac ttagtcttag ccaaccaaca aattatgagc cagattttgt   9120
ctgctctggg cctgtgtaat agcagtgcca tggcaatgat aattggagca agtggattac   9180
atctcactaa acatgaaaac tttcatggtg ggttggatgc catatcagtt ggggatggat   9240
tatttaccat actgacaacc cttagtaaaa aagcttctac agtccacatg atgctgcagc   9300
caattttaac atacatggcc tgtggatata tgggcagaca aggctctctt gctacttgcc   9360
agttatctga gccattattg tggttcattt tgagagtatt ggatactagt gatgccttga   9420
aagcatttca tgatatgggt ggtgttcagc tcatatgcaa taatatggtt actagtacaa   9480
gggctattgt gaacactgca agaagtatgg tatcaactat tatgaaattt cttgactctg   9540
gtccaaataa agctgttgac agcacattga aaacaagaat actagcttct gagcctgaca   9600
atgctgaagg gattcataac tttgcacccc tcggtacaat cacatctagc agtcctactg   9660
cccaaccagc tgaagtgcta ttgcaggcca cacctcctca cagaagagct cgctctgctg   9720
cttggtccta catctttctt ccagaggagg cttggtgtga ccttaccatt caccttcctg   9780
cagcagtgct gcttaaggag atacatatcc agcctcatct tgcatctctt gcaacctgcc   9840
cttcctcagt gtctgttgaa gtaagtgcag atggggtaaa tatgctacct ttgtccactc   9900
ctgttgtcac aagtggcctc acctacataa aaattcagct tgtaaaagcc gaagtagctt   9960
ctgctgtctg ccttagacta catcgtccac gggatgccag cacattaggc ctttcacaaa  10020
ttaaattatt ggggctcact gcttttggta ccacctcttc tgcaacagtt aataatccat  10080
tccttccatc tgaagatcag gtatccaaaa caagtattgg atggttacgg ttattacatc  10140
attgccttac tcacataagt gatctagaag gaatgatggc aagtgcagct gcacctactg  10200
ctaatctgct gcagacttgt gcggccttat tgatgtcacc ttactgtgga atgcattcac  10260
```

```
ccaacatcga ggttgtgctt gtaaagatag gactgcagtc tactagaatt ggcctgaagc  10320
tcatagacat tctcctgaga aattgtgcag catcaggcag tgatcctaca gatttgaata  10380
gtcctttact ttttggaaga ctaaatggac tctcttctga ctctacgata gatattcttt  10440
accagcttgg aacaactcag gatcctggta caaaagacag aattcaggcc ttgttaaaat  10500
gggttagtga ttctgcaaga gtggctgcta tgaagagaag tggcaggatg aactacatgt  10560
gtcctaactc ctcaacagta gagtatggtc ttctgatgcc atctccttct catttgcact  10620
gtgtagcagc cattctgtgg catagttatg agctgcttgt agaatatgac ttaccagcac  10680
tcctggacca agagctcttt gagttacttt ttaattggtc catgtctctt ccctgcaata  10740
tggttttgaa gaaagctgtt gacagtctac tttgctcaat gtgtcacgta cacccaaact  10800
atttttcttt gctcatgggc tggatgggaa ttacccctcc tccagtgcaa tgtcatcata  10860
gactgtccat gacagatgat agcaaaaagc aggatcttag ttcatcttta acagatgact  10920
ctaaaaatgc acaagcacct ctcgcattaa ctgaatcaca tttggctacc cttgcttcct  10980
cttctcaatc tcctgaagct attaaacaat tactagactc aggtttgcct tctcttcttg  11040
tgaggagtct ggctagtttc tgctttagcc acatttctag ctcagaaagc attgcccagt  11100
caatagatat ttcccaggac aaactcaggc gccatcatgt cccacaacaa tgtaataaga  11160
tgcctatcac agccgaccta gttgctccta ttcttaggtt tttgacagaa gttggcaata  11220
gccatattat gaaagattgg cttggtggtt ctgaagtcaa tccactatgg acagcacttc  11280
tgtttttatt gtgtcactct gggtccactt ctggaagcca taatttaggt gcacaacaga  11340
ccagtgcaag atcagcttct ctttcttcag ctgctacaac aggactgact actcaacagc  11400
gcacagcaat tgagaatgca actgttgcgt tctttctaca gtgcatttca tgccatccta  11460
ataatcaaaa gctgatggca caggttcttt gtgaactatt tcagacatct cctcaaagag  11520
ggaaccttcc aacatctggg aacatttcag ggtttatacg aagattattt ttacagttga  11580
tgctggaaga tgagaaagtg acaatgtttc ttcagtctcc atgtccactg tacaaaggta  11640
gaattaatgc tactagccac gtcatccagc atccaatgta tggagcaggc cacaaattcc  11700
gtactcttca tttgccagtc tcaacaacat tatcagatgt tcttgacaga gtgtcagata  11760
ctccaagtat cacagctaaa ttaattagtg aacaaaaaga tgacaaagaa aagaaaaacc  11820
atgaagagaa agaaaaagtt aaagcggaaa atggatttca agacaattac agtgttgttg  11880
ttgcctctgg gctgaagtct caatctaaac gtgctgtgtc agctacacca cctcgcccac  11940
catccaggag gggaggacaa atacctgata aaataggaag tacttcagga gcagaggctg  12000
ccaacaaaat aattactgtc ccagtgtttc acctgtttca caaactcttg gcaggccagc  12060
cattgccagc tgaaatgaca cttgcccagc ttttaactct cctatatgac cgaaaacttc  12120
ctcagggtta ccgctcaata gatctgactg ttaaattggg atcaagagtt ataacagacc  12180
ccagtctatc aaaaacagat tcttataaaa gactacaccc tgaaaaagat catggagact  12240
tacttgctag ctgtccagaa gatgaggctc tcactccagg tgatgaatgc atggatggga  12300
tactggatga atctttgctt gaaacctgtc caattcagtc accattacaa gtttttgcag  12360
gaatgggtgg actggctctt attgctgaaa gactacccat gctatatcca gaagtaattc  12420
aacaggtgag tgctccagtt gtaacatcta ccactcagga aaagccgaag gatagcgatc  12480
agtttgaatg ggtgaccatt gaacagtcag gggagttagt ttatgaagca ccagaaactg  12540
ttgcggctga acctccacct atcaagtcag cagtacagac catgtctccc atacctgccc  12600
```

```
attctttggc tgcttttgga ttatttcttc gtcttccggg ctatgcggaa gtgctactga  12660
aagagagaaa acatgcccag tgccttcttc gattggtatt gggagtgaca gatgatggag  12720
aaggaagtca tattcttcaa tctccatcag ccaatgtgct tccaaccctt cctttccacg  12780
tccttcgtag cttgtttagc actacacctt tgacaactga tgatggtgta cttctaaggc  12840
ggatggcatt ggaaattgga gccttacacc tcattcttgt ctgtctctct gctttgagcc  12900
accattcccc acgagttcca aactctagcg tgaatcaaac tgagccacag gtgtcaagct  12960
ctcataaccc tacatcaaca gaagaacaac agttatattg ggccaaaggg actggctttg  13020
gaacaggctc tacagcttct gggtgggatg tggaacaagc cttaactaag caaaggctgg  13080
aagaggaaca tgttacctgc cttctgcagg ttcttgccag ttacataaat cccgtcagta  13140
gtgcggtaaa tggagaagct cagtcatctc atgagactag agggcagaac agtaatgccc  13200
ttccttctgt acttctcgag cttctcagtc agtcctgcct catcccagcc atgtcatctt  13260
atctacgaaa tgattcagtt ctggacatgg caagacatgt gccactctat cgggcactgc  13320
tggaattgct tcgggccatt gcttcttgtg ctgccatggt gcccctattg ttgccccttt  13380
ctacagagaa cggtgaagag gaagaagaac agtcagaatg tcaaacttct gttggtacat  13440
tgttagccaa aatgaagacc tgtgttgata cctataccaa ccgtttaaga tctaaaaggg  13500
aaaatgttaa aacaggagta aaaccagatg cgtctgatca agaaccagaa ggacttactc  13560
ttttggtacc agacatccaa aagactgctg agatagttta tgcagccacc accagtttgc  13620
ggcaagcaaa tcaggaaaaa aaactgggtg aatactccaa gaaggcggct atgaaaccca  13680
aaccctttgtc agtattaaag tcacttgaag aaaaatatgt ggctgttatg aagaaattac  13740
agtttgatac gtttgaaatg gtttctgaag atgaagatgg gaaattggga tttaaagtaa  13800
attaccacta catgtctcag gtgaaaaatg ctaatgatgc gaacagtgct gccagagctc  13860
gccgccttgc ccaggaagct gtgacgcttt caacctcact gcctctgtct tcatcctcta  13920
gtgtgtttgt acgctgtgat gaggagcgac ttgatatcat gaaggttcta ataactggtc  13980
cagcggacac cccttatgca aatggctgct ttgagtttga tgtgtatttt cctcaagatt  14040
atcccagttc acccccctctt gtgaatctag agacaactgg tggtcatagc gtgcgattca  14100
atccaaacct ttataatgat ggcaaggttt gtttaagcat cttaaacacg tggcatggaa  14160
gaccagaaga gaagtggaat cctcagacct caagcttttt gcaagtgttg gtgtctgtcc  14220
agtcccttat attagtagct gagccttatt ttaatgaacc gggatatgaa cggtctagag  14280
gcactcccag tggcacacag agttctcgag aatatgatgg aaacattcga caagcaacag  14340
ttaagtgggc aatgctagaa caaatcagaa acccttcacc atgttttaaa gaggtaatac  14400
acaaacattt ttacttgaaa agagttgaga taatggccca atgtgaggag tggattgcgg  14460
atatccagca gtacagcagt gataagcggg taggcaggac tatgtctcac catgcagcag  14520
ctctcaagcg tcacactgct cagctccgcg aagagttgct gaaacttccc tgccctgaag  14580
gcttggatcc tgacactgac gatgccccag aggtgtgcag agccacaaca ggtgctgagg  14640
agactctaat gcatgatcag gttaaaccca gcagcagcaa agaactcccc agtgacttcc  14700
agttatgagc tgcattgatg tggacttcat agacacaaag gcttcgaagc acaagccaaa  14760
tatgtcaata tttgtatgta agaaactaat tatgtaatag gtaatgaaac tgaaactata  14820
ctatgccctt aaggagatcc agtttaattc aaggtgatct tttatttacc tgtacaggag  14880
tgtaaacttt tttgtgcttt tatttttcaa ttgtgagaac cactgattgg tatgttcaac  14940
aaatttgtgt atacaaagaa atggataaat cactgctata taagggaaac taccttagga  15000
```

```
aagaatgttt actgaatgtt tattttattt tatttttttt ttactataga gtgaggggtt  15060

gttaacaaag aatatatatt ggtcattctt acaactacta tttaaagtca gcaacttttc  15120

actgaatttg atagatttta tgtttggcca tatcttcatg ctcacatttg atttctgaag  15180

acctcctaca tacacttcaa taaaagttaa atggacatac tccctctttt ttgatttact  15240

ggtacatttt taaaataata aatctgccat aaaatgcatt atatctggag acttgcactt  15300

gtatggatga atttattaca ttcaacatat ttaattttat gccttctaat tctaagatgc  15360

agaaaaaaat aaatgaacat gattttattc tatgccaaca tttgggcctc tgaatgtatc  15420

tgttatttga atttaagtat ttgaaaagga atggtcaatt tgaaagtcat tctaaactga  15480

ttttttttt ctaaagggct cctttttcc tggactatgt ggttttatga ctaaagtcac  15540

atgtatgtat taaacattga ggctctgtag aggagagagg atgtacctct ctggtgctgt  15600

tacagtacat tctgtacctg ccatacaggc tcattttcat gcaaattctt cctagagcca  15660

aataaataaa gacttaggtg aattagtatg tcttgtttct aaaaaaaaaa aaaaaaaa    15718
```

```
<210> SEQ ID NO 26
<211> LENGTH: 1026
<212> TYPE: DNA
<213> ORGANISM: Homo sapiens

<400> SEQUENCE: 26

gttcgttgca acaaattgat gagcaatgct tttttataat gccaactttg tacaaaaaag    60

ttagcatggg acctaaagac agtgccaagt gcctgcaccg tggaccacag ccgagccact   120

gggcagccgg tgatggtccc acgcaggagc gctgtggacc ccgctctctg ggcagccctg   180

tcctaggcct ggacacctgc agagcctggg accacgtgga tgggcagatc ctgggccagc   240

tgcggcccct gacagaggag gaagaggagg agggcgccgg ggccaccttg tccagggggc   300

ctgccttccc cggcatgggc tctgaggagt tgcgtctggc ctccttctat gactggccgc   360

tgactgctga ggtgccaccc gagctgctgg ctgctgccgg cttcttccac acaggccatc   420

aggacaaggt gaggtgcttc ttctgctatg gggcctgca gagctggaag cgcggggacg   480

acccctggac ggagcatgcc aagtggttcc ccagctgtca gttcctgctc cggtcaaaag   540

gaagagactt tgtccacagt gtgcaggaga ctcactccca gctgctgggc tcctgggacc   600

cgtgggaaga accggaagac gcagcccctg tggccccctc cgtccctgcc tctgggtacc   660

ctgagctgcc cacacccagg agagaggtcc agtctgaaag tgcccaggag ccaggagggg   720

tcagtccagc ccaggcccag agggcgtggt gggttcttga gcccccagga gccagggatg   780

tggaggcgca gctgcggcgg ctgcaggagg agaggacgtg caaggtgtgc ctggaccgcg   840

ccgtgtccat cgtctttgtg ccgtgcggcc acctggtctg tgctgagtgt gcccccggcc   900

tgcagctgtg ccccatctgc agagcccccg tccgcagccg cgtgcgtacc ttcctgtcct   960

acccaacttt cttgtacaaa gttggcatta taagaaagca ttgcttatca atttgttgca  1020

acgaac                                                             1026
```

```
<210> SEQ ID NO 27
<211> LENGTH: 1805
<212> TYPE: DNA
<213> ORGANISM: Homo sapiens

<400> SEQUENCE: 27

ggcttcctct tttcttgctg acccttcgga gctctgggaa gtggctgcac cttggcggct    60
```

```
ccccagagcg cgcggtgcta atcgtgggtc gtcagcctgg gtggctgggc ccggcttagg    120

gcagggtttg gcatttccaa tggtaggggg ctcggaccgt ccctccgcgg gaccctcccg    180

ttgggacaag gccgatcgcc tgggcggttg gagccgctat cctggcgcga gacggtggac    240

aagtcctata ttcaagagaa gataactttg aacagtttcg aaggatctaa aacgtatgtg    300

tctgcagaca tcaatgagga tgaagaatta gtagaagaga ttaatagatc aaaaacgttt    360

gctggctttg caggtggtgg gcctgcctgg gcatcggcgc gttggaggag acgccctggg    420

gggccttagc tgccctgaag cggtagacag gtggcaacgt gggggctcag gagttgacaa    480

acacaagaaa gtagcgccga attgcaggtt tatccgcagc ttttattttg aagacagtgc    540

cacgaaacct gcaaatcctg gtgtcccaaa tagtcaatac caagttgaaa accatctggg    600

agaggaaaag cgttgtgctt tagacaggcc gtctgagact cgtgcagacc ggcttttgag    660

agctggacag gtggtggata gatcagactc catacacccg aggagccccg ccatgcatag    720

tgaagaagct agataacagt cgtttcacaa ctggccagcc tctgcccact tgaccccgag    780

agagctggcc agtgctgggc tgtactacac aggcactgat gaccaagtgc agtgcttctg    840

ttgtggcgga aaactgaaaa actgggaacc tggtgatcgt gcctggtcag aacacaggag    900

acattttcct aattgcttct ttattttggg ccacaacgtt aatattcgag gtgaatctga    960

tgttgcgagt tctgatagga atttctcaaa ttcaacaagt tctccaagga atccatccat   1020

gacgggttat gaagcccggc tcattacttt tgggacatgg atgtactccg ttaacaaaga   1080

gcagcttgca agagctggat tttatgctat aggtcaagag gataaagtac agtgctttca   1140

ctgtggagga gggctagcca actggaagcc caaggaagat ccttgggaac agcatgctaa   1200

atggtatcca ggttgcaaat atctgctaga agagaaggga catgaatata taaacaacat   1260

tcatttaacc cgttcacttg agggagctct ggtacaaact accaagaaaa caccatcact   1320

aactaaaaga atcagtgata ccatcttccc taatcctatg ctacaagaag ctatacgaat   1380

gggatttgat ttcaaggacg ttaagaaaat aatggaggaa agaattcaaa catctgggag   1440

caactataaa acgcttgggg ttcttgttgc agatctagtg agcgctcaga aagacactac   1500

agaaaatgaa ttgaatcaga cttcattgca gagagaaatc agccctgaag agccgctaag   1560

gcgtctgcaa gaggagaagc tttgtaaaat ctgcatggac agacatatcg ctgttgtttt   1620

tattccttgt ggacatctgg tcacttgtaa acaatgtgct gaagcagttg acagatgtcc   1680

catgtgcagc atggttattg atttcaagca aagagttttt atgtcttaat gtaactctac   1740

agtgggtgtg ctatgttctt attaccctga ttaaatgtgt gatgtgacac aaaaaaaaaa   1800

aaaaa                                                                1805
```

<210> SEQ ID NO 28
<211> LENGTH: 1661
<212> TYPE: DNA
<213> ORGANISM: Homo sapiens

<400> SEQUENCE: 28

```
aagtcgcggc caatgggcga cgcggccgca gatccgcccg gccccgccct gccctgtgag     60

ttcctccggc cgggctgcgg ggctccgctc agtccgggag cgcagctggg ccgcggcgct    120

ccgacctccg ctttcccacc gcccgcagct gaagcacatc ccgcagcccg gcgcggactc    180

cgatcgccgc agttgccctc tggcgccatg tcgcagaacg gagcgcccgg gatgcaggag    240

gagagcctgc agggctcctg ggtagaactg cacttcagca ataatgggaa cgggggcagc    300

gttccagcct cggtttctat ttataatgga gacatggaaa aaatactgct ggacgcacag    360
```

```
catgagtctg gacggagtag ctccaagagc tctcactgtg acagcccacc tcgctcgcag    420
acaccacaag ataccaacag agcttctgaa acagataccc atagcattgg agagaaaaac    480
agctcacagt ctgaggaaga tgatattgaa agaaggaaag aagttgaaag catcttgaag    540
aaaaactcag attggatatg ggattggtca agtcggccgg aaaatattcc ccccaaggag    600
ttcctcttta aacacccgaa gcgcacggcc accctcagca tgaggaacac gagcgtcatg    660
aagaaagggg gcatattctc tgcagaattt ctgaaagttt tccttccatc tctgctgctc    720
tctcatttgc tggccatcgg attggggatc tatattggaa ggcgtctgac aacctccacc    780
agcacctttt gatgaagaac tggagtctga cttggttcgt tagtggatta cttctgagct    840
tgcaacatag ctcactgaag agctgttaga tcctggggtg gccacgtcac ttgtgtttat    900
ttgttctgta aatgctgcgt tcctaattta gtaaaataaa agaatagaca ctaaaatcat    960
gttgatctat aattacacct atgggatcaa taagcatgtc agactgatta atgtctactg   1020
tgaaaatttg gtagtaaatt ttcatttgat attagatata aatatctgaa tataaataat   1080
tttaatatac tagtcatgat gtgtgttgta ttttaaaaat tatctgcaac cttaattcag   1140
ctgaagtact ttatatttca aaagaatgaa taacattgat aataaaatcg ctactttaag   1200
gggtttgtcc aaaataaata ttgtggcctt atatatcaca ctattgtaga aagtattatt   1260
taatttaaat ggatgcaggt tgtctactaa agaaagatta tatataacta tgctaattgt   1320
tcataatcaa cagaaaccaa gatagagcta caaactcagc tgtacagttc gtacactaaa   1380
ctcttcttgc ttttgcatta taaggaatta agtctccgat tattaggtga tcaccctgga   1440
tgatcagttt tctgctgaag gcacctactc agtatctttt cctctttatc actctgcatt   1500
ggtgaattta atcctctcct ttgtgttcaa cttttgtgtg cttttaaaat cagctttatt   1560
ctaagcaaat ctgtgtctac tttaaaaaac tggaaatgga aaaaaaaata aatctttgcc   1620
aaatccttca gataaaaaaa aaaaaaaaaa aaaaaaaaaa a                       1661
```

<210> SEQ ID NO 29
<211> LENGTH: 660
<212> TYPE: DNA
<213> ORGANISM: Homo sapiens

<400> SEQUENCE: 29

```
atgtcgtccc acctagtcga gccgccgccg cccctgcaca acaacaacaa caactgcgag     60
gaaaatgagc agtctctgcc cccgccggcc ggcctcaaca gttcctgggt ggagctaccc    120
atgaacagca gcaatggcaa tgataatggc aatgggaaaa atgggggggct ggaacacgta    180
ccatcctcat cctccatcca caatggagac atggagaaga ttcttttgga tgcacaacat    240
gaatcaggac agagtagttc cagaggcagt tctcactgtg acagcccttc gccacaagaa    300
gatgggcaga tcatgtttga tgtggaaatg cacaccagca gggaccatag ctctcagtca    360
gaagaagaag ttgtagaagg agagaaggaa gtcgaggctt tgaagaaaag tgcggactgg    420
gtatcagact ggtccagtag acccgaaaac attccaccca aggagttcca cttcagacac    480
cctaaacgtt ctgtgtcttt aagcatgagg aaaagtggag ccatgaagaa agggggtatt    540
ttctccgcag aatttctgaa ggtgttcatt ccatctctct tcctttctca tgttttggct    600
ttggggctag gcatctatat tggaaagcga ctgagcacac cctctgccag cacctattaa    660
```

<210> SEQ ID NO 30
<211> LENGTH: 2626
<212> TYPE: DNA

<213> ORGANISM: Homo sapiens

<400> SEQUENCE: 30

```
ctctcgccag ctgggagtcg cgcgctgccc acctcgctgc ccaggccccc gacgccgcgg      60
caggagcccc ccaagagcgc gggaagcccc gtggacctgg cgctcccggc tcgggcgtgg     120
acggggcggg cgccggggcg gggcgcgcgt cctcgcgggt ctgaatggaa gggtcgaggt     180
cgtcgtcggc ggcgagcaga tcctgaagcc agaactccac cccggcgccc gcgccatgcg     240
gcgggagagg tgcggcgccc cccacccgcg tcgccgccat ggaggtgctg cggcgctcct     300
cggtcttcgc cgccgagatc atggacgcct ttgaccgctc gcccacagac aaggagctgg     360
tggcccaggc caaggcgctg ggccgggagt acgtgcacgc gcggctgctg cgcgccggcc     420
tctcctggag cgcgcccgag cgtgccgcgc cggtcccggg acgcctggct gaggtgtgcg     480
cggtgctgct gcgcctgggc gatgagctgg agatgatccg gcccagcgtc taccgcaacg     540
tggcgcgtca gctgcacatc tccctgcagt ctgagcctgt ggtgaccgat gcgttcctgg     600
ccgtggctgg ccacatcttc tctgcaggca tcacgtgggg caaggtggtg tccctgtatg     660
cggtggccgc ggggctggcc gtggactgtg tgaggcaggc ccagcctgcc atggtccacg     720
ccctcgtgga ctgcctgggg gagttcgtgc gcaagaccct ggcaacctgg ctgcggagac     780
gcggcggatg gactgatgtc ctcaagtgtg tggtcagcac agaccctggc ctccgctccc     840
actggctggt ggctgcactc tgcagcttcg gccgcttcct gaaggctgcc ttcttcgtgc     900
tgctgccaga gagatgagct gcccacctgg cagtggccgc agcctggccc tctgggccca     960
acgcaggagg ccctcagcac ccgaacacat cttcctcctc cccacccgag cctggagcac    1020
tctaaccctc ggagaccccc taagccccgt tcctccgcag acccaggccc tccggaaggg    1080
gtgagtgggg aggggctttc ctgagcctgg agctgggctt tggggcagcc tgcgaccctc    1140
cccgcttgtg tcccttctcc tgtgatctct gtgttttccc ttttctttct ggggccagga    1200
agtcagggtc aactcccagg cctcagatgc aggggcccag aacacctgct ctcacctgag    1260
ccccaggtga aggggcccgg gaacacctgc tctcacctga gccccaggtg aaggggcccg    1320
ggaacacctg ctctcacctg aaccccaggt gaaggggccc ggaacacctg ctctcacctg    1380
agccccaggt gaaggggccc ggaacacctg ctctcacctg agccccaggt gaaggggccc    1440
gggaacacct gctctcacct gagccccagg tgaaggggcc cgggaacacc tgctctcacc    1500
tgaaccccag gtgaaggggc ccagaacacc tgctctcacc tgagccccag gtgaaggggc    1560
ccggaacacc tgctctcacc tgagccccag gtgaaggggc ccgggaacac ctgctctcac    1620
ctgagcccct ggtgaagggg cccggaacac ttgctctcac ctgagcccca ggtgaagggg    1680
cccggaacac ctgctctcac ctgagccccc ggtgaagggg cccggaacac ttgctctcac    1740
ctgagcccca ggtgaagggg cccggaacac ctcctctcac ctgagcccca ggtgaagggg    1800
cccggaacac ctcctgtcac ctgagcccca ggtgaagggg cccgggaaca cctctcacct    1860
gaacccgggg gtcccatccc aggaagaagg gccatctcag gacatgagtc ctcaggggcc    1920
ctgcacattc aatctgaagg tgaccctggc ctggctgaag ctggaagagc tgtggggact    1980
cagcctgtaa acagagcgta aggttcacat gctggttgct taatccgttt ctggaggaag    2040
agtatgacac ccacttgtga tggggtcctt gtgcggtggg gaccggggcc ggcgggctcc    2100
aggccagcac acctaaccca tggatgtgga acctacggcc gagaaggaat gttgcatgag    2160
tcggatccca gtccattgtc agtggagggt gagggtgacc ccatctgcta tttttgtgct    2220
catcctcata caaccatttg ggatgtgccc tattagggct ccgtaagaac tcagatgcct    2280
```

```
gggaagccca gcccctcagg tgcccccaca cacagccttc ccttgacgcc tacatttcta   2340

ggcacatgtg aggcatcttt cctggagccc cgagccagcc ctgtccctcc ccagtgcagc   2400

atggcactca ggagatacag gctggacatg ggcagtcgt  tctggggagg cctggcctag   2460

cagccaccca cctgagccct cccggccagg cttcgtgctg ggtgggccca tgtgccagga   2520

caggagggtc ccggcggaaa gccagccccg gactcatcgt gacattgaga tcccactgga   2580

gggtaggggt ggtaataaac ttctccaaac gatcgttgtc atttta                  2626
```

<210> SEQ ID NO 31
<211> LENGTH: 4675
<212> TYPE: DNA
<213> ORGANISM: Homo sapiens

<400> SEQUENCE: 31

```
acttacttgt ggcctgtccc ctcgtgaatg tgtctcatgt ccccagtggg gtttttcagt     60

gagggtcatg gtctccagga tgcacaaggc tttgtgccag aattgcttgg aattgcctag    120

ttctggaagg ctggttggcc aactctggcc tccggctttt cctttgggaa tttcccttga    180

aggtggggtt ggtagacaga tccaggctca ccagtcctgt gccactgggc ttttggcgtt    240

ctgcacaagg cctacccgca gatgccatgc ctgctccccc agcctaatgg gctttgatgg    300

gggaagaggg tggttcagcc tctcacgatg aggaggaaag agcaagtgtc ctcctcggac    360

attctccggg ttgtgaaatg tgctcgcagg aggcttttca ggcacagagg agccagctgg    420

tcgagctgct ggtctcaggg tccctggaag gcttcgagag tgtcctggac tggctgctgt    480

cctgggaggt cctctcctgg gaggactacg agggcttcca cctcctgggc cagcctctct    540

cccacttggc caggcgcctt ctggacaccg tctggaataa gggtacttgg gcctgtcaga    600

agctcatcgc ggctgcccaa gaagcccagg ccgacagcca gtcccccaag ctgcatggct    660

gctgggaccc ccactcgctc cacccagccc gagacctgca gagtcaccgg ccagccattg    720

tcaggaggct ccacagccat gtggagaaca tgctggacct ggcatgggag cggggtttcg    780

tcagccagta tgaatgtgat gaaatcaggt tgccgatctt cacaccgtcc cagagggcaa    840

gaaggctgct tgatcttgcc acggtgaaag cgaatggatt ggctgccttc cttctacaac    900

atgttcagga attaccagtc ccattggccc tgcctttgga agctgccaca tgcaagaagt    960

atatggccaa gctgaggacc acggtgtctg ctcagtctcg cttcctcagt acctatgatg   1020

gagcagagac gctctgcctg gaggacatat acacagagaa tgtcctggag gtctgggcag   1080

atgtgggcat ggctggaccc ccgcagaaga gcccagccac cctgggcctg gaggagctct   1140

tcagcacccc tggccacctc aatgacgatg cggacactgt gctggtggtg ggtgaggcgg   1200

gcagtggcaa gagcacgctc ctgcagcggc tgcacttgct gtgggctgca gggcaagact   1260

tccaggaatt tctctttgtc ttcccattca gctgccggca gctgcagtgc atggccaaac   1320

cactctctgt gcggactcta ctctttgagc actgctgttg gcctgatgtt ggtcaagaag   1380

acatcttcca gttactcctt gaccaccctg accgtgtcct gttaaccttt gatggctttg   1440

acgagttcaa gttcaggttc acggatcgtg aacgccactg ctccccgacc gaccccacct   1500

ctgtccagac cctgctcttc aaccttctgc agggcaacct gctgaagaat gcccgcaagg   1560

tggtgaccag ccgtccggcc gctgtgtcgg cgttcctcag gaagtacatc cgcaccgagt   1620

tcaacctcaa gggcttctct gaacagggca tcgagctgta cctgaggaag cgccatcatg   1680

agcccggggt ggcggaccgc ctcatccgcc tgctccaaga gacctcagcc ctgcacggtt   1740
```

```
tgtgccacct gcctgtcttc tcatggatgg tgtccaaatg ccaccaggaa ctgttgctgc   1800
aggagggggg gtccccaaag accactacag atatgtacct gctgattctg cagcattttc   1860
tgctgcatgc caccccccca gactcagctt cccaaggtct gggacccagt cttcttcggg   1920
gccgcctccc caccctcctg cacctgggca gactggctct gtggggcctg ggcatgtgct   1980
gctacgtgtt ctcagcccag cagctccagg cagcacaggt cagccctgat gacatttctc   2040
ttggcttcct ggtgcgtgcc aaaggtgtcg tgccagggag tacggcgccc ctggaattcc   2100
ttcacatcac tttccagtgc ttctttgccg cgttctacct ggcactcagt gctgatgtgc   2160
caccagcttt gctcagacac ctcttcaatt gtggcaggcc aggcaactca ccaatggcca   2220
ggctcctgcc cacgatgtgc atccaggcct cggagggaaa ggacagcagc gtggcagctt   2280
tgctgcagaa ggccgagccg cacaaccttc agatcacagc agccttcctg gcagggctgt   2340
tgtcccggga gcactggggc ctgctggctg agtgccagac atctgagaag gccctgctcc   2400
ggcgccaggc ctgtgcccgc tggtgtctgg cccgcagcct ccgcaagcac ttccactcca   2460
tcccgccagc tgcaccgggt gaggccaaga gcgtgcatgc catgcccggg ttcatctggc   2520
tcatccggag cctgtacgag atgcaggagg agcggctggc tcggaaggct gcacgtggcc   2580
tgaatgttgg gcacctcaag ttgacatttt gcagtgtggg ccccactgag tgtgctgccc   2640
tggcctttgt gctgcagcac ctccggcggc ccgtggccct gcagctggac tacaactctg   2700
tgggtgacat tggcgtggag cagctgctgc cttgccttgg tgtctgcaag gctctgtatt   2760
tgcgcgataa caatatctca gaccgaggca tctgcaagct cattgaatgt gctcttcact   2820
gcgagcaatt gcagaagtta gctctattca acaacaaatt gactgacggc tgtgcacact   2880
ccatggctaa gctccttgca tgcaggcaga acttcttggc attgaggctg gggaataact   2940
acatcactgc cgcgggagcc caagtgctgg ccgagggggct ccgaggcaac acctccttgc   3000
agttcctggg attctggggc aacagagtgg gtgacgaggg ggcccaggcc ctggctgaag   3060
ccttgggtga tcaccagagc ttgaggtggc tcagcctggt ggggaacaac attggcagtg   3120
tgggtgccca agccttggca ctgatgctgg caaagaacgt catgctagaa gaactctgcc   3180
tggaggagaa ccatctccag gatgaaggtg tatgttctct cgcagaagga ctgaagaaaa   3240
attcaagttt gaaaatcctg aagttgtcca ataactgcat cacctaccta ggggcagaag   3300
ccctcctgca ggcccttgaa aggaatgaca ccatcctgga agtctggctc cgagggaaca   3360
ctttctctct agaggaggtt gacaagctcg gctgcaggga caccagactc ttgctttgaa   3420
gtctccggga ggatgttcgt ctcagtttgt ttgtgagcag gctgtgagtt tgggccccag   3480
aggctgggtg acatgtgttg gcagcctctt caaaatgagc cctgtcctgc ctaaggctga   3540
acttgttttc tgggaacacc ataggtcacc tttattctgg cagaggaggg agcatcagtg   3600
ccctccagga tagacttttc ccaagcctac ttttgccatt gacttcttcc caagattcaa   3660
tcccaggatg tacaaggaca gcccctcctc catagtatgg gactggcctc tgctgatcct   3720
cccaggcttc cgtgtgggtc agtggggccc atggatgtgc ttgttaactg agtgcctttt   3780
ggtggagagg cccggcctct cacaaaagac cccttaccac tgctctgatg aagaggagta   3840
cacagaacac ataattcagg aagcagcttt ccccatgtct cgactcatcc atccaggcca   3900
ttccccgtct ctggttcctc ccctcctcct ggactcctgc acacgctcct tcctctgagg   3960
ctgaaattca gaatattagt gacctcagct ttgatatttc acttacagca cccccaaccc   4020
tggcacccag ggtgggaagg gctacacctt agcctgccct cctttccggt gtttaagaca   4080
tttttggaag ggacacgtg acagccgttt gttccccaag acattctagg tttgcaagaa   4140
```

```
aaatatgacc acactccagc tgggatcaca tgtggacttt tatttccagt gaaatcagtt   4200
actcttcagt taagcctttg gaaacagctc gactttaaaa agctccaaat gcagctttaa   4260
aaaattaatc tgggccagaa tttcaaacgg cctcactagg cttctggttg atgcctgtga   4320
actgaactct gacaacagac ttctgaaata gacccacaag aggcagttcc atttcatttg   4380
tgccagaatg ctttaggatg tacagttatg gattgaaagt ttacaggaaa aaaaattagg   4440
ccgttccttc aaagcaaatg tcttcctgga ttattcaaaa tgatgtatgt tgaagccttt   4500
gtaaattgtc agatgctgtg caaatgttat tattttaaac attatgatgt gtgaaaactg   4560
gttaatattt ataggtcact ttgttttact gtcttaagtt tatactctta tagacaacat   4620
ggccgtgaac tttatgctgt aaataatcag aggggaataa actgttgagt caaaa        4675
```

<210> SEQ ID NO 32
<211> LENGTH: 4390
<212> TYPE: DNA
<213> ORGANISM: Homo sapiens

<400> SEQUENCE: 32

```
ctctagctct cagcggctgc gaagtctgta aacctggtgg ccaagtgatt gtaagtcagg     60
agactttcct tcggtttctg cctttgatgg caatttcctt cggtttctgc ctttgatggc    120
aagaggtgga gattgtggcg gcgattacag agaacgtctg ggaagacaag ttgctgtttt    180
tatgggaatc gcaggcttgg aagagacaga agcaattcca gaaataaatt ggaaattgaa    240
gatttaaaca atgttgtttt aaaatattct aacttcaaag aatgatgcca gaaacttaaa    300
aaggggctgc gcagagtagc aggggccctg gagggcgcgg cctgaatcct gattgccctt    360
ctgctgagag gacacacgca gctgaagatg aatttgggaa aagtagccgc ttgctacttt    420
aactatggaa gagcagggcc acagtgagat ggaaataatc ccatcagagt ctcacccccca    480
cattcaatta ctgaaaagca atcgggaact tctggtcact cacatccgca atactcagtg    540
tctggtggac aacttgctga agaatgacta cttctcggcc gaagatgcgg agattgtgtg    600
tgcctgcccc acccagcctg acaaggtccg caaaattctg gacctggtac agagcaaggg    660
cgaggaggtg tccgagttct tcctctactt gctccagcaa ctcgcagatg cctacgtgga    720
cctcaggcct tggctgctgg agatcggctt ctccccttcc ctgctcactc agagcaaagt    780
cgtggtcaac actgacccag tgagcaggta tacccagcag ctgcgacacc atctgggccg    840
tgactccaag ttcgtgctgt gctatgccca gaaggaggag ctgctgctgg aggagatcta    900
catggacacc atcatggagc tggttggctt cagcaatgag agcctgggca gcctgaacag    960
cctggcctgc ctcctggacc acaccaccgg catcctcaat gagcagggtg agaccatctt   1020
catcctgggt gatgctgggg tggcaagtc catgctgcta cagcggctgc agagcctctg   1080
ggccacgggc cggctagacg caggggtcaa attcttcttc cactttcgct gccgcatgtt   1140
cagctgcttc aaggaaagtg acaggctgtg tctgcaggac ctgctcttca agcactactg   1200
ctacccagag cgggaccccg aggaggtgtt tgccttcctg ctgcgcttcc cccacgtggc   1260
cctcttcacc ttcgatggcc tggacgagct gcactcggac ttggacctga gccgcgtgcc   1320
tgacagctcc tgcccctggg agcctgccca cccccctggtc ttgctggcca acctgctcag   1380
tgggaagctg ctcaaggggg ctagcaagct gctcacagcc cgcacaggca tcgaggtccc   1440
gcgccagttc ctgcggaaga aggtgcttct ccggggcttc tcccccagcc acctgcgcgc   1500
ctatgccagg aggatgttcc ccgagcgggc cctgcaggac cgcctgctga gccagctgga   1560
```

-continued

```
ggccaacccc aacctctgca gcctgtgctc tgtgcccctc ttctgctgga tcatcttccg   1620
gtgcttccag cacttccgtg ctgcctttga aggctcacca cagctgcccg actgcacgat   1680
gaccctgaca gatgtcttcc tcctggtcac tgaggtccat ctgaacagga tgcagcccag   1740
cagcctggtg cagcggaaca cacgcagccc agtggagacc ctccacgccg gccgggacac   1800
tctgtgctcg ctggggcagg tggcccaccg gggcatggag aagagcctct ttgtcttcac   1860
ccaggaggag gtgcaggcct ccgggctgca ggagagagac atgcagctgg gcttcctgcg   1920
ggctttgccg gagctgggcc ccgggggtga ccagcagtcc tatgagtttt tccacctcac   1980
cctccaggcc ttctttacag ccttcttcct cgtgctggac gacagggtgg gcactcagga   2040
gctgctcagg ttcttccagg agtggatgcc ccctgcgggg gcagcgacca cgtcctgcta   2100
tcctcccttc ctcccgttcc agtgcctgca gggcagtggt ccggcgcggg aagacctctt   2160
caagaacaag gatcacttcc agttcaccaa cctcttcctg tgcgggctgt tgtccaaagc   2220
caaacagaaa ctcctgcggc atctggtgcc cgcggcagcc ctgaggagaa agcgcaaggc   2280
cctgtgggca cacctgtttt ccagcctgcg gggctacctg aagagcctgc cccgcgttca   2340
ggtcgaaagc ttcaaccagg tgcaggccat gcccacgttc atctggatgc tgcgctgcat   2400
ctacgagaca cagagccaga aggtggggca gctggcggcc aggggcatct gcgccaacta   2460
cctcaagctg acctactgca acgcctgctc ggccgactgc agcgccctct ccttcgtcct   2520
gcatcacttc cccaagcggc tggccctaga cctagacaac aacaatctca acgactacgg   2580
cgtgcgggag ctgcagccct gcttcagccg cctcactgtt ctcagactca gcgtaaacca   2640
gatcactgac ggtggggtaa aggtgctaag cgaagagctg accaaataca aaattgtgac   2700
ctatttgggt ttatacaaca accagatcac cgatgtcgga gccaggtacg tcaccaaaat   2760
cctggatgaa tgcaaaggcc tcacgcatct taaactggga aaaaacaaaa taacaagtga   2820
aggagggaag tatctcgccc tggctgtgaa gaacagcaaa tcaatctctg aggttgggat   2880
gtggggcaat caagttgggg atgaaggagc aaaagccttc gcagaggctc tgcggaacca   2940
ccccagcttg accaccctga gtcttgcgtc caacggcatc tccacagaag gaggaaagag   3000
ccttgcgagg gccctgcagc agaacacgtc tctagaaata ctgtggctga cccaaaatga   3060
actcaacgat gaagtggcag agagtttggc agaaatgttg aaagtcaacc agacgttaaa   3120
gcatttatgg cttatccaga atcagatcac agctaagggg actgcccagc tggcagatgc   3180
gttacagagc aacactggca taacagagat ttgcctaaat ggaaacctga taaaaccaga   3240
ggaggccaaa gtctatgaag atgagaagcg gattatctgt ttctgagagg atgctttcct   3300
gttcatgggg tttttgccct ggagcctcag cagcaaatgc cactctgggc agtcttttgt   3360
gtcagtgtct taaaggggcc tgcgcaggcg ggactatcag gagtccactg cctccatgat   3420
gcaagccagc ttcctgtgca gaaggtctgg tcggcaaact ccctaagtac ccgctacaat   3480
tctgcagaaa aagaatgtgt cttgcgagct gttgtagtta cagtaaatac actgtgaaga   3540
gactttattg cctattataa ttatttttat ctgaagctag aggaataaag ctgtgagcaa   3600
acagaggagg ccagcctcac ctcattccaa cacctgccat agggaccaac gggagcgagt   3660
tggtcaccgc tcttttcatt gaagagttga ggatgtggca caaagttggt gccaagcttc   3720
ttgaataaaa cgtgtttgat ggattagtat tatacctgaa atattttctt ccttctcagc   3780
actttcccat gtattgatac tggtcccact tcacagctgg agacaccgga gtatgtgcag   3840
tgtgggattt gactcctcca aggttttgtg gaaagttaat gtcaaggaaa ggatgcacca   3900
cgggctttta attttaatcc tggagtctca ctgtctgctg gcaaagatag agaatgccct   3960
```

```
cagctcttag ctggtctaag aatgacgatg ccttcaaaat gctgcttcca ctcagggctt   4020

ctcctctgct aggctaccct cctctagaag gctgagtacc atgggctaca gtgtctggcc   4080

ttgggaagaa gtgattctgt ccctccaaag aaatagggca tggcttgccc ctgtggccct   4140

ggcatccaaa tggctgcttt tgtctccctt acctcgtgaa gaggggaagt ctcttcctgc   4200

ctcccaagca gctgaagggt gactaaacgg gcgccaagac tcaggggatc ggctgggaac   4260

tgggccagca gagcatgttg gacacccccc accatggtgg gcttgtggtg gctgctccat   4320

gagggtgggg gtgatactac tagatcactt gtcctcttgc ccgctcattt gttaataaaa   4380

tactgaaaac                                                          4390

<210> SEQ ID NO 33
<211> LENGTH: 4038
<212> TYPE: DNA
<213> ORGANISM: Homo sapiens

<400> SEQUENCE: 33

agaggaaaca ggaacaatgg ctaccgagag tactccctca gagatcatag aaagagaaag     60

aaaaaagttg cttgaaatcc ttcaacatga tcctgattct atcttagaca cgttaacttc    120

tcggaggctg atttctgagg aagagtatga gactctggag aatgttacag atctcctgaa    180

gaaaagtcgg aagctgttaa ttttggtaca gaaaaaggga gaggcgacct gtcagcattt    240

tctcaagtgt ttatttagta cttttccaca gtcagctgcc atttgcggct taaggcatga    300

agttttaaaa catgagaata cagtacctcc tcaatctatg ggggcaagca gtaattcaga    360

agatgctttt tctcctggaa taaaacagcc tgaagcccct gagatcacag tgttcttcag    420

tgagaaggaa cacttggatt tggaaacctc tgagtttttc agggacaaga aaactagtta    480

tagggaaaca gctttgtctg ccaggaagaa tgagaaggaa tatgacacac cagaagtcac    540

attatcatat tcagttgaga aagttggatg tgaagttcca gcaactatta catatataaa    600

agatggacag agatatgagg agctagatga ttctttatac ttaggaaaag aggaatatct    660

aggatctgtt gacacccctg aagatgcaga agccactgtg gaagaggagg tttatgatga    720

cccagagcac gttggatatg atggtgaaga ggacttcgag aattcagaaa ccacagagtt    780

ctctggtgaa gaaccaagtt atgagggatc agaaaccagc ctttcattgg aggaggaaca    840

ggagaaaagt atagaagaaa gaaaaaaggt gtttaaagat gtcctgttat gtttgaacat    900

ggatagaagc agaaaggttc tgccagattt tgttaaacaa ttctccttag atcgaggatg    960

taagtggacc cctgagagtc caggagactt agcctggaat ttcctgatga aagttcaagc   1020

acgagatgtg acggctaggg attcaatcct cagtcacaag gttctggatg aagatagcaa   1080

ggaggatttg ctggctggag tggagaattt ggaaattcga gacatacaaa ccattaatcc   1140

ccttgacgtg ctttgtgcca ccatgctgtg ttcagatagc tctttgcaac gccaagtcat   1200

gtcaaacatg tatcagtgcc agtttgctct tcccctgcta ctgccagatg cagaaaacaa   1260

caaaagcatc ttaatgctgg gggccatgaa agacattgtg aagaagcagt caacacagtt   1320

ttcagggggg cctacagagg atacagaaaa gtttctgact ctcatgaaga tgcctgtcat   1380

ctcttttgtg cgtctaggat actgtagctt ctctaagtcc agaatcctca acacacttct   1440

cagccctgcc cagttgaaat tacacaaaat ctttcttcat caagatttgc ctcttttggt   1500

gcttccccgg caaatctctg atggcctggt tgagataaca tggtgttttc ctgatagcga   1560

tgatagaaag gaaaacccct tttccaaaa gcctgttgct ctggctaatc tccgtggaaa   1620
```

-continued

```
tctagaaagc ttttggactc agtttggttt tttgatggaa gtttcttcag ctgtgttttt   1680
tttcactgac tgtttaggtg agaaggaatg ggacttgcta atgtttttag gagaggctgc   1740
cattgaaaga tgctactttg ttctcagttc ccaagccagg gagagtgaag aggctcaaat   1800
ttttcagagg atactgaact tgaagccagc acagctactg ttttgggaga ggggagatgc   1860
tggggataga aggaagaaca tggagggcct tcaagctgcc ctccaggaag tgatgttctc   1920
ttcttgcctc agatgtgtgt ctgtggagga tatggccgcc ctggccaggg agctggggat   1980
tcaggtagat gaagactttg aaaacactca gagaattcaa gtttcctctg gagaaaacat   2040
ggctgggaca gctgaaggtg agggtcagca aagacacagt cagctaaaaa gctcatctaa   2100
aagccaggct ctaatgccaa ttcaagagcc tgggactcaa tgtgagctca gccagaatct   2160
tcagaatctc tatggtaccc cagtattcag gcctgttcta gagaactcct ggctctttcc   2220
aaccagaatt ggaggtaact ttaaccatgt ttccttgaaa gcctcctggg ttatgggccg   2280
ccccttttggg tcagagcaga ggcctaagtg gttccatcct ttgccttttc agaatgcagg   2340
ggcccagggc cgaggtaaaa gttttggtat tcaatccttc catccccaga tattttattc   2400
aggtgaaaga ttcatgaaat tttccagagt tgctcgggga tgtcactcga atggaacatt   2460
tgggagactg ccaagaccca tttgtcagca tgtacaggcc tgccctgaga gaccacaaat   2520
gatgggaact cttgaaaggt ctagggcagt agcctccaag ataggtcact cctattccct   2580
ggattcacag ccagcaagag cagtagggaa gccatggcct cagcaagctt gcaccagggt   2640
aacagagtta actgaagcaa ctggaaaact gataagaaca tcccatattg gaaagcctca   2700
ccctcagtcc tttcaaccag cagcagccac acaaaaacta agacctgctt ctcagcaagg   2760
agtccagatg aagacacaag gtggggcttc aaatccagct ctccaaatag ggtcccatcc   2820
catgtgcaag agctctcagt tcaaatccga tcagtccaac ccatccacag tcaaacactc   2880
ccagcctaaa cccttccatt ctgtgccctc tcaacctaaa tcctctcaga caaaatcctg   2940
tcagtcccag ccctcccaaa ctaaaccttc tccatgcaaa tctactcagc ctaagccaag   3000
ccagccctgg cctccccagt ctaagccttc tcagcccaga ccccctcaac ctaagtcatc   3060
ctcaaccaat ccttcacaag ctaaggcaca ccactcaaaa gcagggcaga agaggggagg   3120
gaagcattaa agagctaact ccagagatct ataaagcata tcctttaccc aggccattcc   3180
tatcatatag taagcagaag agttgccatg aaagtaaaag actactgtca ttagcatgta   3240
aaacaaagaa agatatacat gactgaattg gatatctttg tttgtttgtt tgagacagag   3300
tttcactctt gttgcccagg ctggagtgca atggcacgat ctcggctcac cgcaacctct   3360
gcttcctggc ttaaagtgat tctcctgcct cagcctctcg agtagctggg attacaggca   3420
tgcaccacca cacccagcta attttgtatt tttagtagag gcagggtttc tccatgttgg   3480
tcaggctggt cttgaactcc cgacctcagg tgatccgccc acctaggcct ctcaaagtgt   3540
tgggattacg tgtgtaagcc acagtgccca gcccgaattg gatatcttta agatatctgt   3600
aagtgttata tccctaacca agaagaaaaa tatgaaaata attaagacta gaatcaagca   3660
gtagataatt gaatccaatc ttgggtatta ttagataatg tataacttgc acccagggaa   3720
tgggggtcta tgagacaacc ccacttggag aagaatgggg ttagggtctc taattgcaaa   3780
gtgactgtac aataggacga aagttgcctc tgtgtctgag aaagtatctt agttgttggc   3840
tgctccagag gtatctttgt caaaagcttc tggttcaata tcagccactg agcagataac   3900
cctgcttatt tggtgtggtt aaatcaacta gcttctgcta atagccccaa tttgcttgaa   3960
tgggaaaact ctctcatttg acccttatag gtagaaataa tgaattaaca accaataaaa   4020
```

ttaatcattt ggcattaa 4038

<210> SEQ ID NO 34
<211> LENGTH: 2111
<212> TYPE: DNA
<213> ORGANISM: Homo sapiens

<400> SEQUENCE: 34
aagcagaacc catcaggaag tgcacaggcg tccggcgtgc tcctccctcc ctgcagcccc 60
gggcagcatc tcccagaggc tccgcggccc aggctcctgg tgtgtctgca gtgcaggtgg 120
ctcctggaag accctcagcc tgcctgctga ggccatgtcg gactacgaga acgatgacga 180
gtgctggagc gtcctggagg gcttccgggt gacgctcacc tcggtcatcg acccctcacg 240
catcacacct tacctgcggc agtgcaaggt cctgaacccc gatgatgagg agcaggtgct 300
cagcgacccc aacctggtca tccgcaaacg gaaagtgggt gtgctcctgg acatcctgca 360
gcggaccggc cacaagggct acgtggcctt cctcgagagc ctggagctct actacccgca 420
gctgtacaag aaggtcacag gcaaggagcc ggcccgcgtc ttctccatga tcatcgacgc 480
gtccggggag tcaggcctga ctcagctgct gatgactgag gtcatgaagc tgcagaagaa 540
ggtgcaggac ctgaccgcgc tgctgagctc caaagatgac ttcatcaagg agctgcgggt 600
gaaggacagc ctgctgcgca agcaccagga gcgtgtgcag aggctcaagg aggagtgcga 660
ggccggcagc cgcgagctca agcgctgcaa ggaggagaac tacgacctgg ccatgcgcct 720
ggcgcaccag agtgaggaga agggcgccgc gctcatgcgg aaccgtgacc tgcagctgga 780
gattgaccag ctcaagcaca gcctcatgaa ggccgaggac gactgcaagg tggagcgcaa 840
gcacacgctg aagctcaggc acgccatgga gcagcggccc agccaggagc tgctgtggga 900
gctgcagcag gagaaggccc tgctccaggc ccgggtgcag gagctggagg cctccgtcca 960
ggaggggaag ctggacagga gcagccccta catccaggta ctggaggagg actggcggca 1020
ggcgctgcgg gaccaccagg agcaggccaa caccatcttc tccctgcgca aggacctccg 1080
ccagggcgag gcccgacgcc tccggtgcat ggaggagaag gagatgttcg agctgcagtg 1140
cctggcacta cgtaaggact ccaagatgta caaggaccgc atcgaggcca tcctgctgca 1200
gatggaggag gtcgccattg agcgggacca ggccatagcc acgcgggagg agctgcacgc 1260
acagcacgcc cggggcctgc aggagaagga cgcgctgcgc aagcaggtgc gggagctggg 1320
cgagaaggcg gatgagctgc agctgcaggt gttccagtgt gaggcgcagc tactggccgt 1380
ggagggcagg ctcaggcggc agcagctgga gacgctcgtc ctgagctccg acctggaaga 1440
tggctcaccc aggaggtccc aggagctctc actcccccag gacctggagg acacccagct 1500
ctcagacaaa ggctgccttg ccggcggggg gagcccgaaa cagccctttg cagctctgca 1560
ccaggagcag gttttgcgga acccccatga cgcaggcctg agcagcgggg agccgcccga 1620
gaaggagcgg cggcgcctca aagagagttt tgagaactac cgcaggaagc gcgccctcag 1680
gaagatgcag aaaggatggc ggcaggggga ggaggaccgg gagaacacca cgggcagcga 1740
caacaccgac actgagggct cctagccgca gcagcgcagg ccccgaccag ggcacaccca 1800
ccggcccggc ctcctgccac ccgggggtgc cgacgccctg ggcgcagac ttccccgagc 1860 cgtcgctgac ttggcctgga acgaggaatc tggtgccctg aaaggcccag ccggactgcc 1920
gggcattggg gccgtttgtt aagcggcact cattttgcgg aggccatgcg ggtgctcacc 1980
acccccatgc acacgccatc tgtgtaactt caggatctgt tctgtttcac catgtaacac 2040
acaatacatg catgcattgt attagtgtta gaaaacacag ctgcgtaaat aaacagcacg 2100
ggtgacccgc a 2111

<210> SEQ ID NO 35
<211> LENGTH: 1436
<212> TYPE: DNA
<213> ORGANISM: Homo sapiens

<400> SEQUENCE: 35
cagtcacaca agaagggagg agagaaaagc catggccgac aaggtcctga aggagaagag 60
aaagctgttt atccgttcca tgggtgaagg tacaataaat ggcttactgg atgaattatt 120
acagacaagg gtgctgaaca aggaagagat ggagaaagta aaacgtgaaa atgctacagt 180
tatggataag acccgagctt tgattgactc cgttattccg aaaggggcac aggcatgcca 240
aatttgcatc acatacattt gtgaagaaga cagttacctg gcagggacgc tgggactctc 300
agcagatcaa acatctggaa attaccttaa tatgcaagac tctcaaggag tactttcttc 360
ctttccagct cctcaggcag tgcaggacaa cccagctatg cccacatcct caggctcaga 420
agggaatgtc aagctttgct ccctagaaga agctcaaagg atatggaaac aaaagtcggc 480
agagatttat ccaataatgg acaagtcaag ccgcacacgt cttgctctca ttatctgcaa 540
tgaagaattt gacagtattc ctagaagaac tggagctgag gttgacatca caggcatgac 600
aatgctgcta caaaatctgg ggtacagcgt agatgtgaaa aaaaatctca ctgcttcgga 660
catgactaca gagctggagg catttgcaca ccgcccagag cacaagacct ctgacagcac 720
gttcctggtg ttcatgtctc atggtattcg ggaaggcatt tgtgggaaga aacactctga 780
gcaagtccca gatatactac aactcaatgc aatctttaac atgttgaata ccaagaactg 840
cccaagtttg aaggacaaac cgaaggtgat catcatccag gcctgccgtg gtgacagccc 900
tggtgtggtg tggtttaaag attcagtagg agtttctgga aacctatctt taccaactac 960
agaagagttt gaggatgatg ctattaagaa agcccacata gagaaggatt ttatcgcttt 1020
ctgctcttcc acaccagata atgtttcttg gagacatccc acaatgggct ctgtttttat 1080
tggaagactc attgaacata tgcaagaata tgcctgttcc tgtgatgtgg aggaaatttt 1140
ccgcaaggtt cgattttcat ttgagcagcc agatggtaga gcgcagatgc ccaccactga 1200
aagagtgact ttgacaagat gtttctacct cttcccagga cattaaaata aggaaactgt 1260
atgaatgtct gtgggcagga agtgaagaga tccttctgta aaggtttttg gaattatgtc 1320
tgctgaataa taaacttttt tgaaataata aatctggtag aaaaatgaaa acttgtcctc 1380
atttttctcc cacactgaag aaacagggac tggaacttag agtgactaag gaattt 1436

<210> SEQ ID NO 36
<211> LENGTH: 6357
<212> TYPE: DNA
<213> ORGANISM: Homo sapiens

<400> SEQUENCE: 36
gcgacgctgt ctctccatgc caggactgag ttgtggggga gggaggcggt tagcgggctt 60
tagcgccttt tctggcggcg gtagatttga agcgcttcaa aggaccggac ccagagaaga 120
ggaaaactct accggtgcag gagcacaggg atcagttgtc cttgtttttt tttggtcttt 180
tcttcatttg aagattaagt attggagcca tgggaataaa ggttcaacgt cctcgatgtt 240
tttttgacat tgccattaac aatcaacctg ctggaagagt tgtctttgaa ttattttctg 300
atgtgtgccc caaaacatgc gagaactttc gttgtctttg tacaggtgaa aaggggaccg 360

```
ggaaatcaac tcagaaacca ttacattata agagttgtct ctttcacaga gttgtcaagg    420
attttatggt tcaaggtggt gacttcagtg aaggaaatgg acgaggaggg gaatctatct    480
atggaggatt ttttgaagac gagagtttcg ctgttaaaca caacaaagaa tttctcttgt    540
caatggccaa cagagggaag gatacaaatg gttcacagtt cttcataaca acgaaaccaa    600
ctcctcattt agatgggcat catgttgttt ttggacaagt aatctctggt caagaagttg    660
taagagagat tgaaaaccag aaaacagatg cagctagcaa accgtttgcg gaggtacgga    720
tactcagttg tggagagctg attcccaaat ctaaagttaa gaaagaagaa aagaaaaggc    780
ataaatcatc atcatcttcc tcctcctcat ctagtgactc agatagctca agtgattctc    840
agtcctcttc tgattcctct gattccgaaa gtgctactga agagaaatca aagaaaagaa    900
aaaagaaaca tcggaaaaat tcccgaaaac acaagaaaga aaagaaaaag cgaaagaaaa    960
gcaagaagag tgcatctagt gagagtgaag ctgaaaatct tgaagcacaa ccccagtcta   1020
ctgtccgtcc agaagagatc cctcctatac ctgaaaatag attcctaatg agaaaaagtc   1080
ctcctaaagc tgatgagaag gaaaggaaaa acagagagag agaaagggaa agagagtgta   1140
atccacctaa ctcccagcct gcttcatacc agagacgact tttagttact agatctggca   1200
ggaaaattaa aggaagagga ccaaggcgtt atcgaactcc ttccagatcc agatcaaggg   1260
atcgtttcag acgtagtgag actcctccac attggaggca agagatgcag agagctcaaa   1320
gaatgagggt atcaagtggt gaaagatgga tcaaggggga taagagtgag ttgaatgaaa   1380
taaaagaaaa tcagagaagt ccagttagag taaaagagag aaaaataaca gatcacagga   1440
atgtatctga gagtccaaac agaaaaaatg aaaaggagaa gaaagttaaa gaccataaat   1500
ctaacagcaa agagagagac atcagaagaa attcagaaaa agatgacaag tataaaaaca   1560
aagtgaagaa aagggccaaa tctaaaagta ggagtaagag caaagagaaa tcaaagagta   1620
aagaaagaga ttcaaaacat aatagaaatg aagaaaagag gatgaggtca aggagtaaag   1680
gaagggatca tgaaaatgtt aaagaaaaag aaaagcagtc tgattctaaa ggaaaagatc   1740
aggaaaggag tagaagtaaa gagaagtcta aacagttaga atcaaagagt aatgagcatg   1800
atcacagtaa aagtaaggaa aaggatagac gcgcacaatc caggagtaga gaatgtgata   1860
taactaaagg taaacacagt tataatagca gaacaagaga acgaagcaga agtagggaca   1920
gaagcagaag agtgcgatca agaacccatg acagagatcg cagcagaagc aaggagtacc   1980
atagatacag agaacaggaa tacaggagaa gaggacggtc acgaagccga gagagaagaa   2040
caccaccagg aagatcaaga agtaaagata ggaggagaag gaggagagac tcacggagct   2100
cagagagaga agaaagtcaa agcagaaaca aagacaaata cagaaaccaa gagagtaaga   2160
gctcacacag aaaagaaaat tctgagagtg agaaaagaat gtactctaaa agtcgtgatc   2220
ataatagctc aaataacagc agggaaaaaa aggctgatag agatcaaagt cccttctcaa   2280
aaataaaaca aagcagtcag gacaatgaat taaagtcctc catgttgaaa aataaggagg   2340
atgagaagat cagatcctca gtggaaaaag aaaaccaaaa atcaaaaggt caagaaaatg   2400
accatgtaca tgaaaaaaat aaaaaatttg atcatgaatc aagccctgga acagatgaag   2460
acaaaagcgg atgagtgagt tatataaact tacttccatt ctgtttcgga ttttaagttt   2520
gagagacttg ctaatgaatc tcctttatgt tgttttcctt ttcattgttt ttggattgtt   2580
ttatgtttgt ccttttttt cttaatgtgg atttcattga gttgattttt tgataatctg   2640
caatctggat aatttgtact gctaaagttt taataaactc gacatgagaa aaacactttg   2700
```

```
gtgtagtact gtgtgctgtg tttaactatt ttatgtatgc attactgtgt tgcaacaatt   2760
agccaatagc atcctaattt gtttagtcag ccatttggaa tggttgcaat gcattgttgc   2820
aaaagcttgt gtttctcatg attaaagtaa ctttagaagc cactagaaga catcttgtat   2880
agattttctg attgcgttat aaatagaggt ttgcagcggt ttcttttaat tacacagaag   2940
cagggtccta ataacctgag atcttaaatc atcacttttg attttatagt aatttgtgct   3000
ttaaaataga tgtatttata ttgcacttca tactctattc tttatagttc gagccatagc   3060
ttgtttccta ttaatgcttt tcctgtctag ttgtgtttta cttaactgcc tataaaaatc   3120
gtaagagtaa ttttttcag ttgatgtact gattgagctt gagttgctgt tatacagcat    3180
ttgacaggaa ctataccttg gaaaatcaga ttgtgattct cagttctgtg ttgcttttgg   3240
tttgaagagt tttgggaacg ttttaattat taattaccct tctctaaact ttaaaaaaaa   3300
aaaagctttt ctcattaaaa cataccattt gtgcaggtcc ttaagctata cagattctaa   3360
aaattgttag tattgagaca ttaacttcta agatttctct tttttggcct ccaacctata   3420
tagaattgag tgttaactct gcatggattt tgtttgtttt aattgaactg acttctctaa   3480
ctctcatagc tgtgagttcc aaatggcaag aaaatgcatc ttttctatat atgtatcacg   3540
ataggctata gcatgtttat gactctggtt tctttctctt caggtggttt tataccatta   3600
ctgttaatgt tattttaact tggcatgtat aacattgcca tatagagtag agtagaaagt   3660
tgcaaatttt gatagtttac agagttaaac actaaacata tccaaagtcc atttagagtt   3720
ttgggtgttg tattttgcca tttttgtgat gtgtggcctt ttattctgta atctcttcta   3780
aataaaacat tgaacatcca gcaaacataa aacctgcctc atttgaaaag gaatttcaaa   3840
attccaatta ataggattct ctagagagtt ttgtacttta atatttgtca gtgtagtgtc   3900
aactctgtta ccaaggtagc ttcttggtaa atccagtagc tactcaatgc tatttgtact   3960
gaataaagca attattaaca tgatacttcc cactattgat taatgcaata ttgatatatt   4020
tggcgttgtg gtagctgttg cagaatgaat agtgtaatga ccataagatt gcttggaaaa   4080
ttgtaataca gatatccaca atgaattctt tccaaaattt tttttccga tgataaaagt    4140
agtagatgtt tattataaaa tccaaggtga ttgattcctt agagactgac cacaaaccca   4200
cattagggat aattgagtct gagtgcccaa gctatataac gttatgtagt ttaagcaagt   4260
tattgtttgt cttaatttca gttaactgca ttttaaaatt gttgttataa actatttgag   4320
ctttaagaaa ggtgctattt aagaaaggat ttctaataac agttaaatat tttttttaag   4380
tccatgctaa gtaaaaattc ttacatgttg tctgatccca gagctttatc tactaaaaat   4440
tatacataag gatttccaaa tcttagagtt tcaaaaagta accataggga aaaaaattgt   4500
agtaatttct ataggcaata ttctgtttgg gttatcaaaa gagcaactcc atgctccgca   4560
ttatttatag tccttatttt aaagttttat tagctctctt tacagaacag atgtgaagga   4620
gttgagagga caatcaacta gattttattt ttagaatata aagaacattt ttaaaatgat   4680
taaacagcat taactgtacc tcaggatctg cgcatgcatc tgaatagcac acggctcaaa   4740
tggtcctttc cttttgttac atttagtagt tgtgccatct ttagtttttg ctttgaacat   4800
tgttttccta aaagtcaact attactttcc catcaagttg gttttatagt tatgtctaaa   4860
tttatggttc atgtcaaagt atttttgact taatatcctt ttaaaaatat ttaaactgat   4920
ttattgctca attggtgata gctgagaaaa ttttttcaat atgtagaatt ttcatggtta   4980
ttttgtatga attatttttc tgggtaagcc atctgccaca gaaattgaca ctatggtgag   5040
attaatgtta atgaaatgag cagtagagaa gctactggat tgctttaaaa cattctttga   5100
```

ttaaattact acatagttgg taagttcata gttttaagtt acttaattga agccctcaga 5160
agttgcaaag aatttatctg ataaatctgc ctttgcacaa atgtgatact gatgcatgga 5220
cggctttgcg gaatgacctt tgatatttgt gcctagtgga aggtatggag ctaaacaatt 5280
aaagaactct tcattatgga taggcacata ttggatctct ggtattttgg gtagtggtat 5340
taacttgaca attctaattt attttagtta gtatatgtag caagttagta tgtttgttag 5400
tagtttattg tacttcattc cagttggtaa tatagttttc atcacactaa actttttata 5460
ctaaatttct gtagaagctt gttgggtttg ccttcaccag aaggtacttt aaatacctac 5520
catagctgat ttgttataaa gaaacaaaat gggtgttctt ctgtttcctt ttgattatgt 5580
ttactgtaat tatttcattt tggatttata catttacaat tgaataagga ttataggttg 5640
ataagctgtt tattgtgaaa agatgtgttt tgttacaaat acttgtttta aaaattaata 5700
agcccccagg aagtacagca ttgactggca caactgccca tagtgagctt cccaactaac 5760
tgccttcagt ggattcgggc aagtgcaaag tctttggcct attgtgtgac aaagaggtat 5820
atattaaagg aaaagaaaaa tgacatgaat aagaaaattc cgtcaacaag gttggagtag 5880
ggagttgttg aggggtttag tttgttttaa aaggtatgtg agggagtggt ggggtggatt 5940
tgtgtttctg acttttttc tttaagcaaa ttccatatgt taccaaaagc acatgctgta 6000
tattttcttc cccttttgtg tgtatatagt attttgaaag ataaatgaat tgggtatttg 6060
tatgtgggat gtacaaaatt gtggccgctc tctttgtgga aggaaaaaac ataaatgaag 6120
ttaatgcact tcttttccta gcccaaaagt cactgtgatt atattttttt aatgaagttt 6180
agaaaaaaag ctgttgtctt ctcaattgta aaattagttt caaaatgctg cttctcttat 6240
cattagtcta gtaattgttg aacttttctg caaactgcat tttacaaaat tgaaacttgg 6300
aagctgtatt aacttttata gttaaacatt gtattaaata aactatacta taataaa 6357

<210> SEQ ID NO 37
<211> LENGTH: 777
<212> TYPE: DNA
<213> ORGANISM: Homo sapiens

<400> SEQUENCE: 37
aggatcagac aagggtgctg agagccggga ctcacaacca aaggagaaat gagcaatccg 60
cggtctttgg aagaggagaa atatgatatg tcaggtgccc gcctggccct aatactgtgt 120
gtcaccaaag cccgggaagg ttccgaagaa gacctggatg ctctggaaca catgtttcgg 180
cagctgagat tcgaaagcac catgaaaaga gaccccactg ccgagcaatt ccaggaagag 240
ctggaaaaat tccagcaggc catcgattcc cgggaagatc ccgtcagttg tgccttcgtg 300
gtactcatgg ctcacgggag ggaaggcttc ctcaagggag aagatgggga gatggtcaag 360
ctggagaatc tcttcgaggc cctgaacaac aagaactgcc aggccctgcg agctaagccc 420
aaggtgtaca tcatacaggc ctgtcgagga gaacaaaggg accccggtga aacagtaggt 480
ggagatgaga ttgtgatggt catcaaagac agcccacaaa ccatcccaac atacacagat 540
gccttgcacg tttattccac ggtagaggga tacatcgcct accgacatga tcagaaaggc 600
tcatgcttta tccagaccct ggtggatgtg ttcacgaaga ggaaaggaca tatcttggaa 660
cttctgacag aggtgacccg gcggatggca gaagcagagc tggttcaaga aggaaaagca 720
aggaaaacga accctgaaat ccaaagcacc ctccggaaac ggctgtatct gcagtag 777

<210> SEQ ID NO 38

<211> LENGTH: 1488
<212> TYPE: DNA
<213> ORGANISM: Homo sapiens

<400> SEQUENCE: 38

```
gttcgttgca acaaattgat gagcaatgct tttttataat gccaactttg tacaaaaaag     60
ttggcatggc ggcgccgagc gcggggtctt ggtccacctt ccagcacaag gagctgatgg    120
ccgctgacag ggacgcaggg atattgggag tgtgtggcat gcatcctcat catcaggaaa    180
ctctaaaaaa gaaccgagtg gtgctagcca aacagctgtt gttgagcgaa ttattagaac    240
atcttctgga gaaggacatc atcaccttgg aaatgaggga gctcatccag gccaaagtgg    300
gcagtttcag ccagaatgtg gaactcctca acttgctgcc taagaggggt ccccaagctt    360
ttgatgcctt ctgtgaagca ctgagggaga ccaagcaagg ccacctggag gatatgttgc    420
tcaccaccct ttctgggctt cagcatgtac tcccaccgtt gagctgtgac tacgacttga    480
gtctcccttt tccggtgtgt gagtcctgtc ccctttacaa gaagctccgc ctgtcgacag    540
atactgtgga acactcccta gacaataaag atggtcctct ctgccttcag gtgaagcctt    600
gcactcctga attttatcaa acacacttcc agctggcata taggttgcag tctcggcctc    660
gtggcctagc actggtgttg agcaatgtgc acttcactgg agagaaagaa ctggaatttc    720
gctctggagg ggatgtggac cacagtactc tagtcaccct cttcaagctt ttgggctatg    780
acgtccatgt tctatgtgac cagactgcac aggaaatgca agagaaactg cagaattttg    840
cacagttacc tgcacaccga gtcacggact cctgcatcgt ggcactcctc tcgcatggtg    900
tggagggcgc catctatggt gtggatggga aactgctcca gctccaagag gtttttcagc    960
tctttgacaa cgccaactgc ccaagcctac agaacaaacc aaaaatgttc ttcatccagg   1020
cctgccgtgg agatgagact gatcgtgggg ttgaccaaca agatggaaag aaccacgcag   1080
gatcccctgg gtgcgaggag agtgatgccg gtaaagaaaa gttgccgaag atgagactgc   1140
ccacgcgctc agacatgata tgcggctatg cctgcctcaa agggactgcc gccatgcgga   1200
acaccaaacg aggttcctgg tacatcgagg ctcttgctca agtgttttct gagcgggctt   1260
gtgatatgca cgtggccgac atgctggtta aggtgaacgc acttatcaag gatcgggaag   1320
gttatgctcc tggcacagaa ttccaccggt gcaaggagat gtctgaatac tgcagcactc   1380
tgtgccgcca cctctacctg ttcccaggac accctcccac atgcccaact ttcttgtaca   1440
aagttggcat tataagaaag cattgcttat caatttgttg caacgaac                1488
```

<210> SEQ ID NO 39
<211> LENGTH: 963
<212> TYPE: DNA
<213> ORGANISM: Homo sapiens

<400> SEQUENCE: 39

```
gttcgttgca acaaattgat gagcaatgct tttttataat gccaactttg tacaaaaaag     60
ttggcatgga gaacactgaa aactcagtgg attcaaaatc cattaaaaat ttggaaccaa    120
agatcataca tggaagcgaa tcaatggact ctggaatatc cctggacaac agttataaaa    180
tggattatcc tgagatgggt ttatgtataa taattaataa taagaatttt cataaaagca    240
ctggaatgac atctcggtct ggtacagatg tcgatgcagc aaacctcagg gaaacattca    300
gaaacttgaa atatgaagtc aggaataaaa atgatcttac acgtgaagaa attgtggaat    360
tgatgcgtga tgtttctaaa gaagatcaca gcaaaaggag cagttttgtt tgtgtgcttc    420
tgagccatgg tgaagaagga ataatttttg gaacaaatgg acctgttgac ctgaaaaaaa    480
```

```
taacaaactt tttcagaggg gatcgttgta gaagtctaac tggaaaaccc aaacttttca    540

ttattcaggc ctgccgtggt acagaactgg actgtggcat tgagacagac agtggtgttg    600

atgatgacat ggcgtgtcat aaaataccag tggaggccga cttcttgtat gcatactcca    660

cagcacctgg ttattattct tggcgaaatt caaaggatgg ctcctggttc atccagtcgc    720

tttgtgccat gctgaaacag tatgccgaca agcttgaatt tatgcacatt cttacccggg    780

ttaaccgaaa ggtggcaaca gaatttgagt ccttttcctt tgacgctact tttcatgcaa    840

agaaacagat tccatgtatt gtttccatgc tcacaaaaga actctatttt tatcactacc    900

caactttctt gtacaaagtt ggcattataa gaaagcattg cttatcaatt tgttgcaacg    960

aac                                                                  963
```

<210> SEQ ID NO 40
<211> LENGTH: 1296
<212> TYPE: DNA
<213> ORGANISM: Homo sapiens

<400> SEQUENCE: 40

```
actctgaggc tctttccaac gctgtaaaaa aggacagagg ctgttcccta tggcagaagg     60

caaccacaga aaaaagccac ttaaggtgtt ggaatccctg ggcaaagatt tcctcactgg    120

tgttttggat aacttggtgg aacaaaatgt actgaactgg aaggaagagg aaaaaaagaa    180

atattacgat gctaaaactg aagacaaagt tcgggtcatg gcagactcta tgcaagagaa    240

gcaacgtatg gcaggacaaa tgcttcttca aaccttttt aacatagacc aaatatcccc    300

caataaaaaa gctcatccga atatggaggc tggaccacct gagtcaggag aatctacaga    360

tgccctcaag ctttgtcctc atgaagaatt cctgagacta tgtaaagaaa gagctgaaga    420

gatctatcca ataaaggaga gaaacaaccg cacacgcctg gctctcatca tatgcaatac    480

agagtttgac catctgcctc cgaggaatgg agctgacttt gacatcacag ggatgaagga    540

gctacttgag ggtctggact atagtgtaga tgtagaagag aatctgacag ccagggatat    600

ggagtcagcg ctgagggcat ttgctaccag accagagcac aagtcctctg acagcacatt    660

cttggtactc atgtctcatg gcatcctgga gggaatctgc ggaactgtgc atgatgagaa    720

aaaaccagat gtgctgcttt atgacaccat cttccagata ttcaacaacc gcaactgcct    780

cagtctgaag gacaaaccca aggtcatcat tgtccaggcc tgcagaggtg caaaccgtgg    840

ggaactgtgg gtcagagact ctccagcatc cttggaagtg gcctcttcac agtcatctga    900

gaacctagag gaagatgctg tttacaagac ccacgtggag aaggacttca ttgctttctg    960

ctcttcaacg ccacacaacg tgtcctggag agacagcaca atgggctcta tcttcatcac   1020

acaactcatc acatgcttcc agaaatattc ttggtgctgc cacctagagg aagtatttcg   1080

gaaggtacag caatcatttg aaactccaag ggccaaagct caaatgccca ccatagaacg   1140

actgtccatg acaagatatt tctacctctt tcctggcaat tgaaaatgga agccacaagc   1200

agcccagccc tccttaatca acttcaagga gcaccttcat tagtacagct tgcatattta   1260

acattttgta tttcaataaa agtgaagaca aacgaa                             1296
```

<210> SEQ ID NO 41
<211> LENGTH: 1446
<212> TYPE: DNA
<213> ORGANISM: Homo sapiens

<400> SEQUENCE: 41

```
agtgctgtac aaagagacag aggctgttag ctatggctga agacagtggc aaaaaaaaaa     60
ggcgtaagaa ttttgaagct atgttcaaag gtatccttca gagtggattg gataacttcg    120
tgataaacca catgctaaag aacaacgtgg ctggacaaac atctatccag accctagtac    180
ctaatacgga tcaaaagtcg accagtgtaa aaaaagacaa ccacaaaaaa aaaacagtta    240
agatgttgga atacctgggc aaagatgttc ttcatggtgt ttttaattat ttggcaaaac    300
acgatgttct gacattgaag gaagaggaaa agaaaaaata ttatgatacc aaaattgaag    360
acaaggccct gatcttggta gactctttgc gaaagaatcg cgtggctcat caaatgttta    420
cccaaacact tctcaatatg gaccaaaaga tcaccagtgt aaaacctctt ctgcaaatcg    480
aggctggacc acctgagtca gcagaatcta caaatatact caaactttgt cctcgtgaag    540
aattcctgag actgtgtaaa aaaaatcatg atgagatcta tccaataaaa aagagagagg    600
accgcagacg cctggctctc atcatatgca atacaaagtt tgatcacctg cctgcaagga    660
atggggctca ctatgacatc gtggggatga aaaggctgct tcaaggcctg ggctacactg    720
tggttgacga aaagaatctc acagccaggg atatggagtc agtgctgagg gcatttgctg    780
ccagaccaga gcacaagtcc tctgacagca cgttcttggt actcatgtct catggcatcc    840
tagagggaat ctgcggaact gcgcataaaa agaaaaaacc ggatgtgctg ctttatgaca    900
ccatcttcca gatattcaac aaccgcaact gcctcagtct aaaggacaaa cccaaggtca    960
tcattgtcca ggcctgcaga ggtgaaaaac atggggaact ctgggtcaga gactctccag   1020
catccttggc actcatctct tcacagtcat ctgagaacct ggaggcagat tctgtttgca   1080
agatccacga ggagaaggac ttcattgctt tctgttcttc aacaccacat aacgtgtcct   1140
ggagagaccg cacaaggggc tccatcttca ttacggaact catcacatgc ttccagaaat   1200
attcttgctg ctgccaccta atggaaatat ttcggaaggt acagaaatca tttgaagttc   1260
cacaggctaa agcccagatg cccaccatag aacgagcaac cttgacaaga gatttctacc   1320
tctttcctgg caattgaaaa tgaaaccaca ggcagcccag ccctcctctg tcaacatcaa   1380
agagcacatt taccagtata gcttgcatag tcaatatttg gtatttcaat aaaagtaaag   1440
actgta                                                               1446
```

<210> SEQ ID NO 42
<211> LENGTH: 1634
<212> TYPE: DNA
<213> ORGANISM: Homo sapiens

<400> SEQUENCE: 42

```
gtggcttcag gaagaggagg gcaaggtgtc tggctgcgcg tttggctgca atgagctcgg     60
cctcggggct ccgcaggggg cacccggcag gtggggaaga aaacatgaca gaaacagatg    120
ccttctataa aagagaaatg tttgatccgg cagaaaagta caaaatggac cacaggagga    180
gaggaattgc tttaatcttc aatcatgaga ggttcttttg gcacttaaca ctgccagaaa    240
ggcggggcac ctgcgcagat agagacaatc ttacccgcag gttttcagat ctaggatttg    300
aagtgaaatg ctttaatgat cttaaagcag aagaactact gctcaaaatt catgaggtgt    360
caactgttag ccacgcagat gccgattgct ttgtgtgtgt cttcctgagc catggcgaag    420
gcaatcacat ttatgcatat gatgctaaaa tcgaaattca gacattaact ggcttgttca    480
aaggagacaa gtgtcacagc ctggttggaa aacccaagat atttatcatt caggcatgtc    540
ggggaaacca gcacgatgtg ccagtcattc ctttggatgt agtagataat cagacagaga    600
agttggacac caacataact gaggtggatg cagcctccgt ttacacgctg cctgctggag    660
```

```
ctgacttcct catgtgttac tctgttgcag aaggatatta ttctcaccgg gaaactgtga    720

acggctcatg gtacattcaa gatttgtgtg agatgttggg aaaatatggc tcctccttag    780

agttcacaga actcctcaca ctggtgaaca ggaaagtttc tcagcgccga gtggactttt    840

gcaaagaccc aagtgcaatt ggaaagaagc aggttccctg ttttgcctca atgctaacta    900

aaaagctgca tttctttcca aaatctaatt aattaataga ggctatctaa ttttacactc    960

tgtattgaaa atggctttct cagccaggcg tggttactca cacctgtaat cccagcactt   1020

tgggagtcca aggtgggcgg atcacctgag gtcgggagtt cgagaccagc ctgaccaaca   1080

tggagaagcc ccgtctctac taaaaatgca aaaaaaaatt tagctaggca tggcggcgca   1140

tgcctgcaat cccagctact tggaaggctg aggcaggaga atcacttgaa cccaggaggt   1200

ggaggctgcg gtgagccgag attgcgccat tgcactccag cctgggcaac gagtgaaact   1260

ccgtctcaaa aaaaagaaaa tgtctttctc ttccttttat ataaatatcg ttagggtgaa   1320

gcattatggt ctaatgattc aaatgtttta aagtttaatg cctagcagag aactgcctta   1380

aaaaaaaaaa aaaaaagttc atgttggcca tggtgaaagg gtttgatatg gagaaacaaa   1440

atcctcagga aattagataa ataaaaattt ataagcattt gtattatttt ttaataaact   1500

gcagggttac acaaaaatct agctgattta acttgtattt tgtcactttt ttataaaagt   1560

ttattgtttg atgtttttaa aggtttttga aatccaggaa ttaaatcatc ccttaataaa   1620

atattcgaaa ttca                                                     1634
```

<210> SEQ ID NO 43
<211> LENGTH: 1041
<212> TYPE: DNA
<213> ORGANISM: Homo sapiens

<400> SEQUENCE: 43

```
gttcgttgca acaaattgat gagcaatgct tttttataat gccaactttg tacaaaaaag     60

ttggcatggc agatgagcag ggctgtattg aagagcaggg ggttgaggat tcagcaaatg    120

aagattcagt ggatgctaag ccagaccggt cctcgtttgt accgtccctc ttcagtaaga    180

agaagaaaaa tgtcaccatg cgatccatca agaccacccg ggaccgagtg cctacatatc    240

agtacaacat gaattttgaa aagctgggca aatgcatcat aataaacaac aagaactttg    300

ataaagtgac aggtatgggc gttcgaaacg gaacagacaa agatgccgag gcgctcttca    360

agtgcttccg aagcctgggt tttgacgtga ttgtctataa tgactgctct tgtgccaaga    420

tgcaagatct gcttaaaaaa gcttctgaag aggaccatac aaatgccgcc tgcttcgcct    480

gcatcctctt aagccatgga gaagaaaatg taatttatgg gaaagatggt gtcacaccaa    540

taaaggattt gacagcccac tttagggggg atagatgcaa aaccctttta gagaaaccca    600

aactcttctt cattcaggct tgccgaggga ccgagcttga tgatggcatc caggccgact    660

cggggcccat caatgacaca gatgctaatc ctcgatacaa gatcccagtg gaagctgact    720

tcctcttcgc ctattccacg gttccaggct attactcgtg gaggagccca ggaagaggct    780

cctggtttgt gcaagccctc tgctccatcc tggaggagca cggaaaagac ctggaaatca    840

tgcagatcct caccagggtg aatgacagag ttgccaggca ctttgagtct cagtctgatg    900

acccacactt ccatgagaag aagcagatcc cctgtgtggt ctccatgctc accaaggaac    960

tctacttcag tcaataccca actttcttgt acaaagttgg cattataaga aagcattgct   1020

tatcaatttg ttgcaacgaa c                                             1041
```

<210> SEQ ID NO 44
<211> LENGTH: 2659
<212> TYPE: DNA
<213> ORGANISM: Homo sapiens

<400> SEQUENCE: 44
agacgtttgc tcttgtctta gatgctcaga tggtagtgga taggcctgtg acgaaggtgc 60
taccatcgtg agagtaagat tatattctcc tgccttttaa aaagatggac ttcagcagaa 120
atctttatga tattggggaa caactggaca gtgaagatct ggcctccctc aagttcctga 180
gcctggacta cattccgcaa aggaagcaag aacccatcaa ggatgccttg atgttattcc 240
agagactcca ggaaaagaga atgttggagg aaagcaatct gtccttcctg aaggagctgc 300
tcttccgaat taatagactg gatttgctga ttacctacct aaacactaga aaggaggaga 360
tggaaaggga acttcagaca ccaggcaggg ctcaaatttc tgcctacagg gtcatgctct 420
atcagatttc agaagaagtg agcagatcag aattgaggtc ttttaagttt cttttgcaag 480
aggaaatctc caaatgcaaa ctggatgatg acatgaacct gctggatatt ttcatagaga 540
tggagaagag ggtcatcctg ggagaaggaa agttggacat cctgaaaaga gtctgtgccc 600
aaatcaacaa gagcctgctg aagataatca acgactatga agaattcagc aaagagagaa 660
gcagcagcct tgaaggaagt cctgatgaat tttcaaatgg ggaggagttg tgtggggtaa 720
tgacaatctc ggactctcca agagaacagg atagtgaatc acagactttg gacaaagttt 780
accaaatgaa aagcaaacct cggggatact gtctgatcat caacaatcac aattttgcaa 840
aagcacggga gaaagtgccc aaacttcaca gcattaggga caggaatgga acacacttgg 900
atgcaggggc tttgaccacg acctttgaag agcttcattt tgagatcaag ccccacgatg 960
actgcacagt agagcaaatc tatgagattt tgaaaatcta ccaactcatg gaccacagta 1020
acatggactg cttcatctgc tgtatcctct cccatggaga caagggcatc atctatggca 1080
ctgatggaca ggaggccccc atctatgagc tgacatctca gttcactggt ttgaagtgcc 1140
cttcccttgc tggaaaaccc aaagtgtttt ttattcaggc ttgtcagggg gataactacc 1200
agaaaggtat acctgttgag actgattcag aggagcaacc ctatttagaa atggatttat 1260
catcacctca aacgagatat atcccggatg aggctgactt tctgctgggg atggccactg 1320
tgaataactg tgtttcctac cgaaaccctg cagagggaac ctggtacatc cagtcacttt 1380
gccagagcct gagagagcga tgtcctcgag gcgatgatat tctcaccatc ctgactgaag 1440
tgaactatga agtaagcaac aaggatgaca agaaaaacat ggggaaacag atgcctcagc 1500
ctactttcac actaagaaaa aaacttgtct tcccttctga ttgatggtgc tattttgttt 1560
gttttgtttt gttttgtttt tttgagacag aatctcgctc tgtcgcccag gctggagtgc 1620
agtggcgtga tctcggctca ccgcaagctc cgcctcccgg gttcaggcca ttctcctgcc 1680
tcagcctccc gagtagctgg gactacaggg gcccgccacc acacctggct aatttttttaa 1740 aaatattttt agtagagaca gggtttcact gtgttagcca gggtggtctt gatctcctga 1800
cctcgtgatc cacccacctc ggcctcccaa agtgctggga ttacaggcgt gagccaccgc 1860
gcctggccga tggtactatt tagatataac actatgttta tttactaatt ttctagattt 1920
tctactttat taattgtttt gcactttttt ataagagcta aagttaaata ggatattaac 1980
aacaataaca ctgtctcctt tctcttatgc ttaaggcttt gggaatgttt ttagctggtg 2040
gcaataaata ccagacacgt acaaaatcca gctatgaata tagagggctt atgattcaga 2100
ttgttatcta tcaactataa gcccactgtt aatattctat taactttaat tctctttcaa 2160

```
agctaaattc cacactacca cattaaaaaa attagaaagt agccacgtat ggtggctcat   2220

gtctataatc ccagcacttt gggaggttga ggtgggagga ttgcttgaac ccaagaggtc   2280

aaggctgcag tgagccatgt tcacaccgct gcactcaagc ttgggtgaca gaacaagacc   2340

ccgtctcaaa aaaaattttt tttttaataa aacaaaattt gtttgaaatc ttttaaaaat   2400

tcaaatgatt tttacaagtt ttaaataagc tctccccaaa cttgctttat gccttcttat   2460

tgcttttatg atatatatat gcttggctaa ctatatttgc tttttgctaa caatgctctg   2520

gggtcttttt atgcatttgc atttgctctt tcatctctgc ttggattatt ttaaatcatt   2580

aggaattaag ttatctttaa aatttaagta tctttttttca aaaacatttt ttaatagaat   2640

aaaatataat ttgatctta                                                2659
```

<210> SEQ ID NO 45
<211> LENGTH: 6792
<212> TYPE: DNA
<213> ORGANISM: Homo sapiens

<400> SEQUENCE: 45

```
agggagacct cggtgggcag aaaggaaccg ggttgtcttg ggccgggcag ggcgggtaag     60

ttgtcgtagg ggcccggtcc gtgagggact gctaaggaag aggctgcatg gcgcggtagt    120

cccccgagtg gaggtcggct gcccctggga aaccagagag tcggagggag tccatctgga    180

gcggccaagt ggtgactctc aaaaggaaat aggatcatgg cagcagatga tgacaatggt    240

gatggaacaa gtttatttga tgtcttttct gcttctcctc ttaagaacaa tgatgaaggc    300

tcactggaca tatacgctgg gttggacagt gctgtttctg acagcgcttc caaatcctgt    360

gtaccatcaa gaaattgttt ggacttatat gaagagatcc tgactgaaga aggaactgca    420

aaggaggcaa catataatga tttgcaagta gaatatggaa aatgtcaact acaaatgaaa    480

gagctgatga aaaaatttaa agaaatacag acacagaatt tcagcttaat aaacgaaaac    540

cagtctctta agaagaatat ttcagcactt atcaaaactg ccagagtgga aataaaccgc    600

aaggatgaag aaataagtaa tcttcaccaa agattgtctg agtttccaca ttttcgaaat    660

aatcataaaa ctgcaaggac atttgataca gttaaaacaa aagatcttaa atctagatct    720

ccacatttgg atgattgttc aaagactgat cacagagcta aaagtgatgt ttctaaagat    780

gtacatcata gcacttcact gccaaatctg gaaaaggaag gaaaaccaca ttctgataaa    840

aggagtactt cacatttacc tacatctgtt gagaaacact gcactaatgg tgtttggtca    900

cgttctcatt atcaggttgg cgagggtagc tcaaatgagg atagtagaag aggaagaaaa    960

gatattagac atagccagtt taacagagga actgaaagag tacgaaaaga cttaagtact   1020

ggctgtggtg atggtgaacc aaggatattg gaggctagtc aaaggctaca aggacatcct   1080

gagaaatatg gtaaaggtga accaaagact gaaagcaaaa gttcgaagtt taaaagtaac   1140

tcagattctg actataaagg tgaacgcatt aactcttctt gggagaaaga gacccctgga   1200

gaaaggtcac acagtcgagt agactctcaa agtgacaaaa aactagaaag acaaagtgaa   1260

agatcacaaa atataaatag gaaagaagtt aaatcacaag acaaagaaga aagaaaagtt   1320

gatcaaaaac ctaaatcagt agtaaaggac caagatcact ggagaagatc tgaacgagca   1380

tcacttcctc attccaagaa tgaaataaca ttttctcata attcaagtaa ataccatcta   1440

gaagagagaa gaggatggga agattgtaaa agagacaaga gtgtaaacag tcatagtttt   1500

caagatggaa gatgtccatc ttctctttca aacagtagaa ctcacaaaaa cattgactct   1560
```

```
aaggaagttg atgccatgca tcagtgggaa aatacacctt taaaagcaga aagacataga   1620
actgaagata agaggaaaag agaacaagaa agcaaagaag aaaataggca tattagaaat   1680
gaaaaaagag tacctacaga acatttgcag aagactaata aggaaactaa gaaaaccact   1740
actgatttaa agaaacagaa tgaaccaaag actgataagg gagaagtcct tgataatggt   1800
gtttctgaag gagcagataa taaagagctt gcaatgaaag ctgagagtgg tccaaatgaa   1860
acaaaaaaca aggacctaaa attgagtttt atgaaaaaat tgaacttaac tctttctcct   1920
gctaaaaagc aacctgtttc ccaggataat cagcataaaa taactgatat tcccaagtcc   1980
agtggtgtat gtgattcaga gtcttcaatg caagttaaaa cagtggcata tgttccctcc   2040
ataagtgaac atatcttggg ggaagcagct gtcagtgaac ataccatggg ggaaaccaag   2100
tcaacgttat tggaaccaaa ggttgctctt ctagcagtga ctgaacccag gatcggtatc   2160
tcagaaacca acaaggaaga cgaaaatagt ttgttagtta ggtctgttga caatactatg   2220
cattgtgaag agcccatttg tggtacagag acttccttcc catctcctat ggaaatacaa   2280
cagacagaat ccttgtttcc atcaacagga atgaaacaaa ccattaataa tggaagggca   2340
gcagctcctg tggtaatgga tgtattacaa acagatgtgt ctcaaaactt tggcttggaa   2400
ttggatacca aaagaaatga taattcagat tattgtggta tttctgaagg tatggagatg   2460
aaggtggcac tttcaacaac agtgagtgaa accactgaaa gcattttgca gccttcaatt   2520
gaggaagctg atattttgcc aataatgctt tcagaagata ataacccaaa atttgagcct   2580
tctgttatag ttacaccact ggttgagagt aagtcgtgtc atctggagcc ttgcttacct   2640
aaagagactc tagattcttc acttcagcag actgagttaa tggaccacag aatggcaact   2700
ggtgaaacaa actcagtata tcatgatgat gataactcgg ttttgagcat tgaccttaat   2760
cacctgagac ctattccaga agccatcagt cctctgaata gtccagtgag acctgtagca   2820
aaagttctta gaaatgaaag cccacctcaa gttccagtgt ataataacag tcataaagat   2880
gtgtttttac caaattcagc tcattctacc tctaagagtc agtctgatct caataaggaa   2940
aatcaaaagc caatttacaa atctgacaaa tgtacagaag cagacacatg taagaattca   3000
ccattagatg aattagaaga aggagaaatt agaagtgata gtgaaacatc taaaccacaa   3060
gaaagttttg aaaaaaattc caaacgtaga gtgtcagctg atgtgcggaa gtcaaagact   3120
atcccacgac gtgggaaaag tactgtgtgt ttagataaag acagtaggaa aacacatgta   3180
agaatccatc agaccaataa caaatggaat aaaagacctg ataaatctag cagatcttca   3240
aaaacagaga agaaagataa agtgatgagc acttccagct tggaaaaaat agttccaatt   3300
attgctgtac cctcttctga acaagagatc atgcacatgt tacgaatgat aagaaaacat   3360
gtaagaaaaa attatatgaa attcaaggca aaattttcat taatacaatt tcacagaatt   3420
attgagtcag caattttgag ttttacatct ttaattaaac atctcaactt acacaaaatc   3480
tctaagtcag tgactacctt acagaagaat ctctgtgata ttatagagtc taaacttaag   3540
caagttaaaa agaatggcat agttgatcgt ttatttgaac agcaactacc agatatgaaa   3600
aaaaaattgt ggaagtttgt agatgaccaa cttgattatt tgtttgcaaa gcttaagaaa   3660
atcttagtat gtgattccaa aagctttgga agagatagtg atgaaggcaa acttgaaaaa   3720
acaagtaaac agaatgcaca gtattcaaat agtcagaaaa ggagtgtgga caactccaac   3780
agagaattgc tgaaagaaaa attatcaaaa tcagaagacc ctgttcatta taagtcttta   3840
gtgggatgta aaaaatctga ggaaaattat caagaccaaa ataactccag tattaacact   3900
gtaaagcatg acattaaaaa aaattttaac atctgctttg ataatataaa gaactctcaa   3960
```

```
tccgaagagc gctccttgga agtacactgt ccaagcaccc caaagtcaga aaaaaacgaa   4020
ggaagcagca tagaggatgc acagacatcc cagcatgcaa ctttgaagcc agaacgaagt   4080
ttcgagattc ttaccgaaca gcaagcatcg agccttactt ttaatttagt gagtgatgca   4140
caaatgggtg aaatatttaa aagtttgttg caaggttctg atcttttaga cagcagtgtt   4200
aactgtactg aaaaaagtga gtgggagtta aagactccag agaagcagct gctagagact   4260
cttaagtgcg agtctatacc agcttgtaca acagaagagc tagtttcagg ggtggcttct   4320
ccatgtccta aaatgattag tgatgataat tggtcattat tatcatctga aaaaggtcca   4380
tctctgtctt cagggctttc attgccggtt catcctgatg tgttggatga aagttgtatg   4440
tttgaagtgt ctactaacct acctttaagt aaagataatg tgtgtagtgt agaaaagagc   4500
aagccctgcg tttcttccat acttcttgaa gatctagcag tctctttaac agtaccatcg   4560
cctctgaagt cagatggtca tctcagtttt ttaaagcctg atatgtcgtc cagttcaact   4620
cctgaagaag tcattagtgc tcattttagt gaagatgcct tacttgagga agaggatgca   4680
tctgagcaag atattcattt agctctggag tctgataatt caagcagtaa atcaagttgt   4740
tcttcttcct ggacaagccg atctgttgct ccaggctttc agtaccaccc taatctacct   4800
atgcatgccg tcataatgga aaagtccaat gatcatttca ttgtgaaaat acgacgtgca   4860
acaccatcta cctcttctgg ccttaaacag agtatgatgc ctgatgaatt attgacatct   4920
ttgcccagac atggaaagga agctgatgaa ggaccagaga aagaatatat ttcatgtcag   4980
aacacagttt ttaaatctgt ggaggaattg gaaaactcca acaaaaatgt tgatggcagc   5040
aagtcaactc atgaagaaca gagctctatg atacaaacac aggttcctga tatatatgaa   5100
tttcttaaag atgcttcaga taagatgggt catagtgatg aagtggctga tgaatgtttc   5160
aaattgcatc aagtatggga aacaaaagtg cctgaaagca ttgaagaatt gccttcaatg   5220
gaagaaatct cacactctgt tggggaacat cttccaaaca catacgtaga tctaacgaaa   5280
gatccagtca ctgaaaccaa aaacttgggg gaattcatag aagtaacagt tttacatatt   5340
gatcagttgg gatgttctgg aggcaattta aatcagagtg ctcaaatatt agacaattct   5400
ttgcaggctg atactgtagg tgcttttatt gatttgacac aagatgcttc aagtgaggct   5460
aaaagtgaag gtaatcatcc tgcattagct gtggaagact tgggatgtgg ggtgatacag   5520
gtagatgaag ataattgtaa ggaagaaaag gcacaagtgg caaacaggcc tttaaaatgc   5580
attgttgagg aaacctatat cgacttgacc acagaatctc ccagttcatg tgaagtaaaa   5640
aaagatgagt taaaatcaga gccaggatca aattgtgata actcggagtt gcctgggact   5700
ttgcataatt ctcacaaaaa gagaagaaac atttctgatc taaatcatcc tcataaaaaa   5760
caaagaaagg aaacagactt aactaataag gaaaagacca agaaacctac ccaagattct   5820
tgtgagaata ctgaagctca ccaaaagaaa gccagtaaga agaaggcccc tcctgtgact   5880
aaagatccct catcattaaa ggcaacccca gggattaagg attcatcagc agcacttgcc   5940
acttctacaa gtctttctgc aaaaaatgtt attaaaaaga agggagaaat tatcatttta   6000
tggacaagaa atgatgaccg ggaaatttta ttggagtgtc agaaaagagg gccatcattt   6060
aaaacatttg catatttagc cgccaagttg gataaaaatc caaatcaggt ctcagaaaga   6120
ttccagcagc taatgaagct ctttgaaaag tcaaaatgca gataagttgc tgaattcctg   6180
ggactcttaa ctgatattgc atactacaca gaagcttcaa attcctcatg ttttaaatga   6240
gcactagagg gaggtttatc accttttttgg ttaccagatg ataatctata tttgttatta   6300
```

```
ctcagtgact ctctaatttc acatcagcat gttcagcttg tgctagtcat cattctgatt   6360

tgcttatctg tttttggtca aaatatttat ttttaaacat gttagaactt accaaaatga   6420

aagcaacagt gatgtattga aatcttagtt ttgatatttt aaagaaatga ctttctagat   6480

taaaaaaata gttttgtagc attttaaact tagtgactat ttagttcaat tgttcatcca   6540

tttttattt gcttttataa ttgcctcctt gttttggtat attgtaaaat aatttaaata    6600

atgtatttat aaatatgtat aattatgatg taaaataccg tgtgtatatg tatgtatgtg   6660

tgtttctgta tatgcacaca cataaacggc tttgcctagc caaggatttt ttttatctgt   6720

ataaaacttt ttgtataaag tttgctttca ataacagtaa tgtataataa aaccatgtaa   6780

agttttgttg ta                                                      6792
```

<210> SEQ ID NO 46
<211> LENGTH: 1380
<212> TYPE: DNA
<213> ORGANISM: Homo sapiens

<400> SEQUENCE: 46

```
gttcgttgca acaaattgat gagcaatgct tttttataat gccaactttg tacaaaaaag     60

ttggcatgga cgaagcggat cggcggctcc tgcggcggtg ccggctgcgg ctggtggaag    120

agctgcaggt ggaccagctc tgggacgccc tgctgagccg cgagctgttc aggccccata    180

tgatcgagga catccagcgg gcaggctctg gatctcggcg ggatcaggcc aggcagctga    240

tcatagatct ggagactcga gggagtcagg ctcttccttt gttcatctcc tgcttagagg    300

acacaggcca ggacatgctg gcttcgtttc tgcgaactaa caggcaagca gcaaagttgt    360

cgaagccaac cctagaaaac cttaccccag tggtgctcag accagagatt cgcaaaccag    420

aggttctcag accggaaaca cccagaccag tggacattgg ttctggagga tttggtgatg    480

tcggtgctct tgagagtttg aggggaaatg cagatttggc ttacatcctg agcatggagc    540

cctgtggcca ctgcctcatt atcaacaatg tgaacttctg ccgtgagtcc gggctccgca    600

cccgcactgg ctccaacatc gactgtgaga agttgcggcg tcgcttctcc tcgctgcatt    660

tcatggtgga ggtgaagggc gacctgactg ccaagaaaat ggtgctggct ttgctggagc    720

tggcgcagca ggaccacggt gctctggact gctgcgtggt ggtcattctc tctcacggct    780

gtcaggccag ccacctgcag ttcccagggg ctgtctacgg cacagatgga tgccctgtgt    840

cggtcgagaa gattgtgaac atcttcaatg ggaccagctg ccccagcctg ggagggaagc    900

ccaagctctt tttcatccag gcctgtggtg gggagcagaa agaccatggg tttgaggtgg    960

cctccacttc ccctgaagac gagtcccctg gcagtaaccc cgagccagat gccaccccgt   1020

tccaggaagg tttgaggacc ttcgaccagc tggacgccat atctagtttg cccacaccca   1080

gtgacatctt tgtgtcctac tctactttcc caggttttgt ttcctggagg gaccccaaga   1140

gtggctcctg gtacgttgag accctggacg acatctttga gcagtgggct cactctgaag   1200

acctgcagtc cctcctgctt agggtcgcta atgctgtttc ggtgaaaggg atttataaac   1260

agatgcctgg ttgctttaat ttcctccgga aaaaactttt ctttaaaaca tcatacccaa   1320

ctttcttgta caaagttggc attataagaa agcattgctt atcaatttgt tgcaacgaac   1380
```

<210> SEQ ID NO 47
<211> LENGTH: 1572
<212> TYPE: DNA
<213> ORGANISM: Homo sapiens

<400> SEQUENCE: 47

```
gttcgttgca acaaattgat gagcaatgct tttttataat gccaactttg tacaaaaaag      60

ttggcatgtc tgctgaagtc atccatcagg ttgaagaagc acttgataca gatgagaagg     120

agatgctgct ctttttgtgc cgggatgttg ctatagatgt ggttccacct aatgtcaggg     180

accttctgga tattttacgg gaaagaggta agctgtctgt cggggacttg gctgaactgc     240

tctacagagt gaggcgattt gacctgctca aacgtatctt gaagatggac agaaaagctg     300

tggagaccca cctgctcagg aaccctcacc ttgtttcgga ctatagagtg ctgatggcag     360

agattggtga ggatttggat aaatctgatg tgtcctcatt aattttcctc atgaaggatt     420

acatgggccg aggcaagata agcaaggaga agagtttctt ggaccttgtg gttgagttgg     480

agaaactaaa tctggttgcc ccagatcaac tggatttatt agaaaaatgc ctaaagaaca     540

tccacagaat agacctgaag acaaaaatcc agaagtacaa gcagtctgtt caaggagcag     600

ggacaagtta caggaatgtt ctccaagcag caatccaaaa gagtctcaag gatccttcaa     660

ataacttcag gctccataat gggagaagta aagaacaaag acttaaggaa cagcttggcg     720

ctcaacaaga accagtgaag aaatccattc aggaatcaga agctttttttg cctcagagca     780

tacctgaaga gagatacaag atgaagagca agcccctagg aatctgcctg ataatcgatt     840

gcattggcaa tgagacagag cttcttcgag acaccttcac ttccctgggc tatgaagtcc     900

agaaattctt gcatctcagt atgcatggta tatcccagat tcttggccaa tttgcctgta     960

tgcccgagca ccgagactac gacagctttg tgtgtgtcct ggtgagccga ggaggctccc    1020

agagtgtgta tggtgtggat cagactcact cagggctccc cctgcatcac atcaggagga    1080

tgttcatggg agattcatgc ccttatctag cagggaagcc aaagatgttt tttattcaga    1140

actatgtggt gtcagagggc cagctggagg acagcagcct cttggaggtg gatgggccag    1200

cgatgaagaa tgtggaattc aaggctcaga agcgagggct gtgcacagtt caccgagaag    1260

ctgacttctt ctggagcctg tgtactgcgg acatgtccct gctggagcag tctcacagct    1320

caccatccct gtacctgcag tgcctctccc agaaactgag acaagaaaga aaacgcccac    1380

tcctggatct tcacattgaa ctcaatggct acatgtatga ttggaacagc agagtttctg    1440

ccaaggagaa atattatgtc tggctgcagc acactctgag aaagaaactt atcctctcct    1500

acacataccc aactttcttg tacaaagttg gcattataag aaagcattgc ttatcaattt    1560

gttgcaacga ac                                                        1572
```

<210> SEQ ID NO 48
<211> LENGTH: 3600
<212> TYPE: DNA
<213> ORGANISM: Homo sapiens

<400> SEQUENCE: 48

```
atcggcggcc cggaaccggc cttggaacaa ctgtggaacc tgaggccgct tgccctcccg      60

ccccatggag cggcccccgg ggctgcggcc gggcgcgggc gggccctggg agatgcggga     120

gcggctgggc accggcggct tcgggaacgt ctgtctgtac cagcatcggg aacttgatct     180

caaaatagca attaagtctt gtcgcctaga gctaagtacc aaaaacagag aacgatggtg     240

ccatgaaatc cagattatga agaagttgaa ccatgccaat gttgtaaagg cctgtgatgt     300

tcctgaagaa ttgaatattt tgattcatga tgtgcctctt ctagcaatgg aatactgttc     360

tggaggagat ctccgaaagc tgctcaacaa accagaaaat tgttgtggac ttaaagaaag     420

ccagatactt tctttactaa gtgatatagg gtctgggatt cgatatttgc atgaaaacaa     480
```

```
aattatacat cgagatctaa aacctgaaaa catagttctt caggatgttg gtggaaagat    540
aatacataaa ataattgatc tgggatatgc caaagatgtt gatcaaggaa gtctgtgtac    600
atcttttgtg ggaacactgc agtatctggc cccagagctc tttgagaata agccttacac    660
agccactgtt gattattgga gctttgggac catggtattt gaatgtattg ctggatatag    720
gccttttttg catcatctgc agccatttac ctggcatgag aagattaaga agaaggatcc    780
aaagtgtata tttgcatgtg aagagatgtc aggagaagtt cggtttagta gccatttacc    840
tcaaccaaat agcctttgta gtttagtagt agaacccatg gaaaactggc tacagttgat    900
gttgaattgg gaccctcagc agagaggagg acctgttgac cttactttga agcagccaag    960
atgttttgta ttaatggatc acattttgaa tttgaagata gtacacatcc taaatatgac   1020
ttctgcaaag ataatttctt ttctgttacc acctgatgaa agtcttcatt cactacagtc   1080
tcgtattgag cgtgaaactg gaataaatac tggttctcaa gaacttcttt cagagacagg   1140
aatttctctg gatcctcgga aaccagcctc tcaatgtgtt ctagatggag ttagaggctg   1200
tgatagctat atggtttatt tgtttgataa aagtaaaact gtatatgaag ggccatttgc   1260
ttccagaagt ttatctgatt gtgtaaatta tattgtacag gacagcaaaa tacagcttcc   1320
aattatacag ctgcgtaaag tgtgggctga agcagtgcac tatgtgtctg gactaaaaga   1380
agactatagc aggctctttc agggacaaag ggcagcaatg ttaagtcttc ttagatataa   1440
tgctaactta acaaaaatga agaacacttt gatctcagca tcacaacaac tgaaagctaa   1500
attggagttt tttcacaaaa gcattcagct tgacttggag agatacagcg agcagatgac   1560
gtatgggata tcttcagaaa aaatgctaaa agcatggaaa gaaatggaag aaaaggccat   1620
ccactatgct gaggttggtg tcattggata cctggaggat cagattatgt ctttgcatgc   1680
tgaaatcatg gagctacaga agagccccta tggaagacgt cagggagact tgatggaatc   1740
tctggaacag cgtgccattg atctatataa gcagttaaaa cacagacctt cagatcactc   1800
ctacagtgac agcacagaga tggtgaaaat cattgtgcac actgtgcaga gtcaggaccg   1860
tgtgctcaag gagctgtttg gtcatttgag caagttgttg ggctgtaagc agaagattat   1920
tgatctactc cctaaggtgg aagtggccct cagtaatatc aaagaagctg acaatactgt   1980
catgttcatg cagggaaaaa ggcagaaaga aatatggcat ctccttaaaa ttgcctgtac   2040
acagagttct gcccggtccc ttgtaggatc cagtctagaa ggtgcagtaa cccctcagac   2100
atcagcatgg ctgcccccga cttcagcaga acatgatcat tctctgtcat gtgtggtaac   2160
tcctcaagat ggggagactt cagcacaaat gatagaagaa aatttgaact gccttggcca   2220
tttaagcact attattcatg aggcaaatga ggaacagggc aatagtatga tgaatcttga   2280
ttggagttgg ttaacagaat gagttgtcac ttgttcactg tccccaaacc tatggaagtt   2340
gttgctatac atgttggaaa tgtgtttttc ccccatgaaa ccattcttca gacatcagtc   2400
aatggaagaa atggctatga acagaaacta catttctact atgatcagaa gaacatgatt   2460
ttacaagtat aacagttttg agtaattcaa gcctctaaac agacaggaat ttagaaaaag   2520
tcaatgtact tgtttgaata tttgttttaa taccacagct atttagaagc atcatcacga   2580
cacatttgcc ttcagtcttg gtaaaacatt acttatttaa ctgattaaaa ataccttcta   2640
tgtattagtg tcaactttta acttttgggc gtaagaccaa atgtagtttt gtatacagag   2700
aagaaaacct caagtaatag gcattttaag taaaagtcta cctgtgtttt tttctaaaaa   2760
ggctgctcac aagttctatt tcttgaagaa taaattctac ctccttgtgt tgcactgaac   2820
aggttctctt cctggcatca taaggagttg gtgtaatcat tttaaattcc actgaaaatt   2880
```

```
taacagtatc cccttctcat cgaagggatt gtgtatctgt gcttctaata ttagttggct   2940

ttcataaatc atgttgttgt gtgtatatgt atttaagatg tacatttaat aatatcaaag   3000

agaagatgcc tgttaattta taatgtattt gaaaattaca tgtttttca tttgtaaaaa   3060

tgagtcattt gtttaaacaa tctttcatgt cttgtcatac aaatttataa aggtctgcac   3120

tcctttatct gtaattgtaa ttccaaaatc caaaaagctc tgaaaacaag gtttccataa   3180

gcttggtgac aaaattcatt tgcttgcaat ctaatctgaa ctgaccttga atctttttat   3240

cccatttagt gtgaatattc ctttattttg ctgcttgatg atgagaggga gggctgctgc   3300

cacagactgt ggtgagggct ggttaatgta gtatggtata tgcacaaaac tacttttcta   3360

aaatctaaaa tttcataatt ctgaaacaac ttgccccaag ggtttcagag aaaggactgt   3420

ggacctctat catctgctaa gtaatttaga agatattatt tgtcttaaaa aatgtgaaat   3480

gcttttatat tctaatagtt tttcactttg tgtattaaat ggtttttaaa ttactttctt   3540

gatctctatt cattataaaa atcagattat aataaaacag ttgaatatgg cttaggaaaa   3600
```

```
<210> SEQ ID NO 49
<211> LENGTH: 597
<212> TYPE: DNA
<213> ORGANISM: Homo sapiens

<400> SEQUENCE: 49

atggaggcca gagacaaaca agtactccgc tcacttcgcc tggagctggg tgcagaggta     60

ttggtggagg gactggttct tcagtacctc taccaggaag gaatcttgac ggaaaaccat    120

attcaagaaa tcaatgctca aaccacaggc ctccggaaaa caatgctcct gctggatatc    180

ctaccttcca ggggccctaa agcatttgat acattcctag attccctaca ggagtttccc    240

tgggtcaggg agaagctgaa gaaggcaagg gaagaggcca tgaccgacct gcctgcaggt    300

gacagattga ctgggatccc ctcgcacatc ctcaacagct ccccatcaga ccggcagatt    360

aaccagctgg cccagaggct gggccctgag tgggagccca tggtgctgtc tctgggactg    420

tcccagacgg atatctaccg ctgtaaggcc aaccaccccc acaacgtgca gtcgcaggtg    480

gtggaggcct tcatccgttg gcggcagcgc ttcgggaagc aggccacctt ccagagcctg    540

cacaacgggc tgcgggctgt ggaggtggac cctcgctgc tcctgcacat gttggag       597
```

```
<210> SEQ ID NO 50
<211> LENGTH: 4425
<212> TYPE: DNA
<213> ORGANISM: Homo sapiens

<400> SEQUENCE: 50

gttcgttgca acaaattgat gagcaatgct tttttataat gccaactttg tacaaaaaag     60

ttggcaccat gaccgtgttc aggcaggaaa acgtggatga ttactacgac accggcgagg    120

aacttggcag tggacagttt gcggttgtga agaaatgccg tgagaaaagc accggcctcc    180

agtatgccgc caaattcatc aagaaaagga ggactaagtc cagccggcgg ggtgtgagcc    240

gcgaggacat cgagcgggag gtcagcatcc tgaaggagat ccagcacccc aatgtcatca    300

ccctgcacga ggtctatgag aacaagacgg acgtcatcct gatcttggaa ctcgttgcag    360

gtggcgagct gtttgacttc ttagctgaaa aggaatcttt aactgaagag gaagcaactg    420

aatttctcaa acaaattctt aatggtgttt actacctgca ctcccttcaa atcgcccact    480

ttgatcttaa gcctgagaac ataatgcttt tggatagaaa tgtccccaaa cctcggatca    540
```

```
agatcattga ctttgggttg gcccataaaa ttgactttgg aaatgaattt aaaaacatat    600
ttgggactcc agagtttgtc gctcctgaga tagtcaacta tgaacctctt ggtcttgagg    660
cagatatgtg gagtatcggg gtaataacct atatcctcct aagtggggcc tccccatttc    720
ttggagacac taagcaagaa acgttagcaa atgtatccgc tgtcaactac gaatttgagg    780
atgaatactt cagtaatacc agtgccctag ccaaagattt cataagaaga cttctggtca    840
aggatccaaa gaagagaatg acaattcaag atagtttgca gcatccctgg atcaagccta    900
aagatacaca acaggcactt agtagaaaag catcagcagt aaacatggag aaattcaaga    960
agtttgcagc ccggaaaaaa tggaaacaat ccgttcgctt gatatcactg tgccaaagat   1020
tatccaggtc attcctgtcc agaagtaaca tgagtgttgc cagaagcgat gatactctgg   1080
atgaggaaga ctcctttgtg atgaaagcca tcatccatgc catcaacgat gacaatgtcc   1140
caggcctgca gcaccttctg ggctcattat ccaactatga tgttaaccaa cccaacaagc   1200
acgggacacc tccattactc attgctgctg gctgtgggaa tattcaaata ctacagttgc   1260
tcattaaaag aggctcgaga atcgatgtcc aggataaggg cgggtccaat gccgtctact   1320
gggctgctcg gcatggccac gtcgatacct tgaaatttct cagtgagaac aaatgccctt   1380
tggatgtgaa agacaagtct ggagagatgg ccctccacgt ggcagctcgc tatggccatg   1440
ctgacgtggc tcagttactg tgcagcttcg gctcaaatcc caatatccag gacaaggaag   1500
aagaaacccc cctgcactgt gctgcttggc acggctatta ctctgtggcc aaagcccttt   1560
gtgaagccgg ctgtaacgtg aacatcaaga accgagaagg agagacgccc ctcctgacag   1620
cctctgccag ggctaccac gacatcgtgg agtgtctggc cgaacatgga gccgacctta    1680
atgcttgcga caaggacgga cacattgccc ttcatctggc tgtaagacgg tgtcagatgg   1740
aggtaatcaa gactctcctc agccaagggt gtttcgtcga ttatcaagac aggcacggca   1800
atactcccct ccatgtggca tgtaaagatg gcaacatgcc tatcgtggtg gccctctgtg   1860
aagcaaactg caatttggac atctccaaca agtatgggcg aacgcctctg caccttgcgg   1920
ccaacaacgg aatcctagac gtggtccggt atctctgtct gatgggagcc agcgttgagg   1980
cgctgaccac ggacggaaag acggcagaag atcttgctag atcggaacag cacgagcacg   2040
tagcaggtct ccttgcaaga cttcgaaagg atacgcaccg aggactcttc atccagcagc   2100
tccgacccac acagaacctg cagccaagaa ttaagctcaa gctgtttggc cactcgggat   2160
ccgggaaaac cacccttgta gaatctctca agtgtgggct gctgaggagc tttttcagaa   2220
ggcgtcggcc cagactgtct tccaccaact ccagcaggtt cccaccttca cccctggctt   2280
ctaagcccac agtctcagtg agcatcaaca acctgtaccc aggctgcgag aacgtgagtg   2340
tgaggagccg cagcatgatg ttcgagccgg gtcttaccaa agggatgctg gaggtgtttg   2400
tggccccgac ccaccacccg cactgctcgg ccgatgacca gtccaccaag gccatcgaca   2460
tccagaacgc ttatttgaat ggagttggcg atttcagcgt gtgggagttc tctggaaatc   2520
ctgtgtattt ctgctgttat gactattttg ctgcaaatga tcccacgtca atccatgttg   2580
ttgtctttag tctagaagag ccctatgaga tccagctgaa ccaagtgatt ttctggctca   2640
gtttcctgaa gtcccttgtc ccagttgaag aacccatagc cttcggtggc aagctgaaga   2700
acccactcca agttgtcctg gtggccaccc acgctgacat catgaatgtt cctcgaccgg   2760
ctggaggcga gtttggatat gacaaagaca catcgttgct gaaagagatt aggaacaggt   2820
ttggaaatga tcttcacatt tcaaataagc tgtttgttct ggatgctggg gcttctgggt   2880
caaaggacat gaaggtactt cgaaatcatc tgcaagaaat acgaagccag attgtttcgg   2940
```

```
tctgtcctcc catgactcac ctgtgtgaga aaatcatctc cacgctgcct tcctggagga   3000
agctcaatgg acccaaccag ctgatgtcgc tgcagcagtt tgtgtacgac gtgcaggacc   3060
agctgaaccc cctggccagc gaggaggacc tcaggcgcat tgctcagcag ctccacagca   3120
caggcgagat caacatcatg caaagtgaaa cagttcagga cgtgctgctc ctggaccccc   3180
gctggctctg cacaaacgtc ctggggaagt tgctgtccgt ggagacccca cgggcgctgc   3240
accactaccg ggccgctac accgtggagg acatccagcg cctggtgccc gacagcgacg   3300
tggaggagct gctgcagatc ctcgatgcca tggacatctg cgcccgggac ctgagcagcg   3360
ggaccatggt ggacgtccca gccctgatca agacagacaa cctgcaccgc tcctgggctg   3420
atgaggagga cgaggtgatg gtgtatggtg gcgtgcgcat cgtgcccgtg gaacacctca   3480
ccccttccc atgtggcatc tttcacaagg tccaggtgaa cctgtgccgg tggatccacc   3540
agcaaagcac agagggcgac gcggacatcc gcctgtgggt gaatggctgc aagctggcca   3600
accgtggggc cgagctgctg gtgctgctgg tcaaccacgg ccagggcatt gaggtccagg   3660
tccgcggcct ggagacggag aagatcaagt gctgcctgct gctggactcg gtgtgcagca   3720
ccattgagaa cgtcatggcc accacgctgc cagggctcct gaccgtgaag cattacctga   3780
gcccccagca gctgcgggag caccatgagc ccgtcatgat ctaccagcca cgggacttct   3840
tccgggcaca gactctgaag gaaacctcac tgaccaacac catgggggg tacaaggaaa   3900
gcttcagcag catcatgtgc ttcgggtgtc acgacgtcta ctcacaggcc agcctcggca   3960
tggacatcca tgcatcagac ctgaacctcc tcactcggag gaaactgagt cgcctgctgg   4020
acccgcccga ccccctgggg aaggactggt gccttctcgc catgaactta ggcctccctg   4080
acctcgtggc aaagtacaac accagtaacg gggctcccaa ggatttcctc cccagccccc   4140
tccacgccct gctgcgggaa tggaccacct accctgagag cacagtgggc accctcatgt   4200
ccaaactgag ggagctgggt cgccgggatg ccgcagactt tttgctgaag gcatcctctg   4260
tgttcaaaat caacctggat ggcaatggcc aggaggccta tgcctcgagc tgcaacagcg   4320
gcacctctta caattccatt agctctgttg tatcccggtt gccaactttc ttgtacaaag   4380
ttggcattat aagaaagcat tgcttatcaa tttgttgcaa cgaac                   4425
```

<210> SEQ ID NO 51
<211> LENGTH: 957
<212> TYPE: DNA
<213> ORGANISM: Homo sapiens

<400> SEQUENCE: 51

```
atggcgggcc taaagcggcg ggcaagccag gtgtggccag aagagcatgg tgagcaggaa     60
catgggctgt acagcctgca ccgcatgttt gacatcgtgg gcactcatct gacacacaga    120
gatgtgcgcg tgctttcttt cctctttgtt gatgtcattg atgaccacga gcgtggactc    180
atccgaaatg gacgtgactt cttattggca ctggagcgcc agggccgctg tgatgaaagt    240
aactttcgcc aggtgctgca gctgctgcgc atcatcactc gccacgacct gctgccctac    300
gtcaccctca agaggagacg ggctgtgtgc cctgatcttg tagacaagta tctggaggag    360
acatcaattc gctatgtgac ccccagagcc ctcagtgatc cagaaccaag gcctccccag    420
ccctctaaaa cagtgcctcc ccactatcct gtggtgtgtt gccccacttc gggtcctcag    480
atgtgtagca agcggccagc ccgagggaga gccacacttg ggagccagcg aaaacgccgg    540
aagtcagtga caccagatcc caaggagaag cagacatgtg acatcagact gcgggttcgg    600
```

gctgaatact gccagcatga gactgctctg cagggcaatg tcttctctaa caagcaggac 660
ccacttgagc gccagtttga gcgctttaac caggccaaca ccatcctcaa gtcccgggac 720
ctgggctcca tcatctgtga catcaagttc tctgagctca cctacctcga tgcattctgg 780
cgtgactaca tcaatggctc tttattagag gcacttaaag gtgtcttcat cacagactcc 840
ctcaagcaag ctgtgggcca tgaagccatc aagctgctgg taaatgtaga cgaggaggac 900
tatgagctgg gccgacagaa actcctgagg aacttgatgc tgcaagcatt gccctga 957

<210> SEQ ID NO 52
<211> LENGTH: 1110
<212> TYPE: DNA
<213> ORGANISM: Homo sapiens

<400> SEQUENCE: 52
gttcgttgca acaaattgat gagcaatgct tttttataat gccaactttg tacaaaaaag 60
ttggcatggc gctatccggg tcgaccccgg ccccgtgctg ggaggaggat gagtgcctgg 120
actactacgg gatgctgtcg cttcaccgta tgttcgaggt ggtgggcggg caactgaccg 180
agtgcgagct ggagctcctg gcctttctgc tggatgaggc tcctggcgcc gccggaggct 240
tagcccgggc ccgcagcggc ctagagctcc tgctggagct ggagcgccgc gggcagtgcg 300
acgagagcaa cctgcggctg ctggggcaac tcctgcgcgt gctggcccgc cacgacctgc 360
tgccgcacct ggcgcgcaag cggcgccggc cagtgtctcc agaacgctat agctatggca 420
cctccagctc ttcaaagagg acagagggta gctgccgtcg ccgtcggcag tcaagcagtt 480
ctgcaaattc tcagcagggt cagtgggaga caggctcccc cccaaccaag cggcagcggc 540
ggagtcgggg ccggcccagt ggtggtgcca gacggcggcg gagaggggcc ccagccgcac 600
cccagcagca gtcagagccc gccagacctt cctctgaagg caaagtgacc tgtgacatcc 660
ggctccgggt tcgagcagag tactgcgagc atgggccagc cttggagcag ggcgtggcat 720
cccggcggcc ccaggcgctg gcgcggcagc tggacgtgtt tgggcaggcc accgcagtgc 780
tgcgctcaag ggacctgggc tccgtggttt gtgacatcaa gttctcagag ctctcctatc 840
tggacgcctt ctggggcgac tacctgagtg gtgccctgct gcaggccctg cggggcgtgt 900
tcctgactga ggccctgcga gaggctgtgg gccgggaggc tgttcgcctg ctggtcagtg 960
tggatgaggc tgactatgag gctggccggc gccgcctgtt gctgatggag gaggaagggg 1020
ggcggcgccc gacagaggcc tcctgcccaa ctttcttgta caaagttggc attataagaa 1080
agcattgctt atcaatttgt tgcaacgaac 1110

<210> SEQ ID NO 53
<211> LENGTH: 2173
<212> TYPE: DNA
<213> ORGANISM: Homo sapiens

<400> SEQUENCE: 53
agttctgccg agatcgcaga atacacacaa gctacctttg ggcaccagag cagacagaac 60
cgcggagctt cagggtggaa gattcgtgga aactttgcca aggccaggac ctcgtgtgtt 120
cccgtccgcc cctctgggac ggcgccagcc cggcaggccg ccgaccgtcc tggggctccc 180
gcgcagcgcg atgccggcct cgtccaccgt ccacgtgctg cagctgctgc gggagctgct 240
cgccttcgtg ctcctcagct acacggtgct catcggggcg ctgctgctgg ccggctggac 300
cacttacttc ctggtgctga agtgacagcg ccgtcgccgc gcccggcccc gcctcccgcc 360
cggccccgcc tcccgcccgg ccccgcctcc ctaactcacc aggaaattcc cttcaagccc 420

```
tggcccgaac tgagtccccg cccacccgcc agcgtcacgg cgcccgactc agctccgcgc    480
cggacccacc tccgcgccct caggccctgc atatgccccg ccccgcgcgg aagttccggc    540
ggttggttgc cttgcgcggc cgttacagcc tttgccctaa gcctcgcccc ctttcccccct    600
gcctgcccaa tcccgactgc ttccttgggt gggggcgtgg ctatggggcg aggcgctctc    660
aggtggaggc cgtgccccgc tccgcgctca cgaagctgcg tcacttccgg cgtgtgcgtc    720
tggcgtccgc gcgctgcaca atggcggctc tgaagagttg gctgtcgcgc agcgtaactt    780
cattcttcag gtacagacag tgtttgtgtg ttcctgttgt ggctaacttt aagaagcggt    840
gtttctcaga attgataaga ccatggcaca aaactgtgac gattggcttt ggagtaaccc    900
tgtgtgcggt tcctattgca cagaaatcag agcctcattc ccttagtagt gaagcattga    960
tgaggagagc agtgtctttg gtaacagata gcacctctac ctttctctct cagaccacat   1020
atgcgttgat tgaagctatt actgaatata ctaaggctgt ttatacctta acttctcttt   1080
accgacaata tacaagttta cttgggaaaa tgaattcaga ggaggaagat gaagtgtggc   1140
aggtgatcat aggagccaga gctgagatga cttcaaaaca ccaagagtac ttgaagctgg   1200
aaaccacttg gatgactgca gttggtcttt cagagatggc agcagaagct gcatatcaaa   1260
ctggcgcaga tcaggcctct ataaccgcca ggaatcacat tcagctggtg aaactgcagg   1320
tggaagaggt gcaccagctc tcccggaaag cagaaaccaa gctggcagaa gcacagatag   1380
aagagctccg tcagaaaaca caggaggaag gggaggagcg ggctgagtcg gagcaggagg   1440
cctacctgcg tgaggattga gggcctgagc acactgccct gtctccccac tcagtgggga   1500
aagcaggggc agatgccacc ctgcccaggg ttggcatgac tgtctgtgca ccgagaagag   1560
gcggcagatc ctgccctggc caatcaggcg agacgccttt gtgagctgtg agtgcctcct   1620
gtggtctcag gcttgcgctg gacctggttc ttagcccttg ggcactgcac cctgtttaac   1680
atttcacccc actctgtaca gctgctctta cccatttttt ttacctcaca cccaaagcat   1740
tttgcctacc tgggtcagag agaggagtcc tttttgtcat gcccttaagt tcagcaactg   1800
tttaacctgt tttcagtctt atttacgtcg tcaaaaatga tttagtactt gttccctctg   1860
ttgggatgcc agttgtggca gggggagggg aacctgtcca gtttgtacga tttctttgta   1920
tgtatttctg atgtgttctc tgatctgccc ccactgtcct gtgaggacag ctgaggccaa   1980
ggagtgaaaa acctattact actaagagaa ggggtgcaga gtgtttacct ggtgctctca   2040
acaggactta acatcaacag gacttaacac aggcctcttg ttccttcctt tctttccgtt   2100
tctctattgt atccaaagga gaagagtgta agattttgtt tgcatctgaa agagaaaatg   2160
cgtctctcct ggg                                                      2173
```

<210> SEQ ID NO 54
<211> LENGTH: 3057
<212> TYPE: DNA
<213> ORGANISM: Homo sapiens

<400> SEQUENCE: 54

```
gcctggtaac cggtcgtggc tgtactggcg gcggcagggc tggcggctta ggccgcagag     60
gtctgtgggc ctgagcccac gctggactct gtccgttctg cgatgactgc tgctctggcc    120
gtcgtcacga cgtcgggttt ggaagatggg gtgcctaggt cccgtggcga agggaccggg    180
gaagtggtct tggagcgggg gcccggcgcg gcctaccaca tgttcgtggt gatggaggac    240
ttggtggaga agctgaagct gctccgctac gaggaggagt tcctccggaa gagcaacctg    300
```

```
aaggccccgt ccagacacta ttttgcactg cctaccaacc ctggcgaaca gttctacatg    360
ttttgtactc ttgctgcttg gttgattaat aaagcgggac gtccctttga gcagcctcaa    420
gaatatgatg accctaatgc aacaatatct aacatactat ccgagcttcg gtcatttgga    480
agaactgcag attttcctcc ttcaaaatta aagtcaggtt atggagaaca tgtatgctat    540
gttcttgatt gcttcgctga agaagcattg aaatatattg gtttcacctg gaaaaggcca    600
atatacccag tagaagaatt agaagaagaa agcgttgcag aagatgatgc agaattaaca    660
ttaaataaag tggatgaaga atttgtggaa gaagagacag ataatgaaga aaactttatt    720
gatctcaacg ttttaaaggc ccagacatat cacttggata tgaacgagac tgccaaacaa    780
gaagatattt tggaatccac aacagatgct gcagaatgga gcctagaagt ggaacgtgta    840
ctaccgcaac tgaaagtcac gattaggact gacaataagg attggagaat ccatgttgac    900
caaatgcacc agcacagaag tggaattgaa tctgctctaa aggagaccaa gggatttttg    960
gacaaactcc ataatgaaat tactaggact ttggaaaaga tcagcagccg agaaaagtac   1020
atcaacaatc agcttgagaa tttggttcaa gaatatcgtg cagctcaagc ccagctgagt   1080
gaggcaaagg agcgatacca gcagggaaat ggaggagtga cggaaagaac cagactcctc   1140
tctgaggtta tggaagaatt agaaaaggta aaacaagaaa tggaagaaaa gggcagcagc   1200
atgactgatg gtgctccttt ggtgaagatt aaacagagct taacaaaact gaagcaagaa   1260
actgtagaga tggacattag aattggcatt gtggaacaca cactactcca atcaaagctg   1320
aaggagaagt ccaacatgac taggaacatg catgccacag ttattccaga accagcaaca   1380
ggcttttatt aaaacatact ggttttcatg tttctgatta gttgggtttt ttatatcaaa   1440
ctatatttca tgttgcatag atttcaaaac ataattttat gttcaatggg tattttttta   1500
catatacata ctcacatatt atatcatggt gattatgatg gttaaagcct ttacactgaa   1560
tgtaatgttt aataaagaaa ttacaaattc tcactttcta agaagctttc actaatcatt   1620
acctatgtta aagctcccac ctggtggctc atttttcata gcattccttg tgtaagccaa   1680
ggtatatgac ctgcgttttc tgcagatgct gctgctgtca caacatgaac tgctgacaca   1740
gtcctttacc ttgctccacc tctgcagtga tcataagtgc tttgtgccca gaggccactg   1800
aagatggtag gcaggattct ttccaagaac ccaaactgcc tttgcctcag ctttatggtt   1860
acctaaaatt gccacttttt ttaggttaaa aaaaacttca gtatcctcat taacatttga   1920
agttggtttc ttatgaatat ttcgtggcta aaatgatttt atagggaatc tatcttctag   1980
gatctaagcc actaaataaa aggataaatg aatgatgata agtcagtcac tcatgtttga   2040
ctctgttctt agaatgaaga gaaggtgcat atgcatgtct caatttctac ctttttctgt   2100
ggtatcggct atactaggga accattttgt agaagaagga acgatgacag gtcgcatgaa   2160
gatcagcctc tagtactgat gatctttact tatgcatctt cctgagcaac tttctaggct   2220
aggatttcta aattggtgaa aaaagcagca ttagagtgcc agaattagca ctggggaaaa   2280
ctggccaggg gaacacaaag caggagacag cctgcgttaa tttttttttt ttaataattt   2340
tcaaaagcag tggtagaaaa tttgataaga atgctttatg tttaggacaa caaaaataat   2400
tttaaaaagt tattttttac cctaatactt ttctccactg aatattatta ttttttttctt  2460
agctttttct ttctagatgt attccccaac atgctcacat acacagatct ttccctttcc   2520
ttactagacc tctctttagt ttaagataag tttagacagg agaaagtgta tgtaaactac   2580
ctgaaaggat gacaatcaat acaatgacaa atatgccagt ttatttaatt tgtttaaaaa   2640
aaaaaaggca gaaaacccac catgggaaaa taagcatttt ttaaaatctg aagttgctct   2700
```

```
tttcctgtgt ggtctttggg aggagtctaa tacaaaaact gaaaaccttt ggtcctggga   2760

atttattttc atggctgttg tcatggctga gtagtttttt gatgaattca atcaatgcag   2820

agaacgcttt tagataaatc agaactctcc ttaaaatgca tttcaatcag aagcaaagta   2880

cacccattat ttatgcagac atgtaaaaaa tctaaaaatt cttgcaatga gtagtataag   2940

ccacctattt ttacttcctt ctctgaaata ttccagttaa ctcagcttgg gttctgtgct   3000

cctcctctct tcctatagaa cactgtgcat accttgaata aagagcttat tatacta      3057


<210> SEQ ID NO 55
<211> LENGTH: 627
<212> TYPE: DNA
<213> ORGANISM: Homo sapiens

<400> SEQUENCE: 55

atggacccgt tcctggtgct gctgcactcg gtgtcgtcca gcctgtcgag cagcgagctg     60

accgagctca agttcctatg cctcgggcgc gtgggcaagc gcaagctgga gcgcgtgcag    120

agcggcctag acctcttctc catgctgctg gagcagaacg acctggagcc cgggcacacc    180

gagctcctgc gcgagctgct cgcctccctg cggcgccacg acctgctgcg gcgcgtcgac    240

gacttcgagg cgggggcggc ggccggggcc gcgcctgggg aagaagacct gtgtgcagca    300

tttaacgtca tatgtgataa tgtggggaaa gattggagaa ggctggctcg tcagctcaaa    360

gtctcagaca ccaagatcga cagcatcgag gacagatacc cccgcaacct gacagagcgt    420

gtgcgggagt cactgagaat ctggaagaac acagagaagg agaacgcaac agtggcccac    480

ctggtggggg ctctcaggtc ctgccagatg aacctggtgg ctgacctggt acaagaggtt    540

cagcaggccc gtgacctcca gaacaggagt ggggccatgt ccccgatgtc atggaactca    600

gacgcatcta cctccgaagc gtcttaa                                        627


<210> SEQ ID NO 56
<211> LENGTH: 2755
<212> TYPE: DNA
<213> ORGANISM: Homo sapiens

<400> SEQUENCE: 56

cctacccgcg cgcaggccaa gttgctgaat caatggagcc ctccccaacc cgggcgttcc     60

ccagcgaggc ttccttccca tcctcctgac caccggggct tttcgtgagc tcgtctctga    120

tctcgcgcaa gagtgacaca caggtgttca aagacgcttc tggggagtga gggaagcggt    180

ttacgagtga cttggctgga gcctcagggg cgggcactgg cacggaacac accctgaggc    240

cagccctggc tgcccaggcg gagctgcctc ttctcccgcg ggttggtgga cccgctcagt    300

acggagttgg ggaagctctt tcacttcgga ggattgctca acaaccatgc tgggcatctg    360

gaccctccta cctctggttc ttacgtctgt tgctagatta tcgtccaaaa gtgttaatgc    420

ccaagtgact gacatcaact ccaagggatt ggaattgagg aagactgtta ctacagttga    480

gactcagaac ttggaaggcc tgcatcatga tggccaattc tgccataagc cctgtcctcc    540

aggtgaaagg aaagctaggg actgcacagt caatggggat gaaccagact gcgtgccctg    600

ccaagaaggg aaggagtaca cagacaaagc ccattttttct tccaaatgca gaagatgtag    660

attgtgtgat gaaggacatg gcttagaagt ggaaataaac tgcacccgga cccagaatac    720

caagtgcaga tgtaaaccaa acttttttttg taactctact gtatgtgaac actgtgaccc    780

ttgcaccaaa tgtgaacatg gaatcatcaa ggaatgcaca ctcaccagca acaccaagtg    840
```

```
caaagaggaa ggatccagat ctaacttggg gtggctttgt cttcttcttt tgccaattcc    900

actaattgtt tgggtgaaga gaaaggaagt acagaaaaca tgcagaaagc acagaaagga    960

aaaccaaggt tctcatgaat ctccaacttt aaatcctgaa acagtggcaa taaatttatc   1020

tgatgttgac ttgagtaaat atatcaccac tattgctgga gtcatgacac taagtcaagt   1080

taaaggcttt gttcgaaaga atggtgtcaa tgaagccaaa ataggtgaga tcaagaatga   1140

caatgtccaa gacacagcag aacagaaagt tcaactgctt cgtaattggc atcaacttca   1200

tggaaagaaa gaagcgtatg acacattgat taaagatctc aaaaaagcca atctttgtac   1260

tcttgcagag aaaattcaga ctatcatcct caaggacatt actagtgact cagaaaattc   1320

aaacttcaga aatgaaatcc aaagcttggt ctagagtgaa aaacaacaaa ttcagttctg   1380

agtatatgca attagtgttt gaaaagattc ttaatagctg gctgtaaata ctgcttggtt   1440

ttttactggg tacattttat catttattag cgctgaagag ccaacatatt tgtagatttt   1500

taatatctca tgattctgcc tccaaggatg tttaaaatct agttgggaaa acaaacttca   1560

tcaagagtaa atgcagtggc atgctaagta cccaaatagg agtgtatgca gaggatgaaa   1620

gattaagatt atgctctggc atctaacata tgattctgta gtatgaatgt aatcagtgta   1680

tgttagtaca aatgtctatc cacaggctaa ccccactcta tgaatcaata gaagaagcta   1740

tgaccttttg ctgaaatatc agttactgaa caggcaggcc actttgcctc taaattacct   1800

ctgataattc tagagatttt accatatttc taaactttgt ttataactct gagaagatca   1860

tatttatgta aagtatatgt atttgagtgc agaatttaaa taaggctcta cctcaaagac   1920

ctttgcacag tttattggtg tcatattata caatatttca attgtgaatt cacatagaaa   1980

acattaaatt ataatgtttg actattatat atgtgtatgc attttactgg ctcaaaacta   2040

cctacttctt tctcaggcat caaaagcatt ttgagcagga gagtattact agagctttgc   2100

cacctctcca tttttgcctt ggtgctcatc ttaatggcct aatgcacccc caaacatgga   2160

aatatcacca aaaaatactt aatagtccac caaaaggcaa gactgccctt agaaattcta   2220

gcctggtttg gagatactaa ctgctctcag agaaagtagc tttgtgacat gtcatgaacc   2280

catgtttgca atcaaagatg ataaaataga ttcttatttt tcccccaccc ccgaaaatgt   2340

tcaataatgt cccatgtaaa acctgctaca aatggcagct tatacatagc aatggtaaaa   2400

tcatcatctg gatttaggaa ttgctcttgt catacccccca agtttctaag atttaagatt   2460

ctccttacta ctatcctacg tttaaatatc tttgaaagtt tgtattaaat gtgaatttta   2520

agaaataata tttatatttc tgtaaatgta aactgtgaag atagttataa actgaagcag   2580

atacctggaa ccacctaaag aacttccatt tatggaggat ttttttgccc cttgtgtttg   2640

gaattataaa atataggtaa aagtacgtaa ttaaataatg tttttggtaa aaaaaaaaaa   2700

aaaaaaaaaa aaaaaaaaaa aaaaaaaaaa aaaaaaaaaa aaaaaaaaaa aaaaa        2755
```

<210> SEQ ID NO 57
<211> LENGTH: 975
<212> TYPE: DNA
<213> ORGANISM: Homo sapiens

<400> SEQUENCE: 57

```
gttcgttgca acaaattgat gagcaatgct tttttataat gccaactttg tacaaaaaag     60

ttggcatgca gcagcccttc aattacccat atccccagat ctactgggtg gacagcagtg    120

ccagctctcc ctgggcccct ccaggcacag ttcttccctg tccaacctct gtgcccagaa    180

ggcctggtca aaggaggcca ccaccaccac cgccaccgcc accactacca cctccgccgc    240
```

```
cgccgccacc actgcctcca ctaccgctgc cacccctgaa gaagagaggg aaccacagca    300

caggcctgtg tctccttgtg atgtttttca tggttctggt tgccttggta ggattgggcc    360

tggggatgtt tcagctcttc cacctacaga aggagctggc agaactccga gagtctacca    420

gccagatgca cacagcatca tctttggaga agcaaatagg ccaccccagt ccaccccctg    480

aaaaaaagga gctgaggaaa gtggcccatt taacaggcaa gtccaactca aggtccatgc    540

ctctggaatg ggaagacacc tatggaattg tcctgctttc tggagtgaag tataagaagg    600

gtggccttgt gatcaatgaa actgggctgt actttgtata ttccaaagta tacttccggg    660

gtcaatcttg caacaacctg cccctgagcc acaaggtcta catgaggaac tctaagtatc    720

cccaggatct ggtgatgatg gaggggaaga tgatgagcta ctgcactact gggcagatgt    780

gggcccgcag cagctacctg ggggcagtgt tcaatcttac cagtgctgat catttatatg    840

tcaacgtatc tgagctctct ctggtcaatt ttgaggaatc tcagacgttt ttcggcttat    900

ataagctcta cccaactttc ttgtacaaag ttggcattat aagaaagcat tgcttatcaa    960

tttgttgcaa cgaac                                                      975
```

```
<210> SEQ ID NO 58
<211> LENGTH: 3246
<212> TYPE: DNA
<213> ORGANISM: Homo sapiens

<400> SEQUENCE: 58
```

```
gttcgttgca acaaattgat gagcaatgct tttttataat gccaactttg tacaaaaaag     60

ttggcaccat ggatcggatg gccagctcca tgaagcaggt gcccaaccca ctgcccaagg    120

tgctgagccg gcgcggggtc ggcgctgggc tggaggcggc ggagcgcgag agcttcgagc    180

ggactcagac tgtcagcatc aataaggcca ttaatacgca ggaagtggct gtaaaggaaa    240

aacacgccag aacgtgcata ctgggcaccc accatgagaa aggggcacag accttctggt    300

ctgttgtcaa ccgcctgcct ctgtctagca acgcagtgct ctgctggaag ttctgccatg    360

tgttccacaa actcctccga gatggacacc cgaacgtcct gaaggactct ctgagataca    420

gaaatgaatt gagtgacatg agcaggatgt ggggccacct gagcgagggg tatggccagc    480

tgtgcagcat ctacctgaaa ctgctaagaa ccaagatgga gtaccacacc aaaaatccca    540

ggttcccagg caacctgcag atgagtgacc gccagctgga cgaggctgga gaaagtgacg    600

tgaacaactt tttccagtta acagtggaga tgtttgacta cctggagtgt gaactcaacc    660

tcttccaaac agtattcaac tccctggaca tgtcccgctc tgtgtccgtg acggcagcag    720

ggcagtgccg cctcgccccg ctgatccagg tcatcttgga ctgcagccac ctttatgact    780

acactgtcaa gcttctcttc aaactccact cctgcctccc agctgacacc ctgcaaggcc    840

accgggaccg cttcatggag cagtttacaa agttgaaaga tctgttctac cgctccagca    900

acctgcagta cttcaagcgg ctcattcaga tcccccagct gcctgagaac ccacccaact    960

tcctgcgagc ctcagccctg tcagaacata tcagccctgt ggtggtgatc cctgcagagg   1020

cctcatcccc cgacagcgag ccagtcctag agaaggatga cctcatggac atggatgcct   1080

ctcagcagaa tttatttgac aacaagtttg atgacatctt tggcagttca ttcagcagtg   1140

atcccttcaa tttcaacagt caaaatggtg tgaacaagga tgagaaggac cacttaattg   1200

agcgactata cagagagatc agtggattga aggcacagct agaaaacatg aagactgaga   1260

gccagcgggt tgtgctgcag ctgaagggcc acgtcagcga gctggaagca gatctggccg   1320
```

```
agcagcagca cctgcggcag caggcggccg acgactgtga attcctgcgg gcagaactgg   1380

acgagctcag gaggcagcgg gaggacaccg agaaggctca gcggagcctg tctgagatag   1440

aaaggaaagc tcaagccaat gaacagcgat atagcaagct aaaggagaag tacagcgagc   1500

tggttcagaa ccacgctgac ctgctgcgga agaatgcaga ggtgaccaaa caggtgtcca   1560

tggccagaca agcccaggta gatttggaac gagagaaaaa agagctggag gattcgttgg   1620

agcgcatcag tgaccagggc cagcggaaga ctcaagaaca gctggaagtt ctagagagct   1680

tgaagcagga acttgccaca agccaacggg agcttcaggt tctgcaaggc agcctggaaa   1740

cttctgccca gtcagaagca aactgggcag ccgagttcgc cgagctagag aaggagcggg   1800

acagcctggt gagtggcgca gctcataggg aggaggaatt atctgctctt cggaaagaac   1860

tgcaggacac tcagctcaaa ctggccagca cagaggaatc tatgtgccag cttgccaaag   1920

accaacgaaa aatgcttctg gtggggtcca ggaaggctgc ggagcaggtg atacaagacg   1980

ccctgaacca gcttgaagaa cctcctctca tcagctgcgc tgggtctgca gatcacctcc   2040

tctccacggt cacatccatt tccagctgca tcgagcaact ggagaaaagc tggagccagt   2100

atctggcctg cccagaagac atcagtggac ttctccattc cataaccctg ctggcccact   2160

tgaccagcga cgccattgct catggtgcca ccacctgcct cagagcccca cctgagcctg   2220

ccgactcact gaccgaggcc tgtaagcagt atggcaggga aaccctcgcc tacctggcct   2280

ccctggagga agagggaagc cttgagaatg ccgacagcac agccatgagg aactgcctga   2340

gcaagatcaa ggccatcggc gaggagctcc tgcccagggg actggacatc aagcaggagg   2400

agctggggga cctggtggac aaggagatgg cggccacttc agctgctatt gaaactgcca   2460

cggccagaat agaggagatg ctcagcaaat cccgagcagg agacacagga gtcaaattgg   2520

aggtgaatga aaggatcctt ggttgctgta ccagcctcat gcaggctatt caggtgctca   2580

tcgtggcctc taaggacctc cagagagaga ttgtggagag cggcaggggt acagcatccc   2640

ctaaagagtt ttatgccaag aactctcgat ggacagaagg acttatctca gcctccaagg   2700

ctgtgggctg gggagccact gtcatggtgg atgcagctga tctggtggta caaggcagag   2760

ggaaatttga ggagctaatg gtgtgttctc atgaaattgc tgctagcaca gcccagcttg   2820

tggctgcatc caaggtgaaa gctgataagg acagccctaa cctagcccag ctgcagcagg   2880

cctctcgggg agtgaaccag gccactgccg gcgttgtggc ctcaaccatt tccggcaaat   2940

cacagatcga agagacagac aacatggact tctcaagcat gacgctgaca cagatcaaac   3000

gccaagagat ggattctcag gttagggtgc tagagctaga aaatgaattg cagaaggagc   3060

gtcaaaaact gggagagctt cggaaaaagc actacgagct tgctggtgtt gctgagggct   3120

gggaagaagg aacagaggca tctccaccta cactgcaaga agtggtaacc gaaaaagaat   3180

tgccaacttt cttgtacaaa gttggcatta taagaaagca ttgcttatca atttgttgca   3240

acgaac                                                              3246
```

<210> SEQ ID NO 59
<211> LENGTH: 716
<212> TYPE: DNA
<213> ORGANISM: Homo sapiens

<400> SEQUENCE: 59

```
gaaacttggt gtccagggga ggcccccggc ggctggagcg cggcggcagc gggcgcagag     60

gccggaggga gaggaggcga ggggcggccc gagcgcgggg cgggagcgag gccagcggtc    120

atgtgcccgt gccccctgca ccgcggccgc ggcccccccgg ccgtgtgcgc ctgcagcgcg    180
```

```
ggtcgcctgg ggctgcgctc gtccgccgcg cagctcaccg ccgcccggct caaggcgcta    240

ggcgacgagc tgcaccagcg caccatgtgg cggcgccgcg cgcggagccg gagggcgccg    300

gcgcccggcg cgctccccac ctactggcct tggctgtgcg cggccgcgca ggtggcggcg    360

ctggcggcct ggctgctcgg caggcggaac ttgtaggaac gcggggcttc ttggtggggc    420

cggagccgag acccagccgg agcgagcaac aggttggtga aaccctgtg tccttggaga     480

aagctggttc ccgttttcca gagggggagc ccagagcttg aaaggccgcg gttggcactt    540

cgagaaggaa gtggagagta aagacagcgc ctggagcgat cgtagaaaca cagaatggga    600

ctggggaagc cctttggaaa tccagctgca gaaacagaca ccccaatgct atttacatac    660

agctctatat atataaaaaa agaaaatatg aatattaaaa aaaaaaaaaa aaaaaa        716
```

<210> SEQ ID NO 60
<211> LENGTH: 1506
<212> TYPE: DNA
<213> ORGANISM: Homo sapiens
<220> FEATURE:
<221> NAME/KEY: misc_feature
<222> LOCATION: (71)..(71)
<223> OTHER INFORMATION: n is a, c, g, or t

<400> SEQUENCE: 60

```
gttcgttgca acaaattgat gagcaatgct tttttataat gccaactttg tacaaaaaag     60

ttggcatggc ngcgccgagg gcggggcggg gtgcaggctg gagccttcgg gcatggcggg    120

ctttgggggg cattcgctgg gggaggagac cccgtttgac ccctgacctc cgggccctgc    180

tgacgtcagg aacttctgac ccccgggccc gagtgactta tgggaccccc agtctctggg    240

cccggttgtc tgttggggtc actgaacccc gagcatgcct gacgtctggg accccgggtc    300

cccgggcaca actgactgcg gtgaccccag ataccaggac ccgggaggcc tcagagaact    360

ctggaacccg ttcgcgcgcg tggctggcgg tggcgctggg cgctgggggg gcagtgctgt    420

tgttgttgtg gggcgggggt cggggtcctc cggccgtcct cgccgccgtc cctagcccgc    480

cgcccgcttc tccccggagt cagtacaact tcatcgcaga tgtggtggag aagacagcac    540

ctgccgtggt ctatatcgag atcctggacc ggcacccttt cttgggccgc gaggtcccta    600

tctcgaacgg ctcaggattc gtggtggctg ccgatgggct cattgtcacc aacgcccatg    660

tggtggctga tcggcgcaga gtccgtgtga gactgctaag cggcgacacg tatgaggccg    720

tggtcacagc tgtggatccc gtggcagaca tcgcaacgct gaggattcag actaaggagc    780

ctctccccac gctgcctctg ggacgctcag ctgatgtccg gcaaggggag tttgttgttg    840

ccatgggaag tccctttgca ctgcagaaca cgatcacatc cggcattgtt agctctgctc    900

agcgtccagc cagagacctg ggactccccc aaaccaatgt ggaatacatt caaactgatg    960

cagctattga ttttggaaac tctggaggtc ccctggttaa cctggatggg gaggtgattg   1020

gagtgaacac catgaaggtc acagctggaa tctcctttgc catcccttct gatcgtcttc   1080

gagagtttct gcatcgtggg gaaaagaaga attcctcctc cggaatcagt gggtcccagc   1140

ggcgctacat tggggtgatg atgctgaccc tgagtcccag catccttgct gaactacagc   1200

ttcgagaacc aagctttccc gatgttcagc atggtgtact catccataaa gtcatcctgg   1260

gctcccctgc acaccgggct ggtctgcggc ctggtgatgt gattttggcc attggggagc   1320

agatggtaca aaatgctgaa gatgtttatg aagctgttcg aacccaatcc cagttggcag   1380

tgcagatccg gcggggacga gaaacactga ccttatatgt gacccctgag gtcacagaat   1440
```

gcccaacttt cttgtacaaa gttggcatta taagaaagca ttgcttatca atttgttgca 1500
acgaac 1506

<210> SEQ ID NO 61
<211> LENGTH: 702
<212> TYPE: DNA
<213> ORGANISM: Homo sapiens

<400> SEQUENCE: 61
attgcaagtg taacacacat tgcaagtgcc aacgtgagga gccatggctg accaactctt 60
gcgtaaaaag agaagaattt ttatccattc agtgggtgca ggcacaataa atgccttgct 120
ggattgccta ttagaggatg aagttattag ccaggaagac atgaacaaag tgagagatga 180
aaatgacact gtcatggata aggctcgagt cttgattgac cttgttactg gaaaaggacc 240
caagtcttgc tgcaaattta tcaagcatct ctgtgaagaa gaccctcaac ttgcctcaaa 300
gatgggtttg cactaagaga gaagatggaa ctctggagca cttcagagac ttcccagagc 360
ttcttccaag ggagaagata ttctcgtgaa agaaaaaaac aaaacaaaac aacagtgctt 420
ttttcaaacc tgattaattt catcaatttc caataaatct ttcattctct catattactt 480
tcttcttatt ctttctctcc tcataccaac agaggataat tcatcaataa taatgaaggt 540
catgatgatt gtaatgtaat taagaaagtc cctccctttc ccttcctttc tgtttagttc 600
ctttgcaatc ctgtagagac atgtacagct tactttggtg cttttagcac tgagagtctg 660
ctgtgatggg aataaaatga agtcccagct cagaatttta aa 702

<210> SEQ ID NO 62
<211> LENGTH: 3938
<212> TYPE: DNA
<213> ORGANISM: Homo sapiens

<400> SEQUENCE: 62
gtgacgtcag agcaggaagt gtttgaggaa gtcgcgccgc gctgcccgcg ttaagattcc 60
cgcattttaa tgttttcagg ggggtgtcat agccccgggt ttggccgccc cagccccgcc 120
ttccccgccc cggggagccc gccccctgcc ccgcgtccct gccgacagag ttagcacgac 180
atcagtatga gctggtcacc ttccctgaca acgcagacat gtggggcctg ggaaatgaaa 240
gagcgccttg ggacaggggg atttggaaat gtcatccgat ggcacaatca ggaaacaggt 300
gagcagattg ccatcaagca gtgccggcag gagctcagcc cccggaaccg agagcggtgg 360
tgcctggaga tccagatcat gagaaggctg acccacccca atgtggtggc tgcccgagat 420
gtccctgagg ggatgcagaa cttggcgccc aatgacctgc ccctgctggc catggagtac 480
tgccaaggag gagatctccg gaagtacctg aaccagtttg agaactgctg tggtctgcgg 540
gaaggtgcca tcctcacctt gctgagtgac attgcctctg cgcttagata ccttcatgaa 600
aacagaatca tccatcggga tctaaagcca gaaaacatcg tcctgcagca aggagaacag 660
aggttaatac acaaaattat tgacctagga tatgccaagg agctggatca gggcagtctt 720
tgcacatcat tcgtggggac cctgcagtac ctggccccag agctactgga gcagcagaag 780
tacacagtga ccgtcgacta ctggagcttc ggcaccctgg cctttgagtg catcacgggc 840
ttccggccct tcctccccaa ctggcagccc gtgcagtggc attcaaaagt gcggcagaag 900
agtgaggtgg acattgttgt tagcgaagac ttgaatggaa cggtgaagtt ttcaagctct 960
ttaccctacc ccaataatct taacagtgtc ctggctgagc gactggagaa gtggctgcaa 1020
ctgatgctga tgtggcaccc ccgacagagg ggcacggatc ccacgtatgg gcccaatggc 1080

```
tgcttcaagg ccctggatga catcttaaac ttaaagctgg ttcatatctt gaacatggtc   1140
acgggcacca tccacaccta ccctgtgaca gaggatgaga gtctgcagag cttgaaggcc   1200
agaatccaac aggacacggg catcccagag gaggaccagg agctgctgca ggaagcgggc   1260
ctggcgttga tccccgataa gcctgccact cagtgtattt cagacggcaa gttaaatgag   1320
ggccacacat tggacatgga tcttgttttt ctctttgaca acagtaaaat cacctatgag   1380
actcagatct ccccacggcc ccaacctgaa agtgtcagct gtatccttca agagcccaag   1440
aggaatctcg ccttcttcca gctgaggaag gtgtggggcc aggtctggca cagcatccag   1500
accctgaagg aagattgcaa ccggctgcag cagggacagc gagccgccat gatgaatctc   1560
ctccgaaaca acagctgcct ctccaaaatg aagaattcca tggcttccat gtctcagcag   1620
ctcaaggcca agttggattt cttcaaaacc agcatccaga ttgacctgga gaagtacagc   1680
gagcaaaccg agtttgggat cacatcagat aaactgctgc tggcctggag ggaaatggag   1740
caggctgtgg agctctgtgg gcgggagaac gaagtgaaac tcctggtaga acggatgatg   1800
gctctgcaga ccgacattgt ggacttacag aggagcccca tgggccggaa gcagggggga   1860
acgctggacg acctagagga gcaagcaagg gagctgtaca ggagactaag ggaaaaacct   1920
cgagaccagc gaactgaggg tgacagtcag gaaatggtac ggctgctgct tcaggcaatt   1980
cagagcttcg agaagaaagt gcgagtgatc tatacgcagc tcagtaaaac tgtggtttgc   2040
aagcagaagg cgctggaact gttgcccaag gtggaagagg tggtgagctt aatgaatgag   2100
gatgagaaga ctgttgtccg gctgcaggag aagcggcaga aggagctctg gaatctcctg   2160
aagattgctt gtagcaaggt ccgtggtcct gtcagtggaa gcccggatag catgaatgcc   2220
tctcgactta gccagcctgg gcagctgatg tctcagccct ccacggcctc caacagctta   2280
cctgagccag ccaagaagag tgaagaactg gtggctgaag cacataacct ctgcaccctg   2340
ctagaaaatg ccatacagga cactgtgagg gaacaagacc agagtttcac ggccctagac   2400
tggagctggt tacagacgga agaagaagag cacagctgcc tggagcaggc ctcatgatgt   2460
ggggggactc gacccccctga catggggcag cccatagcag gccttgtgca gtggggggac   2520
tcgacccccct gacatggggc tgcctggagc aggccgcgtg acgtggggct gcctggccgc   2580
ggctctcaca tggtggttcc tgctgcactg atggcccagg ggtctctggt atccagatgg   2640
agctctcgct tcctcagcag ctgtgacttt cacccaggac ccaggacgca gccctccgtg   2700
ggcactgccg gcgccttgtc tgcacactgg aggtcctcca ttacagaggc ccagcgcaca   2760
tcgctggccc cacaaacgtt caggggtaca gccatggcag ctccttcctc tgccgtgaga   2820
aaagtgcttg gagtacggtt tgccacacac gtgactggac agtgtccaat tcaaatcttt   2880
cagggcagag tccgagcagc gcttggtgac agcctgtcct ctcctgctct ccaaaggccc   2940
tgctccctgt cctctctcac tttacagctt gtgtttcttc tggattcagc ttctcctaaa   3000
cagacagttt aattatagtt gcggcctggc cccatcctca cttcctcttt ttatttcact   3060
gctgctaaaa ttgtgttttt acctactact ttggtggttg tcctcttttc ggcaaagttg   3120
gagcgagtgc caagctctcc atctgtggtc ctttctgcca agagcgactc atagtaacca   3180
ggatgggaga gcagctgcct tattctgaat cccaaaaatt acttgggggt gattgtcaca   3240
gaggagggac agaaagggta tctgctgacc accagcctgc ctacccatgc ccatgtctcc   3300
attcctgctc aagcgtgtgt gctgggccgg ggagtccctg tctctcacag catctagcag   3360
tattattaaa tggattcatt ttaaaaatag ctcctatatt ttgtaacatg tctcaaacac   3420
```

```
tcatactggg ttccacaatc cactgttaga atacctatgg ttagggcttc tgaactaaaa   3480
taatggaaaa ttttaacaat ttgtatagtg cctggatcat tactagtgcc ataaccctgc   3540
ttcttcaaca tttcacagaa cttctctttt atataaaggc aagagcacaa aatgagttca   3600
gatgatcaca aacaggtgag ttttgttgga gaagaaagtt ggagtaggag actttcacaa   3660
gtggtttcca tggagataga atgaagcatt ctgtggtcaa gtaagtttag ggagctattc   3720
atgtttcact tgctttgtgg agattcacac tatgcactgg gaaagtatct gaaaagtctt   3780
ataataaaga aacaggctta actttgtgta agaacactgt ttatcaatgt catttggcta   3840
tagaaacatt ttctcctgct gattgtgtgt gtgaaacatg tattaacatt ccaatgaact   3900
agcatttaat aaagcacaat tttggaaacc ctggtaaa                           3938
```

<210> SEQ ID NO 63
<211> LENGTH: 3240
<212> TYPE: DNA
<213> ORGANISM: Homo sapiens

<400> SEQUENCE: 63

```
agtgctgagc ttggtgtccc accgccacaa ggaggcaggg aagaaaccca ctagtcccag     60
ctcctggggt ggcacagaca ttgcaactgg ccctgcctgt gggtcctagg ggcccttggc    120
taccaggagg ctaagaacac tgctcatgaa tgacagtgag ccctgaaagc tctgggggtg    180
tcacccagtc ccacaagcct gcatcccctg cagtggagat gggctcagct cctggacgtg    240
ccacagacag aaagcataac atacactcgc caggaagagc ctttgcctga ctcagggcag    300
ctcagagtgt ggggcagaag gtgaccagcc agctcagggc aggagatgca gagcacagcc    360
aattacctgt ggcacacaga tgacctgctg gggcaggggg ccactgccag tgtgtacaag    420
gcccgcaaca agaaatccgg agagctggtt gctgtgaagg tcttcaacac taccagctac    480
ctgcggcccc gcgaggtgca ggtgagggag tttgaggtcc tgcggaagct gaaccaccag    540
aacattgtca agctctttgc ggtggaggag acgggcggaa gccggcagaa ggtactggtg    600
atggagtact gctccagtgg gagcctgctg agtgtgctgg agagccctga gaatgccttt    660
gggctgcctg aggatgagtt cctggtggtg ctgcgctgtg tggtggccgg catgaaccac    720
ctgcgggaga acggcattgt gcatcgcgac atcaagccgg ggaacatcat gcgcctcgta    780
ggggaggagg ggcagagcat ctacaagctg acagacttcg gcgctgcccg ggagctggat    840
gatgatgaga agttcgtctc ggtctatggg actgaggagt acctgcatcc cgacatgtat    900
gagcgggcgg tgcttcgaaa gccccagcaa aaagcgttcg ggtgactgt ggatctctgg     960
agcattggag tgaccttgta ccatgcagcc actggcagcc tgcccttcat cccctttggt   1020
gggccacggc ggaacaagga gatcatgtac cggatcacca cggagaagcc ggctggggcc   1080
attgcaggtg cccagaggcg ggagaacggg cccctggagt ggagctacac cctccccatc   1140
acctgccagc tgtcactggg gctgcagagc cagctggtgc ccatcctggc caacatcctg   1200
gaggtggagc aggccaagtg ctggggcttc gaccagttct ttgcggagac cagtgacatc   1260
ctgcagcgag ttgtcgtcca tgtcttctcc ctgtcccagg cagtcctgca ccacatctat   1320
atccatgccc acaacacgat agccattttc caggaggccg tgcacaagca gaccagtgtg   1380
gccccccgac accaggagta cctctttgag ggtcacctct gtgtcctcga gcccagcgtc   1440
tcagcacagc acatcgccca cacgacggca agcagccccc tgaccctctt cagcacagcc   1500
atccctaagg ggctggcctt cagggaccct gctctggacg tccccaagtt cgtccccaaa   1560
gtggacctgc aggcggatta caacactgcc aagggcgtgt tgggcgccgg ctaccaggcc   1620
```

ctgcggctgg cacgggccct gctggatggg caggagctaa tgtttcgggg gctgcactgg 1680
gtcatggagg tgctccaggc cacatgcaga cggactctgg aagtggcaag gacatccctc 1740
ctctacctca gcagcagcct gggaactgag aggttcagca gcgtggctgg aacgcctgag 1800
atccaggaac tgaaggcggc tgcagaactg aggtccaggc tgcggactct agcggaggtc 1860
ctctccagat gctcccaaaa tatcacggag acccaggaga gcctgagcag cctgaaccgg 1920
gagctggtga agagccggga tcaggtacat gaggacagaa gcatccagca gattcagtgc 1980
tgtttggaca agatgaactt catctacaaa cagttcaaga agtctaggat gaggccaggg 2040
cttggctaca acgaggagca gattcacaag ctggataagg tgaatttcag tcatttagcc 2100
aaaagactcc tgcaggtgtt ccaggaggag tgcgtgcaga agtatcaagc gtccttagtc 2160
acacacggca agaggatgag ggtggtgcac gagaccagga accacctgcg cctggttggc 2220
tgttctgtgg ctgcctgtaa cacagaagcc cagggggtcc aggagagtct cagcaagctc 2280
ctggaagagc tatctcacca gctccttcag gaccgagcaa agggggctca ggcctcgccg 2340
cctcccatag ctccttaccc cagccctaca cgaaaggacc tgcttctcca catgcaagag 2400
ctctgcgagg ggatgaagct gctggcatct gacctcctgg acaacaaccg catcatcgaa 2460
cggctaaata gagtcccagc acctcctgat gtctgagctc catggggcac atgaggcatc 2520
ctgaagcatt agaatgattc caacactgct cttctgcacc atgagaccaa cccagggcaa 2580
gatcccatcc catcacatca gcctacctcc ctcctggctg ctggccagga tgtcgccagc 2640
attaccttcc actgcctttc tccctgggaa gcagcacagc tgagactggg caccaggcca 2700
cctctgttgg gacccacagg aaagagtgtg gcagcaactg cctggctgac ctttctatct 2760
tctctaggct caggtactgc tcctccatgc ccatggctgg gccgtgggga gaagaagctc 2820
tcatacgcct tcccactccc tctggtttat aggacttcac tccctagcca acaggagagg 2880
aggcctcctg ggggtttccccc agggcagtag gtcaaacgac ctcatcacag tcttccttcc 2940
tcttcaagcg tttcatgttg aacacagctc tctccgctcc cttgtgattt ctgagggtca 3000
ccactgccag cctcaggcaa catagagagc ctcctgttct ttctatgctt ggtctgactg 3060
agcctaaagt tgagaaaatg ggtggccaag gccagtgcca gtgtcttggg gccccttttgg 3120 ctctccctca ctctctgagg ctccagctgg tcctgggaca tgcagccagg actgtgagtc 3180
tgggcaggtc caaggcctgc accttcaaga agtggaataa atgtggcctt tgcttctgtt 3240

<210> SEQ ID NO 64
<211> LENGTH: 1990
<212> TYPE: DNA
<213> ORGANISM: Homo sapiens

<400> SEQUENCE: 64
gacaccggaa gccggaagcg tggtagggaa gggcgaccgc gaaactggga ctttctcgga 60
gcgccggggc ccttccagcg ttcacagtcc gccgctccca cccttctcac gtctgacgga 120
ctctgctgac agcccttgcc ctgttggatg aataggcacc tctggaagag ccaactgtgt 180
gagatggtgc agcccagtgg tggcccggca gcagatcagg acgtactggg cgaagagtct 240
cctctgggga agccagccat gctgcacctg ccttcagaac agggcgctcc tgagaccctc 300
cagcgctgcc tggaggagaa tcaagagctc cgagatgcca tccggcagag caaccagatt 360
ctgcgggagc gctgcgagga gcttctgcat ttccaagcca gccagaggga ggagaaggag 420
ttcctcatgt gcaagttcca ggaggccagg aaactggtgg agagactcgg cctggagaag 480

```
ctcgatctga agaggcagaa ggagcaggct ctgcgggagg tggagcacct gaagagatgc    540

cagcagcaga tggctgagga caaggcctct gtgaaagccc aggtgacgtc cttgctcggg    600

gagctgcagg agagccagag tcgcttggag gctgccacta aggaatgcca ggctctggag    660

ggtcgggccc gggcggccag cgagcaggcg cggcagctgg agagtgagcg cgaggcgctg    720

cagcagcagc acagcgtgca ggtggaccag ctgcgcatgc agggccagag cgtggaggcc    780

gcgctccgca tggagcgcca ggccgcctcg gaggagaaga ggaagctggc ccagttgcag    840

gtggcctatc accagctctt ccaagaatac gacaaccaca tcaagagcag cgtggtgggc    900

agtgagcgga agcgaggaat gcagctggaa gatctcaaac agcagctcca gcaggccgag    960

gaggccctgg tggccaaaca ggaggtgatc gataagctga aggaggaggc cgagcagcac   1020

aagattgtga tggagaccgt tccggtgctg aaggcccagg cggatatcta caaggcggac   1080

ttccaggctg agaggcaggc ccgggagaag ctggccgaga agaaggagct cctgcaggag   1140

cagctggagc agctgcagag ggagtacagc aaactgaagg ccagctgtca ggagtcggcc   1200

aggatcgagg acatgaggaa gcggcatgtc gaggtctccc aggccccctt gcccccgcc   1260

cctgcctacc tctcctctcc cctggccctg cccagccaga ggaggagccc ccccgaggag   1320

ccacctgact tctgctgtcc caagtgccag tatcaggccc ctgatatgga caccctgcag   1380

atacatgtca tggagtgcat tgagtagggc cggccagtgc aaggccactg cctgccgagg   1440

acgtgcccgg gaccgtgcag tctgcgcttt cctctcccgc ctgcctagcc caggatgaag   1500

ggctgggtgg ccacaactgg gatgccacct ggagccccac ccaggagctg gccgcggcac   1560

cttacgcttc agctgttgat ccgctggtcc cctcttttgg ggtagatgcg gccccgatca   1620

ggcctgactc gctgctcttt ttgttccctt ctgtctgctc gaaccacttg cctcgggcta   1680

atccctccct cttcctccac ccggcactgg ggaagtcaag aatggggcct ggggctctca   1740

gggagaactg cttcccctgg cagagctggg tggcagctct tcctcccacc ggacaccgac   1800

ccgcccgctg ctgtgccctg ggagtgctgc cctcttacca tgcacacggg tgctctcctt   1860

ttgggctgca tgctattcca ttttgcagcc agaccgatgt gtatttaacc agtcactatt   1920

gatggacatt tgggttgttt cccatctttt tgttaccata aataatggca tagtaaaaaa   1980

aaaaaaaaaa                                                          1990
```

<210> SEQ ID NO 65
<211> LENGTH: 2984
<212> TYPE: DNA
<213> ORGANISM: Homo sapiens

<400> SEQUENCE: 65

```
aggcgccgag cgcccgctga gcagccaccc tttgcgcgcc gcctgcagcg cagcttcccc     60

gggcgctgcc tggacaggcc tgcctgcgtg ctgggacatg tctggcctcc aaggaccgtc    120

ggtgggcgat ggctgcaacg gtggaggggc cagagctgga ggcagctgct gccgcaggag    180

atgcttcaga ggattcggac gcagggtcca gggcgctgcc tttcctgggc ggcaaccggc    240

tgagcttgga cctgtacccc gggggctgcc agcagctgct gcacctgtgt gtccagcagc    300

ctctgcagct gctgcaggtg gaattcttgc gtctgagcac tcacgaggac cctcagctgc    360

tggaggccac cctggcccag ctgcctcaga gcctgtcctg cctccgctcc ctggtcctca    420

aaggagggca acgccgggac acactgggtg cctgtctccg ggtgccctg accaacctgc     480

ccgctggtct gagtggcctg gcccatctgg cccacctgga cctgagcttc aacagcctgg    540

agacactgcc ggcctgtgtc ctgcagatgc gaggtctggg tgcgctcttg ctgtctcaca    600
```

```
actgcctctc tgagctgcct gaggctctgg gggccctccc cgccctcacc ttcctcacag    660
tgacacacaa ccgcctgcag acgctgcccc cagcactggg ggccctatcc accctgcagc    720
gcctcgatct ctctcagaat ctgctggaca cgctacctcc tgagattgga ggcctgggca    780
gcctcctgga gctcaacctg gcctccaacc ggctgcagag cctcccagcc tctctggcgg    840
gacttcggtc cttgcggctc cttgtcctgc acagcaacct cctggcctct gtgccagctg    900
acttggcccg ccttccactc ctcacccggc tcgacctgag ggacaaccag ctccgggacc    960
tgccccctga gctgctagac gccccctttg tgcgcctgca ggggaacccc ctgggtgagg   1020
cctcgccaga cgcccccgagt tcaccagtgg cagccctcat tccagaaatg cccagactgt  1080
tcctgacctc agatttggac agctttcctg tgacccctca aggctgctca gtgaccctgg   1140
cctgtggcgt ccgcctgcag ttcccagcgg gagccaccgc cacccccatc accatccgct   1200
atcggctgct gctgccggag ccaggcctcg tccccctggg tcctcatgac gccctgctca   1260
gccatgtgct ggagctgcag ccccatgggg tggccttcca gcaggatgtg gggctgtggc   1320
tgctcttcac cccaccgcag gcccggcgct gccgtgaagt ggtggtcagg acccggaatg   1380
acaacagctg gggtgacctg gagacctacc tggaggaaga ggcaccccag cggctctggg   1440
ctcactgcca ggtgccccac ttctcctggt tccttgtggt ttcccgccct gtgtccaatg   1500
cctgcctggt gccaccggag gggacactgc tgtgctcctc gggtcatcct ggggtcaaag   1560
tcatcttccc ccctggggcc actgaggagc ctcgtcgagt ctccatgcag gtggtgcgca   1620
tggctggccg agagctgcag gccctcctgg gagaaccaga ggctgcagtg agccccctgc   1680
tgtgcctgtc acagagcggt ccccccagct tcctccaacc ggtcaccgtg cagctgcctc   1740
tgccctctgg catcacaggc ctcagtctgg accgctcccg cctgcacctg ttgtactggg   1800
cccctcctgc agccacctgg gatgacatca cagctcaggt ggtcctggag ctcacccacc   1860
tgtacgcacg cttccaggtc acacacttct cctggtactg gctctggtac accaccaaga   1920
actgtgtggg aggcctggct cggaaggcct gggagcggct gcggctgcac cgtgtgaacc   1980
tcatcgctct gcagcggcgc cgggaccctg agcaggtcct gctgcagtgc ctgccccgaa   2040
acaaggtgga cgccaccctt cggcggctgc tggagcggta ccggggcccc gagccctctg   2100
acacggtgga gatgttcgag ggcgaagagt tctttgcggc cttcgagcgc ggcatcgacg   2160
tggatgctga ccgccctgac tgtgtggagg gcagaatctg ctttgtcttc tactcgcacc   2220
tgaagaatgt gaaggaggta tacgtgacca ccactctgga ccgggaggct caggctgtgc   2280
ggggccaggt gtccttctac cgtggcgcgg tgcctgtgcg ggtgcccgag gaggctgagg   2340
ctgcccggca gaggaagggc gcagacgccc tgtggatggc cactctgccc atcaagctgc   2400
cgagacttcg agggtccgag gggccacggc gggggctgg cctctccttg gcacccttga    2460
atctgggaga tgccgagacc ggctttctga cgcagagcaa cctgctgagt gtggctgggc   2520
gtctgggtct ggactggcca gccgtggccc tgcacctggg ggtgtcctac cgggaggtgc   2580
agcgcatccg gcacgagttc cgggatgatc tggatgagca gatccgtcac atgctcttct   2640
cctgggctga gcgccaggct gggcagccag ggctgtgggg gctcctggtg caggccctgg   2700
agcagagtga ccggcaggac gtggctgaag aggtgcgcgc agtcttggag ctcggccgcc   2760
gcaagtacca ggacagcatc cgacgcatgg gcttggcccc caaggacccc gctctgcctg   2820
gctcctcggc tccacagccc ccagagcctg cccaggccta ggccccacag acttttaggc   2880
tggcccagat attccccagt ggatgggcag agcccccacc ttcaagtctc tccagtgtgt   2940
```

ggggacgggt ccctgtgagc aacaaaactg cactgtttct ttca 2984

<210> SEQ ID NO 66
<211> LENGTH: 618
<212> TYPE: DNA
<213> ORGANISM: Homo sapiens

<400> SEQUENCE: 66
atgacaccac ctgaacgtct cttcctccca agggtgcgtg gcaccaccct acacctcctc 60
cttctggggc tgctgctggt tctgctgcct ggggcccagg ggctccctgg tgttggcctc 120
acaccttcag ctgcccagac tgcccgtcag caccccaaga tgcatcttgc ccacagcacc 180
ctcaaacctg ctgctcacct cattggagac cccagcaagc agaactcact gctctggaga 240
gcaaacacgg accgtgcctt cctccaggat ggtttctcct tgagcaacaa ttctctcctg 300
gtccccacca gtggcatcta cttcgtctac tcccaggtgg tcttctctgg gaaagcctac 360
tctcccaagg ccacctcctc cccactctac ctggcccatg aggtccagct cttctcctcc 420
cagtacccct tccatgtgcc tctcctcagc tcccagaaga tggtgtatcc agggctgcag 480
gaaccctggc tgcactcgat gtaccacggg gctgcgttcc agctcaccca gggagaccag 540
ctatccaccc acacagatgg catcccccac ctagtcctca gccctagtac tgtcttcttt 600
ggagccttcg ctctgtag 618

<210> SEQ ID NO 67
<211> LENGTH: 1709
<212> TYPE: DNA
<213> ORGANISM: Homo sapiens

<400> SEQUENCE: 67
atgggggcac tggggctgga gggcaggggt gggaggctcc aggggagggg ttccctcctg 60
ctagctgtgg caggagccac ttctctggtg accttgttgc tggcggtgcc tatcactgtc 120
ctggctgtgc tggccttagt gccccaggat cagggaggac tggtgagtgg ctgcaacagg 180
ccctggtgga gagttgtatc ttgcggatgc ttggctccct ctggttgtgc ctgtggtctt 240
ttgccccctc tggctcagct ggctcggctg tccctggtgg ggatgtcttg tctctttgct 300
gactctcttt ccatgttcct gtgatgttgt gcttgtgtcc cgacataagc cccttgtgtc 360
tcctctcctc ttcccgaggt acatctgttt ctccgcccaa gtacctatgc cttgcttgtt 420
ctcccttcta aggaggtgtg tgttggggat ggtgctggta ggagaaaccc caggcctgca 480
gcttgggtcc actttcagag ggtaggggt gacatgagct gaatctgaac tctgggcact 540
gtgaccccac ccaaccaggt aacggagacg gccgaccccg gggcacaggc ccagcaagga 600
ctgggtaaga gcagactgtc tctccttccc cgcttcagac cctcaggggc tcccagctcc 660
ctgctgcgtc cccagatacc tcttcctcta ggaatccagg ctccccatcc ctgcgccctg 720
ttctctcaag ggtagcctgc atgggtggct gccctgcccc caatcgtgga ctctttgccc 780
cttccagggt ttcagaagct gccagaggag gagccagaaa cagatctcag ccccgggctc 840
ccagctgccc acctcatagg taaggacctc caagacctga ataagagtgt aaataatccg 900
aaggttccag ttctgctcgc ccagagtcct tcggctccat gattccagtg ctcggtttcc 960
cacccgcttc acgacctttt gtcgctcgtg cccactctta cgctcgtccc cgcagtgtag 1020
tttcttcttc cctccggtgc aagcaaaagc cggcctggag gtccccacta cagcgttctg 1080
caccccacat ccgtgttccc tcggccccca actcgcactc atcccagaaa cagcaccatc 1140
cctcctcccc cggcccggct cggctcccgc aggggctaaa agccgccact tccccagaag 1200

```
tcccaagcct ttaggatcgc attcccaaga gcgcgtcggc ccgtgtctcc gcaggcgctc   1260

cgctgaaggg gcaggggcta ggctgggaga cgacgaagga acaggcgttt ctgacgagcg   1320

ggacgcagtt ctcggacgcc gaggggctgg cgctcccgca ggacggcctc tattacctct   1380

actgtctcgt cggctaccgg ggccgggcgc cccctggcgg cggggacccc cagggccgct   1440

cggtcacgct gcgcagctct ctgtaccggg cggggggcgc ctacgggccg ggcactcccg   1500

agctgctgct cgagggcgcc gagacggtga ctccagtgct ggacccggcc aggagacaag   1560

ggtacgggcc tctctggtac acgagcgtgg ggttcggcgg cctggtgcag ctccggaggg   1620

gcgagagggt gtacgtcaac atcagtcacc ccgatatggt ggacttcgcg agagggaaga   1680

ccttctttgg ggccgtgatg gtggggtga                                     1709
```

<210> SEQ ID NO 68
<211> LENGTH: 1182
<212> TYPE: DNA
<213> ORGANISM: Homo sapiens

<400> SEQUENCE: 68

```
gttcgttgca acaaattgat gagcaatgct tttttataat gccaactttg tacaaaaaag     60

ttggcatgtt tggcctcaaa agaaacgcgg taatcggact caacctctac tgtggggggg    120

ccggcttggg ggccggcagc ggcggcgcca cccgcccggg agggcgactt ttggctacgg    180

agaaggaggc ctcggcccgg cgagagatag gggsagggga ggccggcgcg gtgattggcg    240

gaagcgccgg cgcaagcccc ccgtccaccc tcacgccaga ctcccggagg gtcgcgcggc    300

cgccgcccat tggcgccgag gtccccgacg tcaccgcgac cccgcgaggg ctgcttttct    360

tcgcgcccac ccgccgcgcg gcgccgcttg aggagatgga agccccggcc gctgacgcca    420

tcatgtcgcc cgaagaggag ctggacgggt acgagccgga gcctctcggg aagcggccgg    480

ctgtcctgcc gctgctggag ttggtcgggg aatctggtaa taacaccagt acggacgggt    540

cactaccctc gacgccgccg ccagcagagg aggaggagga cgagttgtac cggcagtcgc    600

tggagattat ctctcggtac cttcgggagc aggccaccgg cgccaaggac acaaagccaa    660

tgggcaggtc tggggccacc agcaggaagg cgctggagac cttacgacgg gttggggatg    720

gcgtgcagcg caaccacgag acggccttcc aaggcatgct tcggaaactg gacatcaaaa    780

acgaagacga tgtgaaatcg ttgtctcgag tgatgatcca tgttttcagc gacggcgtaa    840

caaactgggg caggattgtg actctcattt cttttggtgc ctttgtggct aaacacttga    900

agaccataaa ccaagaaagc tgcatcgaac cattagcaga aagtatcaca gacgttctcg    960

taaggacaaa acgggactgg ctagttaaac aaagaggctg ggatgggttt gtggagttct   1020

tccatgtaga ggacctagaa ggtggcatca ggaatgtgct gctggctttt gcaggtgttg   1080

ctggagtagg agctggtttg gcatatctaa taagataccc aactttcttg tacaaagttg   1140

gcattataag aaagcattgc ttatcaattt gttgcaacga ac                      1182
```

<210> SEQ ID NO 69
<211> LENGTH: 5610
<212> TYPE: DNA
<213> ORGANISM: Homo sapiens

<400> SEQUENCE: 69

```
gttgactagg cgctgttctt gctggctggt gccccagggc ctggagaggt ctgaagaaac     60

ctgggagcca gcagcccggg gctccactct gggttctgaa agcccattcc ctgctctgcg    120
```

```
gctcctccca ccccacctct tctcagcctt gcagctcaag ggttgatctc aggagtccag    180
gacccaggag agggaagaat ctgaggaaca cagaacagtg agcgttgccc acaccccatc    240
tcccgtcacc acatctcccc tcaccctcac cctccctgcc tggccctgga ccccatccca    300
ggacctccct atcagctgac ttcttccagt gtcttgcagg cccctctggg ctcctccctc    360
ccctggcttt tcctaccact ccccctctat cggcgtctat ctgtaggtgc cctgggattt    420
ataaaactgg gttccgaatg ctgaataaga gacggtaaga gccaaggcaa aggacagcac    480
tgttctctgc ctgcctgata ccctcaccac ctgggaacat cccccagaca ccctcttaac    540
tccgggacag agatggctgg cggagcctgg ggccgcctgg cctgttactt ggagttcctg    600
aagaaggagg agctgaagga gttccagctt ctgctcgcca ataaagcgca ctccaggagc    660
tcttcgggtg agacacccgc tcagccagag aagacgagtg gcatggaggt ggcctcgtac    720
ctggtggctc agtatgggga gcagcgggcc tgggacctag ccctccatac ctgggagcag    780
atggggctga ggtcactgtg cgcccaagcc caggaagggg caggccactc tccctcattc    840
ccctacagcc caagtgaacc ccacctgggg tctcccagcc aacccacctc caccgcagtg    900
ctaatgccct ggatccatga attgccggcg gggtgcaccc agggctcaga gagaagggtt    960
ttgagacagc tgcctgacac atctggacgc cgctggagag aaatctctgc ctcactcctc   1020
taccaagctc ttccaagctc cccagaccat gagtctccaa gccaggagtc acccaacgcc   1080
cccacatcca cagcagtgct ggggagctgg ggatccccac ctcagcccag cctagcaccc   1140
agagagcagg aggctcctgg gacccaatgg cctctggatg aaacgtcagg aatttactac   1200
acagaaatca gagaaagaga gagagagaaa tcagagaaag gcaggccccc atgggcagcg   1260
gtggtaggaa cgcccccaca ggcgcacacc agcctacagc cccaccacca cccatgggag   1320
ccttctgtga gagagagcct ctgttccaca tggccctgga aaaatgagga ttttaaccaa   1380
aaattcacac agctgctact tctacaaaga cctcacccca gaagccaaga tcccctggtc   1440
aagagaagct ggcctgatta tgtggaggag aatcgaggac atttaattga gatcagagac   1500
ttatttggcc caggcctgga tacccaagaa cctcgcatag tcatactgca gggggctgct   1560
ggaattggga agtcaacact ggccaggcag gtgaaggaag cctgggggag aggccagctg   1620
tatggggacc gcttccagca tgtcttctac ttcagctgca gagagctggc ccagtccaag   1680
gtggtgagtc tcgctgagct catcggaaaa gatgggacag ccactccggc tcccattaga   1740
cagatcctgt ctaggccaga gcggctgctc ttcatcctcg atggtgtaga tgagccagga   1800
tgggtcttgc aggagccgag ttctgagctc tgtctgcact ggagccagcc acagccggcg   1860
gatgcactgc tgggcagttt gctggggaaa actatacttc ccgaggcatc cttcctgatc   1920
acggctcgga ccacagctct gcagaacctc attccttctt tggagcaggc acgttgggta   1980
gaggtcctgg ggttctctga gtccagcagg aaggaatatt tctacagata tttcacagat   2040
gaaaggcaag caattagagc ctttaggttg gtcaaatcaa acaaagagct ctgggccctg   2100
tgtcttgtgc cctgggtgtc ctggctggcc tgcacttgcc tgatgcagca gatgaagcgg   2160
aaggaaaaac tcacactgac ttccaagacc accacaaccc tctgtctaca ttaccttgcc   2220
caggctctcc aagctcagcc attgggaccc cagctcagag acctctgctc tctggctgct   2280
gagggcatct ggcaaaaaaa gacccttttc agtccagatg acctcaggaa gcatgggtta   2340
gatggggcca tcatctccac cttcttgaag atgggtattc ttcaagagca ccccatccct   2400
ctgagctaca gcttcattca cctctgtttc caagagttct ttgcagcaat gtcctatgtc   2460
ttggaggatg agaaggggag aggtaaacat tctaattgca tcatagattt ggaaaagacg   2520
```

```
ctagaagcat atggaataca tggcctgttt ggggcatcaa ccacacgttt cctattgggc   2580
ctgttaagtg atgaggggga gagagagatg gagaacatct ttcactgccg gctgtctcag   2640
gggaggaacc tgatgcagtg ggtcccgtcc ctgcagctgc tgctgcagcc acactctctg   2700
gagtccctcc actgcttgta cgagactcgg aacaaaacgt tcctgacaca agtgatggcc   2760
catttcgaag aaatgggcat gtgtgtagaa acagacatgg agctcttagt gtgcactttc   2820
tgcattaaat tcagccgcca cgtgaagaag cttcagctga ttgagggcag gcagcacaga   2880
tcaacatgga gccccaccat ggtagtcctg ttcaggtggg tcccagtcac agatgcctat   2940
tggcagattc tcttctccgt cctcaaggtc accagaaacc tgaaggagct ggacctaagt   3000
ggaaactcgc tgagccactc tgcagtgaag agtctttgta agaccctgag acgccctcgc   3060
tgcctcctgg agaccctgcg gttggctggc tgtggcctca cagctgagga ctgcaaggac   3120
cttgcctttg ggctgagagc caaccagacc ctgaccgagc tggacctgag cttcaatgtg   3180
ctcacggatg ctggagccaa acacctttgc cagagactga gacagccgag ctgcaagcta   3240
cagcgactgc agctggtcag ctgtggcctc acgtctgact gctgccagga cctggcctct   3300
gtgcttagtg ccagccccag cctgaaggag ctagacctgc agcagaacaa cctggatgac   3360
gttggcgtgc gactgctctg tgaggggctc aggcatcctg cctgcaaact catacgcctg   3420
gggctggacc agacaactct gagtgatgag atgaggcagg aactgagggc cctggagcag   3480
gagaaacctc agctgctcat cttcagcaga cggaaaccaa gtgtgatgac ccctactgag   3540
ggcctggata cgggagagat gagtaatagc acatcctcac tcaagcggca gagactcgga   3600
tcagagaggg cggcttccca tgttgctcag gctaatctca aactcctgga cgtgagcaag   3660
atcttcccaa ttgctgagat tgcagaggaa agctccccag aggtagtacc ggtggaactc   3720
ttgtgcgtgc cttctcctgc ctctcaaggg gacctgcata cgaagccttt ggggactgac   3780
gatgacttct ggggccccac ggggcctgtg gctactgagg tagttgacaa agaaaagaac   3840
ttgtaccgag ttcacttccc tgtagctggc tcctaccgct ggcccaacac gggtctctgc   3900
tttgtgatga gagaagcggt gaccgttgag attgaattct gtgtgtggga ccagttcctg   3960
ggtgagatca acccacagca cagctggatg gtggcagggc ctctgctgga catcaaggct   4020
gagcctggag ctgtggaagc tgtgcacctc cctcactttg tggctctcca agggggccat   4080
gtggacacat ccctgttcca aatggcccac tttaaagagg aggggatgct cctggagaag   4140
ccagccaggg tggagctgca tcacatagtt ctggaaaacc ccagcttctc cccttggga    4200
gtcctcctga aaatgatcca taatgccctg cgcttcattc ccgtcacctc tgtggtgttg   4260
ctttaccacc gcgtccatcc tgaggaagtc accttccacc tctacctgat cccaagtgac   4320
tgctccattc ggaaggccat agatgatcta gaaatgaaat tccagtttgt gcgaatccac   4380
aagccacccc cgctgacccc actttatatg ggctgtcgtt acactgtgtc tgggtctggt   4440
tcagggatgc tggaaatact ccccaaggaa ctggagctct gctatcgaag ccctggagaa   4500
gaccagctgt tctcggagtt ctacgttggc cacttgggat cagggatcag gctgcaagtg   4560
aaagacaaga aagatgagac tctggtgtgg gaggccttgg tgaaaccagg agatctcatg   4620
cctgcaacta ctctgatccc tccagcccgc atagccgtac cttcacctct ggatgccccg   4680
cagttgctgc actttgtgga ccagtatcga gagcagctga tagcccgagt gacatcggtg   4740
gaggttgtct tggacaaact gcatggacag gtgctgagcc aggagcagta cgagagggtg   4800
ctggctgaga acacgaggcc cagccagatg cggaagctgt tcagcttgag ccagtcctgg   4860
```

```
gaccggaagt gcaaagatgg actctaccaa gccctgaagg agacccatcc tcacctcatt   4920

atggaactct gggagaaggg cagcaaaaag ggactcctgc cactcagcag ctgaagtatc   4980

aacaccagcc cttgaccctt gagtcctggc tttggctgac ccttctttgg gtctcagttt   5040

ctttctctgc aaacaagttg ccatctggtt tgccttccag cactaaagta atggaacttt   5100

gatgatgcct ttgctgggca ttatgtgtcc atgccaggga tgccacaggg ggccccagtc   5160

caggtggcct aacagcatct cagggaatgt ccatctggag ctggcaagac ccctgcagac   5220

ctcatagagc ctcatctggt ggccacagca gccaagccta gagccctccg gatcccatcc   5280

aggcgcaaag aggaatagga gggacatgga accatttgcc tctggctgtg tcacagggtg   5340

agccccaaaa ttggggttca gcgtgggagg ccacgtggat tcttggcttt gtacaggaag   5400

atctacaaga gcaagccaac agagtaaagt ggaaggaagt ttattcagaa aataaaggag   5460

tatcacagct cttttagaat ttgtctagca ggctttccag tttttaccag aaaaccccta   5520

taaattaaaa atttttttact taaatttaag aattaaaaaa atacaaaaaa gaaaaaatga   5580

aaataaagga ataagaagtt acctactcca                                    5610
```

```
<210> SEQ ID NO 70
<211> LENGTH: 3039
<212> TYPE: DNA
<213> ORGANISM: Homo sapiens

<400> SEQUENCE: 70

gttcgttgca acaaattgat gagcaatgct tttttataat gccaactttg tacaaaaaag     60

ttggcatggc agaagatgat ccatatttgg gaaggcctga acaaatgttt catttggatc    120

cttctttgac tcatacaata tttaatccag aagtatttca accacagatg gcactgccaa    180

cagcagatgg cccatacctt caaatattag agcaacctaa acagagagga tttcgtttcc    240

gttatgtatg tgaaggccca tcccatggtg gactacctgg tgcctctagt gaaaagaaca    300

agaagtctta ccctcaggtc aaaatctgca actatgtggg accagcaaag gttattgttc    360

agttggtcac aaatggaaaa aatatccacc tgcatgccca cagcctggtg ggaaaacact    420

gtgaggatgg gatctgcact gtaactgctg gacccaagga catggtggtc ggcttcgcaa    480

acctgggtat acttcatgtg acaaagaaaa aagtatttga aacactggaa gcacgaatga    540

cagaggcgtg tataaggggc tataatcctg gactcttggt gcaccctgac cttgcctatt    600

tgcaagcaga aggtggaggg gaccggcagc tgggagatcg ggaaaaagag ctaatccgcc    660

aagcagctct gcagcagacc aaggagatgg acctcagcgt ggtgcggctc atgtttacag    720

cttttcttcc ggatagcact ggcagcttca caaggcgcct ggaacccgtg gtatcagacg    780

ccatctatga cagtaaagcc cccaatgcat ccaacttgaa aattgtaaga atggacagga    840

cagctggatg tgtgactgga ggggaggaaa tttatcttct ttgtgacaaa gttcagaaag    900

atgacatcca gattcgattt tatgaagagg aagaaaatgg tggagtctgg gaaggatttg    960

gagatttttc ccccacagat gttcatagac aatttgccat tgtcttcaaa actccaaagt   1020

ataaagatat taatattaca aaaccagcct ctgtgtttgt ccagcttcgg aggaaatctg   1080

acttggaaac tagtgaacca aaacctttcc tctactatcc tgaaatcaaa gataaagaag   1140

aagtgcagag gaaacgtcag aagctcatgc ccaatttttc ggatagtttc ggcggtggta   1200

gtggtgccgg agctggaggc ggaggcatgt ttggtagtgg cggtggagga gggggcactg   1260

gaagtacagg tccagggtat agcttcccac actatggatt tcctacttat ggtgggatta   1320

ctttccatcc tggaactact aaatctaatg ctgggatgaa gcatggaacc atggacactg   1380
```

```
aatctaaaaa ggaccctgaa ggttgtgaca aaagtgatga caaaaacact gtaaacctct   1440
ttgggaaagt tattgaaacc acagagcaag atcaggagcc cagcgaggcc accgttggga   1500
atggtgaggt cactctaacg tatgcaacag gaacaaaaga agagagtgct ggagttcagg   1560
ataacctctt tctagagaag gctatgcagc ttgcaaagag gcatgccaat gcccttttcg   1620
actacgcggt gacaggagac gtgaagatgc tgctggccgt ccagcgccat ctcactgctg   1680
tgcaggatga gaatggggac agtgtcttac acttagcaat catccacctt cattctcaac   1740
ttgtgaggga tctactagaa gtcacatctg gtttgatttc tgatgacatt atcaacatga   1800
gaaatgatct gtaccagacg cccttgcact tggcagtgat cactaagcag gaagatgtgg   1860
tggaggattt gctgagggct ggggccgacc tgagccttct ggaccgcttg ggtaactctg   1920
ttttgcacct agctgccaaa gaaggacatg ataaagttct cagtatctta ctcaagcaca   1980
aaaaggcagc actacttctt gaccaccccca acggggacgg tctgaatgcc attcatctag   2040
ccatgatgag caatagcctg ccatgtttgc tgctgctggt ggccgctggg gctgacgtca   2100
atgctcagga gcagaagtcc gggcgcacag cactgcacct ggctgtggag cacgacaaca   2160
tctcattggc aggctgcctg ctcctggaag gtgatgccca tgtggacagt actacctacg   2220
atggaaccac acccctgcat atagcagctg ggagagggtc caccaggctg gcagctcttc   2280
tcaaagcagc aggagcagat cccctggtgg agaactttga gcctctctat gacctggatg   2340
actcttggga aaatgcagga gaggatgaag gagttgtgcc tggaaccacg cctctagata   2400
tggccaccag ctggcaggta tttgacatat taaatgggaa accatatgag ccagagttta   2460
catctgatga tttactagca caaggagaca tgaaacagct ggctgaagat gtgaagctgc   2520
agctgtataa gttactagaa attcctgatc cagacaaaaa ctgggctact ctggcgcaga   2580
aattaggtct ggggatactt aataatgcct tccggctgag tcctgctcct tccaaaacac   2640
ttatggacaa ctatgaggtc tctgggggta cagtcagaga gctggtggag gccctgagac   2700
aaatgggcta caccgaagca attgaagtga tccaggcagc ctccagccca gtgaagacca   2760
cctctcaggc ccactcgctg cctctctcgc ctgcctccac aaggcagcaa atagacgagc   2820
tccgagacag tgacagtgtc tgcgacagcg gcgtggagac atccttccgc aaactcagct   2880
ttaccgagtc tctgaccagt ggtgcctcac tgctaactct caacaaaatg ccccatgatt   2940
atgggcagga aggacctcta gaaggcaaaa tttacccaac tttcttgtac aaagttggca   3000
ttataagaaa gcattgctta tcaatttgtt gcaacgaac                          3039
```

<210> SEQ ID NO 71
<211> LENGTH: 3125
<212> TYPE: DNA
<213> ORGANISM: Homo sapiens

<400> SEQUENCE: 71

```
ccgcaaccag agccgccgcc acggtgagtg gctggattca gacccctggg tggccgggac     60
aagagaaaag agggaggagg gcctttagcg gacagcgcct ggggctggag agcagcagct    120
gcacacagcc ggaaagggcg cgcaggcgac gacactcgga tccacgtcga caccgttgta    180
caaagatacg cggacccgcg ggcgtctaaa attctgggaa gcagaacctg gccggagcca    240
ctagacagag ccgggcctag cccagagaca tggagagttg ctacaaccca ggtctggatg    300
gtattattga atatgatgat ttcaaattga actcctccat tgtggaaccc aaggagccag    360
ccccagaaac agctgatggc ccctacctgg tgatcgtgga acagcctaag cagagaggct    420
```

```
tccgatttcg atatggctgt gaaggcccct cccatggagg actgcccggt gcctccagtg    480
agaagggccg aaagacctat cccactgtca agatctgtaa ctacgaggga ccagccaaga    540
tcgaggtgga cctggtaaca cacagtgacc cacctcgtgc tcatgcccac agtctggtgg    600
gcaagcaatg ctcggagctg gggatctgcg ccgtttctgt ggggcccaag gacatgactg    660
cccaatttaa caacctgggt gtcctgcatg tgactaagaa gaacatgatg gggactatga    720
tacaaaaact tcagaggcag cggctccgct ctaggcccca gggccttacg gaggccgagc    780
agcgggagct ggagcaagag gccaaagaac tgaagaaggt gatggatctg agtatagtgc    840
ggctgcgctt ctctgccttc cttagagcca gtgatggctc cttctccctg cccctgaagc    900
cagtcatctc ccagcccatc catgacagca aatctccggg ggcatcaaac ctgaagattt    960
ctcgaatgga caagacagca ggctctgtgc ggggtggaga tgaagtttat ctgctttgtg   1020
acaaggtgca gaaagatgac attgaggttc ggttctatga ggatgatgag aatggatggc   1080
aggcctttgg ggacttctct cccacagatg tgcataaaca gtatgccatt gtgttccgga   1140
caccccccta tcacaagatg aagattgagc ggcctgtaac agtgtttctg caactgaaac   1200
gcaagcgagg aggggacgtg tctgattcca aacagttcac ctattaccct ctggtggaag   1260
acaaggaaga ggtgcagcgg aagcggagga aggccttgcc caccttctcc cagcccttcg   1320
ggggtggctc ccacatgggt ggaggctctg gggtgcagc cgggggctac ggaggagctg   1380
gaggaggtgg cagcctcggt ttcttcccct cctccctggc ctacagcccc taccagtccg   1440
gcgcgggccc catgggctgc tacccgggag gcgggggcgg ggcgcagatg gccgccacgg   1500
tgcccagcag ggactccggg gaggaagccg cggagccgag cgccccctcc aggacccccc   1560
agtgcgagcc gcaggccccg gagatgctgc agcgagctcg agagtacaac gcgcgcctgt   1620
tcggcctggc gcagcgcagc gcccgagccc tactcgacta cggcgtcacc gcggacgcgc   1680
gcgcgctgct ggcgggacag cgccacctgc tgacggcgca ggacgagaac ggagacacac   1740
cactgcacct agccatcatc cacgggcaga ccagtgtcat tgagcagata gtctatgtca   1800
tccaccacgc ccaggacctc ggcgttgtca acctcaccaa ccacctgcac cagacgcccc   1860
tgcacctggc ggtgatcacg ggcagacga gtgtggtgag ctttctgctg cgggtaggtg   1920
cagacccagc tctgctggat cggcatggag actcagccat gcatctggcg ctgcgggcag   1980
gcgctggtgc tcctgagctg ctgcgtgcac tgcttcagag tggagctcct gctgtgcccc   2040
agctgttgca tatgcctgac tttgagggac tgtatccagt acacctggcg gtccgagccc   2100
gaagccctga gtgcctggat ctgctggtgg acagtggggc tgaagtggag gccacagagc   2160
ggcagggggg acgaacagcc ttgcatctag ccacagagat ggaggagctg gggttggtca   2220
cccatctggt caccaagctc cggccaacg tgaacgctcg cacctttgcg ggaaacacac   2280
ccctgcacct ggcagctgga ctggggtacc cgaccctcac ccgcctcctt ctgaaggctg   2340
gtgctgacat ccatgctgaa aacgaggagc ccctgtgccc actgccttca ccccctacct   2400
ctgatagcga ctcggactct gaagggcctg agaaggacac ccgaagcagc ttccggggcc   2460
acacgcctct tgacctcact tgcagcacca aggtgaagac cttgctgcta aatgctgctc   2520
agaacaccat ggagccaccc ctgaccccgc ccagcccagc agggccggga ctgtcacttg   2580
gtgatacagc tctgcagaac ctggagcagc tgctagacgg gccagaagcc cagggcagct   2640
gggcagagct ggcagagcgt ctggggctgc gcagcctggt agacacgtac cgacagacaa   2700
cctcacccag tggcagcctc ctgcgcagct acgagctggc tggcggggac ctggcaggtc   2760
tactggaggc cctgtctgac atgggcctag aggagggagt gaggctgctg aggggtccag   2820
```

```
aaacccgaga caagctgccc agcacagcag aggtgaagga agacagtgcg tacgggagcc   2880

agtcagtgga gcaggaggca gagaagctgg gcccaccccc tgagccacca ggagggctct   2940

gccacgggca cccccagcct caggtgcact gacctgctgc ctgcccccag ccccccttccc   3000

ggaccccctg tacagcgtcc ccacctattt caaatcttat ttaacacccc acacccaccc   3060

ctcagttggg acaaataaag gattctcatg ggaaggggag gacccctcct tcccaactta   3120

tggca                                                               3125
```

<210> SEQ ID NO 72
<211> LENGTH: 996
<212> TYPE: DNA
<213> ORGANISM: Homo sapiens

<400> SEQUENCE: 72

```
agctcgtccg cgccatgttc caggcggccg agcgccccca ggagtgggcc atggagggcc     60

cccgcgacgg gctgaagaag gagcggctac tggacgaccg ccacgacagc ggcctggact    120

ccatgaaaga cgaggagtac gagcagatgg tcaaggagct gcaggagatc cgcctcgagc    180

cgcaggaggt gccgcgcggc tcggagccct ggaagcagca gctcaccgag gacggggact    240

cgttcctgca cttggccatc atccatgaag aaaaggcact gaccatggaa gtgatccgcc    300

aggtgaaggg agacctggcc ttcctcaact tccagaacaa cctgcagcag actccactcc    360

acttggctgt gatcaccaac cagccagaaa ttgctgaggc acttctggga gctggctgtg    420

atcctgagct ccgagacttt cgaggaaata ccccccctaca ccttgcctgt gagcagggct    480

gcctggccag cgtgggagtc ctgactcagt cctgcaccac ccccgcacctc cactccatcc    540

tgaaggctac caactacaat ggccacacgt gcctacactt agcctctatc catggctacc    600

tgggcatcgt ggagcttttg gtgtccttgg gtgctgatgt caatgctcag gagccctgta    660

atggccggac tgcccttcac ctcgcagtgg acctgcaaaa tcctgacctg gtgtcactcc    720

tgttgaagtg tggggctgat gtcaacagag ttacctacca gggctattct ccctaccagc    780

tcacctgggg ccgcccaagc acccggatac agcagcagct gggccagctg acactagaaa    840

accttcagat gctgccagag agtgaggatg aggagagcta tgacacagag tcagagttca    900

cggagttcac agaggacgag ctgccctatg atgactgtgt gtttggaggc cagcgtctga    960

cgttatgagt gcaaaggggc tgaaagaaca tggact                              996
```

<210> SEQ ID NO 73
<211> LENGTH: 1200
<212> TYPE: DNA
<213> ORGANISM: Homo sapiens

<400> SEQUENCE: 73

```
gttcgttgca acaaattgat gagcaatgct tttttataat gccaactttg tacaaaaaag     60

ttggcatggc tggggtcgcg tgcttgggaa aagctgccga cgcagatgaa tggtgcgaca    120

gcggcctggg ctccctgggt ccggacgcag cggcccccgg aggacctggg ttgggcgcgg    180

agttgggccc ggggctgtcg tgggctcccc tcgtcttcgg ctacgtcact gaggatgggg    240

acacggcact gcacttggct gtgattcatc agcatgaacc cttcctggat tttcttctag    300

gcttctcggc cggcactgag tacatggacc tgcagaatga cctaggccag acagccctgc    360

acctggcagc catcctgggg gagacatcca cggtggagaa gctgtacgca gcaggcgccg    420

ggctgtgtgt ggcggagcgt aggggccaca cggcgctgca cctggcctgc cgtgtggggg    480
```

```
cacacgcctg tgcccgtgcc ctgcttcagc cccgcccccg gcgccccagg gaagcccccg    540
acacctacct cgctcagggc cctgaccgta ctcccgacac caaccatacc cctgtcgcct    600
tgtaccccga ttccgacttg gagaaggaag aagaggagag tgaggaggac tggaagctgc    660
agctggaggc tgaaaactac gagggccaca ccccactcca cgtggccgtt atccacaaag    720
atgtggagat ggtccggctg ctccgagatg ctggagctga ccttgacaaa ccggagccca    780
cgtgcggccg gagccccctt catttggcag tggaggccca ggcagccgat gtgctggagc    840
ttctcctgag ggcaggcgcg aaccctgctg cccgcatgta cggtggccgc accccactcg    900
gcagtgccat gctccggccc aaccccatcc tcgcccgcct cctccgtgca cacggagccc    960
ctgagcccga gggcgaggac gagaaatccg gcccctgcag cagcagtagc gacagcgaca   1020
gcggagacga gggcgatgaa tacgacgaca ttgtggttca cagcagccgc agccaaaccc   1080
ggctgcctcc caccccagcc tcaaaacctc ttcctgacga cccccgcccc gtgtgcccaa   1140
ctttcttgta caaagttggc attataagaa agcattgctt atcaatttgt tgcaacgaac   1200
```

<210> SEQ ID NO 74
<211> LENGTH: 2344
<212> TYPE: DNA
<213> ORGANISM: Homo sapiens

<400> SEQUENCE: 74

```
agtaaccgct gggtggacct ggccagcgct ccgaaccttg tcctcgctgc gcgccggccc     60
ctcggagccc cacagcccgg gaaggaggcc gccgcgggcc gggcgcccgc tctgccaagc    120
ggacccgcaa cccggaaagg cggcgcggcg gagcctggag ccggatcctg ctcagaccgg    180
gccccggccg gccagagccg cgggcatgtc ggaggcgcgg aaggggccgg acgaggcgga    240
ggagagccag tacgactctg gcattgagtc tctgcgctct ctgcgctccc tacccgagtc    300
cacctcggct ccagcctccg ggccctcgga cggcagcccc cagccctgca cccatcctcc    360
gggacccgtc aaggaaccac aggagaagga agacgcggat ggggagcggg ctgattccac    420
ctatggctcc tcctcgctca cctacaccct gtccttgctg gggggccccg aggctgagga    480
cccggcccca cgcctgccac tcccccacgt gggggcgctg agccctcagc agctggaagc    540
actcacttac atctccgagg acggagacac gctggtccac ctggcagtga ttcatgaggc    600
cccagcggtg ctgctctgtt gcctggcttt gctgccccag gaggtcctgg acattcaaaa    660
taacctttac cagacagcac tccatctggc tgtacatctg gaccaaccgg gcgcagttcg    720
ggcactggtg ctgaaggggg ccagccgggc actacaggac cggcatggtg acacagccct    780
tcatgtggcc tgccagcgcc agcacttggc ctgtgcccgc tgcctgctgg aagggcggcc    840
agagccaggc agaggaacat ctcactctct ggacctccag ctgcaaaact ggcaaggtct    900
ggcttgtctc cacattgcca cccttcagaa gaaccaacca ctcatggaat tgctgcttcg    960
gaatggagct gacattgatg tgcaggaggg caccagtggt aagacagcgc tgcacctggc   1020
tgtggaaacc caagagcggg gcctggtaca gttcctgctc caggctggtg cccaggtaga   1080
tgcccgcatg ctgaacgggt gcacacccct gcacctggca gctggccggg gtctcatggg   1140
catctcatcc actctgtgca aggcgggtgc tgactccctg ctgcggaatg tggaggatga   1200
gacgccccag gacctgactg aggaatccct tgtccttttg ccctttgatg acctgaagat   1260
ctcagggaaa ctgctgctgt gtaccgactg aagccaggca gggtctggga tcctcagggc   1320
tccacctctc catctggaag ccggagccat aactgctgca gtttgggccc aggctatgtg   1380
ctcttctggt gccctaggga ctgctgtggc cagagcctgg ggccagccag tacagtcctg   1440
```

```
agccgaggag gagggactgc aagtggaaga gagccagtct ggaaggaaga gctttccagg   1500

tggacagggc ttcttggaag acccccaaag ccccaggtat cctgggtgaa gcctgtttgc   1560

ctctcttgaa aatggcaggt gctcttgttt tacccatgtt gggtcagcct gaaactgcca   1620

accagtagga agcatggact ctcctgagtg agaagagact gaaataggag caagcagaac   1680

cctgagaggt gtcccatctt attgctgttg aggaccctga aacaccgttg tttaaagact   1740

tcacacagaa ggctctgaac tgagccactg ggaagggaa gtttcagtaa catgacacta   1800

aaatggcaga gacgttaaaa aaagtttttc ccttctagag ctgttttgcg cgcatgcatg   1860

tctgtgtgca ttggggcttt ttagacaggc ctgccctgtg actttgtggt agaggcagag   1920

agaaggaaat tgtcccctga gcacggtagg gccttgctgg gtggggtcag aggccagtag   1980

ttccaggcct ttctctgtgt ccagcacaga cccttgtcct tgctgtggaa atgatgaggg   2040

atggagggac aagaggaaga atgagaggac acacgccctg gagccctcac cactgccctg   2100

ggggttgcca tctggaggag cctggggata agggtaaccc agggaggctg ggcacgaggg   2160

agctgactcc acgtttttcc ccccgttcct caccttcgag ggccctgcta ggtcacccct   2220

atgctggcat gaagagcatg gggcaataaa ccagcacagt ctctgaccac ttggagcgtc   2280

tcatccagtg agagagacag ccgttaaaag cataaacatc caaataaaga tgcctttcca   2340

agtt                                                                2344
```

<210> SEQ ID NO 75
<211> LENGTH: 3923
<212> TYPE: DNA
<213> ORGANISM: Homo sapiens

<400> SEQUENCE: 75

```
gtactggccc gcgccgtccg cccgccgaca gctccctgag ccagcccggg aggcagccgc     60

gcgcagcgag ccggtggcgc aggtgtcggg gtcctcgagc gcccagcctg ggagcatgat    120

tgtggacaag ctgctggacg acagccgcgg cggagagggg ctgcgggacg cggcgggcgg    180

ctgcggcctc atgaccagcc cgctcaacct gagctacttc tacggcgcgt cgccgcccgc    240

cgccgccccg ggcgcctgcg acgccagctg ctcggtcttg ggcccctcgg cgcccggctc    300

gcccggctcc gactcctccg acttctcctc tgcctcgtcg gtgtcctcct gcggcgccgt    360

ggagtcccgg tcgagaggcg gcgcccgcgc cgagcgccag ccagttgagc cccatatggg    420

ggttggcagg cagcagagag gcccctttca aggtgttcgg gtaaagaact cagtgaagga    480

actcctgttg cacatccgaa gtcataaaca gaaggcttct ggccaagctg tggatgattt    540

taagacacaa ggtgtgaaca tagaacagtt cagagaattg aagaacacag tatcatacag    600

tgggaaaagg aaagggcccg attcgttgtc tgatggacct gcttgcaaaa ggccagctct    660

gttgcattcc caatttttga caccacctca aacaccaacg cccggggaga gcatggaaga    720

tgttcatctc aatgaaccca aacaggagag cagtgctgat ctgcttcaga acattatcaa    780

cattaagaat gaatgcagcc ccgtttccct gaacacagtt caagttagct ggctgaaccc    840

cgtggtggtc cctcagagct cccccgcaga gcagtgtcag gacttccatg gagggcaggt    900

cttttctcca cctcagaaat gccaaccatt ccaagtcagg ggctcccaac aaatgataga    960

ccaggcttcc ctgtaccagt attctccaca gaaccagcat gtagagcagc agccacacta   1020

cacccacaaa ccaactctgg aatacagtcc ttttcccata cctccccagt cccccgctta   1080

tgaaccaaac ctctttgatg gtccagaatc acagttttgc ccaaaccaaa gcttagtttc   1140
```

-continued

```
ccttcttggt gatcaaaggg aatctgagaa tattgctaat cccatgcaga cttcctccag   1200
tgttcagcag caaaatgatg ctcacttgca cagcttcagc atgatgccca gcagcgcctg   1260
tgaggccatg gtggggcacg agatggcctc tgactcttca aacacttcac tgccattctc   1320
aaacatggga aatccaatga acaccacaca gttagggaaa tcactttttc agtggcaggt   1380
ggagcaggaa gaaagcaaat tggcaaatat ttcccaagac cagtttcttt caaaggatgc   1440
agatggtgac acgttccttc atattgctgt tgcccaaggg agaagggcac tttcctatgt   1500
tcttgcaaga aagatgaatg cacttcacat gctggatatt aaagagcaca atggacagag   1560
tgcctttcag gtggcagtgg ctgccaatca gcatctcatt gtgcaggatc tggtgaacat   1620
cggggcacag gtgaacacca cagactgctg ggaagaaca cctctgcatg tgtgtgctga   1680
gaagggccac tcccaggtgc ttcaggcgat tcagaaggga gcagtgggaa gtaatcagtt   1740
tgtggatctt gaggcaacta actatgatgg cctgactccc cttcactgtg cagtcatagc   1800
ccacaatgct gtggtccatg aactccagag aaatcaacag cctcattcac ctgaagttca   1860
ggagctttta ctgaagaata agagtctggt tgataccatt aagtgcctaa ttcaaatggg   1920
agcagcggtg gaagcgaagg atcgcaaaag tggccgcaca gccctgcatt tggcagctga   1980
agaagcaaat ctggaactca ttcgcctctt tttggagctg cccagttgcc tgtcttttgt   2040
gaatgcaaag gcttacaatg gcaacactgc cctccatgtt gctgccagct tgcagtatcg   2100
gttgacacaa ttagatgctg tccgcctgtt gatgaggaag ggagcagacc caagtactcg   2160
gaacttggag aacgaacagc cagtgcattt ggttcccgat ggccctgtgg gagaacagat   2220
ccgacgtatc ctgaagggaa agtccattca gcagagagct ccaccgtatt agctccatta   2280
gcttggagcc tggctagcaa cactcactgt cagttaggca gtcctgatgt atctgtacat   2340
agaccatttg ccttatattg gcaaatgtaa gttgtttcta tgaaacaaac atatttagtt   2400
cactattata tagtgggtta tattaaaaga aaagaagaaa aatatctaat ttctcttggc   2460
agatttgcat atttcatacc caggtatctg ggatctagac atctgaattt gatctcaatg   2520
gtaacattgc cttcaattaa cagtagcttt tgagtaggaa aggactttga tttgtggcac   2580
aaaacattat taatatagct attgacagtt tcaaagcagg taaattgtaa atgtttcttt   2640
aagaaaaagc atgtgaaagg aaaaaggtaa atacagcatt gaggcttcat ttggccttag   2700
tccctgggag ttactggcgt tggacaggct tcagtcattg gactagatga aaggtgtcca   2760
tggttagaat ttgatctttg caaactgtat ataattgtta tttttgtcct taaaaatatt   2820
gtacatactt ggttgttaac atggtcatat ttgaaatgta taagtccata aaatagaaaa   2880
gaacaagtga attgttgcta tttaaaaaaa ttttacaatt cttactaagg agtttttatt   2940
gtgtaatcac taagtctttg tagataaagc agatggggag ttacggagtt gttcctttac   3000
tggctgaaag atatattcga attgtaaaga tgctttttct catgcattga aattatacat   3060
tatttgtagg gaattgcatg cttttttttt tttttctccc gagacagggt cttgctctgg   3120
cgcccaggct ggagtacagt ggcatgatct tggctcactt cagccttgac ttgggctcaa   3180
gtgatcctcc tacctgagcc ttctgagtaa ctggaactac aggtgtgcac tcctcgcctg   3240
gctaattttt tattttttgt acaggcagga tcttgccacc ttgcccaggc tggtcttgaa   3300
ctcctgagct catgccatct gcctgcctta gtctcccaaa atgctgggat tacaggagtg   3360
agccaccatg cccggctggc agttgcatgg aagagaacac ctctttatgg cttaccctct   3420
agaatttcta atttatgtgt tctgttgaaa tttttgtttt tttaccttta ttgaaacaac   3480
aaaaagtcag tattgaaaca tatcttcctg ttttctgttg tcaaatgatg ataatgtgcc   3540
```

```
atgatgtttt atatatatca ttcagaaaaa gttttatttt ttaataacat tctattaaca   3600

ttattttgct tgccgctggc atgcctgagg aatgtatttg gctttgatta cacactaagt   3660

ttttgtaata aatttgactc attaaaaacc tttttttttt aaaaaaaaaa aaaaagaaaa   3720

tctcattagt gaacttatct ttgcagctga gtacttaaat tctttttaaa aagataccct   3780

ttggattgat cacattgttt gacccagtat gtcttgtaga cacgttagtt ataatcacct   3840

tgtatctcta aatatggtgt gatatgaacc agtccattca cattggaaaa actgatggtt   3900

ttaaataaac taattcacta ata                                           3923
```

<210> SEQ ID NO 76
<211> LENGTH: 393
<212> TYPE: DNA
<213> ORGANISM: Homo sapiens

<400> SEQUENCE: 76

```
atggttgagt acgggaccct cttgcaagac ctgaccaaca acatcaccct tgaagatcta     60

gaacagctca agtcggcctg caaggaagac atccccagcg aaaagagtga ggagatcact    120

actggcagtg cctggtttag cttcctggag agccacaaca agctggacaa agacaacctc    180

tcctacattg agcacatctt tgagatctcc cgccgtcctg acctactcac tatggtggtt    240

gactacagaa cccgtgtgct gaagatctct gaggaggatg agctggacac caagctaacc    300

cgtatcccca gtgccaagaa gtacaaagac attatccggc agccctctga ggaagagatc    360

atcaaattgg ctcccccacc gaagaaggcc tga                                 393
```

<210> SEQ ID NO 77
<211> LENGTH: 1899
<212> TYPE: DNA
<213> ORGANISM: Homo sapiens

<400> SEQUENCE: 77

```
agagtttccc gggcactcac cgtgtgtagt tggcatctcc gcgcgtccgg acacccgatc     60

ccagcatccc tgcctgcagg actgttcgtg ttcagctcgc gtcctgcagc tgtccgaggt    120

gctccagttg gaggctgagg ttcccgggct ctgtagctga gtgggcggcg gcaccggcgg    180

agatgcctgg gaagaaggcg cgcaagaacg ctcaaccgag ccccgcgcgg gctccagcag    240

agctggaagt cgagtgtgct actcaactca ggagatttgg agacaaactg aacttccggc    300

agaaacttct gaatctgata tccaaactct tctgctcagg aacctgactg catcaaaaac    360

ttgcatgagg ggactccttc aaaagagttt tctcaggagg tgcacgtttc atcaatttga    420

agaaagactg cattgtaatt gagaggaatg tgaaggtgca ttcatgggtg cccttggaaa    480

cggaagatgg aatacatcaa agtgaatttc tgttcaagtt ttcccagatt atcattcttt    540

gggatgagag aacattataa aaccactttg tttattttaa agcaagaatg gaagaccctt    600

gaaaataaag aagtaattat tgacacattt ctttttttact tagagaatcg ttctagtgtt    660

tttgccgaag attaccgctg gcctactgtg aagggagatg acctgtgatt agactgggcg    720

gctggggaga aacagttcag tgcattgttg ttgttgctgt ttttggtgtt ttgcttttca    780

gtgccaactc agcacattgt atatgattcg gtttatacat attaccttgt tataatgaaa    840

aaactcattc tgagaacact gaaatgttat actcagtgtt gatttcttcg gtcactacac    900

aacgtaaaat catttgtttc ttttgactca aattgtattg cttctgttca gatgatcttt    960

cattcaatgt gttcctgttg ggcgttacta gaaactatgg aaaactggaa aataactttg   1020
```

```
aaaaaattgg ataaagtata ggagggttac ttggggccag taaatcagta gactgaacat   1080
tcaatataat aaaagaacat ggggattttg tataaccagg gataataaaa agaaaaaaga   1140
agttaatttt taattgatgt ttttgaaact tagtagaaca aatattcaga agtaacttga   1200
taagatatga atgtttctaa agaagtttct aaaggttcgg aaaatgctcc ttgtcacatt   1260
agtgtgcatc ctacaaaaag tgatctctta atgtaaatta agaatatttt cataattgga   1320
atatactttt cttaaaaaaa aggaacagtt agttctcatc tagaatgaaa gttccatata   1380
tgcattggtg aatatatatg tatacacata cttacatact tatatgggta tctgtataga   1440
taatttgtat tagagtatta tatagcttct tagtagggtc tcaagtaagt ttcatttttt   1500
ttatctgggc tatatacagt cctcaaataa ataatgtctt gattttattt cagcaggaat   1560
aattttattt attttgccta tttataatta aagtattttt ctttagtttg aaaatgtgta   1620
ttaaagttac atttttgagt tacaagagtc ttataactac ttgaattttt agttaaaatg   1680
tcttaatgta ggttgtagtc actttagatg gaaaattacc tcacatctgt tttcttcagt   1740
attacttaag attgtttatt tagtggtaga gagttttttt tttcagccta gaggcagcta   1800
ttttaccatc tggtatttat ggtctaattt gtatttaaac atatgcacac atataaaagt   1860
tgatactgtg gcagtaaact attaaaagtt ttcactgtt                          1899
```

<210> SEQ ID NO 78
<211> LENGTH: 712
<212> TYPE: DNA
<213> ORGANISM: Homo sapiens

<400> SEQUENCE: 78

```
atggggcgcg cgcgcgacgc catcctggat gcgctggaga acctgaccgc cgaggagctc     60
aagaagttca agctgaagct gctgtcggtg ccgctgcgcg agggctacgg gcgcatcccg    120
cggggcgcgc tgctgtccat ggacgccttg gacctcaccg acaagctggt cagcttctac    180
ctggagacct acggcgccga gctcaccgct aacgtgctgc gcgacatggg cctgcaggag    240
atggccgggc agctgcaggc ggccacgcac cagggctctg gagccgcgcc agctgggatc    300
caggcccctc ctcagtcggc agccaagcca ggcctgcact ttatagacca gcaccgggct    360
gcgcttatcg cgagggtcac aaacgttgag tggctgctgg atgctctgta cgggaaggtc    420
ctgacggatg agcagtacca ggcagtgcgg gccgagccca ccaacccaag caagatgcgg    480
aagctcttca gtttcacacc agcctggaac tggacctgca aggacttgct cctccaggcc    540
ctaagggagt cccagtccta cctggtggag gacctggagc ggagctgagg ctccttccca    600
gcaacactcc ggtcagcccc tggcaatccc accaaatcat cctgaatctg atctttttat    660
acacaatata cgaaaagcca gcttgaaaaa aaaaaaaaaa aaaaaaaaaa aa            712
```

<210> SEQ ID NO 79
<211> LENGTH: 11204
<212> TYPE: DNA
<213> ORGANISM: Homo sapiens

<400> SEQUENCE: 79

```
actcggctct ccccgctccg ccccctgccc ctggctcccg tacggtggac ggcgacgctg     60
ggtgacccgg ggtgcaagaa ttcaggggtt gggaaggtgt gagccgcaaa cccagcggag    120
ggcgggaaga aggaggaggc ctctagggtg gtcgggggac tgggggcccc gccggcagag    180
gtccctcggc ctcctgactg actgactgcg gccgcctccg gccaggacgc tgggagctgc    240
ctgcgggaag gtgcggggag cggagccatg gcctccggtg cgtataaccc gtatatagag    300
```

```
ataattgaac aacccaggca gaggggaatg cgttttagat acaaatgtga agggcgatca    360
gcaggcagca ttccagggga gcacagcaca gacaacaacc gaacataccc ttctatccag    420
attatgaact attatggaaa aggaaaagtg agaattacat tagtaacaaa gaatgaccca    480
tataaacctc atcctcatga tttagttgga aaagactgca gagacggcta ctatgaagca    540
gaatttggac aagaacgcag acctttgttt ttccaaaatt tgggtattcg atgtgtgaag    600
aaaaaagaag taaaagaagc tattattaca agaataaagg caggaatcaa tccattcaat    660
gtccctgaaa aacagctgaa tgatattgaa gattgtgacc tcaatgtggt gagactgtgt    720
tttcaagttt ttctccctga tgaacatggt aatttgacga ctgctcttcc tcctgttgtc    780
tcgaacccaa tttatgacaa ccgtgctcca aatactgcag aattaaggat ttgtcgtgta    840
aacaagaatt gtggaagtgt cagaggagga gatgaaatat ttctactttg tgacaaagtt    900
cagaaagatg acatagaagt tcgttttgtg ttgaacgatt gggaagcaaa aggcatcttt    960
tcacaagctg atgtacaccg tcaagtagcc attgttttca aaactccacc atattgcaaa   1020
gctatcacag aacccgtaac agtaaaaatg cagttgcgga gaccttctga ccaggaagtt   1080
agtgaatcta tggattttag atatctgcca gatgaaaaag atacttacgg caataaagca   1140
aagaaacaaa agacaactct gcttttccag aaactgtgcc aggatcacgt agaaacaggg   1200
tttcgccatg ttgaccagga tggtcttgaa ctcctgacat caggtgatcc acccaccttg   1260
gcctcccaaa gtgctgggat tacagttaat tttcctgaga gaccaagacc tggtctcctc   1320
ggttcaattg gagaaggaag atacttcaaa aaagaaccaa acttgttttc tcatgatgca   1380
gttgtgagag aaatgcctac aggggtttca agtcaagcag aatcctacta tccctcacct   1440
gggcccatct caagtggatt gtcacatcat gcctcaatgg cacctctgcc ttcttcaagc   1500
tggtcatcag tggcccaccc caccccacgc tcaggcaata caaacccact gagtagtttt   1560
tcaacaagga cacttccttc taattcgcaa ggtatcccac cattcctgag aatacctgtt   1620
gggaatgatt taaatgcttc taatgcttgc atttacaaca atgccgatga catagtcgga   1680
atggaagcgt catccatgcc atcagcagat ttatatggta tttctgatcc caacatgctg   1740
tctaattgtt ctgtgaatat gatgacaacc agcagtgaca gcatgggaga gactgataat   1800
ccaagacttc tgagcatgaa tcttgaaaac ccctcatgta attcagtgtt agacccaaga   1860
gacttgagac agctccatca gatgtcctct tccagtatgt cagcaggcgc caattccaat   1920
actactgttt ttgtttcaca atcagatgca tttgagggat ctgacttcag ttgtgcagat   1980
aacagcatga taaatgagtc gggaccatca aacagtacta atccaaacag tcatggtttt   2040
gttcaagata gtcagtattc aggtattggc agtatgcaaa atgagcaatt gagtgactcc   2100
tttccatatg aatttttca agtataactt gcaagattta aatcctttta aatcttgata    2160
ccacctatat agatgcagca ttttgtattt gtctaactgg ggatataata ctatatttat   2220
actgtatata taatactgac tgagaatata atactgtatt tgagaatata aaaaactttt   2280
ttcagggaag aagcatacaa ctttggacat agcgaataca aaattggaag ctgtcataaa   2340
aagacaactc agaggccagg cgcaggggct cacacctgta atcctagcac tttgggaggc   2400
caaggcgggt ggatcacttg agaccaggaa ttcgagacca gcctggccaa catggtgaaa   2460
ccccgtctct actaaaaata caaaaattag ctgagcatgg tggtacgtgc ctgtactgtc   2520
agctacttgg gaggctgagg cacaataatt gtttgaaccc aggaagcaga ggttgcagtg   2580
agctgagatc acaccaccgc actccagcct gggtgacaga gtgagactct gtctcaaaaa   2640
```

```
aaaaaaaaca aaaaaaacac actttttttat atttcttttt ataatgtttt aatgtattct   2700
taaatttcaa gcaaatttaa gataaaactt gtaatggcta tgccattgaa aaacttaatt   2760
ttttattttt gaggcccatg ggccaaggta acccctaagg ggttttctta ggcttcttgg   2820
agcttagatt tgtatgtata tcaaaatgtc tttaaaatgt taagttgggc agaaggcagt   2880
tgaagtgagc tttcaaggta tgggaggttt tctacatttt atactatttc aatctatgcc   2940
tttaaagttg cttatgattt tagctgtaca ctcatttttt aaggggaaga agtttccttg   3000
gaccattcgc ctttcttaga tgtcctcact ccctgtgatc tcataaaact gcctatttga   3060
catctctatc tagaaatcta attaaagctc acactcagca tatccaaaac tgaattcttg   3120
gtcttccctc ccaaacttgc ttctccttca gtcttctcca actcagtaaa tggcaatgcc   3180
atacttctgg ttgctcaggc caaaaaccct gaagtcatcc ttgattcttc ttttagcacc   3240
catatccaat ccattagcaa atctggtaga ccctaccttc acaatatatc taaagctgac   3300
cacctctttt gacctctact attaacgccc tattccaagc caccatcatc tcttccctgg   3360
attgaagctg tcatctacaa aaattcttct tatatccttg cattcctaca gtctgttccc   3420
cataaagtag ccagaatgat tatttttaaa acaagtcaac tcataccatt catctgctca   3480
aaaccattca ttggcttctc atctcactca gagcagtcaa agtccttaaa agttgcaggc   3540
ctagactccc tgtcctacct caggtaccac catatcccac ctcctcatgc agctccaggc   3600
accttggcct cagtgctcct caaagcatca agtatgcact tgccttggac agtctgtact   3660
tggtattccc tctgccttga atgttgttct cccagaaaaa tgcatagttc actcttacat   3720
ccttcaggtg tcactccact gttacctgag caggtcgtcc ttgaatatat acatcagcat   3780
tccctttccc ccctgcttta tgtatgtcca tagcactcac cacgatctga ctttactaag   3840
tatttattca tttactgttt gttttcccat accgaaatat aaactttcta aggacagaaa   3900
tttttgtgct ttattgttga atctccaatt tgtagaaaaa tgcctacctt atattaaaca   3960
ctcagtaaat gtttattgaa cattaaaagt attactaata gaactttggt ttttgaaaga   4020
aataataact ttaattataa gacgtatatg atttttgcag ttttacttag tgtgacattg   4080
ggtttatgag aatcgtgtac attcaagtcc aggaataata atggtcatcc aaattgtttg   4140
aaaggaaaat aatcccagtg gcaaaatgat ggtagaattt gggtaatctt ttttttcctt   4200
ttatgaaaag agattttatt gaaggtaaaa cattagaggt tcattgagaa tctctaaatc   4260
catgttttga cattgtcaag ctcattgcaa cttccagatt gagtaacact tataacacat   4320
ttccttttca aagtgcaaga tttttaaaag agacttgtca catattcatt tggctggttt   4380
caaatggtga gctgaatgct gggtaatctc tactagctcc ttaatcagat ttaaaattct   4440
cagtgtttcc tagttgtttc tgcatacttt atgtgagttg ttatagctgt aacattacac   4500
tttatttgct gtttgtgttt cgtgactttt ggtaattctg gcatttagaa acctttcact   4560
ttgcttcaaa acgtagttat attttggagt tttcatttga tatataatta tttattttgc   4620
ccttttattt cccaaagaca ttgtaagggt taattagatc attatatttt attattacag   4680
attaaagttg ggcagtaatc ttaattatga tggaattatc attatgctaa gtaattaact   4740
ttacctagtt tgttttacaa ctagaacctg ccctaaatgt tgaatatctt cctagcaaga   4800
aacagtctgt cattttactt acacgatgtc taaccaaacc ataactttac ataaactagt   4860
cgtttcggtc aaatagaaaa atgtgtgaat gccataaaaa caaaaattct cagttaaatg   4920
atactgggaa atagggaaga cagcaaagtg agacttgggc tcaggatggt tcaggaagaa   4980
aaaaaaagaa agacccctga gtaccattaa tattcctcag aaattattat ttcaaaagga   5040
```

```
aatatttctg tattataaat ttttcatgag cagccattat gaaatctcac aagaatcata   5100
gaattcaata aaaaaggtag aaagtaattt ttttacttaa aaatataaat taaaataaat   5160
ttttaaaatc ataagcacat aaatagaact taccagggag aaagaaaaac ctgaaggcac   5220
aatttctttt ctgttcaaaa tgtgaaccca ggatgtctct agatgatgat ggatgatagg   5280
tggggagatt tttttttttt ttaatacaga atctcatagt tttggattaa ttagcaccaa   5340
tcagtttaaa cactgactgt tagaatagct gcatgggttt ttttctttaa actaattaag   5400
cgttggctac ttagtataag taagtataag ccgaattaag gttctgctac atctgtgttt   5460
agaatatttt tttaaaacta aataagtgtt ggctagtttt gcggtgtaag cagaattaag   5520
gttctgctac ctctgtgtgt agaatattcc caatggattt ttcatttttc aggtgctatt   5580
ttttgaccct gtatagactt taatttaaaa tgaatttggt aacgtttctc ctctgtctct   5640
acatatattc atgctttcac ctgctctttt aacacctgct tttagtatct gaggcacttt   5700
ttctgaactc tacttgtgca ctggatccct cctcctttct ctgccaggct gtgtttactt   5760
tatccttaca tcaccactta gtgattcctt tctttgtata aacatggtaa atgtcttcat   5820
tagcctaaaa ggaaagacca aataaaacct ttcctaccac ttggatgcat ttgcatcctg   5880
acttctgaaa tgcctccagc ctccattttc tcccttccca gttattcctt agcccagcca   5940
tctctgtctt tagctcctac aattttctta ggatattctg ggaaagatga gcggagactg   6000
cccgccttgt caaatctagt gtcttttttt cagtcctcac actgcttgac ctatgtataa   6060
cctcctatac ttccctcttt gcatactcct ctgggttttc tgtggtagtc aagattcctc   6120
cctgagattt atttcccatg agtcttgacc cctcccctca gttggtgcta tttcccccta   6180
cccgccctcc gatgatctta tcagagccca caggttcagt tttctttcat gctacctgaa   6240
tgtcctgata aactggctcg ctctcttctt taccttccat aatggcatta ccatttacca   6300
cgccacccaa gatacttact aggaacctca aagtattgta ttctttttct ccatcacact   6360
catacttaat catcaagtcc ttttgagctt gtctcctctt gaatatgtcc cttcttaatt   6420
cctgctgcct tcttagtaaa ggccttcatt ctttttttccc tagtaataat cttttccata   6480
tgttccagtt aaaataccat gttctcccta ttccttatta catagctagc attccttgaa   6540
aaaaaacaat tctctcaggc ctccatacct ttagcatgtt acccactctg cctctgctct   6600
tctggaacta gaacactcat ccttgaaggc tgggcttctg tatgaaggtt ggtcctgcct   6660
ccttacttga ggtgaagctt tgtacatgcc tgtattacgg acatcctctt atttaagtgt   6720
ttgtctcttt cgtcattggg actccagcac ccagcatagt ccctagtata ctagttggtg   6780
ctgaataaat agtagctatt attagaaaag gaagggtgaa attgacatgg gagttagtaa   6840
aatgtatatg gaaatgattt ttaaagggaa aggtaatgat tttctggcag gaaaagcagc   6900
aatgacaaga ttacttaagt cttgtgaaat aacacttctc ttccttgacc tgctgcttcc   6960
ctttttttacc acacacacac gcacacatac cacagccctt tgagactgaa agcagctcta   7020
ttgagaatag tagtgtcaac tgtattatgt agaaattcta aagtttttgg gattatttca   7080
tagccctgac cttgctactt ctctccactt tatgtggcag gtttaatctc aggtctccct   7140
catacacttc tcagcctcag cacctaaccc tcacacaaca ctccagtatt gatgcagtca   7200
atcttgtata acatttttttg aatgtccaat gtgcaaagca cgatgttgga aattatacag   7260
aggtgaataa gacaaaaact cttgctctca aagatgtcag tctttttctt tgcaaggata   7320
acacatgtag agtaaaatgc ataaagggga ctaattttaa atgtacagct taattaattt   7380
```

-continued ttatgtatgt taacacccat gtcaccacca tgtttaggac atttccagca cccctgaaat 7440
ttccttcatg ccccttccca gtctgtacct acacctctaa atctattttc aatcttaatg 7500
gccttttaaa taactgggct tctcacaacc atagtgaaca gaaacagctg ggttgtcaac 7560
gtctaaccta atacttcagg aaaactcatg atggtttcca tgttaagaga gacatggagc 7620
agggcactgg catggtggat ggatcacgcc tgtaatccca gcactttggg aggccgaggt 7680
agggggattg cttgagccca ggagttcaag actagcctgg gtaatataag gaaaacctgt 7740
ctctgcaaaa aaaaaaaaaa aaagaggata caaccaaatg gaagaacatt ccatgctcat 7800
gggtaggaag aatcaatatc gtgaaaatgg ccatactgcc caaggtaatt tacagattca 7860
gtgccatccc catcaagcta ccaatgcctt tcttcacaga attggaaaaa actactttaa 7920
agttcatatg gaaccaaaaa agagcccata tcgccaagtc aatcctaagc caaaagaaca 7980
aagctggagg catcacacta cctgacttca aactatacta caaggctaca gtaaccaaaa 8040
cagcatggta ctggtaccaa aacagagata tagatcactg gaacagaaca gagccctcag 8100
aaataacgcc gcatatctac aactatctga tctttgacaa acctgagaaa aacaagcaat 8160
ggggaaagga ttccctattt aataaatggt gctgggaaaa ctggctagcc atatgtagaa 8220
agctgaaact ggatcccttc cttacacctt atacaaaaat caattcaaga tggattaaag 8280
acttaaacgt tagacctaaa accataaaaa ccctagaaga aaacctaggc attaccattc 8340
aggacatagg catgggcaag gacttcatgt ctaaaacacc aaaagcaatg gcaacaaaag 8400
ccaaaattga caaatgggat ctaattaaac taaagagctg ctgcacagca aaagaaacta 8460
ccatcagagt gaacaggcaa cctacaaaat gggagaaaat tttcgcaacc tacttatctg 8520
acaaagggct aatatccaga atctacaatg aactcaaaca aatttacaag aaaaaaacaa 8580
ccccatcaaa aagtgggcga aggacatgaa cagacacttc tcaaaagaag acatttatgc 8640
agccaaaaaa cacatgaaaa aatgctcatc atgactggcc atcagagaaa tgcaaatcaa 8700
aaccacaatg agataccatc tcacaccagt tagaatggca atcattaaaa agtcaggaga 8760
caacaggtgc tggagaggat gtggagaaat aggaacactt ttacactgtt ggtgggactg 8820
taaactagtt caaccattgt ggaagtcagt gtggcgattc ctcagggatg tagaactgga 8880
aataccgttt gacccagcca tcccattact gggtatatac ccaaaggact ataaatcatg 8940
ctgctataaa gacacatgca cacgtatgtt tattgcggca ttattcacaa tagcaaagac 9000
ttggaaccaa cccaaatgtc caacaatgat agactggatt aagaaaatgt ggcacatata 9060
caccatggaa tactatgcag ccataaaaaa tgatgaattc atgtcctttg tagggacatg 9120
gatgaaattg gaaaacatca ttctcagtaa actatcgcaa gaacaagaaa ccaaacacca 9180
catattctca ctcataggtg ggaattgaac aatgagaaca catggacaca ggaaggggaa 9240
tatcacactg gggactgttg tggggtgggg ggaggggga gggatagcat tgggagatat 9300
acctaatgct agatgacgag ttagtgggtg cagtgcacca gcatggcaca tgtatacata 9360
tgtaagtaac ctgcacaatg tgcacatgta ccctaaagct taaagtataa taaaaaataa 9420
ataaataaat aaataagaaa aagaaagcca ggcatggtga catgtgcctg tggtcccagc 9480
tattagggag gctgaggtgg gaggatccct tgaacccagg aggttgagtc tgtagtgagc 9540
agtgattacg ccactgcact ccagcctggg caagaccctg tctcaaaaaa aaaaaagact 9600
tagaattggt gatccaggcc gcctaatggc atcaaataat ttgttatatc tttaatttat 9660
tgaaggatca ccacatgctt ttaaatagca tggagaaatg gaaagaatag ggacttttta 9720
ctcaggtaat acccagcctg ctacctaaca ggttgtgttg tactaaataa aatggtacat 9780

```
aagaagaaac actgtaaatt atatagtgcg aatcaaatat tgttaataaa ccaatatctg    9840
tatatcctat gtcccggatt aatctttaat ttagatactc cttctagtta tctaatacac    9900
agcagagtga gaaaaatcat tatggattag gttctttagt aagaaacctg agatggactt    9960
ctcattagca ttaactagtt attgcccagc tttggagagc cttcttttgg cttatcattt   10020
attataagcc cagaaatagg tgactaatca gagataaatg tatgggttgt ctgtatctag   10080
ttttatgcct ttttttgcc taagacgtag tcaaattaat attttaacta atacatctta    10140
gcagagttta gttaagcaca aagttaacag tgggtaggat tgaatcttga aagtaatcat   10200
gtctgtaatg tttttcatgc atgcaaaaag cacagacaaa accactcatg ccctattaat   10260
aaacaaaata cagatcaaag ttttcaaaag taatcactct atttattcta aatgtctgtg   10320
gctttaggaa aataccacca gctagtactt acctatttaa agatgtagaa tttattatcc   10380
tctaatattc ttatcagttg tttccacaac tttagtttac tattggactt tcaaaaattt   10440
aaagaattac aagtaaaatt cattaaacac ttgtgtgtga atagtaatac acagtaatta   10500
gtacagcatg ttgcttcttc aacaaattga gttttcaggg aaatcagcaa gtaaatgaaa   10560
tataaatttt tggtaaaagt atcaaacatt catcttgccc atttttcctc ttaaacttta   10620
ttatctaatc aaacatagtt ttccataaga tgtaataaaa tatagataag gttggaatat   10680
ttgaggatcc atttgtggaa ctgaatttaa tgagacttca ttggtgatac actcaatttt   10740
tactgggtaa ttagctaata atgttggtca ctgtctcaca gttcaagtag ctttaagatg   10800
atgtggcaag gaaaacacaa agcttttggg taaccagcgt tcttaaatgt atggtttttg   10860
accaggtgaa ccctttagaa gtgatttctg ttttaaaagt atgtacttaa aatacctttg   10920
gctgtgatga atgtagatcc cagcagaata ccaaaatcct attttttttg actgagtatt   10980
tgtagatgct taatgactga aatgaatttg gaggcactga tgaaagtgat ttttttaaag   11040
ttctcaggta ctgttcaatt atttaatgtt aagtttagta tcaagataca gttgttttta   11100
aaatgccaaa atgctgttta ttatacagaa tattttatta catttgcaat atctttgtat   11160
atagtgattt ttttcttgat aataaatgga aaaattctaa aaca                    11204
```

<210> SEQ ID NO 80
<211> LENGTH: 3199
<212> TYPE: DNA
<213> ORGANISM: Homo sapiens

<400> SEQUENCE: 80

```
ctcgtctgta gtgcacgccg cgggcccagc tgcgaccccg gccccgcccc cgggaccccg      60
gccatggacg aactgttccc cctcatcttc ccggcagagc cagcccaggc ctctggcccc     120
tatgtggaga tcattgagca gcccaagcag cggggcatgc gcttccgcta caagtgcgag     180
ggcgctccg cgggcagcat cccaggcgag aggagcacag ataccaccaa gacccacccc      240
accatcaaga tcaatggcta cacaggacca gggacagtgc gcatctccct ggtcaccaag     300
gaccctcctc accggcctca cccccacgag cttgtaggaa aggactgccg ggatggcttc     360
tatgaggctg agctctgccc ggaccgctgc atccacagtt tccagaacct gggaatccag     420
tgtgtgaaga agcgggacct ggagcaggct atcagtcagc gcatccagac caacaacaac     480
cccttccaag ttcctataga agagcagcgt ggggactacg acctgaatgc tgtgcggctc     540
tgcttccagg tgacagtgcg ggacccatca ggcaggcccc tccgcctgcc gcctgtcctt     600
tctcatccca tctttgacaa tcgtgccccc aacactgccg agctcaagat ctgccgagtg     660
```

-continued

```
aaccgaaact ctggcagctg cctcggtggg gatgagatct tcctactgtg tgacaaggtg    720
cagaaagagg acattgaggt gtatttcacg ggaccaggct gggaggcccg aggctccttt    780
tcgcaagctg atgtgcaccg acaagtggcc attgtgttcc ggacccctcc ctacgcagac    840
cccagcctgc aggctcctgt gcgtgtctcc atgcagctgc ggcggccttc cgaccgggag    900
ctcagtgagc ccatggaatt ccagtacctg ccagatacag acgatcgtca ccggattgag    960
gagaaacgta aaaggacata tgagaccttc aagagcatca tgaagaagag tcctttcagc   1020
ggacccaccg acccccggcc tccacctcga cgcattgctg tgccttcccg cagctcagct   1080
tctgtcccca agccaggtaa ggatttcctt ttgtcccact ggaacgacag gttcagctct   1140
gttcagctga ggagcagtgg agatgaagac tcttgggccc cattacagac ctactgaatc   1200
agaggctttg aaaggatggc gcaggaacca gcgacttcct gggatgctaa tgcacactga   1260
agcctgggaa ccaccgtgcc acttaaattc tatattgggt atcttgggaa tcagaagtta   1320
aaaatgcaga atctctgctc tcatctctca cttgaattgg gggaacaaaa atcacctcta   1380
aattagcaag atgtgtgtgc ctgtgcgagg ctcaaaaact gacaagctct gcacttcagg   1440
ccgctgctca cttggtgctc catgggctca ttgcctctca ggacttagtt tttcagctgt   1500
aaactgagga gtccagctta tctctccaag tgtcccttcc tctaaaaggc tggaagagtt   1560
tcgtgggctt gagtagtcag ggaggactcc aaggtggagg tgtggctaga actggaccct   1620
acaggctggg tcagatgggg taagaggaag gagatagggt gttggcagtg actccctaga   1680
gagggattga gcctgagcac catgaagagg ggctggggta cagaggacgg ggtggatctc   1740
tagggctttc tctgacccct gcctctctgt ctctctcctc cagcacccca gccctatccc   1800
tttacgtcat ccctgagcac catcaactat gatgagtttc ccaccatggt gtttccttct   1860
gggcagatca gccaggcctc ggccttggcc ccggcccctc cccaagtcct gccccaggct   1920
ccagcccctg cccctgctcc agccatggta tcagctctgg cccaggcccc agcccctgtc   1980
ccagtcctag ccccaggccc tcctcaggct gtggccccac ctgcccccaa gcccacccag   2040
gctggggaag gaacgctgtc agaggccctg ctgcagctgc agtttgatga tgaagacctg   2100
ggggccttgc ttggcaacag cacagaccca gctgtgttca cagacctggc atccgtcgac   2160
aactccgagt ttcagcagct gctgaaccag ggcatacctg tggcccccca cacaactgag   2220
cccatgctga tggagtaccc tgaggctata actcgcctag tgacaggggc ccagaggccc   2280
cccgacccag ctcctgctcc actgggggcc ccggggctcc ccaatggcct cctttcagga   2340
gatgaagact tctcctccat tgcggacatg gacttctcag ccctgctgag tcagatcagc   2400
tcctaagggg gtgacgcctg ccctccccag agcactgggt tgcaggggat tgaagccctc   2460
caaaagcact tacggattct ggtggggtgt gttccaactg cccccaactt tgtggatgtc   2520
ttccttggag gggggagcca tattttattc ttttattgtc agtatctgta tctctctctc   2580
tttttggagg tgcttaagca gaagcattaa cttctctgga aagggggggag ctggggaaac  2640
tcaaactttt cccctgtcct gatggtcagc tcccttctct gtagggaact ctggggtccc   2700
ccatccccat cctccagctt ctggtactct cctagagaca gaagcaggct ggaggtaagg   2760
cctttgagcc cacaaagcct tatcaagtgt cttccatcat ggattcatta cagcttaatc   2820
aaaataacgc cccagatacc agcccctgta tggcactggc attgtccctg tgcctaacac   2880
cagcgtttga ggggctggcc ttcctgccct acagaggtct ctgccggctc tttccttgct   2940
caaccatggc tgaaggaaac cagtgcaaca gcactggctc tctccaggat ccagaagggg   3000
tttggtctgg gacttccttg ctctccctct tctcaagtgc cttaatagta gggtaagttg   3060
```

```
ttaagagtgg gggagagcag gctggcagct ctccagtcag gaggcatagt ttttactgaa   3120

caatcaaagc acttggactc ttgctctttc tactctgaac taataaatct gttgccaagc   3180

tggaaaaaaa aaaaaaaaa                                                3199
```

<210> SEQ ID NO 81
<211> LENGTH: 2258
<212> TYPE: DNA
<213> ORGANISM: Homo sapiens

<400> SEQUENCE: 81

```
gcagccccgg gcgccgcgcg tcctgcccgg cctgcggccc cagcccttgc gccgctcgtc     60

cgacccgcga tcgtccacca gaccgtgcct cccggccgcc cggccggccc gcgtgcatgc    120

ttcggtctgg gccagcctct gggccgtccg tccccactgg ccgggccatg ccgagtcgcc    180

gcgtcgccag accgccggct gcgccggagc tgggggcctt agggtccccc gacctctcct    240

cactctcgct cgccgtttcc aggagcacag atgaattgga gatcatcgac gagtacatca    300

aggagaacgg cttcggcctg gacgggggac agccgggccc gggcgagggg ctgccacgcc    360

tggtgtctcg cggggctgcg tccctgagca cggtcaccct gggccctgtg gcgcccccag    420

ccacgccgcc gccttggggc tgccccctgg gccgactagt gtccccagcg ccgggcccgg    480

gcccgcagcc gcacctggtc atcacggagc agcccaagca gcgcggcatg cgcttccgct    540

acgagtgcga gggccgctcg gccggcagca tccttgggga gagcagcacc gaggccagca    600

agacgctgcc cgccatcgag ctccgggatt gtggagggct gcgggaggtg gaggtgactg    660

cctgcctggt gtggaaggac tggcctcacc gagtccaccc ccacagcctc gtggggaaag    720

actgcaccga cggcatctgc agggtgcggc tccggcctca cgtcagcccc cggcacagtt    780

ttaacaacct gggcatccag tgtgtgagga agaaggagat tgaggctgcc attgagcgga    840

agattcaact gggcattgac ccctacaacg ctgggtccct gaagaaccat caggaagtag    900

acatgaatgt ggtgaggatc tgcttccagg cctcatatcg ggaccagcag ggacagatgc    960

gccggatgga tcctgtgctt tccgagcccg tctatgacaa gaaatccaca aacacatcag   1020

agctgcggat ttgccgaatt aacaaggaaa gcgggccgtg caccggtggc gaggagctct   1080

acttgctctg cgacaaggtg cagaaagagg acatatcagt ggtgttcagc agggcctcct   1140

gggaaggtcg ggctgacttc tcccaggccg acgtgcaccg ccagattgcc attgtgttca   1200

agacgccgcc ctacgaggac ctggagattg tcgagcccgt gacagtcaac gtcttcctgc   1260

agcggctcac cgatggggtc tgcagcgagc cattgccttt cacgtacctg cctcgcgacc   1320

atgacagcta cggcgtggac aagaagcgga aacgggggat gcccgacgtc cttggggagc   1380

tgaacagctc tgacccccat ggcatcgaga gcaaacggcg gaagaaaaag ccggccatcc   1440

tggaccactt cctgcccaac cacggctcag gcccgttcct cccgccgtca gccctgctgc   1500

cagaccctga cttcttctct ggcaccgtgt ccctgcccgg cctggagccc cctggcgggc   1560

ctgacctcct ggacgatggc tttgcctacg accctacggc ccccacactc ttcaccatgc   1620

tggacctgct gcccccggca ccgccacacg ctagcgctgt tgtgtgcagc ggaggtgccg   1680

gggccgtggt tggggagacc cccggccctg aaccactgac actggactcg taccaggccc   1740

cgggccccgg ggatggaggc accgccagcc ttgtgggcag caacatgttc cccaatcatt   1800

accgcgaggc ggcctttggg ggcggcctcc tatccccggg gcctgaagcc acgtagcccc   1860

gcgatgccag aggaggggca ctgggtgggg agggaggtgg aggagccgtg caatcccaac   1920
```

caggatgtct agcaccccca tccccttggc ccttcctcat gcttctgaag tggacatatt 1980
cagccttggc gagaagctcc gttgcacggg tttccccttg agcccatttt acagatgagg 2040
aaactgagtc cggagaggaa aagggacatg gctcccgtgc actagcttgt tacagctgcc 2100
tctgtcccca catgtggggg caccttctcc agtaggattc ggaaaagatt gtacatatgg 2160
gaggaggggg cagattcctg gccctccctc cccagacttg aaggtggggg gtaggttggt 2220
tgttcagagt cttcccaata aagatgagtt tttgagcc 2258

<210> SEQ ID NO 82
<211> LENGTH: 4017
<212> TYPE: DNA
<213> ORGANISM: Homo sapiens

<400> SEQUENCE: 82
gggagtccgc ggcgagcgca gcagcagggc ccggtcctgc gcctcgggag tcggcgtcca 60
ggctcggagc gcgacacgga gactaggtgg cagggtacag ctctgccggg gggggaaaaa 120
gtggtaccat tttgggcgtt cttgagcttc agaatgcaac cagacatgtc cttgaatgtc 180
attaagatga aatccagtga cttcctggag agtgcagaac tggacagcgg aggctttggg 240
aaggtgtctc tgtgtttcca cagaacccag ggactcatga tcatgaaaac agtgtacaag 300
gggcccaact gcattgagca caacgaggcc ctcttggagg aggcgaagat gatgaacaga 360
ctgagacaca gccgggtggt gaagctcctg ggcgtcatca tagaggaagg gaagtactcc 420
ctggtgatgg agtacatgga gaagggcaac ctgatgcacg tgctgaaagc cgagatgagt 480
actccgcttt ctgtaaaagg aaggataatt ttggaaatca ttgaaggaat gtgctactta 540
catggaaaag gcgtgataca caaggacctg aagcctgaaa atatccttgt tgataatgac 600
ttccacatta agatcgcaga cctcggcctt gcctccttta agatgtggag caaactgaat 660
aatgaagagc acaatgagct gagggaagtg gacggcaccg ctaagaagaa tggcggcacc 720
ctctactaca tggcgcccga gcacctgaat gacgtcaacg caaagcccac agagaagtcg 780
gatgtgtaca gctttgctgt agtactctgg gcgatatttg caaataagga gccatatgaa 840
aatgctatct gtgagcagca gttgataatg tgcataaaat ctgggaacag gccagatgtg 900
gatgacatca ctgagtactg cccaagagaa attatcagtc tcatgaagct ctgctgggaa 960
gcgaatccgg aagctcggcc gacatttcct ggcattgaag aaaaatttag gcctttttat 1020
ttaagtcaat tagaagaaag tgtagaagag gacgtgaaga gtttaaagaa agagtattca 1080
aacgaaaatg cagttgtgaa gagaatgcag tctcttcaac ttgattgtgt ggcagtacct 1140
tcaagccggt caaattcagc cacagaacag cctggttcac tgcacagttc ccagggactt 1200
gggatgggtc ctgtggagga gtcctggttt gctccttccc tggagcaccc acaagaagag 1260
aatgagccca gcctgcagag taaactccaa gacgaagcca actaccatct tttatggcagc 1320 cgcatggaca ggcagacgaa acagcagccc agacagaatg tggcttacaa cagagaggag 1380
gaaaggagac gcagggtctc ccatgaccct tttgcacagc aaagacctta cgagaatttt 1440
cagaatacag agggaaaagg cactgcttat tccagtgcag ccagtcatgg taatgcagtg 1500
caccagccct cagggctcac cagccaacct caagtactgt atcagaacaa tggattatat 1560
agctcacatg gctttggaac aagaccactg gatccaggaa cagcaggtcc cagagtttgg 1620
tacaggccaa ttccaagtca tatgcctagt ctgcataata tcccagtgcc tgagaccaac 1680
tatctaggaa atacacccac catgccattc agctccttgc caccaacaga tgaatctata 1740
aaatatacca tatacaatag tactggcatt cagattggag cctacaatta tatggagatt 1800

```
ggtgggacga gttcatcact actagacagc acaaatacga acttcaaaga agagccagct   1860
gctaagtacc aagctatctt tgataatacc actagtctga cggataaaca cctggaccca   1920
atcagggaaa atctgggaaa gcactggaaa aactgtgccc gtaaactggg cttcacacag   1980
tctcagattg atgaaattga ccatgactat gagcgagatg gactgaaaga aaaggtttac   2040
cagatgctcc aaaagtgggt gatgagggaa ggcataaagg gagccacggt ggggaagctg   2100
gcccaggcgc tccaccagtg ttccaggatc gaccttctga gcagcttgat ttacgtcagc   2160
cagaactaac cctggatggg ctacggcagc tgaagtggac gcctcactta gtggataacc   2220
ccagaaagtt ggctgcctca gagcattcag aattctgtcc tcactgatag ggttctgtg    2280
tctgcagaaa ttttgtttcc tgtacttcat agctggagaa tggggaaaga aatctgcagc   2340
aaaggggtct cactctgttg ccaggctggt ctcaaacttc tggactcaag tgatcctccc   2400
gcctcggcct tccaaagtgc tgggatatca ggcactgagc cactgcgccc agccaacaat   2460
ccgctctgag gaaagcgtaa gcaggaagac ctcttaatgg catagcacca ataaaaaaat   2520
gactcctagt tgtgtttgga aagggagaga agagatgtct gaggaaggtc atgttctttc   2580
agcttatggc atttcctaga gttttgttga agcaagaaga aaaactcaga gaatataaaa   2640
tcaactttta aaattgtgtg ctctcttctt cacgtaggct cctgttaaaa acaaagtgca   2700
gtcagattct aagccctgtt cagagacttc gtggatcaca gctgcagctc accgccacat   2760
cacaggatcc gttaacgtta atacccaata ctctgtcagc cactgtaggc tctaagaacc   2820
acgtgcagtc ttcagcccat taaattatcg attatttttt aatgaattga atttatattg   2880
agtcttcaaa ttaactgaat ggatttaaag gggtaccaag gagggggaa acatcagaat    2940
ttcccaggca gttgttgcaa ggaattggta ctaaccgtga ctacaacaaa aattcttgat   3000
tgacttttaa agttatttcc tggcattctg gtaccttcac ccagcctgag tgccctggag   3060
agggaacagg aaatgctgat ctctacccct gggtgagacc agaacctcag ggctgatact   3120
gttgagtggc ttcctcggtt tactctgtgt actgtgaaag tattttcata ttttttctgt   3180
gtgccagagt gaaaaaggac agcttctgag tgtggtaatt gtgcctctag cacccagcct   3240
ttcaaagccc acctgaaacc tgggggtgga tgaaagaact agaatagaag actgaagctg   3300
ggtaggccgc tcagtgtcca ctggcatttt gctaaaccga caaggaaggc tgtgtgctta   3360
gctctcccca gagggagggc gagaagggtg tggtgatggt caatctggct gtcggaacag   3420
attctggtgt cttgggctga taacagtgtt gttgattctg attgtgaatc ccctcaactc   3480
tagcagacac atacacaccc ctgaaatggg gctgcagagc aggctgtctc agccttgcca   3540
ctgtcggcat ctcggcctgg gtaattctgt tgtggggact gtcctgttcc ttgtaggatg   3600
tttagtagca tccctgcccc cacctactag atgccagggg cactgttctc cccagccccc   3660
cgccccagtt gtgacaatag tctctaaaca ttgtcaaatg gtccaaggaa aggggaaaat   3720
tgccccggtt gagaagagca ctgctgtaaa gtaatgagcc tcggctctcc tgtctgcacc   3780
tgtccggtta ctacttggcc accacgcagc cttggctcct acagcccaaa agggagaatg   3840
gagggaggct ccaggctttg ctggaggggc ctgggtgagt tctgtttgct ccttgtacca   3900
ccatccaaat ggtgttatca aatctcttag attccaaaga ggttgaataa ttaatgttca   3960
aaggcaagag ggcaaggcat tttttaacac tttttaaaat aaaaatttat accacaa      4017
```

<210> SEQ ID NO 83
<211> LENGTH: 2521
<212> TYPE: DNA

<213> ORGANISM: Homo sapiens

<400> SEQUENCE: 83

```
gaagctcttt cgcggcgcta cggcgttggc accagtctct agaaaagaag tcagctctgg     60
ttcggagaag cagcggctgg cgtgggccat ccggggaatg ggcgccctcg tgacctagtg    120
ttgcggggca aaaagggtct tgccggcctc gctcgtgcag gggcgtatct gggcgcctga    180
gcgcggcgtg ggagccttgg gagccgccgc agcagggggc acacccggaa ccggcctgag    240
cgcccgggac catgaacggg gaggccatct gcagcgccct gcccaccatt ccctaccaca    300
aactcgccga cctgcgctac ctgagccgcg gcgcctctgg cactgtgtcg tccgcccgcc    360
acgcagactg gcgcgtccag gtggccgtga agcacctgca catccacact ccgctgctcg    420
acagtgaaag aaaggatgtc ttaagagaag ctgaaatttt acacaaagct agatttagtt    480
acattcttcc aattttggga atttgcaatg agcctgaatt tttgggaata gttactgaat    540
acatgccaaa tggatcatta aatgaactcc tacataggaa aactgaatat cctgatgttg    600
cttggccatt gagatttcgc atcctgcatg aaattgccct tggtgtaaat tacctgcaca    660
atatgactcc tcctttactt catcatgact tgaagactca gaatatctta ttggacaatg    720
aatttcatgt taagattgca gattttggtt tatcaaagtg gcgcatgatg tccctctcac    780
agtcacgaag tagcaaatct gcaccagaag gagggacaat tatctatatg ccacctgaaa    840
actatgaacc tggacaaaaa tcaagggcca gtatcaagca cgatatatat agctatgcag    900
ttatcacatg ggaagtgtta tccagaaaac agccttttga agatgtcacc aatcctttgc    960
agataatgta tagtgtgtca caaggacatc gacctgttat taatgaagaa agtttgccat   1020
atgatatacc tcaccgagca cgtatgatct ctctaataga aagtggatgg gcacaaaatc   1080
cagatgaaag accatctttc ttaaaatgtt taatagaact tgaaccagtt ttgagaacat   1140
ttgaagagat aacttttctt gaagctgtta ttcagctaaa gaaaacaaag ttacagagtg   1200
tttcaagtgc cattcaccta tgtgacaaga agaaaatgga attatctctg aacatacctg   1260
taaatcatgg tccacaagag gaatcatgtg gatcctctca gctccatgaa aatagtggtt   1320
ctcctgaaac ttcaaggtcc ctgccagctc ctcaagacaa tgattttttta tctagaaaag   1380
ctcaagactg ttattttatg aagctgcatc actgtcctgg aaatcacagt tgggatagca   1440
ccatttctgg atctcaaagg gctgcattct gtgatcacaa gaccactcca tgctcttcag   1500
caataataaa tccactctca actgcaggaa actcagaacg tctgcagcct ggtatagccc   1560
agcagtggat ccagagcaaa agggaagaca ttgtgaacca aatgacagaa gcctgcctta   1620
accagtcgct agatgccctt ctgtccaggg acttgatcat gaaagaggac tatgaacttg   1680
ttagtaccaa gcctacaagg acctcaaaag tcagacaatt actagacact actgacatcc   1740
aaggagaaga atttgccaaa gttatagtac aaaaattgaa agataacaaa caaatgggtc   1800
ttcagcctta cccggaaata cttgtggttt ctagatcacc atctttaaat ttacttcaaa   1860
ataaaagcat gtaagtgact gtttttcaag aagaaatgtg tttcataaaa ggatatttat   1920
atctctgttg ctttgacttt ttttatataa aatccgtgag tattaaagct ttattgaagg   1980
ttctttgggt aaatattagt ctccctccat gacactgcag tattttttttt aattaataca   2040
agtaaaaagt ttgaattttg ctacatagtt caatttttat gtctcttttg ttaacagaaa   2100
ccacttttaa aggatagtaa ttattcttgt ttataacagt gccttaaggt atgatgtatt   2160
tctgatggaa gccattttca cattcatgtt cttcatggat tatttgttac ttgtctaaga   2220
tgcaatttga ttttatgaag tatataccct ttacccacca gagacagtac agaatccctg   2280
```

```
ccctaaaatc ccaggcttaa ttgccctaca aagggttatt aatttaaaac tccattatta   2340

ggattacatt ttaaagtttt atttatgaat tccctttaaa aatgatattt caaaggtaaa   2400

acaatacaat ataaagaaaa aaataaatat attaataccg gcttcctgtc cccattttta   2460

acctcagcct tccctactgt caccaacaac caagctaaat aaagtcaaca gcctgatgtg   2520

t                                                                   2521
```

<210> SEQ ID NO 84
<211> LENGTH: 3022
<212> TYPE: DNA
<213> ORGANISM: Homo sapiens

<400> SEQUENCE: 84

```
ggaagtgtcc tgagtctcga ggaggccgcg ggagcccgcc ggcggtggcg cggcggagac     60

ccggctggta taacaagagg attgcctgat ccagccaaga tgcagagcac ttctaatcat    120

ctgtggcttt tatctgatat tttaggccaa ggagctactg caaatgtctt tcgtggaaga    180

cataagaaaa ctggtgattt atttgctatc aaagtattta ataacataag cttccttcgt    240

ccagtggatg ttcaaatgag agaatttgaa gtgttgaaaa aactcaatca caaaaatatt    300

gtcaaattat ttgctattga agaggagaca acaacaagac ataaagtact tattatggaa    360

ttttgtccat gtgggagttt atacactgtt ttagaagaac cttctaatgc ctatggacta    420

ccagaatctg aattcttaat tgttttgcga gatgtggtgg gtggaatgaa tcatctacga    480

gagaatggta tagtgcaccg tgatatcaag ccaggaaata tcatgcgtgt tataggggaa    540

gatggacagt ctgtgtacaa actcacagat tttggtgcag ctagagaatt agaagatgat    600

gagcagtttg tttctctgta tggcacagaa gaatatttgc accctgatat gtatgagaga    660

gcagtgctaa gaaaagatca tcagaagaaa tatggagcaa cagttgatct ttggagcatt    720

ggggtaacat tttaccatgc agctactgga tcactgccat ttagaccctt tgaagggcct    780

cgtaggaata aagaagtgat gtataaaata attacaggaa agccttctgg tgcaatatct    840

ggagtacaga aagcagaaaa tggaccaatt gactggagtg gagacatgcc tgtttcttgc    900

agtctttctc ggggtcttca ggttctactt acccctgttc ttgcaaacat ccttgaagca    960

gatcaggaaa agtgttgggg ttttgaccag ttttttgcag aaactagtga tatacttcac   1020

cgaatggtaa ttcatgtttt ttcgctacaa caaatgacag ctcataagat ttatattcat   1080

agctataata ctgctactat atttcatgaa ctggtatata aacaaaccaa aattatttct   1140

tcaaatcaag aacttatcta cgaagggcga cgcttagtct tagaacctgg aaggctggca   1200

caacatttcc ctaaaactac tgaggaaaac cctatatttg tagtaagccg ggaacctctg   1260

aataccatag gattaatata tgaaaaaatt tccctcccta aagtacatcc acgttatgat   1320

ttagacgggg atgctagcat ggctaaggca ataacagggg ttgtgtgtta tgcctgcaga   1380

attgccagta ccttactgct ttatcaggaa ttaatgcgaa aggggatacg atggctgatt   1440

gaattaatta aagatgatta caatgaaact gttcacaaaa agacagaagt tgtgatcaca   1500

ttggatttct gtatcagaaa cattgaaaaa actgtgaaag tatatgaaaa gttgatgaag   1560

atcaacctgg aagcggcaga gttaggtgaa atttcagaca tacacaccaa attgttgaga   1620

ctttccagtt ctcagggaac aatagaaacc agtcttcagg atatcgacag cagattatct   1680

ccaggtggat cactggcaga cgcatgggca catcaagaag gcactcatcc gaaagacaga   1740

aatgtagaaa aactacaagt cctgttaaat tgcatgacag agatttacta tcagttcaaa   1800
```

```
aaagacaaag cagaacgtag attagcttat aatgaagaac aaatccacaa atttgataag   1860

caaaaactgt attaccatgc cacaaaagct atgacgcact ttacagatga atgtgttaaa   1920

aagtatgagg catttttgaa taagtcagaa gaatggataa gaaagatgct tcatcttagg   1980

aaacagttat tatcgctgac taatcagtgt tttgatattg aagaagaagt atcaaaatat   2040

caagaatata ctaatgagtt acaagaaact ctgcctcaga aaatgtttac agcttccagt   2100

ggaatcaaac ataccatgac cccaatttat ccaagttcta acacattagt agaaatgact   2160

cttggtatga agaaattaaa ggaagagatg gaaggggtgg ttaaagaact tgctgaaaat   2220

aaccacattt tagaaaggtt tggctcttta accatggatg gtggccttcg caacgttgac   2280

tgtctttagc tttctaatag aagtttaaga aaagtttccg tttgcacaag aaaataacgc   2340

ttgggcatta aatgaatgcc tttatagata gtcacttgtt tctacaattc agtatttgat   2400

gtggtcgtgt aaatatgtac aatattgtaa atacataaaa aatatacaaa tttttggctg   2460

ctgtgaagat gtaattttat cttttaacat ttataattat atgaggaaat ttgacctcag   2520

tgatcacgag aagaaagcca tgaccgacca atatgttgac atactgatcc tctactctga   2580

gtggggctaa ataagttatt ttctctgacc gcctactgga aatattttta agtggaacca   2640

aaataggcat ccttacaaat caggaagact gacttgacac gtttgtaaat ggtagaacgg   2700

tggctactgt gagtggggag cagaaccgca ccactgttat actgggataa caattttttt   2760

gagaaggata aagtggcatt attttatttt acaaggtgcc cagatcccag ttatccttgt   2820

atccatgtaa tttcagatga attattaagc aaacatttta aagtgaattc attattaaaa   2880

actattcatt tttttccttt ggccataaat gtgtaattgt cattaaaatt ctaaggtcat   2940

ttcaactgtt ttaagctgta tatttcttta attctgctta ctatttcatg gaaaaaaata   3000

aatttctcaa ttttaatgta aa                                             3022
```

<210> SEQ ID NO 85
<211> LENGTH: 1798
<212> TYPE: DNA
<213> ORGANISM: Homo sapiens

<400> SEQUENCE: 85

```
atgagcactg aaagcatgat ccgggacgtg gagctggccg aggaggcgct ccccaagaag     60

acaggggggc cccagggctc caggcggtgc ttgttcctca gcctcttctc cttcctgatc    120

gtggcaggcg ccaccacgct cttctgcctg ctgcactttg gagtgatcgg cccccagagg    180

gaagaggtga gtgcctggcc agccttcatc cactctccca cccaagggga aatggagacg    240

caagagaggg agagagatgg gatgggtgaa agatgtgcgc tgatagggag ggatggagag    300

aaaaaaacgt ggagaaagac ggggatgcag aaagagatgt ggcaagagat ggggaagaga    360

gagagagaaa gatggagaga caggatgtct ggcacatgga aggtgctcac taagtgtgta    420

tggagtgaat gaatgaatga atgaatgaac aagcagatat ataaataaga tatggagaca    480

gatgtggggt gtgagaagag agatggggga agaaacaagt gatatgaata aagatggtga    540

gacagaaaga gagcgggaaa tatgacagct aaggagagag atgggggaga taaggagaga    600

agaagatagg gtgtctggca cacagaagac actcagggaa agagctgttg aatgcctgga    660

aggtgaatac acggatgaat ggagagagaa aaccagacac ctcagggcta agagcgcagg    720

ccagacaggc agccagctgt tcctccttta agggtgactc cctcgatgtt aaccattctc    780

cttctcccca acagttcccc agggacctct ctctaatcag ccctctggcc caggcagtca    840

gtaagtgtct ccaaacctct ttcctaattc tgggtttggg tttgggggta gggttagtac    900
```

```
cggtatggaa gcagtggggg aaatttaaag ttttggtctt gggggaggat ggatggaggt    960

gaaagtaggg gggtattttc taggaagttt aagggtctca gctttttctt ttctctctcc   1020

tcttcaggat catcttctcg aaccctgagt gacaagcctg tagcccatgt tgtaggtaag   1080

agctctgagg atgtgtcttg gaacttggag ggctaggatt tggggattga agcccggctg   1140

atggtaggca gaacttggag acaatgtgag aaggactcgc tgagctcaag ggaagggtgg   1200

aggaacagca caggccttag tgggatactc agaacgtcat ggccaggtgg gatgtgggat   1260

gacagacaga gaggacagga accggatgtg gggtgggcag agctcgaggg ccaggatgtg   1320

gagagtgaac cgacatggcc acactgactc tcctctccct ctctccctcc ctccagcaaa   1380

ccctcaagct gaggggcagc tccagtggct gaaccgccgg gccaatgccc tcctggccaa   1440

tggcgtggag ctgagagata accagctggt ggtgccatca gagggcctgt acctcatcta   1500

ctcccaggtc ctcttcaagg gccaaggctg cccctccacc catgtgctcc tcacccacac   1560

catcagccgc atcgccgtct cctaccagac caaggtcaac ctcctctctg ccatcaagag   1620

cccctgccag agggagaccc cagagggggc tgaggccaag ccctggtatg agcccatcta   1680

tctgggaggg gtcttccagc tggagaaggg tgaccgactc agcgctgaga tcaatcggcc   1740

cgactatctc gactttgccg agtctgggca ggtctacttt gggatcattg ccctgtga     1798
```

<210> SEQ ID NO 86
<211> LENGTH: 1536
<212> TYPE: DNA
<213> ORGANISM: Homo sapiens

<400> SEQUENCE: 86

```
gttcgttgca acaaattgat gagcaatgct tttttataat gccaactttg tacaaaaaag     60

ttggcatggc gccaccacca gctagagtac atctaggtgc gttcctggca gtgactccga    120

atcccgggag cgcagcgagt gggacagagg cagccgcggc cacacccagc aaagtgtggg    180

gctcttccgc ggggaggatt gaaccacgag gcgggggccg aggagcgctc cctacctcca    240

tgggacagca cggacccagt gcccgggccc gggcagggcg cgccccagga cccaggccgg    300

cgcgggaagc cagccctcgg ctccgggtcc acaagacctt caagtttgtc gtcgtcgggg    360

tcctgctgca ggtcgtacct agctcagctg caaccatcaa acttcatgat caatcaattg    420

gcacacagca atgggaacat agccctttgg gagagttgtg tccaccagga tctcatagat    480

cagaacatcc tggagcctgt aaccggtgca cagagggtgt gggttacacc aatgcttcca    540

acaatttgtt tgcttgcctc ccatgtacag cttgtaaatc agatgaagaa gagagaagtc    600

cctgcaccac gaccaggaac acagcatgtc agtgcaaacc aggaactttc cggaatgaca    660

attctgctga gatgtgccgg aagtgcagca gagggtgccc cagagggatg gtcaaggtca    720

aggattgtac gccctggagt gacatcgagt gtgtccacaa agaatcaggc aatggacata    780

atatatgggt gattttggtt gtgactttgg ttgttccgtt gctgttggtg gctgtgctga    840

ttgtctgttg ttgcatcggc tcaggttgtg gaggggaccc caagtgcatg gacagggtgt    900

gtttctggcg cttgggtctc ctacgagggc ctggggctga ggacaatgct cacaacgaga    960

ttctgagcaa cgcagactcg ctgtccactt tcgtctctga gcagcaaatg gaaagccagg   1020

agccggcaga tttgacaggt gtcactgtac agtccccagg ggaggcacag tgtctgctgg   1080

gaccggcaga agctgaaggg tctcagagga ggaggctgct ggttccagca aatggtgctg   1140

accccactga gactctgatg ctgttctttg acaagtttgc aaacatcgtg ccctttgact   1200
```

cctgggacca gctcatgagg cagctggacc tcacgaaaaa tgagatcgat gtggtcagag 1260
ctggtacagc aggcccaggg gatgccttgt atgcaatgct gatgaaatgg gtcaacaaaa 1320
ctggacggaa cgcctcgatc cacaccctgc tggatgcctt ggagaggatg gaagagagac 1380
atgcaaaaga gaagattcag gacctcttgg tggactctgg aaagttcatc tacttagaag 1440
atggcacagg ctctgccgtg tccttggagt gcccaacttt cttgtacaaa gttggcatta 1500
taagaaagca ttgcttatca atttgttgca acgaac 1536

<210> SEQ ID NO 87
<211> LENGTH: 1323
<212> TYPE: DNA
<213> ORGANISM: Homo sapiens

<400> SEQUENCE: 87
atggaacaac ggggacagaa cgccccggcc gcttcggggg cccggaaaag gcacggccca 60
ggacccaggg aggcgcgggg agccaggcct gggctccggg tccccaagac ccttgtgctc 120
gttgtcgccg cggtcctgct gttggtctca gctgagtctg ctctgatcac ccaacaagac 180
ctagctcccc agcagagagc ggccccacaa caaaagaggt ccagcccctc agagggattg 240
tgtccacctg gacaccatat ctcagaagac ggtagagatt gcatctcctg caaatatgga 300
caggactata gcactcactg gaatgacctc cttttctgct tgcgctgcac caggtgtgat 360
tcaggtgaag tggagctaag tccctgcacc acgaccagaa acacagtgtg tcagtgcgaa 420
gaaggcacct tccgggaaga agattctcct gagatgtgcc ggaagtgccg cacagggtgt 480
cccagaggga tggtcaaggt cggtgattgt acaccctgga gtgacatcga atgtgtccac 540
aaagaatcag gtacaaagca cagtggggaa gccccagctg tggaggagac ggtgacctcc 600
agcccaggga ctcctgcctc tccctgttct ctctcaggca tcatcatagg agtcacagtt 660
gcagccgtag tcttgattgt ggctgtgttt gtttgcaagt ctttactgtg gaagaaagtc 720
cttccttacc tgaaaggcat ctgctcaggt ggtggtgggg accctgagcg tgtggacaga 780
agctcacaac gacctggggc tgaggacaat gtcctcaatg agatcgtgag tatcttgcag 840
cccacccagg tccctgagca ggaaatggaa gtccaggagc cagcagagcc aacaggtgtc 900
aacatgttgt cccccgggga gtcagagcat ctgctggaac cggcagaagc tgaaaggtct 960
cagaggagga ggctgctggt tccagcaaat gaaggtgatc ccactgagac tctgagacag 1020
tgcttcgatg actttgcaga cttggtgccc tttgactcct gggagccgct catgaggaag 1080
ttgggcctca tggacaatga gataaaggtg gctaaagctg aggcagcggg ccacagggac 1140
accttgtaca cgatgctgat aaagtgggtc aacaaaaccg ggcgagatgc ctctgtccac 1200
accctgctgg atgccttgga gacgctggga gagagacttg ccaagcagaa gattgaggac 1260
cacttgttga gctctggaaa gttcatgtat ctagaaggta atgcagactc tgccatgtcc 1320
taa 1323

<210> SEQ ID NO 88
<211> LENGTH: 1497
<212> TYPE: DNA
<213> ORGANISM: Homo sapiens

<400> SEQUENCE: 88
gttcgttgca acaaattgat gagcaatgct tttttataat gccaactttg tacaaaaaag 60
ttggcatggg cctctccacc gtgcctgacc tgctgctgcc actggtgctc ctggagctgt 120
tggtgggaat atacccctca ggggttattg gactggtccc tcacctaggg gacagggaga 180
agagagatag tgtgtgtccc caaggaaaat atatccaccc tcaaaataat tcgatttgct 240
gtaccaagtg ccacaaagga acctacttgt acaatgactg tccaggcccg gggcaggata 300
cggactgcag ggagtgtgag agcggctcct tcaccgcttc agaaaaccac ctcagacact 360
gcctcagctg ctccaaatgc cgaaaggaaa tgggtcaggt ggagatctct tcttgcacag 420
tggaccggga caccgtgtgt ggctgcagga agaaccagta ccggcattat tggagtgaaa 480
acctttttcca gtgcttcaat tgcagcctct gcctcaatgg gaccgtgcac ctctcctgcc 540
aggagaaaca gaacaccgtg tgcacctgcc atgcaggttt ctttctaaga gaaaacgagt 600
gtgtctcctg tagtaactgt aagaaaaagcc tggagtgcac gaagttgtgc ctaccccaga 660
ttgagaatgt taagggcact gaggactcag gcaccacagt gctgttgccc ctggtcattt 720
tctttggtct ttgcctttta tccctcctct tcattggttt aatgtatcgc taccaacggt 780
ggaagtccaa gctctactcc attgtttgtg ggaaatcgac acctgaaaaa gagggggagc 840
ttgaaggaac tactactaag cccctggccc caaacccaag cttcagtccc actccaggct 900
tcacccccac cctgggcttc agtcccgtgc ccagttccac cttcacctcc agctccacct 960
atacccccgg tgactgtccc aactttgcgg ctccccgcag agaggtggca ccaccctatc 1020
agggggctga ccccatcctt gcgacagccc tcgcctccga ccccatcccc aaccccccttc 1080
agaagtggga ggacagcgcc cacaagccac agagcctaga cactgatgac cccgcgacgc 1140
tgtacgccgt ggtggagaac gtgcccccgt tgcgctggaa ggaattcgtg cggcgcctag 1200
ggctgagcga ccacgagatc gatcggctgg agctgcagaa cgggcgctgc ctgcgcgagg 1260
cgcaatacag catgctggcg acctggaggc ggcgcacgcc gcggcgcgag gccacgctgg 1320
agctgctggg acgcgtgctc cgcgacatgg acctgctggg ctgcctggag gacatcgagg 1380
aggcgctttg cggccccgcc gccctcccgc ccgcgcccag tcttctcaga tgcccaactt 1440
tcttgtacaa agttggcatt ataagaaagc attgcttatc aatttgttgc aacgaac 1497

<210> SEQ ID NO 89
<211> LENGTH: 3687
<212> TYPE: DNA
<213> ORGANISM: Homo sapiens

<400> SEQUENCE: 89
agtcgagggc tagcgagcgc agcggagcct ggagagaagg cgctgggctg cgagggcgcg 60
agggcgcgag ggcagggggc aaccggaccc cgcccgcacc catggcgccc gtcgccgtct 120
gggccgcgct ggccgtcgga ctggagctct gggctgcggc gcacgccttg cccgcccagg 180
tggcatttac accctacgcc ccggagcccg ggagcacatg ccggctcaga gaatactatg 240
accagacagc tcagatgtgc tgcagcaaat gctcgccggg ccaacatgca aaagtcttct 300
gtaccaagac ctcggacacc gtgtgtgact cctgtgagga cagcacatac acccagctct 360
ggaactgggt tcccgagtgc ttgagctgtg gctcccgctg tagctctgac caggtggaaa 420
ctcaagcctg cactcgggaa cagaaccgca tctgcacctg caggcccggc tggtactgcg 480
cgctgagcaa gcaggagggg tgccggctgt gcgcgccgct gcgcaagtgc cgcccgggct 540
tcggcgtggc cagaccagga actgaaacat cagacgtggt gtgcaagccc tgtgccccgg 600
ggacgttctc caacacgact tcatccacgg atatttgcag gccccaccag atctgtaacg 660
tggtggccat ccctgggaat gcaagcatgg atgcagtctg cacgtccacg tcccccaccc 720
ggagtatggc cccaggggca gtacacttac cccagccagt gtccacacga tcccaacaca 780

```
cgcagccaac tccagaaccc agcactgctc caagcacctc cttcctgctc ccaatgggcc    840
ccagcccccc agctgaaggg agcactggcg acttcgctct tccagttgga ctgattgtgg    900
gtgtgacagc cttgggtcta ctaataatag gagtggtgaa ctgtgtcatc atgacccagg    960
tgaaaaagaa gcccttgtgc ctgcagagag aagccaaggt gcctcacttg cctgccgata   1020
aggcccgggg tacacagggc cccgagcagc agcacctgct gatcacagcg ccgagctcca   1080
gcagcagctc cctggagagc tcggccagtg cgttggacag aagggcgccc actcggaacc   1140
agccacaggc accaggcgtg gaggccagtg gggccgggga ggcccgggcc agcaccggga   1200
gctcagattc ttcccctggt ggccatggga cccaggtcaa tgtcacctgc atcgtgaacg   1260
tctgtagcag ctctgaccac agctcacagt gctcctccca agccagctcc acaatgggag   1320
acacagattc cagcccctcg gagtccccga aggacgagca ggtccccttc tccaaggagg   1380
aatgtgcctt tcggtcacag ctggagacgc cagagaccct gctggggagc accgaagaga   1440
agcccctgcc ccttggagtg cctgatgctg ggatgaagcc cagttaacca ggccggtgtg   1500
ggctgtgtcg tagccaaggt gggctgagcc ctggcaggat gaccctgcga aggggccctg   1560
gtccttccag gcccccacca ctaggactct gaggctcttt ctgggccaag ttcctctagt   1620
gccctccaca gccgcagcct ccctctgacc tgcaggccaa gagcagaggc agcgagttgt   1680
ggaaagcctc tgctgccatg gcgtgtccct ctcggaaggc tggctgggca tggacgttcg   1740
gggcatgctg gggcaagtcc ctgactctct gtgacctgcc ccgcccagct gcacctgcca   1800
gcctggcttc tggagccctt gggttttttg tttgtttgtt tgtttgtttg tttgtttctc   1860
cccctgggct ctgccccagc tctggcttcc agaaaacccc agcatccttt tctgcagagg   1920
ggctttctgg agaggaggga tgctgcctga gtcacccatg aagacaggac agtgcttcag   1980
cctgaggctg agactgcggg atggtcctgg ggctctgtgc agggaggagg tggcagccct   2040
gtagggaacg gggtccttca agttagctca ggaggcttgg aaagcatcac ctcaggccag   2100
gtgcagtggc tcacgcctat gatcccagca ctttgggagg ctgaggcggg tggatcacct   2160
gaggttagga gttcgagacc agcctggcca acatggtaaa accccatctc tactaaaaat   2220
acagaaatta gccgggcgtg gtggcgggca cctatagtcc cagctactca gaagcctgag   2280
gctgggaaat cgtttgaacc cgggaagcgg aggttgcagg gagccgagat cacgccactg   2340
cactccagcc tgggcgacag agcgagagtc tgtctcaaaa gaaaaaaaaa agcaccgcct   2400
ccaaatgcca acttgtcctt ttgtaccatg gtgtgaaagt cagatgccca gagggcccag   2460
gcaggccacc atattcagtg ctgtggcctg ggcaagataa cgcacttcta actagaaatc   2520
tgccaatttt ttaaaaaagt aagtaccact caggccaaca agccaacgac aaagccaaac   2580
tctgccagcc acatccaacc ccccacctgc catttgcacc ctccgccttc actccggtgt   2640
gcctgcagcc ccgcgcctcc ttccttgctg tcctaggcca caccatctcc tttcagggaa   2700
tttcaggaac tagagatgac tgagtcctcg tagccatctc tctactccta cctcagccta   2760
gaccctcctc ctcccccaga ggggtgggtt cctcttcccc actccccacc ttcaattcct   2820
gggccccaaa cgggctgccc tgccactttg gtacatggcc agtgtgatcc caagtgccag   2880
tcttgtgtct gcgtctgtgt tgcgtgtcgt gggtgtgtgt agccaaggtc ggtaagttga   2940
atggcctgcc ttgaagccac tgaagctggg attcctcccc attagagtca gccttccccc   3000
tcccagggcc agggccctgc agaggggaaa ccagtgtagc cttgcccgga ttctgggagg   3060
aagcaggttg aggggctcct ggaaaggctc agtctcagga gcatggggat aaaggagaag   3120
gcatgaaatt gtctagcaga gcaggggcag ggtgataaat tgttgataaa ttccactgga   3180
```

cttgagcttg gcagctgaac tattggaggg tgggagagcc cagccattac catggagaca 3240
agaagggttt tccaccctgg aatcaagatg tcagactggc tggctgcagt gacgtgcacc 3300
tgtactcagg aggctgaggg gaggatcact ggagcccagg agtttgaggc tgcagcgagc 3360
tatgatcgcg ccactacact ccagcctgag caacagagtg agaccctgtc tcttaaagaa 3420
aaaaaaagtc agactgctgg gactggccag gtttctgccc acattggacc cacatgagga 3480
catgatggag cgcacctgcc ccctggtgga cagtcctggg agaacctcag gcttccttgg 3540
catcacaggg cagagccggg aagcgatgaa tttggagact ctgtggggcc ttggttccct 3600
tgtgtgtgtg tgttgatccc aagacaatga aagtttgcac tgtatgctgg acggcattcc 3660
tgcttatcaa taaacctgtt tgtttta 3687

<210> SEQ ID NO 90
<211> LENGTH: 3595
<212> TYPE: DNA
<213> ORGANISM: homo

<400> SEQUENCE: 90
agtccctcgc cgaccagtct gggcagcgga ggagggtggt tggcagtggc tggaagcttc 60
gctatgggaa gtcgttcctt tgctctctcg cgcccagtcc tcctccctgg ttctcctcag 120
ccgctgtcgg aggagagcac ccggagacgc gggctgcagt cgcggcggct tctccccgcc 180
tgggcggccg cgccgctggg caggtgctga gcgcccctag agcctccctt gccgcctccc 240
tcctctgccc ggccgcagca gtgcacatgg ggtgttggag gtagatgggc tcccggcccg 300
ggaggcggcg gtggatgcgg cgctgggcag aagcagccgc cgattccagc tgccccgcgc 360
gccccgggcg cccctgcgag tccccggttc agccatgggg acctctccga gcagcagcac 420
cgccctcgcc tcctgcagcc gcatcgcccg ccgagccaca gccacgatga tcgcgggctc 480
ccttctcctg cttggattcc ttagcaccac cacagctcag ccagaacaga aggcctcgaa 540
tctcattggc acataccgcc atgttgaccg tgccaccggc caggtgctaa cctgtgacaa 600
gtgtccagca ggaacctatg tctctgagca ttgtaccaac acaagcctgc gcgtctgcag 660
cagttgccct gtggggacct ttaccaggca tgagaatggc atagagaaat gccatgactg 720
tagtcagcca tgcccatggc caatgattga gaaattacct tgtgctgcct tgactgaccg 780
agaatgcact tgcccacctg gcatgttcca gtctaacgct acctgtgccc cccatacggt 840
gtgtcctgtg ggttggggtg tgcggaagaa agggacagag actgaggatg tgcggtgtaa 900
gcagtgtgct cggggtacct tctcagatgt gccttctagt gtgatgaaat gcaaagcata 960
cacagactgt ctgagtcaga acctggtggt gatcaagccg gggaccaagg agacagacaa 1020
cgtctgtggc acactcccgt ccttctccag ctccacctca ccttcccctg gcacagccat 1080
ctttccacgc cctgagcaca tggaaaccca tgaagtccct tcctccactt atgttcccaa 1140
aggcatgaac tcaacagaat ccaactcttc tgcctctgtt agaccaaagg tactgagtag 1200
catccaggaa gggacagtcc ctgacaacac aagctcagca agggggaagg aagacgtgaa 1260
caagaccctc ccaaaccttc aggtagtcaa ccaccagcaa ggcccccacc acagacacat 1320
cctgaagctg ctgccgtcca tggaggccac tgggggcgag aagtccagca cgcccatcaa 1380
gggccccaag aggggacatc ctagacagaa cctacacaag cattttgaca tcaatgagca 1440
tttgccctgg atgattgtgc ttttcctgct gctggtgctt gtggtgattg tggtgtgcag 1500
tatccggaaa agctcgagga ctctgaaaaa ggggccccgg caggatccca gtgccattgt 1560
ggaaaaggca gggctgaaga aatccatgac tccaacccag aaccgggaga aatggatcta 1620
ctactgcaat ggccatggta tcgatatcct gaagcttgta gcagcccaag tgggaagcca 1680
gtggaaagat atctatcagt ttctttgcaa tgccagtgag agggaggttg ctgctttctc 1740
caatgggtac acagccgacc acgagcgggc ctacgcagct ctgcagcact ggaccatccg 1800
gggccccgag gccagcctcg cccagctaat tagcgccctg cgccagcacc ggagaaacga 1860
tgttgtggag aagattcgtg ggctgatgga agacaccacc cagctggaaa ctgacaaact 1920
agctctcccg atgagcccca gcccgcttag cccgagcccc atccccagcc ccaacgcgaa 1980
acttgagaat tccgctctcc tgacggtgga gccttcccca caggacaaga acaagggctt 2040
cttcgtggat gagtcggagc cccttctccg ctgtgactct acatccagcg gctcctccgc 2100
gctgagcagg aacggttcct ttattaccaa agaaaagaag gacacagtgt tgcggcaggt 2160
acgcctggac ccctgtgact tgcagcctat ctttgatgac atgctccact ttctaaatcc 2220
tgaggagctg cgggtgattg aagagattcc ccaggctgag gacaaactag accggctatt 2280
cgaaattatt ggagtcaaga gccaggaagc cagccagacc ctcctggact ctgtttatag 2340
ccatcttcct gacctgctgt agaacatagg gatactgcat tctggaaatt actcaattta 2400
gtggcagggt ggttttttaa ttttcttctg tttctgattt ttgttgtttg gggtgtgtgt 2460
gtgtgtttgt gtgtgtgtgt gtgtgtgtgt gtgtgtgtgt gtttaacaga gaatatggcc 2520
agtgcttgag ttctttctcc ttctctctct ctcttttttt tttaaataac tcttctggga 2580
agttggttta taagcctttg ccaggtgtaa ctgttgtgaa atacccacca ctaaagtttt 2640
ttaagttcca tatttttctcc attttgcctt cttatgtatt ttcaagatta ttctgtgcac 2700
tttaaattta cttaacttac cataaatgca gtgtgacttt tcccacacac tggattgtga 2760
ggctcttaac ttcttaaaag tataatggca tcttgtgaat cctataagca gtctttatgt 2820
ctcttaacat tcacacctac tttttaaaaa caaatattat tactattttt attattgttt 2880
gtcctttata aattttctta aagattaaga aaatttaaga ccccattgag ttactgtaat 2940
gcaattcaac tttgagttat cttttaaata tgtcttgtat agttcatatt catggctgaa 3000
acttgaccac actattgctg attgtatggt tttcacctgg acaccgtgta gaatgcttga 3060
ttacttgtac tcttcttatg ctaatatgct ctgggctgga gaaatgaaat cctcaagcca 3120
tcaggatttg ctatttaagt ggcttgacaa ctgggccacc aaagaacttg aacttcacct 3180
tttaggattt gagctgttct ggaacacatt gctgcacttt ggaaagtcaa aatcaagtgc 3240
cagtggcgcc ctttccatag agaatttgcc cagctttgct ttaaaagatg tcttgttttt 3300
tatatacaca taatcaatag gtccaatctg ctctcaaggc cttggtcctg gtgggattcc 3360
ttcaccaatt actttaatta aaaatggctg caactgtaag aacccttgtc tgatatattt 3420
gcaactatgc tcccatttac aaatgtacct tctaatgctc agttgccagg ttccaatgca 3480
aaggtggcgt ggactcccctt tgtgtgggtg gggtttgtgg gtagtggtga aggaccgata 3540
tcagaaaaat gccttcaagt gtactaattt attaataaac attaggtgtt tgtta 3595

<210> SEQ ID NO 91
<211> LENGTH: 1638
<212> TYPE: DNA
<213> ORGANISM: Homo sapiens

<400> SEQUENCE: 91
cgggccctgc gggcgcgggg ctgaaggcgg aaccacgacg ggcagagagc acggagccgg 60
gaagcccctg ggcgcccgtc ggagggctat ggagcagcgg ccgcggggct gcgcggcggt 120

```
ggcggcggcg ctcctcctgg tgctgctggg ggcccgggcc cagggcggca ctcgtagccc    180
caggtgtgac tgtgccggtg acttccacaa gaagattggt ctgttttgtt gcagaggctg    240
cccagcgggg cactacctga aggccccttg cacggagccc tgcggcaact ccacctgcct    300
tgtgtgtccc caagacacct tcttggcctg ggagaaccac cataattctg aatgtgcccg    360
ctgccaggcc tgtgatgagc aggcctccca ggtggcgctg gagaactgtt cagcagtggc    420
cgacacccgc tgtggctgta agccaggctg gtttgtggag tgccaggtca gccaatgtgt    480
cagcagttca cccttctact gccaaccatg cctagactgc ggggccctgc accgccacac    540
acggctactc tgttcccgca gagatactga ctgtgggacc tgcctgcctg gcttctatga    600
acatggcgat ggctgcgtgt cctgccccac gagcaccctg ggagctgtc cagagcgctg    660
tgccgctgtc tgtggctgga ggcagatgtt ctgggtccag gtgctcctgg ctggccttgt    720
ggtccccctc ctgcttgggg ccaccctgac ctacacatac cgccactgct ggcctcacaa    780
gcccctggtt actgcagatg aagctgggat ggaggctctg accccaccac cggccaccca    840
tctgtcaccc ttggacagcg cccacaccct tctagcacct cctgacagca gtgagaagat    900
ctgcaccgtc cagttggtgg gtaacagctg gacccctggc taccccgaga cccaggaggc    960
gctctgcccg caggtgacat ggtcctggga ccagttgccc agcagagctc ttggccccgc   1020
tgctgcgccc acactctcgc cagagtcccc agccggctcg ccagccatga tgctgcagcc   1080
gggcccgcag ctctacgacg tgatggacgc ggtcccagcg cggcgctgga aggagttcgt   1140
gcgcacgctg gggctgcgcg aggcagagat cgaagccgtg gaggtggaga tcggccgctt   1200
ccgagaccag cagtacgaga tgctcaagcg ctggcgccag cagcagcccg cgggcctcgg   1260
agccgtttac gcggccctgg agcgcatggg gctggacggc tgcgtggaag acttgcgcag   1320
ccgcctgcag cgcggcccgt gacacggcgc ccacttgcca cctaggcgct ctggtggccc   1380
ttgcagaagc cctaagtacg gttacttatg cgtgtagaca ttttatgtca cttattaagc   1440
cgctggcacg gccctgcgta gcagcaccag ccggccccac ccctgctcgc ccctatcgct   1500
ccagccaagg cgaagaagca cgaacgaatg tcgagagggg gtgaagacat ttctcaactt   1560
ctcggccgga gtttggctga gatcgcggta ttaaatctgt gaaagaaaac aaaacaaaac   1620
aaaaaaaaaa aaaaaaaa                                                 1638
```

<210> SEQ ID NO 92
<211> LENGTH: 846
<212> TYPE: DNA
<213> ORGANISM: Homo sapiens

<400> SEQUENCE: 92

```
atggctatga tggaggtcca gggggaccc agcctgggac agacctgcgt gctgatcgtg      60
atcttcacag tgctcctgca gtctctctgt gtggctgtaa cttacgtgta ctttaccaac    120
gagctgaagc agatgcagga caagtactcc aaaagtggca ttgcttgttt cttaaaagaa    180
gatgacagtt attgggaccc caatgacgaa gagagtatga acagcccctg ctggcaagtc    240
aagtggcaac tccgtcagct cgttagaaag atgattttga gaacctctga ggaaaccatt    300
tctacagttc aagaaaagca acaaaatatt tctcccctag tgagagaaag aggtcctcag    360
agagtagcag ctcacataac tgggaccaga ggaagaagca acacattgtc ttctccaaac    420
tccaagaatg aaaaggctct gggccgcaaa ataaactcct gggaatcatc aaggagtggg    480
cattcattcc tgagcaactt gcacttgagg aatggtgaac tggtcatcca tgaaaaaggg    540
```

ttttactaca tctattccca aacatacttt cgatttcagg aggaaataaa agaaaacaca 600
aagaacgaca aacaaatggt ccaatatatt tacaaataca caagttatcc tgaccctata 660
ttgttgatga aaagtgctag aaatagttgt tggtctaaag atgcagaata tggactctat 720
tccatctatc aagggggaat atttgagctt aaggaaaatg acagaatttt tgtttctgta 780
acaaatgagc acttgataga catggaccat gaagccagtt ttttcggggc ctttttagtt 840
ggttaa 846

<210> SEQ ID NO 93
<211> LENGTH: 1496
<212> TYPE: DNA
<213> ORGANISM: Homo sapiens

<400> SEQUENCE: 93
gcacacccgg aagcggcgga gtagagcgga gcctggcggg cgtgggaacc caggccccgc 60
cgaggcggcc aggttagtgc agcaggaggt gagatggcag ctgggcaaaa tgggcacgaa 120
gagtgggtgg gcagcgcata cctgtttgtg gagtcctcgc tggacaaggt ggtcctgtcg 180
gatgcctacg cgcaccccca gcagaaggtg gcagtgtaca gggctctgca ggctgccttg 240
gcagagagcg gcgggagccc ggacgtgctg cagatgctga agatccaccg cagcgacccg 300
cagctgatcg tgcagctgcg attctgcggg cggcagccct gtggccgctt cctccgcgcc 360
taccgcgagg gggcgctgcg cgccgcgctg cagaggagcc tggcggccgc gctcgcccag 420
cactcggtgc cgctgcaact ggagctgcgc gccggcgccg agcggctgga cgctttgctg 480
gcggacgagg agcgctgttt gagttgcatc ctagcccagc agcccgaccg gctccgggat 540
gaagaactgg ctgagctgga ggatgcgctg cgaaatctga agtgcggctc gggggcccgg 600
ggtggcgacg gggaggtcgc ttcggccccc ttgcagcccc cggtgccctc tctgtcggag 660
gtgaagccgc cgccgccgcc gccacctgcc cagacttttc tgttccaggg tcagcctgta 720
gtgaatcggc cgctgagcct gaaggaccaa cagacgttcg cgcgctctgt gggtctcaaa 780
tggcgcaagg tggggcgctc actgcagcga ggctgccggg cgctgcggga cccggcgctg 840
gactcgctgg cctacgagta cgagcgcgag ggactgtacg agcaggcctt ccagctgctg 900
cggcgcttcg tgcaggccga gggccgccgc gccacgctgc agcgcctggt ggaggcactc 960
gaggagaacg agctcaccag cctggcagag gacttgctgg gcctgaccga tcccaatggc 1020
ggcctggcct agaccagggg tgcagccagc ttttggagaa cctggatggc cttagggttc 1080
cttctgcggc tattgctgaa cccctgtcca tccacgggac cctgaaactc cacttggcct 1140
atctgctgga cctgctgggg cagagttgat tgccttcccc aggagccaga ccactggggg 1200
tgcatcattg gggattctgc ctcaggtact ttgatagagt gtggggtggg ggggacctgc 1260
tttggagatc agcctcacct tctcccatcc cagaagcggg gcttacagcc agcccttaca 1320
gtttcactca tgaagcacct tgatctttgg tgtcctggac ttcatcctgg gtgctgcaga 1380
tactgcagtg aagtaaaaca ggaatcaatc ttgcctgccc ccagctcaca ctcagcgtgg 1440
gaccccgaat gttaagcaat gataataaag tataacacgg attttgatgt gagaaa 1496

IMPLANTATION SUCCESS AS DETERMINED BY BLASTOCOEL FLUID COMPONENTS

BACKGROUND OF THE INVENTION

1) Field of the Invention

The present invention relates to methods and systems using cfDNA levels, specific gene expression profiles (assessed via altered mRNA levels of specific gene transcripts), specific protein levels and potentially noncoding RNAs in blastocoel fluid which may be used to grade embryos for implantation and to help forecast/determine implantation potential in IVF patients.

2) Description of Related Art

Recurrent miscarriages are the presumed result of embryonic chromosomal abnormalities, i.e. aneuploidy, the loss or gain of chromosome(s). Moreover, approximately 30% of conceptions will result in a live birth and this low number is due to both pre- and post-implantation complications. Aneuploidies are most commonly associated with advanced maternal age, since chromosomal abnormalities are often of maternal origin, caused by errors in meiotic oocyte divisions. Nevertheless, chromosomal abnormalities can also occur post-fertilization that are likely caused by errors in mitotic divisions within the developing embryo.

Birth outcomes suggest a small subset of aneuploid embryos form blastocysts, successfully implant and result in a live birth (i.e. a child born with Down syndrome or Turner syndrome). Interestingly, the aneuploidy rate has been demonstrated to fluctuate during the transition from oocyte to blastocyst, suggesting that some mechanism of auto-correction within the preimplantation embryo may be occurring. However, the potential correction mechanism of aneuploidy in certain cells of the embryo during the preimplantation stages remains unknown.

One treatment scheme proposed for improving live birth rates is utilizing in vitro fertilization (IVF) with intracytoplasmic sperm injection (ICSI), embryo biopsy and subsequent chromosomal analysis, referred to as preimplantation genetic testing for aneuploidies or PGT-A. The process of identifying a euploid embryo involves the biopsy of numerable trophectoderm cells from a day-5 or day-6 blastocyst stage embryo generated via IVF methods. Despite significant technical capabilities that clinical embryologists currently employ to identify ploidy status of embryos, IVF-generated euploid embryo implantation remains less than 60%.

Further complicating embryo selection, preimplantation embryos are often mosaics, whereby cells in a single embryo can differ from one another in their genetic makeup and therefore ploidy status. These differences within a single embryo have been mapped by a variety of genetic methods, including microarray analysis, which illustrate the vast differences from even neighboring cells in some mosaic embryos. Considering that prevalence of mosaicism in the human embryo is estimated to be ~20%, alongside the evidence that aneuploidy rates decrease in the blastocyst stage of embryo development, the ability of an embryo to rid itself of aneuploid cells through regulated and systematic means prior to implantation is a likely hypothesis.

The best-known mechanism of selective cellular death is apoptosis. Apoptosis, known as programmed cell death, occurs during preimplantation embryo development and possibly serves as a corrective mechanism, sacrificing cells for overall embryo competence. Additionally, apoptosis requires mitochondrial proteins, and both maternal age as well as aneuploid embryos have been linked to defective mitochondria. Moreover, a recent study detected elevated mitochondrial DNA (mtDNA) levels in aneuploid embryos.

Mechanistically, if mitochondrial function is impaired, this could directly lead to reduced ability for apoptosis to occur during normal preimplantation embryo development. If one role of apoptosis is embryo self-correction via elimination of aneuploid cells, then it is possible that impaired apoptosis may contribute to aneuploid cell retention and therefore result in an embryo which is not competent for implantation.

Patients often seek assisted reproductive technology (ART) such as in vitro fertilization (IVF) after experiencing recurrent miscarriage which are most likely due to chromosomal aberrations. Selection of an embryo for transfer is often achieved by assessing the embryo morphology or more recently with preimplantation genetic testing for aneuploidies (PGT-A) which involves biopsy of trophectoderm cells of the embryo at day 5 or 6 followed by next-generation sequencing to assess ploidy status. Those embryos harboring the euploid number of chromosomes are considered suitable for uterine transfer. However, transfer of a euploid embryo does not guarantee successful implantation as highlighted in a recent study that reported IVF-generated euploid implantation rates with single embryo transfers occurred in a range of 50-90% in their patient cohort. The reason why some IVF-generated euploid embryos fail to implant could be due to an inherent biological issue in the embryo not detected by PGT-A and/or a uterine issue. To enhance uterine implantation rates of IVF-generated euploid embryos, more evidence is needed regarding the status of the preimplantation embryo at the cellular and molecular level.

A candidate biological source to obtain this information is the blastocoel fluid. Blastocoel fluid resides in the blastocoel cavity of the developing preimplantation embryo and is known to contain various molecules including cell-free DNA (cfDNA), proteins, mitochondrial DNA, miRNAs and extracellular vesicles. The origin of these molecules within the blastocoel fluid may be the remnants of apoptotic cells from the developing preimplantation embryo while this conjecture is not fully substantiated, evidence to support this rationale includes the detection of fragmented cfDNA and mitochondrial DNA in the blastocoel fluid which is consistent with what would be expected to be the remnants of cells that underwent apoptosis. Apoptosis is known to occur in the preimplantation embryo in both the inner cell mass and trophectoderm as an essential regulatory mechanism of embryonic development. An early report from 1996 detected apoptosis within human embryos via TUNEL analysis and was later shown to occur predominately at day 5 of blastocyst development. A more recent study investigated the mechanism of apoptotic initiation and reported that activation of the spindle assembly checkpoint activated apoptosis at day 5 of embryo development.

Apoptotic gene expression and caspase activity were also detected in human preimplantation embryos and apoptotic gene expression was shown to change at various stages in development. Collectively, these studies provide substantial evidence of apoptosis during early embryo development, yet why apoptosis occurs in this setting may be due to multiple reasons. One possibility is that apoptosis serves as a corrective mechanism for the embryo in order to sacrifice aneuploid or otherwise defective cells for overall embryo fitness. Apoptosis as a means of self-correction was recently shown in a mouse model for mosaicism whereby aneuploidy was induced in mouse embryos resulting in mosaic embryos. Apoptosis was seen selectively in aneuploid cells of these mosaic embryos suggestive of a purging of these cells incompatible with a healthy embryo. Ideally, this information could be obtained by assessing the media post-biopsy in order to perform PGT-A or has been induced to collapse prior to cryopreservation.

Uncovering the molecular mechanisms that regulate early development is crucial to understanding why transfer of euploid embryos does not always result in a live birth. Apoptosis occurs during pre-implantation development and possibly serves as a corrective mechanism to sacrifice cells for overall embryo competence. Remnants of early apoptosis can be detected in blastocoel fluid. Not all euploid embryos successfully implant which may be due in part to altered apoptosis during preimplantation development.

Accordingly, it is an object of the present invention to assess cfDNA gene expression (via RT-PCR) and potentially protein levels and noncoding RNAs found in the blastocoel fluid of IVF blastocysts to determine if there was a correlation with embryo morphology and if these factors allow prediction of euploid embryo implantation potential in IVF patients.

BRIEF SUMMARY OF THE INVENTION

The above objectives are accomplished according to the present invention by providing a method for determining embryonic morphology. The method may include obtaining blastocel fluid via blastocentesis, analyzing cell free DNA/RNA levels in the blastocel fluid, determining apoptic cell elimination based on an amount of cell free DNA/RNA, determining an average cell free DNA/RNA content, and wherein average cell free DNA/RNA content is higher in euploid embryos as compared to aneuploid embryos. Further, extruded trophectoderm cells may be biopsied. Still yet, the extruded trophectoderm cells may be obtained via laser pulses between cellular junctions. Again, cell free DNA/RNA may be assessed using fluorospectronomy. Yet again, analysis of variance may be employed to compare cell free DNA/RNA levels. Still again, elevated cell free DNA/RNA levels may distinguish aneuploid from euploid embryos. Further, extent of chromosomal defects in an embryo may be gauged based on cell free DNA/RNA content. Again yet, detectable molecular differences between embryos may be used to determine embryo ploidy status. Still again, determining implantation success of an embryo may be determined via an amount of apoptotic cell elimination. Further, presence of pro-apoptotic genes indicates increased embryo viability.

In an alternative embodiment, a noninvasive embryo evaluation method is provided. The method may include employing blastocentesis to obtain blastocel fluid, analyzing cell free DNA/RNA levels in the blastocel fluid, using the cell free DNA/RNA levels to derive a level of apoptic cell elimination, determining an average cell free DNA/RNA content, and wherein average cell free DNA/RNA content is higher in euploid embryos as compared to aneuploid embryos. Further, the method may include biopsying extruded trophectoderm cells. Again, laser pulses may be used to obtain the trophectoderm cells. Still yet, fluorospectrometry may be employed to determine cell free DNA/RNA content. Again, analysis of variance may be employed to compare cell free DNA/RNA levels. Still again, embryos may be graded based on cell free DNA/RNA content. Further, cell free DNA/RNA content may indicate an amount of chromosomal defects in an embryo. Yet further, detectable molecular differences between embryos may correspond with embryo ploidy status. Still yet, determining an amount of apoptotic cell elimination may indicate future implantation success of an embryo. Further, presence of pro-apoptotic genes may indicate increased embryo viability.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 1 shows Table 1, which displays means for weighted embryo morphology score, blastocel cfDNA content, and caspase-3 activity for 32 day-5 embryos.

FIG. 5 shows Table 2, Ploidy status (PGT-A), age, and implantation result (if applicable) associated with the embryos that harbored the blastocoel fluid-conditioned media used for this study.

Figure 2:
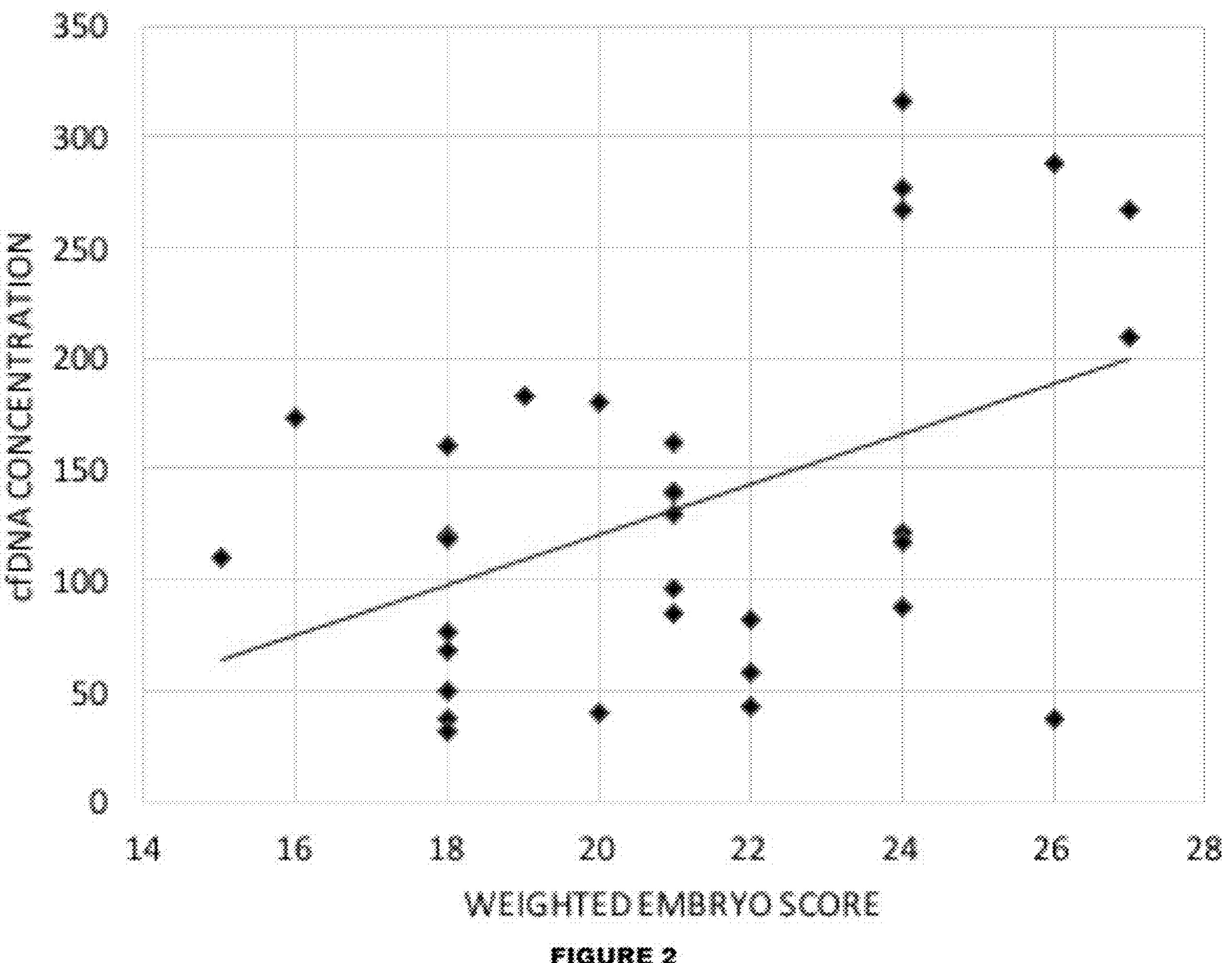
FIG. 2 shows a scatter plot of the weighted embryo score against cfDNA concentration for each of the 32 embryos–cfDNA=104.753+(11.281*score); $R^2$=0.200.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

The current disclosure compared apoptotic gene expression in an embryo that resulted in a live birth, with other euploid (3 leading to pregnancy and 3 resulting in loss of pregnancy) and aneuploid embryos using blastocoel fluid from each day-5 embryo. The design of the current disclosure involved retrospective analysis of day-5 euploid blastocoel apoptotic gene expression and implantation outcome. Following laser-assisted trophectoderm biopsy of IVF-generated day-5 blastocysts, each individual blastocoel fluid-conditioned medium (25 μL) was saved. Biopsied cells were assessed for ploidy status via next-generation sequencing. Gene expression in blastocoel fluid was assessed by RT-PCR utilizing TaqMan arrays for human apoptosis genes (92 genes total). The results showed increased gene expression of caspase-7, an executioner caspase, was observed in pregnancy positive blastocoel fluid samples, but was not detected in pregnancy negative samples (or in aneuploidy samples). Increased gene expression of Bcl-2-like protein 13 (Bcl2-L-13) was detected in embryos that did not implant.

The current disclosure provides evidence that apoptotic gene expression in blastocoel fluid from day-5 euploid embryos differs between embryos that successfully implant versus those that do not. Successfully implanted embryos (one yielding live birth) exhibited increased expression of an apoptosis activator, caspase-7. Bcl2-L-13 gene expression was detected to a higher degree in embryos that failed to implant. This mitochondrial gene plays a role in mitophagy as well as inhibiting apoptosis in some cancer cells.

Purpose:

Cell free DNA (cfDNA) which is present in the blastocoel cavity of embryos is believed to result from either physiological apoptosis during development. This study assessed cfDNA content in day 5 IVF blastocysts to determine if there was a correlation with embryo morphology and to source a cellular explanation.

Methods:

Day 5 IVF blastocysts were scored according to the Gardner and Schoolcraft system (modified to generate a numerical value) and cfDNA was collected following laser-induced blastocoel collapsing prior to cryopreservation in 25 μL of media. cfDNA was quantified via fluorospectrometry and apoptotic activity was assessed via a caspase-3 fluorescence assay. Data were compared by linear regression.

Blastocoel fluid was obtained following standardized IVF procedures including fertilization of the eggs via intracytoplasmic sperm injection and embryo culture (Institutional Review Board approved). The blastocyst-stage embryos were graded via Gardner and Schoolcraft System, see Balaban B, Gardner D K. Morphological assessment of blastocyst stage embryos: types of grading systems and their reported outcomes. In Human Gametes and Preimplantation Embryos: Assessment and Diagnosis. Gardner, D, Sakkas, D, Seli, E, Wells, D. (Eds) 13 New York: Springer Science and Media; 2013:31-43, which is hereby incorporated by reference, and cfDNA was collected from blastocoel fluid from 32 embryos following laser-induced blastocoel collapsing prior to cryopreservation. As the blastocyst collapsed in on itself following the laser destruction between the cell junctions of trophectoderm cells, the blastocoel fluid, containing cfDNA, was extruded into the culture medium. The blastocyst was removed and cryopreserved, and 25 μL of culture media plus blastocoel fluid was collected and stored at −70° C. for further analysis.

An algorithm was created to convert the Gardner system's alphabetical and numerical grading of embryos based on expansion grade, inner cell mass, and trophectoderm to a single numerical score. Rehman, et al., see Rehman K S, Bukulmez O, Langley M, Carr B R, Nackley A C, Doody K M. *Late Stages Of Embryo Progression Are A Much Better Predictor Of Clinical Pregnancy Than Early Cleavage In Intracvtoplasmic Sperm Injection And In Vitro Fertilization Cycles With Blastocvst-Stage Transfer*. Fertil Steril. 2007; 87:1041-52, which is hereby incorporated by reference, devised a numerical score for embryos by assigning a number to each category of the Gardner scale and multiplying them (i.e. 4AB would become 4*4*3=48).

The new algorithm of the current disclosure includes a weighted significance to determine the most viable embryo as follows: weighted embryo morphology score=(Expansion grade*3)+(ICM grade*2)+(TE grade*1). Expansion grade: Grade 1 blastocysts are those where the blastocoel cavity is less than half of the volume of the embryo; in Grade 2 blastocysts, the blastocoel cavity is at least half of the volume of the embryo; Grade 3 blastocysts have the blastocoel cavity completely filling the embryo; Grade 4 blastocysts have a blastocyst cavity greater than the original volume of the embryo; Grade 5 blastocysts, hatching blastocysts, the blastocoel cavity is greater than the original volume of the embryo and trophectoderm is herniating through the zona pellucida and Grade 6 are hatched blastocysts. Once the blastocyst has reached an expansion grade of 3 or more, a clear distinction can be made between the two newly formed cell populations, i.e. the inner cell mass (ICM) and the trophectoderm (TE). The ICM will eventually develop into the embryo/fetus while the TE will form the fetal component of the placenta. Inner cell mass (ICM)

grade: Morphologically, the ICM can range from being very large with tightly packed cells to almost non-existent with loosely bound cells. The best ICM category (1) contains many cells that are tightly packed together, the second ICM category (2) is composed of several cells that are loosely grouped and the last category (3) has an ICM that contains very few cells that are loosely bound. Trophectoderm (TE) grade: The TE cells are scored similarly as the ICM, i.e. by number and epithelium cellular cohesiveness according to three different grades (1-3). The best TE category (1) contains many cells that form a cohesive epithelium, the second TE category (2) has few, loose epithelium cells and the third category (3) has very few and large epithelial cells that form a loose TE. Each grade is subsequently multiplied by a factor (1, 2 or 3) that was predetermined according to its importance, as determined following a survey of experienced embryologists.

To quantify the cfDNA concentration in the blastocoel fluid, an ACCUBLUE NEXTGEN DSDNA QUANTIFICATION KIT (Biotium, Fremont, CA) was used with emissions detected by a NANODROP 3300 Fluorospectrometer (Thermo Fisher Scientific, Waltham, MA) per manufacturer instructions. After a standard curve was generated, 2 μL of blastocyst media for each embryo was quantified independently. Linear regression with statistics via SIGMAPLOT 14.0 (SysStat Software, Inc., San 40 Jose, CA) were then run comparing embryo morphology scores to cfDNA concentrations. Once the cfDNA had been quantified, the blastocoel fluid was then analyzed for caspase-3 apoptotic activity. A caspase-3 enzyme-linked immunosorbent assay was performed with a caspase-3 cellular assay kit (Enzo Life Sciences, Farmingdale, NY). As per the manufacturer's instructions, 10 μL of blastocoel fluid was placed in a buffer in a 96 well plate and 40 μL of Ac49 DEVD-AMC Caspase-3 fluorogenic substrate was added to each individual well. This substrate was cleaved by activated caspase-3 as apoptosis occurred and the emission of the substrate was detected in the 420-460 nm wavelength range. That emission represents the cleavage of the fluorogenic substrate by caspase-3. The well plate with the blastocoel fluid and substrate was run on a TECAN INFINITE M1000 (Mannedorf, Switzerland) monochromator based fluorescence microplate reader to analyze the emissions. The emissions generated from each well were measured every minute over a total of forty-five minutes. The recorded value represented the stabilized emission data point following subtraction of the background buffer emission prior to analysis with the cfDNA concentration data. Linear regression with statistics via SigmaPlot were analyzed comparing caspase-3 activity to cfDNA concentration.

Results:

A total of 32 embryos were evaluated. There was a significant ($p<0.01$) and positive correlation (cfDNA=104.753+(11.281*score); R2=0.200) between embryo score and cfDNA content. A significant ($p<0.05$) and positive correlation (cfDNA=115.9+(0.05*caspase-3); R2=0.128) was observed between caspase-3 activity and cfDNA levels. There was no significant relationship between caspase-3 activity and embryo morphology score.

The current disclosure discovered that cfDNA present in blastocoel fluid, can be quantified, and positively correlates with embryonic morphology. There is also evidence that at least a portion of the cfDNA is due to apoptotic activity. Additional studies are warranted to determine other cellular sources physiological sources of the cfDNA in blastocyst fluid and to determine the relationship with cfDNA content and embryo morphology plus implantation potential.

Cell free DNA (cfDNA) which is present in the blastocoel cavity of embryos is believed to result from physiological apoptosis during development. The current disclosure assessed cfDNA content in day 5 IVF blastocysts to determine if there was a correlation with embryo morphology and to source a cellular explanation.

Blastocoel fluid from a total of 32 day 5 embryos were analyzed as described with the mean values presented in Table 1, see FIG. 1. FIG. 1 shows Table 1, which displays means for weighted embryo morphology score, blastocel cfDNA content, and caspase-3 activity for 32 day-5 embryos. The table reports the total number of embryos used (32) and the average embryo score based on the algorithm described earlier (21.125). The percentage of blastocoel fluid samples that were positive for cfDNA was also recorded (100%) along with the mean cfDNA concentration (133.55 ng/mL) and the percentage of blastocoel fluid samples that were positive for caspase-3 activity (78.1%). Embryo morphology scores ranged from 15 to 27, with a mean of 21.125. cfDNA content (ng/mL) ranged from a low of 32.3 ng/mL to a high of 315.3, with a mean of 133.55. Caspase-3 activity (AFU) ranged from undetectable levels to a high of 2,226.6 AFU, with a mean of 383.8 AFU.

Figure 3:
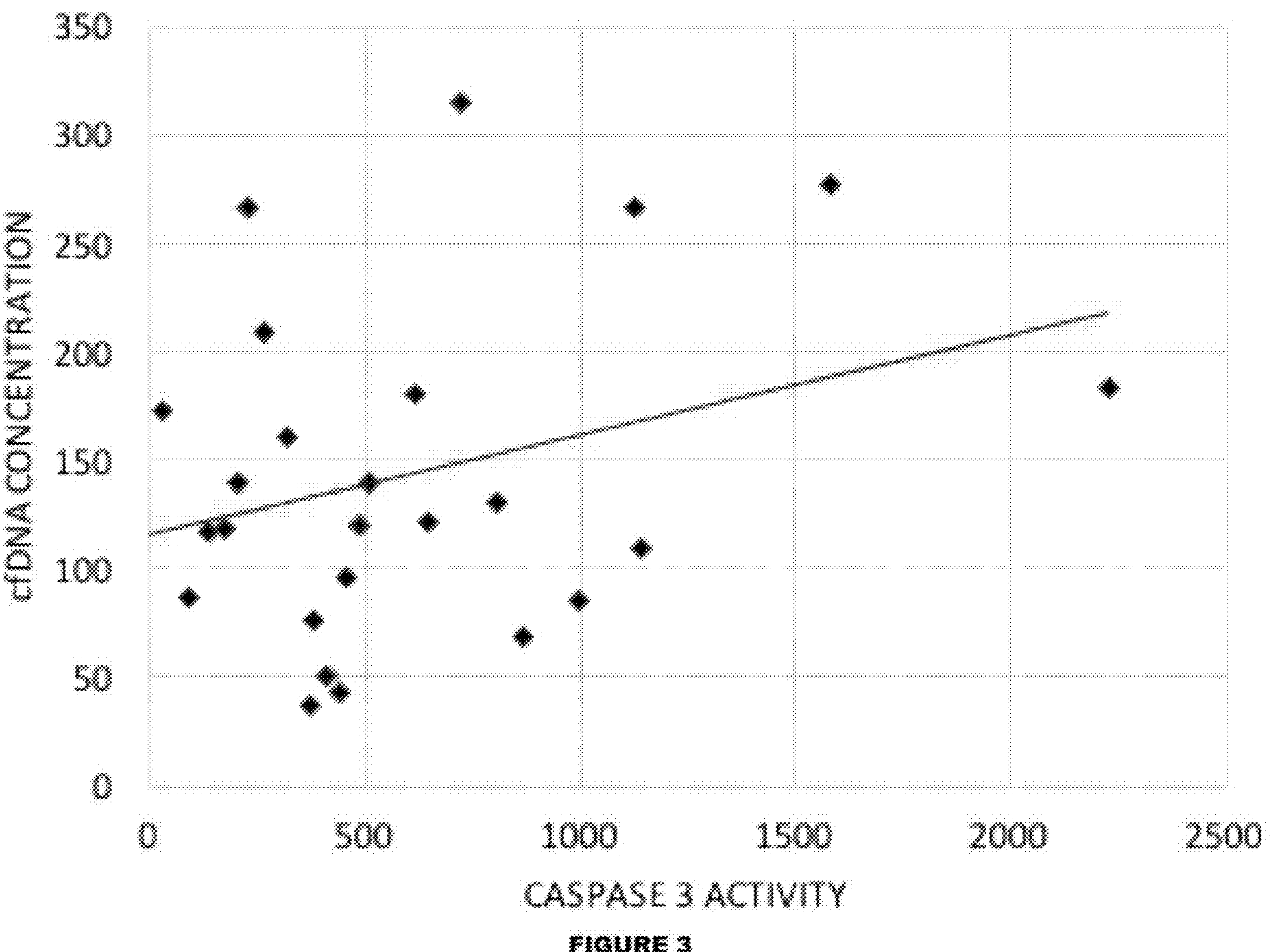
FIG. 3 shows a scatter plot of the caspase-3 activity (AFU) against cfDNA concentration for all 32 embryos–cfDNA=115.9+(0.05*caspase-3); $R^2$=0.128.

The maximum embryo morphology score of 27 had a cfDNA concentration of 266.5 pg/μL and the minimum embryo score of 15 had a cfDNA concentration of 109.9 pg/μL, see FIG. 2, which shows a scatter plot of the weighted embryo score against cfDNA concentration for each of the 32 embryos–cfDNA=104.753+(11.281*score); $R^2=0.200$. There was a significant ($p<0.01$) and positive correlation [cfDNA=104.753+(11.281*29 score); R2=0.200] between embryo morphology score and cfDNA. There was a significant ($p<0.05$) and positive correlation [cfDNA=115.9+(0.05*caspase-3); $R^2=0.128$] between caspase-3 activity and cfDNA, see FIG. 3, which shows a scatter plot of the caspase-3 activity (AFU) against cfDNA concentration for all 32 embryos–cfDNA=115.9+(0.05*caspase-3); R2=0.128. The weighed embryo score was also compared to the caspase-3 activity, however, there was no significant relationship between the two.

Discussion To develop the algorithm used in this disclosure, several studies were evaluated. Rehman, et al (2007) devised a numerical score for embryos by assigning a number to each category of the Gardner scale and multiplying them (for example, 4AB would become 4*4*3=48). While this numerical score did correlate with implantation potential, live birth did not. The algorithm developed with respect to the current disclosure modified this calculation to reflect literature studies that found that the blastocyst expansion and inner cell mass grades predicted live birth rates while there was no association of trophectoderm score with live birth rates. However, the importance of the trophectoderm has been debated in other papers. Palini, et al., see Palini S. Galluzzi L, De Stefani S., Bianchi M, Wells D, Magnani M, Bulletti C. *Genomic DNA In Blatocoel Fluid*. Reprod BioMed. 2013; 26:603-610, discovered that cell free DNA was found in about 90% of blastocoel fluid samples produced from IVF. The current disclosure provides further evidence that cfDNA is present in blastocoel fluid, and is quantifiable supporting this previous research. The current disclosure also indicates that cfDNA positively correlates with a high embryonic morphology score, which suggests that the better the embryo morphology, the higher the cfDNA concentration.

One theory as to why this occurs comes from Tobler et al., see, Tobler K J, Zhao Y, Ross R, Benner A T, Xu X, Du L, Broman K, Thrift K, Brezina P R, Kearns W G. *Blastocoel*

*Fluid Harbors Embryonic DNA That May Result From The Marginalization Of Aneuploidy Cells During Embryogenesis*. Fertil Steril. 2014; 102:205, which is hereby incorporated by reference that reported that euploid blastocysts can marginalize aneuploid cells to the blastocoel fluid during early embryogenesis. Therefore, the cfDNA would be representative of aneuploid cells that a viable embryo had marked for apoptosis. Another theory is that cfDNA could represent normal development from the breaking and repairing of DNA as the embryo develops and thus higher cfDNA concentrations could represent remodeling of the viable embryo. These avenues of causes will be further researched in future studies.

Cell free DNA has also been previously correlated with apoptotic events, which can be measured via caspase activity. In the current disclosure, we discovered that there is caspase-3 activity in the blastocoel fluid and that it positively correlates with cfDNA. This confirms that cfDNA in the blastocoel fluid may be present, in part, due to apoptosis. However, due to the undetectable amounts in 7 samples, this suggests that apoptosis might not be the complete explanation of cfDNA presence.

Other mechanisms may include another caspase pathway (e.g., caspase-8), cellular remodeling, or autophagy. In relation to the caspase-3 activity, Spanos et al., see Spanos S, Rice S, Karagiannis P, Taylor D, Becker D L, Winston R M, Hardy K. *Caspase Activity And Expression Of Cell Death Genes During Development Of Human Preimplantation Embryos*. Reproduction 2002; 124:353-63, were able to identify BAX and BCL2 in blastocyst using immunohistochemistry and further detected caspase activity after compaction at the morula and blastocyst stages. This finding correlates with the current disclosure's detection of caspase activity in the blastocoel fluid. More studies are needed to further elucidate the role of cfDNA in blastocoel fluid.

Overall, the current disclosure confirms the presence of cfDNA in blastocoel fluid and that is due in part to apoptosis during preimplantation embryo development. Further defining the role of cfDNA in embryogenesis will allow for more avenues to determine the best viable embryo in the future. This has the possibility of effecting the way in which the best embryos are selected in the future, with further confirmation of viable embryos with higher cfDNA concentrations.

This current disclosure provides evidence that cfDNA is present in blastocoel fluid, can be quantified, and positively correlates with embryonic morphology. There is also evidence that at least a portion of the cfDNA is due to apoptotic activity. Additional studies are warranted to determine other cellular sources physiological sources of the cfDNA in blastocyst fluid and to determine the relationship with cfDNA content and embryo morphology plus implantation potential.

In addition to chromosomal analysis, one method proposed to improve the implantation rates of euploid IVF embryos is to identify biological markers that are unique to implanted euploid embryos versus those that did not. An ideal biomarker is one easily obtained using non-invasive or minimally-invasive means from the early embryo at trophectoderm biopsy. Upon inspection of the IVF procedure, it is evident that the blastocoel fluid fits the criteria. During IVF, upon completion of the blastocyst biopsy for subsequent chromosomal analysis (preimplantation genetic testing for aneuploidies or PGT-A), the embryo collapses upon itself. This collapse results in the blastocoel fluid extruding into the surrounding culture medium. The blastocyst fluid-conditioned culture medium (which is generally discarded) can be frozen and subsequently assessed. This collection method, known as blastocentesis, is minimally-invasive and provides blastocoel fluid from day-5/6 embryos for study, while mitigating risk to future developmental potential of the embryo. This blastocoel fluid is a recognized source of cell-free DNA (cfDNA), which may serve as a proxy for discovering ploidy status of the embryo. Several studies have reported a limited concordance between the chromosomal status detected using cfDNA compared to PGT-A from embryonic trophectoderm biopsy. Proteins, mitochondrial DNA, miRNAs, along with cfDNA have also been detected in the blastocoel fluid and the origin of these molecules may potentially be the remnants of apoptotic cells from the blastocyst. Most recently, microRNAs, some of which were linked to apoptosis, and extracellular vesicles were found in blastocoel fluid from human embryos. Therefore, if apoptosis purges the embryo of aneuploid cells in the preimplantation embryo, detection of this activity may be possible through measuring cfDNA content in the blastocoel fluid.

In the current study, we assessed cfDNA levels in blastocoel fluid conditioned media from 89 day-5 blastocyst embryos and found higher levels of cfDNA in euploid embryos compared to aneuploid embryos.

One source of the elevated cfDNA in euploid embryos may be remnants of apoptotic cells in the embryo. We hypothesize that human embryos classified as aneuploid (based on PGT-A) would have undergone less and or incomplete apoptotic cell elimination which resulted in the embryo retaining cells that harbored chromosomal abnormalities. We propose that analysis of cfDNA content in blastocoel fluid is a potential biomarker for selecting the embryo having the best chance at uterine implantation.

In addition to chromosomal analysis, one method proposed to improve the implantation rates of euploid IVF embryos is to identify biological markers that are unique to implanted euploid embryos versus those that did not. An ideal biomarker is one easily obtained using non-invasive or minimally-invasive means from the early embryo at trophectoderm biopsy. Upon inspection of the IVF procedure, it is evident that the blastocoel fluid fits the criteria. During IVF, upon completion of the blastocyst biopsy for subsequent chromosomal analysis (preimplantation genetic testing for aneuploidies or PGT-A), the embryo collapses upon itself. This collapse results in the blastocoel fluid extruding into the surrounding culture medium. The blastocyst fluid-conditioned culture medium (which is generally discarded) can be frozen and subsequently assessed. This collection method, known as blastocentesis, is minimally-invasive and provides blastocoel fluid from day-5/6 embryos for study, while mitigating risk to future developmental potential of the embryo. This blastocoel fluid is a recognized source of cell-free DNA (cfDNA), which may serve as a proxy for discovering ploidy status of the embryo. Proteins, mitochondrial DNA, miRNAs, along with cfDNA have also been detected in the blastocoel fluid and the origin of these molecules may potentially be the remnants of apoptotic cells from the blastocyst. Most recently, microRNAs, some of which were linked to apoptosis, and extracellular vesicles were found in blastocoel fluid from human embryos. Therefore, if apoptosis purges the embryo of aneuploid cells in the preimplantation embryo, detection of this activity may be possible through measuring cfDNA content in the blastocoel fluid.

In the current study, we assessed cfDNA levels in blastocoel fluid conditioned media from 89 day-5 blastocyst embryos and found higher levels of cfDNA in euploid embryos compared to aneuploid embryos. One source of the elevated cfDNA in euploid embryos may be remnants of apoptotic cells in the embryo. We hypothesize that human embryos classified as aneuploid (based on PGT-A) would have undergone less and or incomplete apoptotic cell elimination which resulted in the embryo retaining cells that harbored chromosomal abnormalities. We propose that analysis of cfDNA content in blastocoel fluid is a potential biomarker for selecting the embryo having the best chance at uterine implantation.

Methods

Research approval was granted by the Institutional Review Board (IRB) of the University of South Carolina Office of Research Compliance. Blastocoel fluid conditioned media, which is generally discarded, was collected and saved post-biopsy from day-5 blastocyst stage human embryos obtained from patients undergoing IVF cycles at collaborating clinics (San Antonio, TX, Swansea, I L and Raleigh, NC).

Following procedures for preimplantation genetic testing, extruded trophectoderm (TE) cells were biopsied following laser pulses between cellular junctions from the day-5 blastocyst stage embryos. The biopsied TE cells were removed by pipette and placed into buffer for PGT-A analysis via Next-Gen Sequencing (NGS) at a commercial sequencing company. Upon completion of the blastocyst biopsy, the embryo self-collapses, resulting in blastocoel fluid being extruded out into the surrounding medium. The blastocyst fluid-conditioned culture media with a volume of approximately 25 μL is snap frozen prior to shipment. Biopsied embryos are cryopreserved pending outcome of the sequencing results. De-identified data including patient age, blastocyst morphology scores and ploidy status were provided by the collaborating fertility clinics.

Cell-Free DNA Quantitation

Cell-free DNA in the blastocoel fluid-conditioned media from 89 embryos was quantified using fluorospectrometry. An AccuBlue NextGen dsDNA Quantification Kit (Biotium) was utilized, with resulting emissions detected by a NanoDrop 3300 Fluorospectrometer (ThermoScientific) per manufacturer's instructions. After generating a standard curve, 2 μL of blastocoel fluid-conditioned media from each of the 89 embryos was quantified independently. Ploidy status (≤−2, −1, 0, +1, ≥+2) and cfDNA content were compared by analysis of variance (ANOVA) and Students' t-test.

Results

Figure 4:
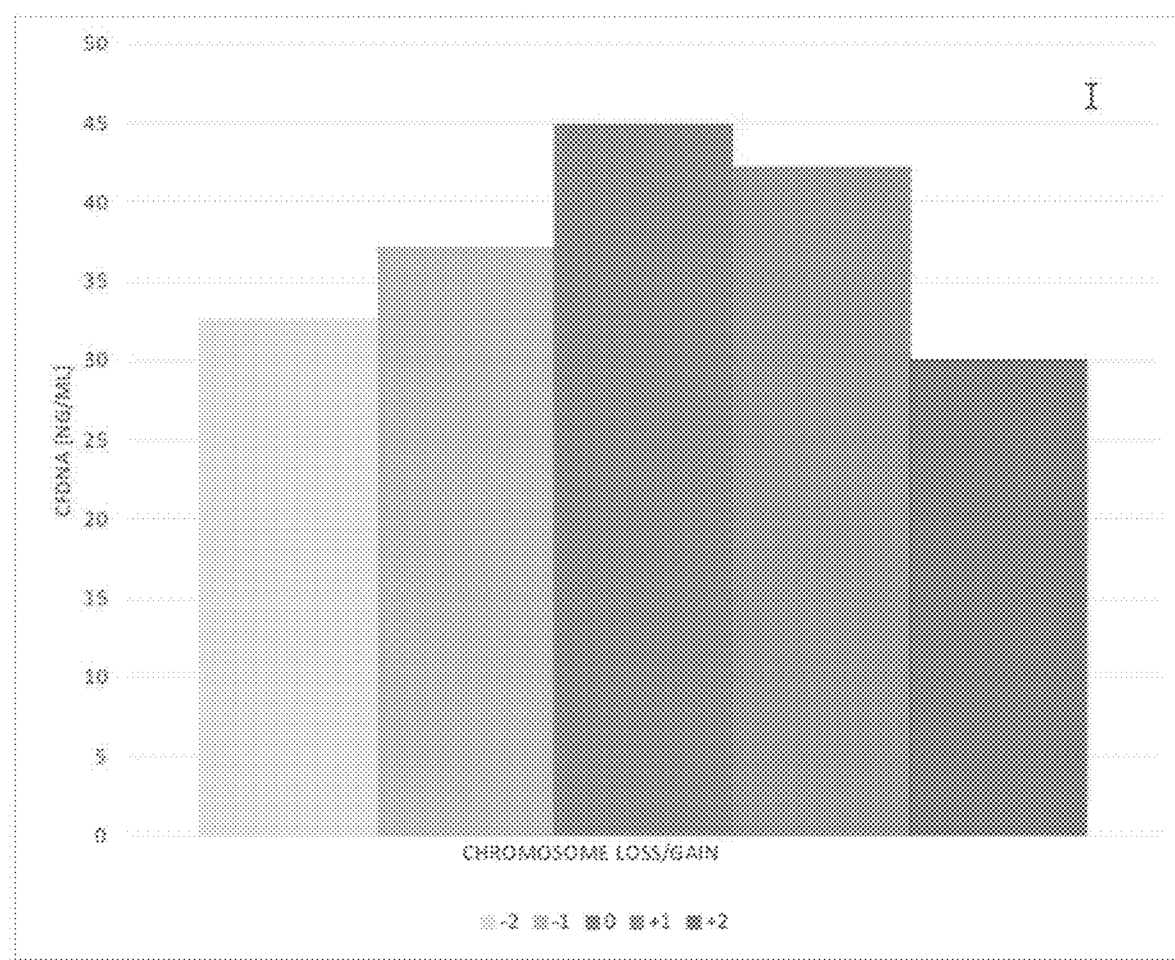
FIG. 4 shows elevated levels of Cell-free DNA content were detected in blastocoel fluid conditioned media from euploid embryos as compared to aneuploid embryos.

Average Cell-free DNA content is higher in euploid embryos compared to aneuploid embryos Cell-free DNA (cfDNA) was quantified in 89 blastocoel fluid conditioned medium samples from day-5 blastocyst embryos, characterized by ploidy status and subsequently averaged see FIG. 4. FIG. 4 shows Elevated levels of Cell-free DNA content were detected in blastocoel fluid conditioned media from euploid embryos as compared to aneuploid embryos. Blastocoel fluid-conditioned medium samples (N=89) from day-5 blastocyst embryos were assessed for DNA content using a fluorescent Nanodrop. cfDNA from each blastocyst stage embryo was determined by fluorospectromety and the mean is reported from 45 euploid blastocyst stage embryos (green bar), 18 blastocyst stage embryos exhibiting a single chromosomal loss, 6 blastocyst stage embryos with 2 or more missing chromosomes, 15 blastocyst stage embryos exhibiting a single chromosome gain and 5 blastocyst stage embryos with a 2 or more chromosome gain. ANOVA revealed a significant ($p<0.05$) difference between chromosomal status (gain/loss/euploid) and cfDNA levels. Normal, euploid blastocyst stage embryos (n=45) had a mean cfDNA content of 44.9 ng/mL. Blastocyst embryos (n=18) exhibiting a single chromosomal loss had a mean cfDNA content of 37.1 ng/mL, those with 2 or more missing (n=6) had a mean cfDNA content of 32.6 ng/mL. Blastocyst embryos (n=15) exhibiting a single chromosome gain had a mean cfDNA content of 42.2 ng/mL, those with 2 or more chromosomes (n=5) had a mean cfDNA content of 30.1 ng/mL. There was a significant ($p<0.05$) difference in cfDNA between euploid (44.9 ng/mL) and aneuploid (36.8 ng/mL) day-5 blastocysts. ANOVA revealed a significant ($p<0.05$) correlation linking chromosomal status (gain/loss/euploid) and cfDNA content. Elevated cfDNA in blastocoel fluid from euploid embryos may represent the apoptotic remnants from aneuploid cells within the euploid embryo that underwent selective elimination, whereby aneuploid embryos may have been unable to selectively remove these cells via apoptosis to the same extent as euploid embryos. Thus, a grading system may be employed to help distinguish euploid embryos from aneuploid embryos based on cell free DNA content.

Discussion

We have identified a molecular feature in blastocoel fluid conditioned media that differs between euploid and aneuploid human embryos. Specifically, cfDNA levels are higher in fluid from euploid embryos when compared with aneuploid embryos. In addition, cfDNA content decreased as more than one chromosome was gained or lost in our pool of aneuploid embryos analyzed. One source of the cfDNA in the blastocoel fluid-conditioned media may be cellular remnants from aneuploid cells that underwent selective apoptosis early in preimplantation development. These results suggest that blastocoel fluid-conditioned media provides detectable molecular differences that vary with embryo ploidy status, see FIG. 4. Furthermore, the blastocoel fluid-conditioned media may retain evidence of apoptotic cell elimination of specific aneuploid cells during early preimplantation development. The extent to which apoptotic cell elimination occurred may be an indicator of future implantation success of the embryo.

The current disclosure's results support the concept that blastocoel fluid-conditioned media contains the molecular remnants of apoptotic cells selectively sacrificed by the preimplantation embryo, therefore cfDNA in blastocoel fluid may not be the best indicator of ploidy status as suggested by others. The current disclosure poses that the level of apoptotic remnants (i.e. cfDNA) may represent a molecular indicator of embryo ploidy statues, and future, embryo implantation potential. We propose that selective self-sacrificing of aneuploid cells via apoptosis within the preimplantation embryo is a natural process, and if carried out to the necessary extent, will yield a euploid embryo, or potentially an aneuploidy embryo, competent for uterine implantation. Therefore, assessing the apoptotic process in preimplantation embryos, resides in the blastocoel fluid-conditioned media.

The current disclosure provides that the identification of molecular markers for use during selection of embryos for intrauterine implantation can enhance in vitro fertilization-embryo transfer success rates. Assessing apoptotic gene expression in blastocoel fluid-conditioned media from human embryos with known ploidy and implantation status provides the opportunity to study patterns and processes occurring during early embryo development. Apoptosis occurs during preimplantation development and may serve to selectively eliminate aneuploid cells from the developing embryo thereby enhancing implantation potential. Therefore, apoptotic remnants (i.e. mRNAs) may reside within the embryo's blastocoel fluid and vary in relation to the embryo's implantation potential. This study compared apoptotic gene expression in blastocoel fluid-conditioned media using Real-Time PCR from euploid embryos with known implantation outcomes.

Blastocoel fluid-conditioned media (25 μL) was collected following trophectoderm (TE) biopsy of ICSI-generated day-5 blastocysts. Biopsied TE cells were sent for preimplantation genetic testing for aneuploidies using NGS. The blastocoel-fluid conditioned media from 10 euploid embryos (6 that implanted; 4 that did not implant) were each subjected to DNase I treatment prior to cDNA synthesis before assessing gene expression via RT-PCR using TaqMan Fast Array-Human Apoptosis plates (assessing 92 apoptosis associated genes).

Of the 92 genes analyzed, CASP7 and MCL1 gene expression were only detected in euploid embryos that successfully implanted. Conversely, expression of TNFRSF25 and BCL2L11 genes were only detected in euploid embryos that failed to implant. Several other apoptotic genes (BAD, BCL2L13, BCAP31, NOD1 and CARD18) were expressed more often in embryos that failed to implant versus those that successfully implanted.

This study poses that specific apoptotic remnants (mRNAs encoding apoptotic genes) may represent a molecular indicator of euploid embryo future implantation potential. Specifically, we detected the expression of seven pro-apoptotic genes associated with negative implantation outcomes. Apoptosis is initiated within the developing embryo in response to the presence of aneuploidies and/or ROS-induced damaged cells. Our results suggest that altered cells may still reside within some euploid blastocysts, thus initiating apoptosis. Evidence of apoptotic cell elimination may be detected by expression of pro-apoptotic gene products found within the blastocoel fluid.

The current disclosure, demonstrates the expression of apoptotic genes in human blastocoel fluid-conditioned media. We assessed apoptotic gene expression levels (92 genes) in human blastocoel fluid-conditioned media from 21 embryos (10 euploid and 11 aneuploid). The discovery of pro-apoptotic genes in those embryos compatible with life aligns with the notion that apoptosis occurs within the embryo as a means of self-correction. Characterizing the gene expression patterns in blastocoel fluid may serve as an additional tool for embryologists to use when selecting which euploid embryo to transfer.

Materials and Methods

Blastocoel Fluid-Conditioned Media Collection

Following standard procedures for PGT-A, extruded trophectoderm (TE) cells were biopsied following laser pulses between cellular junctions from ICSI-generated day-5 blastocyst stage embryos. The biopsied TE cells were removed by pipette and placed into buffer for PGT-A analysis via Next-Gen Sequencing (NGS) at a commercial sequencing company. Upon completion of the blastocyst biopsy procedure, the embryo self-collapses, resulting in blastocoel fluid being extruded out into the surrounding medium. Blastocoel fluid-conditioned media (~25 μL biopsy medium plus ~5 μL blastocoel fluid for each embryo), which is generally discarded, was collected and saved post biopsy from day-5 blastocyst stage human embryos obtained from patients undergoing IVF cycles at collaborating clinics (San Antonio, TX, Swansea, IL and 112 Raleigh, NC). The blastocyst fluid-conditioned culture media with a volume of approximately 30 μL is snap frozen prior to shipment for further analysis. Biopsied embryos are cryopreserved pending outcome of the NGS results. De-identified data including patient age, and ploidy status were provided by the collaborating fertility centers.

Apoptotic Gene Expression with TaqMan Arrays

Blastocoel fluid-conditioned media from ten euploid embryos and eleven aneuploid embryos were each subjected to DNase I (RNAase free, Thermo) treatment step for 30 minutes at 37° C. 120 followed by inactivation at 65° C. for 10 minutes. Next cDNA synthesis (High-Capacity cDNA Reverse Transcription Kit, Applied Biosystems) was performed per manufacturers' instructions. cDNA concentration was subsequently assessed using an Eppendorf Bio Spectrometer. A total of 40 ng of cDNA were required for each well of the 96-well TaqMan Fast Array-Human Apoptosis plate (Applied Biosystems). cDNA obtained from each blastocoel fluid sample was diluted in 540 μL of nuclease free water and combined with 540 μL of 2× TaqMan Master Mix. cDNA-Master Mix (10 μL) was then added to each well in the 96-well plate and prepared for thermal cycler as per manufacturer's instructions. Each plate was run using a 7500 Fast Real-Time PCR System (Applied Biosystems) at 50° C. for 2 minutes, 95° C. for 20 seconds, followed by 40 cycles of 95° C. for 3 seconds and 60° C. for 30 seconds, all as per manufacturer's instructions.

The GAPDH housekeeping gene included in each array plate and fluid sample was utilized to calculate negative ΔCt (define value) values for each apoptotic gene analyzed in the array (negative ΔCt=Ct GAPDH−Ct Apoptotic Gene). Apoptotic genes showing no expression were assigned a Ct value of 40. Negative ΔCt values per apoptotic gene were compared among samples to identify genes that exhibited gene expression versus no expression. Apoptotic genes yielding −ΔCt values above zero were assigned as "expressed" in the specific fluid samples and those below zero were assigned as "no expression".

Ethics Approval and Consent to Participate

Research approval was granted by the Institutional Review Board (IRB) of the University of South Carolina Office of Research Compliance. The study itself is conducted as Not Human Research (since the fluid samples are normally discarded and de-identified) set forth by the Code of Federal Regulations (45 CFR 46) and therefore was exempt from further IRB review. The collection of blastocoel-fluid conditioned media was conducted under informed patient consent. The informed consent for treatment (American Society for Reproductive Medicine-Society for Assisted Reproductive Technology consent template; asrm.org) was modified to include that any unused biological material may be used for current or future research. Additionally, all patients signed a consent permitting PGT-A.

Facility: Vios Fertility Institute. All methods were performed in accordance with the relevant guidelines and regulations.

Facility: University of Texas Health Sciences Center San Antonio. All methods were performed in accordance with the relevant guidelines and regulations.

Facility: Atlantic Reproductive Medicine Specialists. All methods were performed in accordance 154 with the relevant guidelines and regulations.

Results

Apoptotic gene expression was detected in blastocoel fluid-conditioned media Blastocoel fluid-conditioned media from euploid (n=12) and aneuploid (n=11) blastocysts (ploidy status determined via PGT-A) was assessed for apoptotic gene expression via Real-Time PCR (see FIG. 5, Table 2). Briefly, fluid samples were treated with DNase I prior to cDNA synthesis. The resulting cDNA for each sample was added to individual Human Apoptosis array plates and mRNA expression levels were determined by Real-Time PCR, normalized to GAPDH and reported as negative ΔCt values, see FIG. 6. Genes corresponding to negative ΔCt values greater than zero were categorized as expressed genes and those with negative ΔCt values less than zero were considered not expressed. We identified five pro-apoptotic genes (BCAP31, BCL2L13, CASP1, DEDD and NOD1) that showed expression in fluid from both euploid blastocysts and aneuploid blastocysts that harbored chromosomal changes compatible with life (see FIGS. 6A-6C). Fluid from two-three blastocysts harboring an extra copy of chromosome 21 collectively exhibited expression of the five pro-apoptotic genes, while two aneuploid blastocysts containing one less X chromosome expressed only the NOD1 pro-apoptotic gene (see FIG. 7 at A-E). In addition, the pro-apoptotic gene CASP7 was expressed in three euploid embryos all associated with positive implantation as well as two aneuploid embryos harboring survivable chromosomal aberrations (see FIG. 7 at F).

Implantation status was also reported for all ten of the fluid samples from the transferred euploid embryos assessed in this study (see FIG. 5, Table 2). Two anti-apoptotic genes (XIAP and NOD2) yielded expression in the fluid analyzed from one-two euploid blastocysts resulting in failed implantation as well as in four aneuploid embryos, see FIG. 8 at A-B). The anti-apoptotic gene BCL3 was expressed in six aneuploid embryos, including all three associated with non-survivable aneuploidies, see FIG. 8 at C.

Collectively, these results strongly support the understanding that apoptosis occurs in both euploid and aneuploid blastocysts stage embryos prior to day-5, but potentially at different rates or to different extents.

Discussion

Analysis of apoptotic gene expression in blastocoel fluid-conditioned media from euploid (successful and unsuccessful implantation outcome) and aneuploid embryos revealed variations in expression patterns. Our findings reveal pro-apoptotic gene expression that is shared among euploid embryos and specifically aneuploid embryos harboring chromosomal mutations compatible with life (i.e. Down syndrome, Turner syndrome, Edwards syndrome). In contrast, anti-apoptotic genes were found to be expressed in the fluid from euploid embryos that resulted in failed implantation along with several aneuploid embryos analyzed. Collectively, these findings support the premise that apoptosis is occurring in the preimplantation embryo and this process can be detected via apoptotic gene expression in the blastocoel fluid. Blastocoel fluid from euploid embryos and embryos harboring aneuploidies compatible with life both exhibited elevated expression of a subset of pro-apoptotic genes (BCAP3, BCL2L13, CASP1, DEDD, NOD1 and CASP7). In contrast, blastocoel fluid from euploid embryos resulting in failed implantation shared expression of anti-apoptotic genes (XIAP, NOD2 and BCL3) with blastocoel fluid from aneuploid embryos.

Five pro-apoptotic genes were found to be expressed in blastocoel fluid-conditioned media from euploid embryos as well as aneuploid embryos that harbor chromosomal loss or gain that is compatible with life. BCL2L13 (Bcl-2-like protein 13), BCAP31 (B-cell receptor-associated protein 31), DEDD (Death effector domain containing) and CASP1 (caspase-1) were expressed in the blastocoel fluid from several euploid embryos as well as in the fluid from aneuploid embryos with an extra copy of chromosome 21. BCL2L13 is a pro-apoptotic gene found in the mitochondria that in *Drosophila* is known to promote fragmentation of mitochondria and help activate caspases as part of the apoptotic process (Matsubara et al., 2019, Otsu et al., 2015). Similarly, in yeast BCL2L13 has been reported to induce mitochondrial fragmentation as part of the process of autophagy (Otsu et al., 2015). BCAP31 (or BAP31) is also a pro-apoptotic gene that is active in cervical cancer cells and activates both the intrinsic and extrinsic apoptotic pathways (Wang et al., 2019, Lee et al., 2016). Specifically, BCAP31 is an ER protein and once cleaved, may aid in inducing mitochondrial fragmentation (Lee et al., 2016). DEDD is a pro-apoptotic gene that promotes caspase-3 activation (Mori et al., 2011, Zalckvar et al., 2010) and interestingly, has been shown in mice to be essential in early pregnancy (Mori et al., 2011)

NOD1 (Nucleotide-binding oligomerization domain-containing protein 1) showed expression in the blastocoel-fluid conditioned media from several euploid embryos, aneuploid embryos containing an additional copy of chromosome 21 and embryos missing one X chromosome. This pro-apoptotic gene is involved in promoting caspase-9 activation (Inohara et al., 1999). These pro-apoptotic genes were found expressed in euploid embryos and those with an additional copy of chromosome 21 which relates to findings from transcriptome analysis performed on whole embryos. The recent study reported that there were no global differences in the transcriptome when comparing these two groups of day-5 blastocysts (Sanchez-Ribas et al., 2019). The CASP7 gene was expressed in three euploid embryos yielding successful implantation, two aneuploid embryos with an additional copy of chromosome 21 and one aneuploid embryo with an additional copy of chromosome 21 and lacking chromosome 17. Caspase-7 is an executioner caspase and a study in cultured human cells suggested that this enzyme's main role may be to remove apoptotic cells within a given tissue as opposed to promoting cell death (Brentnall et al., 227 2013).

XIAP (X-linked inhibitor of apoptosis) along with NOD2 (Nucleotide-binding oligomerization domain-containing protein 2) are both anti-apoptotic genes. XIAP functions to inhibit caspase-3 and caspase-7 via a protein-protein interaction (Chirieleison et al., 2017, Scott et al., 2005).

NOD2, a cell receptor known to play a role in innate immunity, is also regulated by binding of XIAP (Krieg et al., 2009). Both genes were expressed in the fluid of two euploid embryos that resulted in failed implantation as well as four aneuploid embryos. BCL3 (B-Cell Lymphoma 3 Protein) was expressed in the fluid from all three aneuploid embryos that were incompatible with life. This anti-apoptotic, proto-oncogene functions to inhibit apoptosis via the STAT3 pathway in cancer cells (Wu et al., 2016).

The pro-apoptotic gene IFT57 (Intraflagellar transport 57), also known as HIPPI and TRADD (Tumor necrosis factor receptor type 1-associated DEATH domain) was expressed in several aneuploid embryos is known to activate caspase-8 to initiate apoptosis (Gervais et al., 2002, Anderton et al., 2019).

Among the apoptotic genes identified in our study was MCL1, an anti-apoptotic gene that was expressed in the fluid of two euploid embryos. Expression of MCL1 and other apoptotic genes has been detected in preimplantation human embryos (Jurisicova, et al., 2003). Interestingly, mouse embryos deficient in MCL1 expression resulted in embryos that were unable to implant in the mouse uterus (Rinkenberger et al., 2000). These results suggest that MCL-1 is needed for mouse uterine implantation.

Overall, our findings collectively show that apoptotic remnants, specifically mRNA, can be detected in blastocoel fluid-conditioned media and that differences in apoptotic gene expression are seen among blastocysts with varying ploidy and implantation status. These results lend further support the idea that apoptosis is occurring in the developing blastocyst and that this mechanism of possible self-correction (i.e. elimination of specific aneuploid cells) is occurring in euploid blastocysts and those containing aneuploidies known to be compatible with life. We detected pro-apoptotic gene expression in euploid embryos and those compatible with life which advocates for the utility of apoptosis as a normal part of early embryo developments, and possibly one required for an embryo to be viable after implantation. Expression of the anti-apoptotic genes associated with failed implantation and those with aneuploidies incompatible with life provides evidence that inhibition of apoptosis might be detrimental to overall embryo survival after implantation. This study was limited in sample number, and whole embryo transcriptome analysis was impossible with this cohort, therefore this study provides support for the apoptotic process as necessary for embryo survival. Gaining more insight into the molecular mechanisms of early embryo development is likely to reveal new molecular markers to exploit in selecting the very best IVF-generated euploid embryos for transfer. It is likely that there exists a balance of the correct amount of pro- and anti-apoptotic gene expression within developing embryos, and when this balance is perturbed in one way or the other leading to more or less apoptotic activity, the implantation potential of the embryo may be diminished. Defining this balance will require additional studies to assess the transcriptome of whole embryos of varying ploidy status in combination with the transcriptome of blastocoel fluid.

A recent study used TE biopsy cells for RNASeq analysis to assay for differences in embryos that implanted versus unsuccessful implantation. Though the study had a small samples size, several genes varied between the two groups including the pro-apoptotic gene BAK1 expressed in incompetent blastocysts (Ntostis et al., 2019).

Gene expression in the preimplantation human embryo has revealed expression patters that differ between euploid and aneuploid embryos (Licciardi et al., 2018). Alterations in embryo gene expression were assessed by Vera-Rodriguez and colleagues when comparing cells from human blastomeres leading to the identification of 12 genes with expression patterns that allowed discrimination between aneuploid and euploid human embryos (Vera-Rodriguez et al., 2015).

Assessing gene expression in TE biopsied cells has revealed differences when comparing blastocysts resulting in implantation (Parks et al., 2011, Kirkegaard et al., 2015), with advanced maternal age (McCallie et al., 2019) as well as infertility diagnosis (McCallie et al., 2017). Most recently, profiling the blastocoel fluid for microRNAs revealed their expression as well as the presence of extracellular vesicles suggesting a potential signaling role for the microRNAs within the developing embryo (Battaglia et al., 2019). This study further illustrated the potential for blastocoel fluid analysis to support embryo selection for transfer.

Figure 6A:
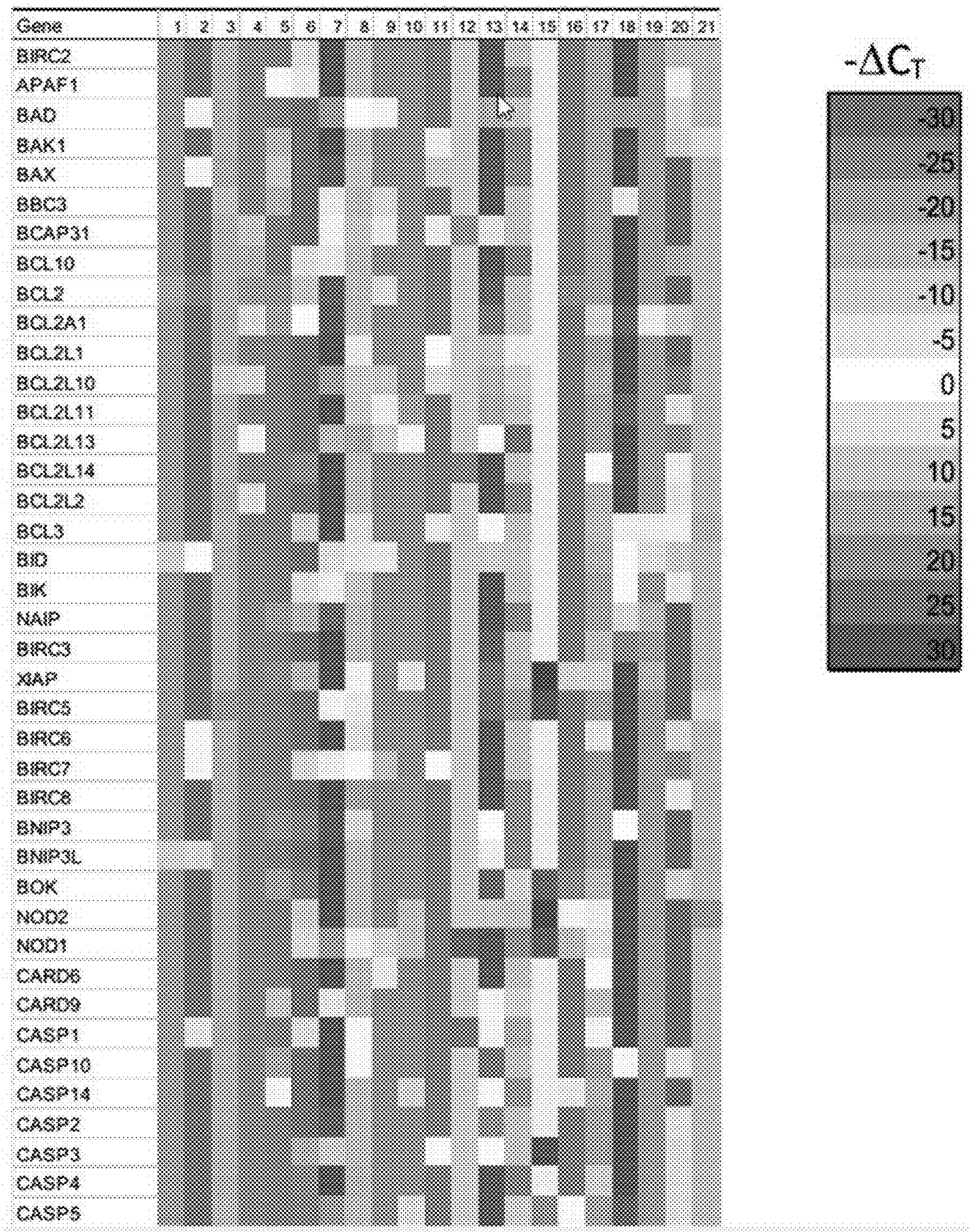
FIGS. 6A, 6B and 6C show apoptotic gene expression in human blastocoel-fluid conditioned media as detected by Real-Time PCR.
Figure 6B:
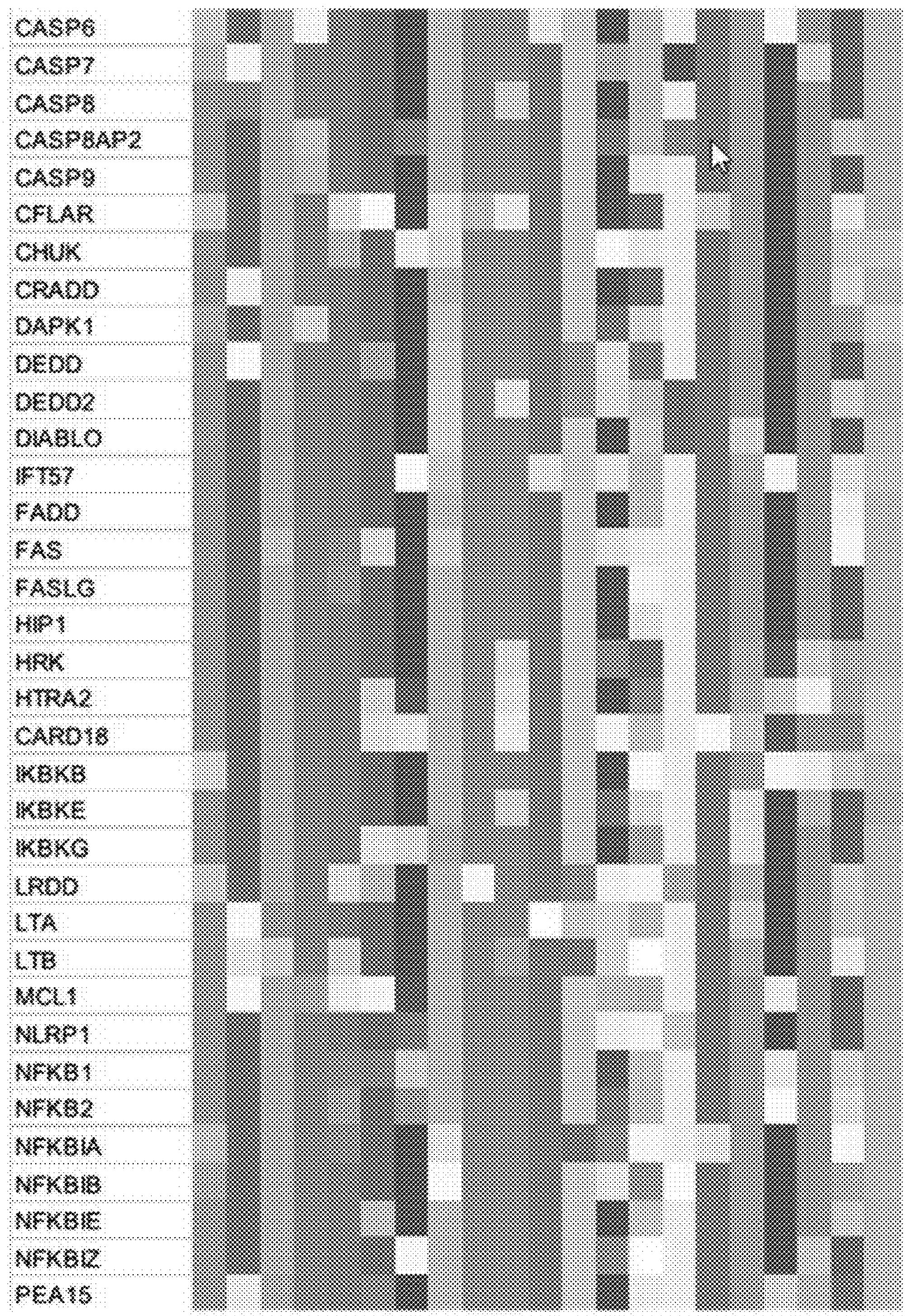
Figure 6C:
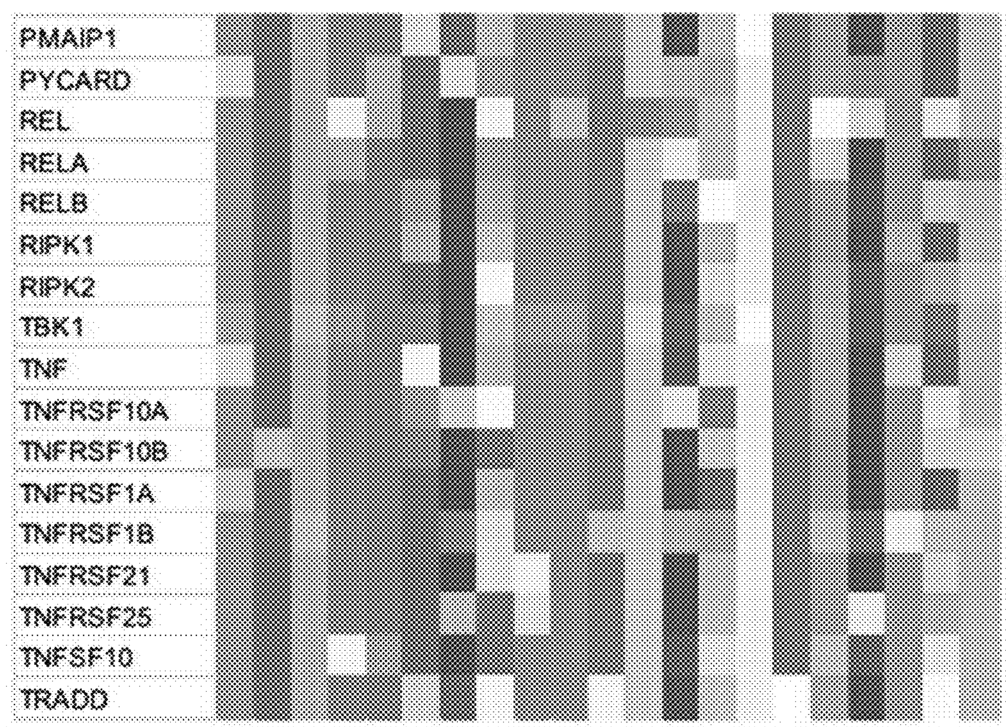

FIGS. 6A, 6B, and 6C show apoptotic gene expression in human blastocoel-fluid conditioned media as detected by Real-Time PCR. The number of each fluid sample (1-21) in the first row corresponds to the embryos listed in Table 2, see FIG. 5. The first row lists the name of each apoptotic gene assessed in the array. The heat map illustrates differential expression of mRNAs in blastocoel fluid from both euploid and aneuploid embryos, reported as negative ΔCt values normalized to GAPDH. Legend shows higher expression indicated by the red shades and lower expression by the blue shades.

Figure 7:
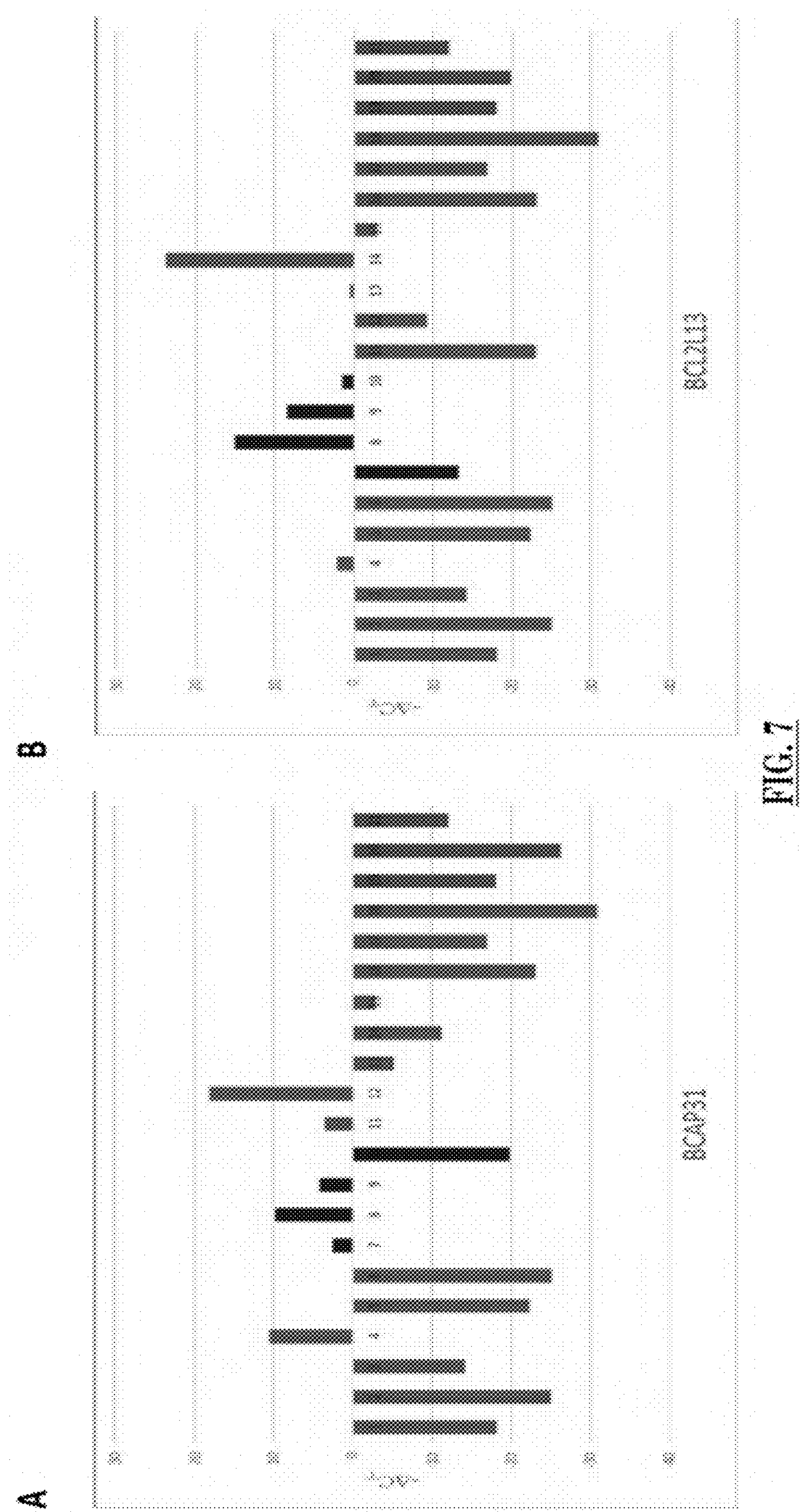
FIG. 7 shows apoptotic gene expression in human blastocoel-fluid conditioned media as detected by 499 Real-Time PCR in euploid blastocysts and specific aneuploid blastocysts.
Figure 7:
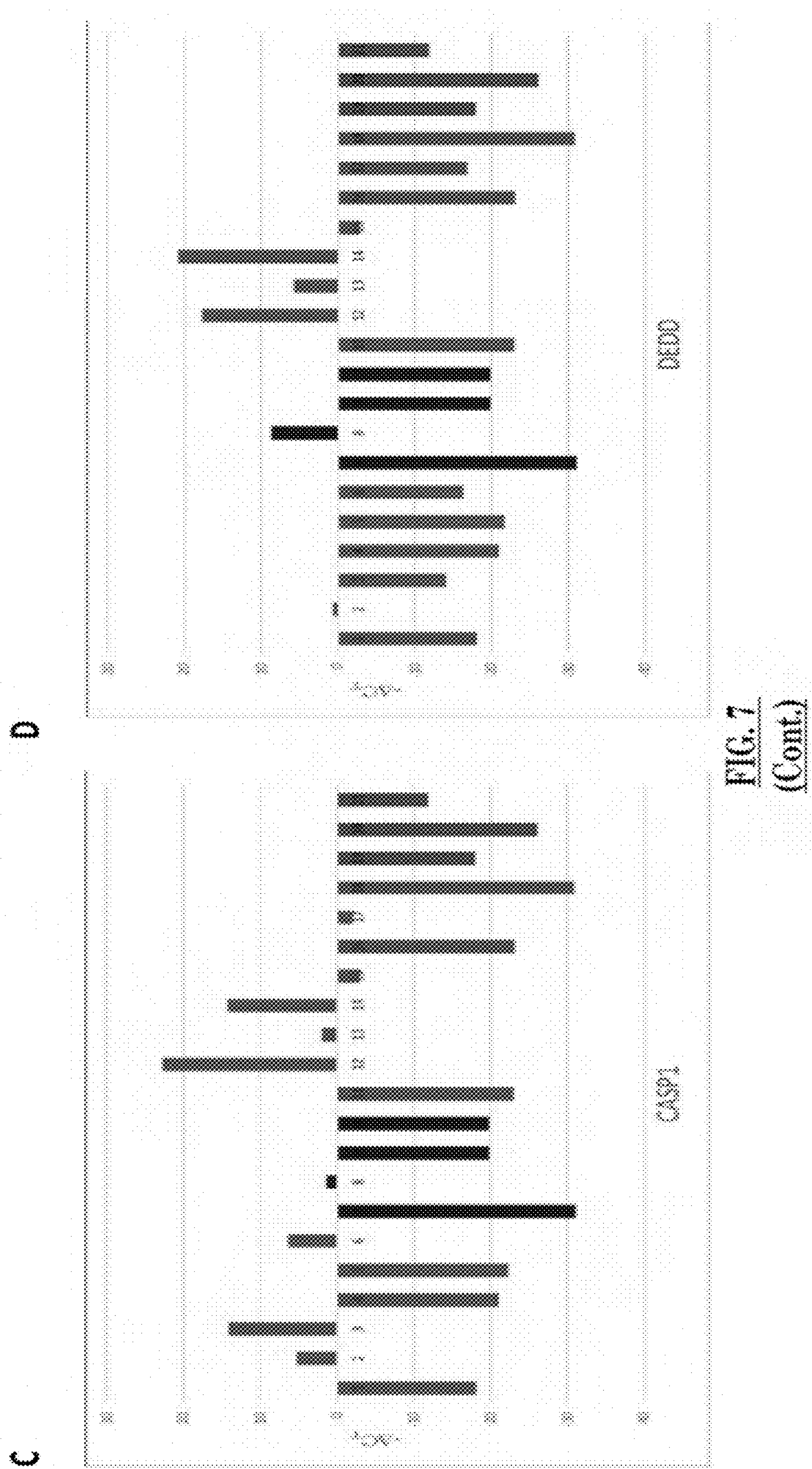
Figure 7:
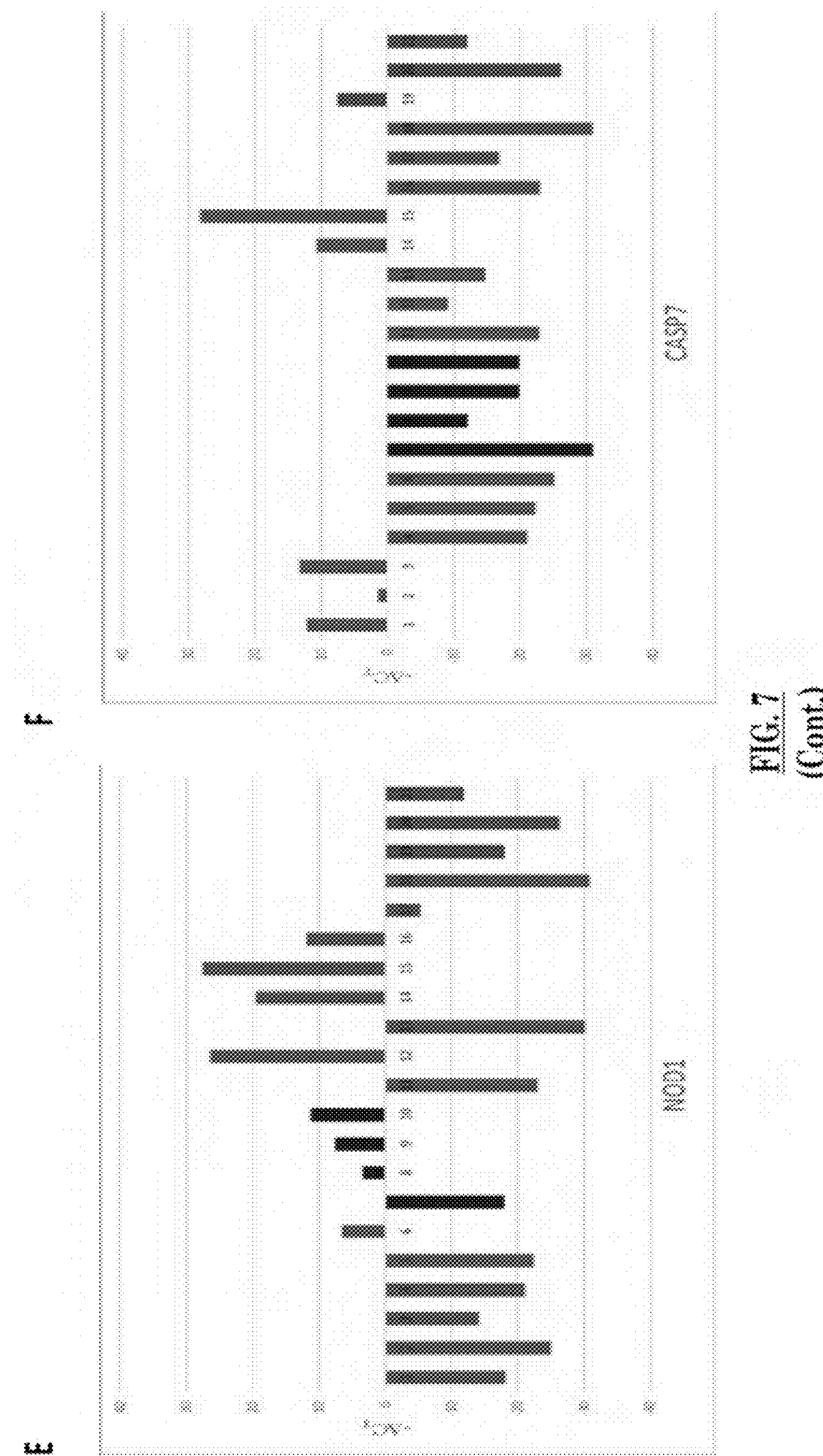

FIG. 7 shows apoptotic gene expression in human blastocoel-fluid conditioned media as detected by Real-Time PCR in euploid blastocysts and specific aneuploid blastocysts. Each bar represents the negative ΔCt value for a specific gene detected in each fluid sample from the numbered blastocysts described in Table 2. A. Expression of BCAP31 was detected in blastocoel fluid from four euploid embryos and two aneuploid embryos harboring an extra copy of chromosome 21. B. Expression of BCL2L13 was detected in blastocoel fluid from four euploid embryos and two aneuploid embryos harboring an extra copy of chromosome 21. C. Expression of CASP1 was detected in blastocoel fluid from four euploid embryos and three aneuploid embryos harboring an extra copy of chromosome 21. D. Expression of DEDD was detected in blastocoel fluid from two euploid embryos and three aneuploid embryos harboring an extra copy of chromosome 21. E. Expression of NOD1 was detected in blastocoel fluid from four euploid embryos and four aneuploid embryos harboring an extra copy of chromosome 21 or one less X chromosome. F. Expression of CASP7 was detected in blastocoel fluid from three euploid embryos resulting in successful implantation and three aneuploid embryos harboring an extra copy of chromosome 21 (embryo numbers 14 and 15) and missing a copy of chromosome 17 (embryo number 19). Green bars indicate euploid embryos resulting in successful implantation, blue bars indicate euploid embryos that did not successfully implant, magenta bars indicate aneuploid embryos compatible with life and purple bars indicate aneuploid embryos incompatible with life.

Figure 8:
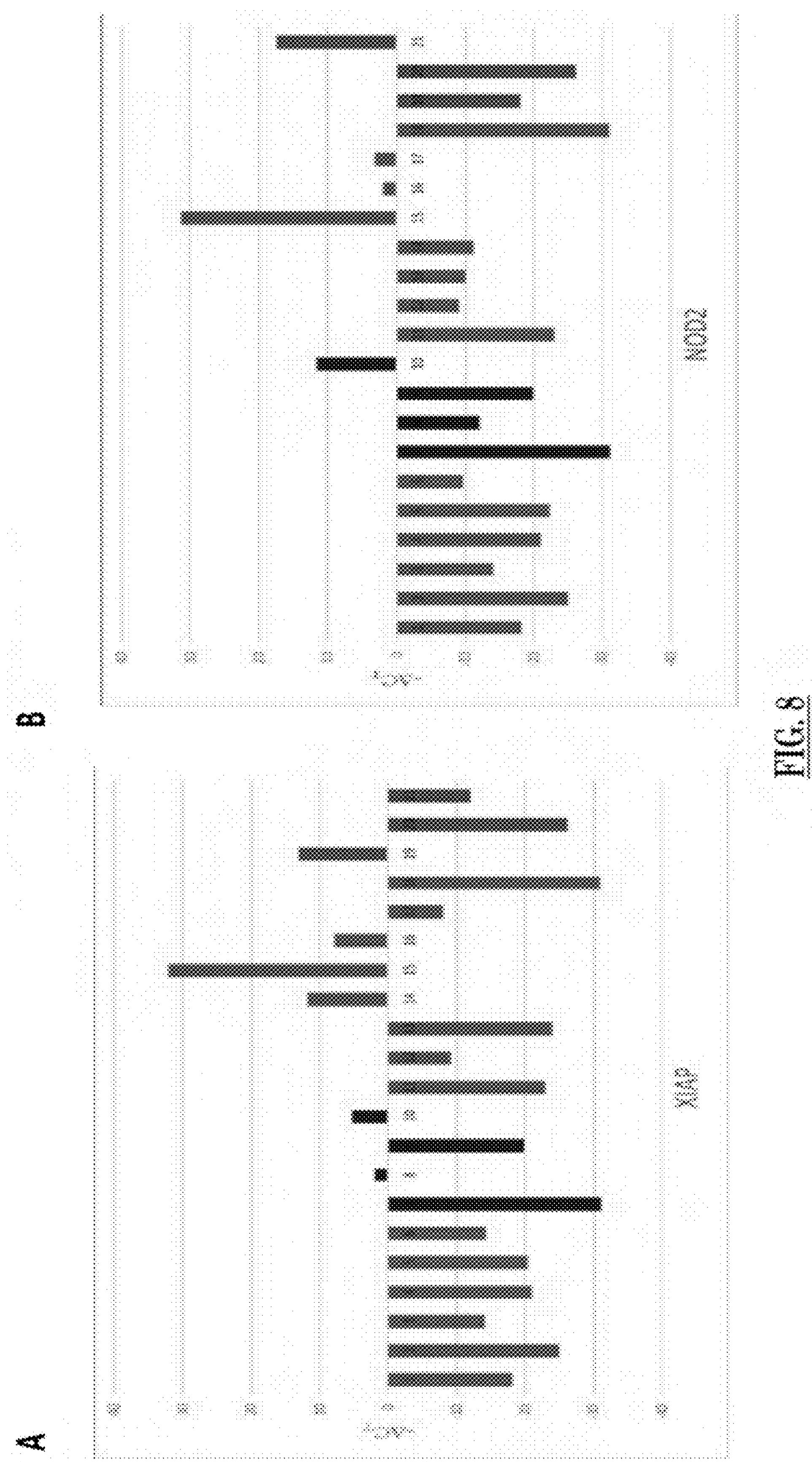
FIG. 8 shows apoptotic gene expression in human blastocoel-fluid conditioned media as detected by Real-Time PCR in euploid blastocysts resulting in failed implantation and aneuploid blastocysts.
Figure 8:
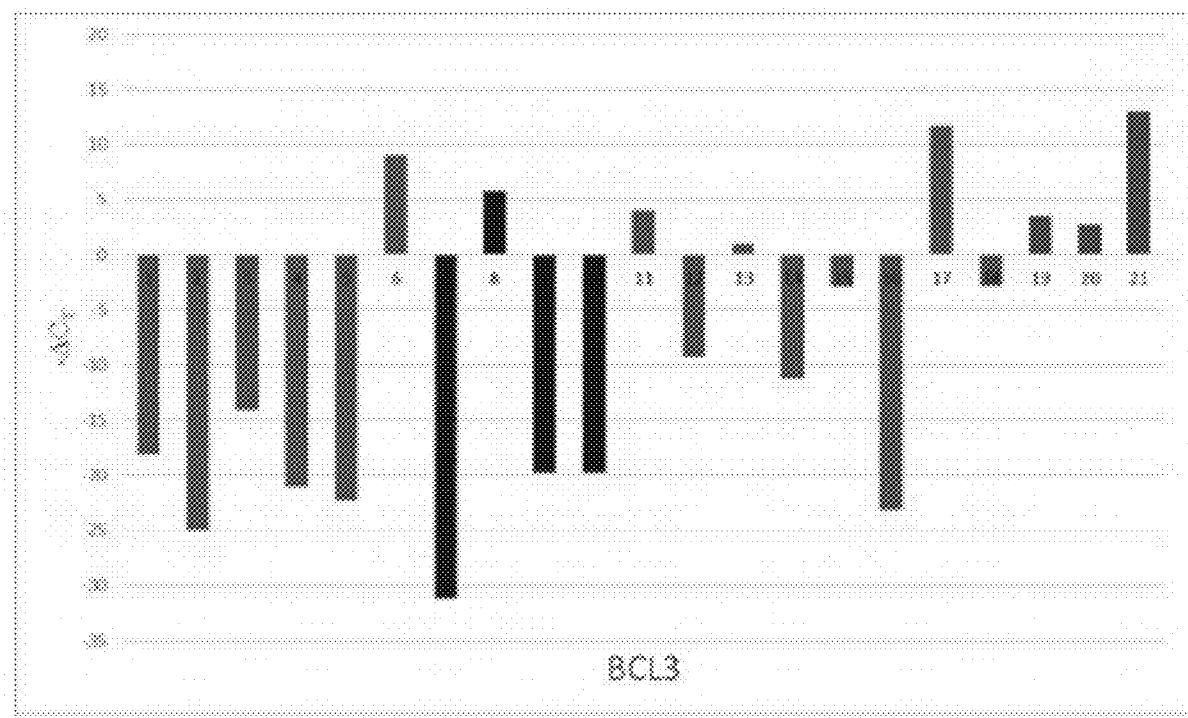

FIG. 8 shows apoptotic gene expression in human blastocoel-fluid conditioned media as detected by Real-Time PCR in euploid blastocysts resulting in failed implantation and aneuploid blastocysts. Each bar represents the negative ΔCt value for a specific gene detected in each fluid sample from the numbered blastocysts described in Table 2. A. Expression of XIAP was detected in blastocoel 521 fluid from two euploid embryos resulting in failed implantation and four aneuploid embryos. B. Expression of NOD2 was detected in blastocoel fluid from one euploid embryo resulting in failed implantation and four aneuploid embryos. C. Expression of BCL3 was detected in blastocoel fluid from two euploid embryos: one resulting in failed implantation and one resulting in successful implantation. This gene was also detected in four aneuploid embryos including all three analyzed harboring aneuploidies incompatible with life. Green bars indicate euploid embryos resulting in successful implantation, blue bars indicate euploid embryos that did not successfully implant, magenta bars indicate aneuploid embryos compatible with life and purple bars indicate aneuploid embryos incompatible with life.

FIG. 5, shows Table 2 Ploidy status (PGT-A), age, and implantation result (if applicable) associated with the embryos that harbored the blastocoel fluid-conditioned media used for this study. Green font indicates euploid embryos resulting in successful implantation, blue font indicates euploid embryos that did not successfully implant, magenta font indicates aneuploid embryos compatible with life and purple font indicates aneuploid embryos incompatible with life.

Discovering a molecular signature in day-5 blastocysts that is suggestive for a successful uterine implantation would provide reproductive specialists an additional tool for selecting the very best embryo for transfer. Identifying the molecules occupying the blastocoel fluid provides a snapshot into the embryos developmental past. During embryo development various cellular signaling pathways are activated to coordinate cell growth. Specific proteins must be expressed at the correct level, time and location for cellular processes to precisely occur. Therefore, any pathway disruption may render an embryo, even a euploid one, unsuitable for implantation. This study assessed global gene expression using RNA-Seq in blastocoel fluid-conditioned media from euploid embryos resulting in (un)successful implantations.

Blastocoel fluid-conditioned media was obtained following biopsy (ploidy status via NextGen sequencing) of ICSI-generated day-5 blastocysts. RNA was extracted and libraries prepared using a SMART-Seq Stranded kit. Following Illumina NextSeq500 sequencing, sequences were aligned to the human genome, reads counted and gene expression determined (~60 million reads). The PANTHER classification system (pantherdb.org) was used to identify signaling pathways that were most represented in the RNA-Seq gene lists per sample. Embryo implantation-related genes were included in the PANTHER analysis (Sanchez-Ribas et al., Fert Steril 2019; 111:991).

A greater number of expressed genes (n=1484) were found associated with no euploid implants than embryos (n=778) that did implant (Table 2). A greater percentage of genes belonging to apoptotic (1.2 vs 0.6%), GnRH (2.4 vs 1.4%), inflammation (3.1 vs 0.8%) and Wnt (2.3 vs 1.5%) signaling pathways were found to be associated with a successful vs unsuccessful implants. These pathways are elevated in the embryo implantation-related genes. The ubiquitin-proteasome signaling pathway had a greater expression percentage in the negative (0.9%) pregnancy outcomes than positive (0.3%) outcomes.

This cutting-edge data for the first time identifies specific gene expression in unique signaling pathways in conditioned media from euploid embryos capable of establishing a successful pregnancy outcome. Additional studies will confirm the use of a novel gene expression signature by euploid embryos as a means for selection of the most ideal embryo for transfer.

| Pathway | Negative Implantation 1484 genes | Positive Implantation 778 genes |
|---|---|---|
| Apoptosis | 0.6% | 1.2% |
| GnRH | 1.4% | 2.4% |
| Inflammation | 0.8% | 3.1% |
| Ubiquitin-proteasome | 0.9% | 0.3% |
| Wnt | 1.5% | 2.3% |

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A method for determining embryonic viability comprising:

obtaining blastocoel fluid via blastocentesis from at least one embryo;

employing an algorithm via software on a processor to calculate a weighted significance for embryo viability of the at least one embryo wherein the algorithm is expressed as:

Weighted Embryo Morphology Score=(Expansion grade*3)+(ICM grade*2)+(TE grade*1), wherein ICM is inner cell mass and TE is trophectoderm grade;

next, analyzing cell free DNA levels in the blastocoel fluid for apoptotic gene expression levels via real-time PCR for at least one human apoptosis gene;

determining apoptotic cell elimination based on an amount of apoptotic remnant of cell free DNA in the blastocoel fluid cell;

determining an average apoptotic remnant of cell free DNA amount in the blastocoel fluid via fluorospectrometer content;

wherein average apoptotic remnant of cell free DNA in the blastocoel fluid content is higher in euploid embryos as compared to aneuploid embryos; and combining the weighted significance for embryo viability with average apoptotic remnant of cell free DNA in the blastocoel fluid to calculate embryo implantation success of the at least one embryo wherein viable embryo implantation success based on implanting the at least one embryo into a subject includes confirming a presence of at least one molecular marker present in the at least one embryo that enhances an in vitro fertilization embryo transfer success rate for the at least one embryo and implanting the at least one embryo based on the presence of the at least one molecular marker present in the at least one embryo.

2. The method of claim 1, wherein extruded trophectoderm cells are biopsied.

3. The method of claim 2, wherein the extruded trophectoderm cells were obtained via laser pulses between cellular junctions.

4. The method of claim 1, wherein analysis of variance is employed to compare cell free DNA levels from different embryos.

5. The method of claim 1, wherein extent of chromosomal defects in an embryo are gauged based on cell free DNA content.

6. The method of claim 1, wherein detectable molecular differences between embryos are used to determine embryo ploidy status.

7. There method of claim 1, further comprising determining implantation success of an embryo via determining an amount of apoptotic cell elimination.

8. The method of claim 1, wherein presence of pro-apoptotic genes in addition to apoptotic remnant in the blastocoel fluid indicates increased embryo viability.

9. A minimally invasive embryo evaluation method comprising:

employing blastocentesis to obtain blastocoel fluid from at least one embryo;

employing an algorithm via software on a processor to calculate a weighted significance for embryo viability for the at least one embryo wherein the algorithm is expressed as:

Weighted Embryo Morphology Score=(Expansion grade*3)+(ICM grade*2)+(TE grade*1), wherein ICM is inner cell mass and TE is trophectoderm grade;

analyzing cell free DNA levels in the blastocoel fluid for apoptotic gene expression levels via real time PCR for at least one human apoptosis gene;

using at least one apoptotic remnant of cell free DNA in the blastocoel fluid levels to derive a level of apoptotic cell elimination;

determining an average apoptotic remnant of cell free DNA in the blastocoel fluid via fluorospectrometry;

wherein average apoptotic remnant of cell free DNA in the blastocoel fluid content is higher in euploid embryos as compared to aneuploid embryos; and combining the weighted significance for embryo viability with average apoptotic remnant of cell free DNA in the blastocoel fluid to calculate embryo implantation success of the at least one embryo wherein viable embryo implantation success based on implanting the at least one embryo into a subject includes confirming a presence of at least one molecular marker present in the at least one embryo that enhances an in vitro fertilization embryo transfer success rate for the at least one embryo and implanting the at least one embryo based on the presence of the at least one molecular marker present in the at least one embryo.

10. The method of claim 9, further comprising biopsying extruded trophectoderm cells.

11. The method of claim 10, comprising employing laser pulses to obtain the trophectoderm cells.

12. The method of claim 9, wherein analysis of variance is employed to compare cell free DNA levels from different embryos.

13. The method of claim 9, wherein embryos are graded based on cell free DNA content.

14. The method of claim 9, wherein cell free DNA content indicates an amount of chromosomal defects in an embryo.

15. The method of claim 9, wherein detectable molecular differences between embryos correspond with embryo ploidy status.

16. The method of claim 9, wherein determining an amount of apoptotic cell elimination indicates future implantation success of an embryo.

17. The method of claim 9, wherein presence of pro-apoptotic genes in addition to apoptotic remnant in the blastocoel fluid indicates increased embryo viability.

* * * * *